United States Patent
Feng et al.

(10) Patent No.: US 12,427,187 B2
(45) Date of Patent: Sep. 30, 2025

(54) GLUCOSE-RESPONSIVE INSULIN CONJUGATES

(71) Applicant: Merck Sharp & Dohme LLC, Rahway, NJ (US)

(72) Inventors: Danqing Feng, Green Brook, NJ (US); Songnian Lin, Holmdel, NJ (US); Dmitri A. Pissarnitski, Scotch Plains, NJ (US); Brenda Pipik, Edison, NJ (US); Lin Yan, East Brunswick, NJ (US); Yuping Zhu, Basking Ridge, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 853 days.

(21) Appl. No.: 17/614,680

(22) PCT Filed: Jun. 1, 2020

(86) PCT No.: PCT/US2020/035503
§ 371 (c)(1),
(2) Date: Nov. 29, 2021

(87) PCT Pub. No.: WO2020/247297
PCT Pub. Date: Dec. 10, 2020

(65) Prior Publication Data
US 2022/0233647 A1    Jul. 28, 2022

Related U.S. Application Data

(60) Provisional application No. 62/931,504, filed on Nov. 6, 2019, provisional application No. 62/858,080, filed on Jun. 6, 2019.

(51) Int. Cl.
| | | |
|---|---|---|
| A61K 38/00 | (2006.01) | |
| A61K 38/28 | (2006.01) | |
| A61K 47/54 | (2017.01) | |
| A61K 47/65 | (2017.01) | |
| A61P 3/10 | (2006.01) | |

(52) U.S. Cl.
CPC .......... *A61K 38/28* (2013.01); *A61K 47/549* (2017.08); *A61K 47/65* (2017.08); *A61P 3/10* (2018.01)

(58) Field of Classification Search
CPC ...... A61K 38/28; A61K 47/549; A61K 47/65; A61P 3/10; C07K 5/0215; C07K 14/62
See application file for complete search history.

(56) References Cited

U.S. PATENT DOCUMENTS

| 5,304,473 A | 4/1994 | Belagaje et al. |
|---|---|---|
| 6,630,348 B1 | 10/2003 | Lee et al. |
| 8,722,620 B2 | 5/2014 | Fynbo et al. |
| 9,884,125 B2 | 2/2018 | Lin et al. |
| 2002/0013269 A1 | 1/2002 | Balschmidt et al. |
| 2011/0098439 A1 | 4/2011 | Madsen et al. |
| 2011/0301083 A1 | 12/2011 | Zion et al. |
| 2015/0105317 A1* | 4/2015 | Lin .......................... A61P 3/08 530/399 |
| 2018/0110863 A1 | 4/2018 | Feng et al. |

FOREIGN PATENT DOCUMENTS

| WO | 9516708 A1 | 6/1995 |
|---|---|---|
| WO | 9634882 A1 | 11/1996 |
| WO | 2005054291 A1 | 6/2005 |
| WO | 2006097521 A1 | 9/2006 |
| WO | 2007096332 A1 | 8/2007 |
| WO | 2007/104737 A1 | 9/2007 |
| WO | 2007/104738 A2 | 9/2007 |
| WO | 2007104734 A1 | 9/2007 |
| WO | 2007104736 A2 | 9/2007 |
| WO | 2009099763 A1 | 8/2009 |
| WO | 2009132129 A2 | 10/2009 |
| WO | 2010080606 A1 | 7/2010 |
| WO | 2010080609 A1 | 7/2010 |
| WO | 2015051052 A2 | 4/2015 |
| WO | 2018175272 A1 | 9/2018 |

OTHER PUBLICATIONS

Baudys, Miroslav et al., Extending Insulin Action in vivo by Conjugation to Carboxymethyl Dextran, Bioconjugate Chem., 1998, 176-183, 9.

Dixon, H.B.F., et al., Reversible Blocking of Amino Groups with Citraconic Anhydride, Biochem J., 1968, 312-314, 109.

Hu, Qi-Ying et al., Towards the next generation of biomedicines by site-selective conjugation, Chem. Soc. Rev., 2016, 1691-1719, 45.

Kristensen et al., A single-chain insulin-like growth factor I/insulin hybrid binds with high affinity to the insulin receptor, Biochem. J., 1995, pp. 981-986, 305.

Mei, Hong et al., NB1-C16-Insulin: Site-Specific Synthesis, Purification, and Biological Activity, Pharmaceutical Research, 1999, 1680-1686, vol. 16 No. 11.

Sato, Masaaki et al., Glycoinsulins: Dendritic Sialyloligosaccharide-Displaying Insulins Showing a Prolonged Blood-Sugar-Lowering Activity, J. Am. Chem. Soc., 2004, 14013-14022, 126(43).

(Continued)

*Primary Examiner* — Jeanette M Lieb

(74) *Attorney, Agent, or Firm* — Julie M. Lake; Catherine D. Fitch

(57) ABSTRACT

Glucose-responsive insulin conjugates that contain one or more linear oligomer sugar cluster are provided. Such insulin conjugates that may display a pharmacokinetic (PK) and/or pharmacodynamic (PD) profile that is responsive to the systemic concentrations of a saccharide such as glucose or alpha-methylmannose, even when administered to a subject in need thereof in the absence of an exogenous multivalent saccharide-binding molecule.

2 Claims, 14 Drawing Sheets
Specification includes a Sequence Listing.

(56) References Cited

OTHER PUBLICATIONS

Schuettler et al., Preparation of N,N-Bis(methylsulphonylethoxycarbonyl)insulins, Hoppe Seyler's Z. Physiol. Chem., 1979, 1721—With English Abstract, 360.

Tsai, Yali J. et al., Synthesis and Purification of NB1-Palmitoyl Insulin, Pharm. Sci., 1997, 1264-1268, vol. 86, No. 11.

* cited by examiner

GLUCOSE-RESPONSIVE INSULIN CONJUGATES

CROSS-REFERENCE TO RELATED APPLICATIONS

This application is a National Stage application of International Patent Application No. PCT/US2020/035503, filed Jun. 1, 2020, which claims the benefit of priority to U.S. Provisional Patent Application No. 62/931,504, filed Nov. 6, 2019, and U.S. Provisional Patent Application No. 62/858,080, filed Jun. 6, 2020.

FIELD OF THE INVENTION

The present disclosure relates to glucose-responsive insulin conjugates that contain one or more linear oligomer sugar cluster. In particular aspects, the insulin conjugate that displays a pharmacokinetic (PK) and/or pharmacodynamic (PD) profile that is responsive to the systemic concentrations of a saccharide such as glucose or alpha-methylmannose, even when administered to a subject in need thereof in the absence of an exogenous multivalent saccharide-binding molecule.

REFERENCE TO SEQUENCE LISTING SUBMITTED ELECTRONICALLY

The sequence listing of the present application is submitted electronically via EFS-Web as an ASCII-formatted sequence listing, with a file name of "24725-SEQLIST-MAY2020", a creation date of May 13, 2020, and a size of 3.60 KB. This sequence listing submitted via EFS-Web is part of the specification and is herein incorporated by reference in its entirety.

BACKGROUND OF THE INVENTION

The majority of known "controlled-release" drug delivery systems are incapable of providing drugs to a patient at intervals and concentrations that are in direct proportion to the amount of a molecular indicator (e.g., a metabolite) present in the human body. The drugs in these systems are thus not literally "controlled," but simply provided in a slow release format that is independent of external or internal factors.

The treatment of diabetes mellitus with injectable insulin is a well-known and studied example in which uncontrolled, slow release of insulin is undesirable. In fact, it is apparent that the simple replacement of the hormone is not sufficient to prevent the pathological sequelae associated with this disease. Insulin replacement therapy for glycemic control in diabetic patients is often insufficient due to the inability of these exogenous insulins to function in response to the varying glucose concentration. Among approaches to develop glucose responsive insulins, conjugation of a cluster of sugars, e.g., D-mannose and L-fucose, to insulin has been reported in patent literature that potentially offer such glucose responsive insulins. The cluster of sugar moieties, acting as substrate of endogenous mannose receptor, potentially affect the pharmacokinetic properties of their corresponding insulin conjugates in a way that is sensitive to the endogenous glucose concentration, rendering these insulin conjugates low risk of hypoglycemia.

SUMMARY OF THE INVENTION

The present disclosure relates to glucose-responsive insulin conjugates, which comprise linear glycosylated amino acid oligomers, and their synthesis. These insulin conjugates may display a pharmacokinetic (PK) and/or pharmacodynamic (PD) profile that is responsive to the systemic concentrations of a saccharide such as glucose or alpha-methylmannose when administered to a subject in need thereof. In general, the conjugates comprise an insulin or insulin analog molecule covalently attached at its N-terminal amino groups of A-chain, such as $^{A1}$Gly, and B-chain $^{B1}$Phe, respectively, or 8-amino group of the side chain of $^{B29}$Lys, or any Lys residue engineered into insulin backbone, to a linear glycosylated amino acid oligomer as cluster of sugar moieties. Specifically, the linear glycosylated amino acid oligomers are conjugated onto the side chain amino group of B29 lysine or any other lysine and/or A1 and B1 amino groups of insulins or insulin analogs. Such conjugates offer a balanced binding profile against both insulin receptor and mannose receptor. These conjugates demonstrate glucose lowering in the presence of alpha-methyl mannose, a surrogate for glucose, and are potentially useful for the treatment of diabetes with lower risk of hypoglycemia.

Other embodiments, aspects and features of the present disclosure are either further described in or will be apparent from the ensuing description, examples and appended claims.

DETAILED DESCRIPTION OF THE INVENTION

Definitions

Figure 1:
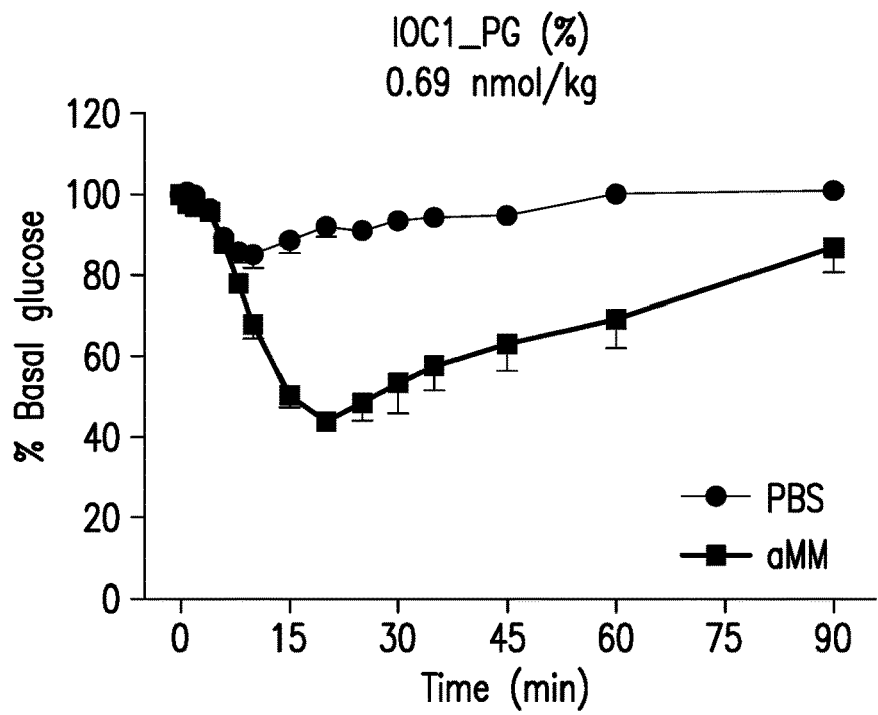
FIG. 1 shows plasma glucose depression curves in non-diabetic male Yucatan minipigs equipped with dual vascular access ports (n=3 per study) following i.v. injection of conjugate IOC-1 at 0.69 nmol/kg under conditions of PBS infusion or i.v. alpha methyl mannose (αMM) infusion.

Definitions of specific functional groups, chemical terms, and general terms used throughout the specification are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987.

As used herein, the term "acyl," refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(=NR^{X1})R^{X1}$, $-C(=NR^{X1})OR^{X1}$, $-C(=NR^{X1})SR$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphatiethioxy, heteroaliphatiethioxy, alkylthioxy, heteroalkylthioxy, arylthioxy, heteroarylthioxy, acyloxy, and the like, each of which may or may not be further substituted).

As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl) alkyl or (cycloalkyl)alkenyl.

As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the disclosure contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, isobutyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like. In embodiments, the alkyl group may be substituted by replacing one or more hydrogen atoms with independently selected substituents.

As used herein, the term "alkenyl" denotes an optionally substituted monovalent group derived from a straight- or branched-chain aliphatic moiety having at least one carbon-carbon double bond by the removal of a single hydrogen atom. In particular embodiments, the alkenyl group employed in the disclosure contains 2-6 carbon atoms. In particular embodiments, the alkenyl group employed in the disclosure contains 2-5 carbon atoms. In some embodiments, the alkenyl group employed in the disclosure contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like. In embodiments, the alkenyl group may be substituted by replacing one or more hydrogen atoms with independently selected substituents.

As used herein, the term "alkynyl" refers to an optionally substituted monovalent group derived from a straight- or branched-chain aliphatic moiety having at least one carbon-carbon triple bond by the removal of a single hydrogen atom. In particular embodiments, the alkynyl group employed in the disclosure contains 2-6 carbon atoms. In particular embodiments, the alkynyl group employed in the disclosure contains 2-5 carbon atoms. In some embodiments, the alkynyl group employed in the disclosure contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like. In embodiments, the alkynyl group may be substituted by replacing one or more hydrogen atoms with independently selected substituents.

As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In particular embodiments of the present invention, "aryl" refers to an aromatic ring system which includes, but not limited to, phenyl ("Ph"), biphenyl, naphthyl, anthracyl and the like, which may bear one or more substituents.

As used herein, the term "arylalkyl" refers to an alkyl group substituted with an aryl group (e.g., an aromatic or heteroaromatic group).

As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

As used herein, the terms "halo" and "halogen" refer to an atom selected from fluorine (fluoro, —F), chlorine (chloro, —Cl), bromine (bromo, —Br), and iodine (iodo, —I).

As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

As used herein, the term "heteroaralkyl" refers to an alkyl group substituted by a heteroaryl, wherein the alkyl and heteroaryl portions independently are optionally substituted.

As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydro-quinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", which are unsubstituted unless otherwise noted.

As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "multivalent hydrocarbon chain" (also referred to as a "multivalent alkylene group") is a polyalkylene group, in which having two or more free valencies or points of connection to other portions of the molecule, for example 2, 3, 4, 5, 6 or more free valencies. For example, the term "bivalent hydrocarbon chain" (also referred to as a "bivalent alkylene group") is a polymethylene group, i.e., —(CH$_2$)—, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described for a substituted aliphatic group. Similarly, the term "trivalent hydrocarbon chain" (also referred to as a "trivalent alkylene group") is a polymethylene group, i.e.,

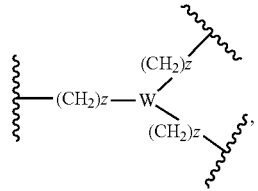

wherein W is independently a carbon atom, a heteroatom, or an optionally substituted group selected from the group consisting of aliphatic, heteroaliphatic, aryl, heteroaryl, and heterocyclic; each z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted trivalent hydrocarbon chain is one in which one or more hydrogen atoms are replaced with a substituent. Suitable substituents include those described for a substituted aliphatic group.

As used herein, the term "unsaturated", means that a moiety has one or more double or triple bonds.

As used herein, the term "partially unsaturated" refers to a ring moiety that includes at least one double or triple bond. The term "partially unsaturated" is intended to encompass rings having multiple sites of unsaturation but is not intended to include aryl or heteroaryl moieties, as herein defined.

As described herein, conjugates of the disclosure may contain "optionally substituted" moieties. In general, conjugates and moieties are unsubstituted unless otherwise noted. The term "substituted" means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable", as used herein, refers to compounds that are not substantially altered when subjected to conditions to allow for their production, detection, and, in particular embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$ that may be substituted with $R^\circ$; $-(CH_2)_{0-4}O(CH_2)_{0-1}Ph$ that may be substituted with $R^\circ$; $-CH=CHPh$ that may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ{}_2$; $-N(R^\circ)C(S)NR^\circ{}_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ{}_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ{}_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ{}_2$; $-C(S)NR^\circ{}_2$; $-C(S)SR^\circ$; $-SC(S)SR^\circ$, $-(CH_2)_{0-4}OC(O)NR^\circ{}_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ{}_2$; $-(CH_2)_{0-4}S(O)R^\circ$; $-N(R^\circ)S(O)_2NR^\circ{}_2$; $-N(R^\circ)S(O)_2R^\circ$; $-N(OR^\circ)R^\circ$; $-C(NH)NR^\circ{}_2$; $-P(O)_2R^\circ$; $-P(O)R^\circ{}_2$; $-OP(O)R^\circ{}_2$; $-OP(O)(OR^\circ)_2$; $SiR^\circ{}_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3- to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet{}_2$, $-NO_2$, $-SiR^\bullet{}_3$, $-OSiR^\bullet{}_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^\bullet{}_2$, $=NNHC(O)R^\bullet$, $=NNHC(O)OR^\bullet$, $=NNHS(O)_2R^\bullet$, $=NR^\bullet$, $=NOR^\bullet$, $-O(C(R^\bullet{}_2))_{2-3}O-$, or $-S(C(R^\bullet{}_2))_{2-3}S-$, wherein each independent occurrence of $R^\bullet$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*{}_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^\bullet$ include halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet{}_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger{}_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger{}_2$, $-C(S)NR^\dagger{}_2$, $-C(NH)NR^\dagger{}_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R are independently halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet{}_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "suitable protecting group," refers to amino protecting groups or hydroxyl protecting groups depending on its location within the compound and includes those described in detail in *Protecting Groups in Organic Synthesis*, T. W. Greene and P. G. M. Wuts, 3rd edition, John Wiley & Sons, 1999.

As used herein, the term "biodegradable" refers to molecules that degrade (i.e., lose at least some of their covalent structure) under physiological or endosomal conditions. Biodegradable molecules are not necessarily hydrolytically degradable and may require enzymatic action to degrade.

As used herein, an "exogenous" molecule is one which is not present at significant levels in a patient unless administered to the patient. In particular embodiments, the patient is a mammal, e.g., a human, a dog, a cat, a rat, a minipig, etc. As used herein, a molecule is not present at significant levels in a patient if normal serum for that type of patient includes less than 0.1 mM of the molecule. In particular embodiments, normal serum for the patient may include less than 0.08 mM, less than 0.06 mM, or less than 0.04 mM of the molecule.

As used herein, a "hyperbranched" structure is a covalent structure that includes at least one branched branch (e.g., a dendrimeric structure). A hyperbranched structure may include polymeric and/or non-polymeric substructures.

As used herein, "normal serum" is serum obtained by pooling approximately equal amounts of the liquid portion of coagulated whole blood from five or more non-diabetic patients. A non-diabetic human patient is a randomly selected 18 to 30 year old who presents with no diabetic symptoms at the time blood is drawn.

As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

As used herein, a "polypeptide" is a polymer made of amino acids that are connected via peptide bonds (or amide bonds). The terms "peptide", "polypeptide", "oligopeptide", and "protein", may be used interchangeably. Polypeptides may contain natural amino acids, non-natural amino acids (i.e., compounds that do not occur in nature but that can be incorporated into a polypeptide chain) and/or amino acid analogs as are known in the art. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

As used herein, a "polysaccharide" is a large polymer made of many individual monosaccharides that are connected via glycosidic bonds. The terms "polysaccharide", "carbohydrate", and "oligosaccharide" may be used interchangeably. The polymer may include natural monosaccharides (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified monosaccharides (e.g., 2'-fluororibose, 2'-deoxyribose, and hexose). Exemplary disaccharides include sucrose, lactose, maltose, trehalose, gentiobiose, isomaltose, kojibiose, laminaribiose, mannobiose, melibiose, nigerose, rutinose, and xylobiose.

As used herein, the term "treat" (or "treating", "treated", "treatment", etc.) refers to the administration of a conjugate of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition. For example, as used herein the term "treating diabetes" will refer in general to maintaining glucose blood levels near normal levels and may include increasing or decreasing blood glucose levels depending on a given situation.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the terms "effective amount" or "therapeutically effective amount" refer to a nontoxic but sufficient amount of an insulin analog to provide the desired effect. For example, one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein, the term "parenteral" means not through the alimentary canal but by some other route such as intranasal, inhalation, subcutaneous, intramuscular, intraspinal, or intravenous.

As used herein, the term "insulin" means the active principle of the pancreas that affects the metabolism of carbohydrates in the animal body and which is of value in the treatment of diabetes mellitus. Herein, "insulin or insulin analog" includes wild-type and modified insulins, including human insulin, porcine insulin, insulin lispro, insulin aspart, insulin glulisine, insulin glargine, and insulin detemir. The term includes synthetic and biotechnologically derived products that are the same as, or similar to, naturally occurring insulins in structure, use, and intended effect and are of value in the treatment of diabetes mellitus.

As used herein, the term "insulin or insulin molecule" is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

As used herein, the terms "insulin analog" or "insulin analogue" as used herein include any heterodimer insulin analog or single-chain insulin analog that comprises one or more modifications of the native A-chain peptide and/or B-chain peptide. Modifications include but are not limited to substituting an amino acid for the native amino acid at a position selected from A1, A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, B30; inserting or adding an amino acid to position A22, A23, A24, B31, B32, B33, B34, or B35; deleting any or all of the amino acids at positions B1, B2, B3, B4, B30, or B26-30; or alkylating with one or more alkyl group(s) to one or both N-terminal amino groups of A-chain, such as $^{A1}$Gly, and B-chain $^{B1}$Phe, respectively, or conjugating directly or by a polymeric or non-polymeric linker one or more acyl, polyethylglycine (PEG), or saccharide moiety (moieties); or any combination thereof. In general, in the insulin analogs the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond. Examples of insulin analogs include but are not limited to the heterodimer and single-chain analogues disclosed in U.S. Pat. No. 8,722,620 and published international application WO20100080606, WO2009099763, and WO2010080609, the disclosures of which are incorporated herein by reference. Examples of single-chain insulin analogues also include but are not limited to those disclosed in published International Applications WO9634882, WO95516708, WO2005054291, WO2006097521, WO2007104734, WO2007104736, WO2007104737, WO2007104738, WO2007096332, WO2009132129; U.S. Pat. Nos. 5,304,473 and 6,630,348; and Kristensen et al., BIOCHEM. J. 305: 981-986 (1995), the disclosures of which are each incorporated herein by reference.

As used herein, the term "amino acid modification" refers to a substitution of an amino acid, or the derivation of an amino acid by the addition and/or removal of chemical groups to/from the amino acid, and it includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein, the term "amino acid substitution" refers to the replacement of one amino acid residue by a different amino acid residue.

As used herein, the term "conservative amino acid substitution" is defined herein as exchanges within one of the following five groups:
 I. Small aliphatic, nonpolar or slightly polar residues: Ala, Ser, Thr, Pro, Gly;
 II. Polar, negatively charged residues and their amides: Asp, Asn, Glu, Gln, cysteic acid and homocysteic acid;
 III. Polar, positively charged residues: His, Arg, Lys; Ornithine (Orn)
 IV. Large, aliphatic, nonpolar residues: Met, Leu, Ile, Val, Cys, Norleucine (Nle), homocysteine
 V. Large, aromatic residues: Phe, Tyr, Trp, acetyl phenylalanine The disclosure provides methods for controlling the pharmacokinetic (PK) and/or pharmacodynamic (PD) profiles of insulin in a manner that is responsive to the systemic concentrations of a saccharide such as glucose. The methods are based in part on the discovery disclosed in U.S. Published Application No. 2011/0301083 that when particular insulin conjugates are modified to include high affinity saccharide ligands such as branched trimannose, they could be made to exhibit PK/PD profiles that responded to saccharide concentration changes even in the absence of an exogenous multivalent saccharide-binding molecule.

In general, the insulin conjugates of the present invention comprise an insulin analog molecule covalently attached to at least one branched linker having or consisting of two arms, each arm independently covalently attached to a ligand comprising or consisting of a saccharide wherein at least one ligand of the linker includes the saccharide fucose. In particular embodiments, the ligands are capable of competing with a saccharide (e.g., glucose or alpha-methylmannose) for binding to an endogenous saccharide-binding molecule. In particular embodiments, the ligands are capable of competing with glucose or alpha-methylmannose for binding to Con A. In particular embodiments, the linker is non-polymeric. In particular embodiments, the conjugate may have a polydispersity index of one and a MW of less than about 20,000 Da. In particular embodiments, the conjugate is of formula (I) or (II) as defined and described herein. In particular embodiments, the conjugate is long acting (i.e., exhibits a PK profile that is more sustained than soluble recombinant human insulin (RHI)).

Insulin Conjugates

This disclosure relates to glucose-responsive insulin conjugates, which comprise linear glycosylated amino acid oligomers, and their synthesis. These insulin conjugates may display a pharmacokinetic (PK) and/or pharmacodynamic (PD) profile that is responsive to the systemic concentrations of a saccharide, such as glucose or alpha-methylmannose, when administered to a subject in need thereof. In one aspect, the insulin conjugates that comprise an insulin analog molecule covalently attached to at least one oligomer sugar cluster having two or more monomers or subunits linked through the amide bond, wherein each monomer or subunit is independently covalently linked through a side chain to a ligand comprising or consisting of a saccharide, which may be a saccharide, bisaccharide, trisaccharide, tetrasaccharide, or branched trisaccharide. In aspects, a ligand comprises or consists of a bisaccharide, trisaccharide, tetrasaccharide, or branched trisaccharide. In some aspects, ligands may comprise or consist of fucose, mannose, glucosamine, or glucose. In some particular aspects, a ligand comprises a bimannose, trimannose, tetramannose, or branched trimannose.

When the insulin conjugate herein is administered to a mammal at least one pharmacokinetic or pharmacodynamic property of the conjugate is sensitive to the serum concentration of a saccharide. In particular embodiments, the PK and/or PD properties of the conjugate are sensitive to the serum concentration of an endogenous saccharide such as glucose. In particular embodiments, the PK and/or PD properties of the conjugate are sensitive to the serum concentration of an exogenous saccharide, e.g., without limitation, mannose, L-fucose, N-acetyl glucosamine and/or alpha-methyl mannose.

PK and PD Properties

In various embodiments, the pharmacokinetic and/or pharmacodynamic behavior of the insulin conjugate herein may be modified by variations in the serum concentration of a saccharide. For example, from a pharmacokinetic (PK) perspective, the serum concentration curve may shift upward when the serum concentration of the saccharide (e.g., glucose) increases or when the serum concentration of the saccharide crosses a threshold (e.g., is higher than normal glucose levels).

In particular embodiments, the serum concentration curve of an insulin conjugate is substantially different when administered to the mammal under fasted and hyperglycemic conditions. As used herein, the term "substantially different" means that the two curves are statistically different as determined by a student t-test ($p<0.05$). As used herein, the term "fasted conditions" means that the serum concentration curve was obtained by combining data from five or more fasted non-diabetic individuals. In particular embodiments, a fasted non-diabetic individual is a randomly selected 18 to 30 year old human who presents with no diabetic symptoms at the time blood is drawn and who has not eaten within 12 hours of the time blood is drawn. As used herein, the term "hyperglycemic conditions" means that the serum concentration curve was obtained by combining data from five or more fasted non-diabetic individuals in which hyperglycemic conditions (glucose $C_{max}$ at least 100 mg/dL above the mean glucose concentration observed under fasted conditions) were induced by concurrent administration of conjugate and glucose. Concurrent administration of conjugate and glucose simply requires that the glucose $C_{max}$ occur during the period when the conjugate is present at a detectable level in the serum. For example, a glucose injection (or ingestion) could be timed to occur shortly before, at the same time or shortly after the conjugate is administered. In particular embodiments, the conjugate and glucose are administered by different routes or at different locations. For example, in particular embodiments, the conjugate is administered subcutaneously while glucose is administered orally or intravenously.

In particular embodiments, the serum $C_{max}$ of the conjugate is higher under hyperglycemic conditions as compared to fasted conditions. Additionally or alternatively, in particular embodiments, the serum area under the curve (AUC) of the conjugate is higher under hyperglycemic conditions as compared to fasted conditions. In various embodiments, the serum elimination rate of the conjugate is slower under hyperglycemic conditions as compared to fasted conditions. In particular embodiments, the serum concentration curve of the conjugates can be fit using a two-compartment bi-exponential model with one short and one long half-life. The long half-life appears to be particularly sensitive to glucose concentration. Thus, in particular embodiments, the long half-life is longer under hyperglycemic conditions as compared to fasted conditions. In particular embodiments, the fasted conditions involve a glucose $C_{max}$ of less than 100 mg/dL (e.g., 80 mg/dL, 70 mg/dL, 60 mg/dL, 50 mg/dL, etc.). In particular embodiments, the hyperglycemic conditions involve a glucose $C_{max}$ in excess of 200 mg/dL (e.g., 300 mg/dL, 400 mg/dL, 500 mg/dL, 600 mg/dL, etc.). It will be appreciated that other PK parameters such as mean serum residence time (MRT), mean serum absorption time (MAT), etc. could be used instead of or in conjunction with any of the aforementioned parameters.

The normal range of glucose concentrations in humans, dogs, cats, and rats is 60 to 200 mg/dL. One skilled in the art will be able to extrapolate the following values for species with different normal ranges (e.g., the normal range of glucose concentrations in miniature pigs is 40 to 150 mg/dl). Glucose concentrations below 60 mg/dL are considered hypoglycemic. Glucose concentrations above 200 mg/dL are considered hyperglycemic. In particular embodiments, the PK properties of the conjugate may be tested using a glucose clamp method (see Examples) and the serum concentration curve of the conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Additionally or alternatively, the serum $T_{max}$, serum $C_{max}$, mean serum residence time (MRT), mean serum absorption time (MAT) and/or serum half-life may be substantially different at the two glucose concentrations. As discussed below, in particular embodiments, 100 mg/dL and 300 mg/dL may be used as comparative glucose concentrations.

It is to be understood however that the present disclosure encompasses each of these embodiments with an alternative pair of comparative glucose concentrations including, without limitation, any one of the following pairs: 50 and 200 mg/dL, 50 and 300 mg/dL, 50 and 400 mg/dL, 50 and 500 mg/dL, 50 and 600 mg/dL, 100 and 200 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc.

Thus, in particular embodiments, the $C_{max}$ of the conjugate is higher when administered to the mammal at the higher of the two glucose concentrations (e.g., 300 vs. 100 mg/dL glucose). In particular embodiments, the $C_{max}$ of the conjugate is at least 50% (e.g., at least 100%, at least 200% or at least 400%) higher when administered to the mammal at the higher of the two glucose concentrations (e.g., 300 vs. 100 mg/dL glucose).

In particular embodiments, the AUC of the conjugate is higher when administered to the mammal at the higher of the two glucose concentrations (e.g., 300 vs. 100 mg/dL glucose). In particular embodiments, the AUC of the conjugate is at least 50% (e.g., at least 100%, at least 200% or at least 400%) higher when administered to the mammal at the higher of the two glucose concentrations (e.g., 300 vs. 100 mg/dL glucose).

In particular embodiments, the serum elimination rate of the insulin conjugate is slower when administered to the mammal at the higher of the two glucose concentrations (e.g., 300 vs. 100 mg/dL glucose). In particular embodiments, the serum elimination rate of the conjugate is at least 25% (e.g., at least 50%, at least 100%, at least 200%, or at least 400%) faster when administered to the mammal at the lower of the two glucose concentrations (e.g., 100 vs. 300 mg/dL glucose).

In particular embodiments, the serum concentration curve of insulin conjugates may be fit using a two-compartment bi-exponential model with one short and one long half-life. The long half-life appears to be particularly sensitive to glucose concentration. Thus, in particular embodiments, the long half-life is longer when administered to the mammal at the higher of the two glucose concentrations (e.g., 300 vs. 100 mg/dL glucose). In particular embodiments, the long half-life is at least 50% (e.g., at least 100%, at least 200% or at least 400%) longer when administered to the mammal at the higher of the two glucose concentrations (e.g., 300 vs. 100 mg/dL glucose).

In particular embodiments, the present disclosure provides a method in which the serum concentration curve of an insulin conjugate is obtained at two different glucose concentrations (e.g., 300 vs. 100 mg/dL glucose); the two curves are fit using a two-compartment bi-exponential model with one short and one long half-life; and the long half-lives obtained under the two glucose concentrations are compared. In particular embodiments, this method may be used as an assay for testing or comparing the glucose sensitivity of one or more insulin conjugates.

In particular embodiments, the present disclosure provides a method in which the serum concentration curves of a conjugated drug (e.g., an insulin conjugate of the present disclosure) and an unconjugated version of the drug (e.g., RHI) are obtained under the same conditions (e.g., fasted conditions); the two curves are fit using a two-compartment bi-exponential model with one short and one long half-life; and the long half-lives obtained for the conjugated and unconjugated drug are compared. In particular embodiments, this method may be used as an assay for identifying conjugates that are cleared more rapidly than the unconjugated drug.

In particular embodiments, the serum concentration curve of an insulin conjugate is substantially the same as the serum concentration curve of an unconjugated version of the drug when administered to the mammal under hyperglycemic conditions. As used herein, the term "substantially the same" means that there is no statistical difference between the two curves as determined by a student t-test (p>0.05). In particular embodiments, the serum concentration curve of the insulin conjugate is substantially different from the serum concentration curve of an unconjugated version of the drug when administered under fasted conditions. In particular embodiments, the serum concentration curve of the insulin conjugate is substantially the same as the serum concentration curve of an unconjugated version of the drug when administered under hyperglycemic conditions and substantially different when administered under fasted conditions.

In particular embodiments, the hyperglycemic conditions involve a glucose $C_{max}$ in excess of 200 mg/dL (e.g., 300 mg/dL, 400 mg/dL, 500 mg/dL, 600 mg/dL, etc.). In particular embodiments, the fasted conditions involve a glucose $C_{max}$ of less than 100 mg/dL (e.g., 80 mg/dL, 70 mg/dL, 60 mg/dL, 50 mg/dL, etc.). It will be appreciated that any of the aforementioned PK parameters such as serum $T_{max}$, serum $C_{max}$, AUC, mean serum residence time (MRT), mean serum absorption time (MAT) and/or serum half-life could be compared.

From a pharmacodynamic (PD) perspective, the bioactivity of the insulin conjugate may increase when the glucose concentration increases or when the glucose concentration crosses a threshold, e.g., is higher than normal glucose levels. In particular embodiments, the bioactivity of an insulin conjugate is lower when administered under fasted conditions as compared to hyperglycemic conditions. In particular embodiments, the fasted conditions involve a glucose $C_{max}$ of less than 100 mg/dL (e.g., 80 mg/dL, 70 mg/dL, 60 mg/dL, 50 mg/dL, etc.). In particular embodiments, the hyperglycemic conditions involve a glucose $C_{max}$ in excess of 200 mg/dL (e.g., 300 mg/dL, 400 mg/dL, 500 mg/dL, 600 mg/dL, etc.).

In particular embodiments, the PD properties of the insulin conjugate may be tested by measuring the glucose infusion rate (GIR) required to maintain a steady glucose concentration. According to such embodiments, the bioactivity of the insulin conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Thus, in particular embodiments, the bioactivity of the insulin conjugate is higher when administered to the mammal at the higher of the two glucose concentrations (e.g., 300 vs. 100 mg/dL glucose). In particular embodiments, the bioactivity of the conjugate is at least 25% (e.g., at least 50% or at least 100%) higher when administered to the mammal at the higher of the two glucose concentrations (e.g., 300 vs. 100 mg/dL glucose).

In particular embodiments, the PD behavior for the insulin analog can be observed by comparing the time to reach minimum blood glucose concentration ($T_{nadir}$), the duration over which the blood glucose level remains below a particular percentage of the initial value (e.g., 70% of initial value or T70% BGL), etc.

In general, it will be appreciated that any of the PK and PD characteristics discussed in this section can be determined according to any of a variety of published pharmacokinetic and pharmacodynamic methods (e.g., see Baudys et al., Bioconjugate Chem. 9:176-183, 1998 for methods suitable for subcutaneous delivery). It is also to be understood that the PK and/or PD properties may be measured in any mammal (e.g., a human, a rat, a cat, a minipig, a dog, etc.). In particular embodiments, PK and/or PD properties are measured in a human. In particular embodiments, PK and/or PD properties are measured in a rat. In particular embodiments, PK and/or PD properties are measured in a minipig. In particular embodiments, PK and/or PD properties are measured in a dog.

It will also be appreciated that while the foregoing was described in the context of glucose-responsive insulin conjugates, the same properties and assays apply to insulin conjugates that are responsive to other saccharides including exogenous saccharides, e.g., mannose, L-fucose, N-acetyl glucosamine, alpha-methyl mannose, etc. As discussed in more detail below and in the Examples, instead of comparing PK and/or PD properties under fasted and hyperglycemic conditions, the PK and/or PD properties may be compared under fasted conditions with and without administration of the exogenous saccharide. It is to be understood that conjugates can be designed that respond to different $C_{max}$ values of a given exogenous saccharide.

This disclosure relates to glucose-responsive insulin conjugates, which comprise linear glycosylated amino acid oligomers, and their synthesis. These insulin conjugates may display a pharmacokinetic (PK) and/or pharmacodynamic (PD) profile that is responsive to the systemic concentrations of a saccharide, such as glucose or alpha-methylmannose, when administered to a subject in need thereof.

In general, the conjugates comprise an insulin or insulin analog molecule covalently attached at its A1Gly, B1Phe, and/or B29Lys amino acid or Lys on another position to one or more linear glycosylated amino acid oligomer as cluster of sugar moieties. In specific embodiments, the conjugates comprise an insulin or insulin analog molecule covalently attached at its A1Gly, B1Phe, and/or B29Lys amino acid or Lys on another position to one or two linear glycosylated amino acid oligomer as cluster of sugar moieties. Specifically, the one or more linear glycosylated amino acid oligomers is conjugated onto the side chain amino group of B29 lysine or A1 and B1 amino groups of insulins.

The present disclosure provides a conjugate comprising an insulin or insulin analog molecule covalently attached via a linker to at least one linear glycosylated amino acid oligomer, which comprises an oligopeptide having amino acid units bound to a sugar containing moiety. Each sugar-containing moiety independently comprises or consists of a saccharide such as a monosaccharide, bisaccharide, trisaccharide, tetrasaccharide, or branched trisaccharide.

In embodiments of the conjugate, the conjugate comprises an insulin or insulin analog molecule conjugated to at least one or more ligands selected from linear glycosylated amino acid oligomers and sugar clusters, and the remaining amino groups modified with another sugar containing moiety, such as a monosaccharide, or organic functional groups, such as aminocarbonyl and methyl.

In embodiments of the conjugate, the conjugate comprises an insulin or insulin analog molecule conjugated to at least two ligands selected from linear glycosylated amino acid oligomers and sugar clusters. In a further embodiment, the conjugate comprises an insulin or insulin analog molecule conjugated to at least three ligands selected from linear glycosylated amino acid oligomers and sugar clusters.

In particular embodiments of the conjugate, the conjugate displays a pharmacodynamic (PD) and/or pharmacokinetic (PK) profile that is sensitive to the serum concentration of a serum saccharide when administered to a subject in need thereof in the absence of an exogenous saccharide binding molecule.

In particular embodiments of the conjugate, the serum saccharide is glucose or alpha-methylmannose.

In particular embodiments of the conjugate, the conjugate binds an endogenous saccharide binding molecule at a serum glucose concentration of 60 mg/dL or less when administered to a subject in need thereof.

In particular embodiments of the conjugate, the endogenous saccharide binding molecule is human mannose receptor 1.

Ligand(s)

This disclosure relates to glucose-responsive insulin conjugates that comprise linear glycosylated amino acid oligomers, and their synthesis. These insulin conjugates may display a pharmacokinetic (PK) and/or pharmacodynamic (PD) profile that is responsive to the systemic concentrations of a saccharide, such as glucose or alpha-methylmannose, when administered to a subject in need thereof.

In general, the insulin conjugates comprise an insulin analog molecule covalently attached to at least one linker having linear glycosylated amino acid oligomer ligands wherein the ligand comprises or consists of one or more saccharides. In particular embodiments, the insulin conjugates may further include one or more linear linkers, each comprising a single ligand, which comprises or consist of one or more saccharides. In particular embodiments, the insulin conjugates may further include one or more branched linkers that each includes at least two, three, four, five, or more ligands, where each ligand independently comprises or consists of one or more saccharides. When more than one ligand is present the ligands may have the same or different chemical structures.

In particular embodiments, the ligands are capable of competing with a saccharide (e.g., glucose, alpha-methylmannose, or mannose) for binding to an endogenous saccharide-binding molecule (e.g., without limitation surfactant proteins A and D or members of the selectin family). In particular embodiments, the ligands are capable of competing with a saccharide (e.g., glucose, alpha-methylmannose, or mannose) for binding to cell-surface sugar receptor (e.g., without limitation macrophage mannose receptor, glucose transporter ligands, endothelial cell sugar receptors, or hepatocyte sugar receptors). In particular embodiments, the ligands are capable of competing with glucose for binding to an endogenous glucose-binding molecule (e.g., without limitation surfactant proteins A and D or members of the selectin family). In particular embodiments, the ligands are capable of competing with glucose or alpha-methylmannose for binding to the human macrophage mannose receptor 1 (MRC1). In particular embodiments, the ligands are capable of competing with a saccharide for binding to a non-human lectin (e.g., Con A). In particular embodiments, the ligands are capable of competing with glucose, alpha-methylmannose, or mannose for binding to a non-human lectin (e.g., Con A). Exemplary glucose-binding lectins include calnexin, calreticulin, N-acetylglucosamine receptor, selectin, asialoglycoprotein receptor, collectin (mannose-binding lectin), mannose receptor, aggrecan, versican, *Pisum sativum* agglutinin (PSA), *Vicia faba* lectin, *Lens culinaris* lectin, soybean lectin, peanut lectin, *Lathyrus ochrus* lectin, sainfoin lectin, *Sophora japonica* lectin, *Bowringia milbraedii* lectin, concanavalin A (Con A), and pokeweed mitogen.

In particular embodiments, the ligand(s) may have a saccharide having the same chemical structure as glucose or may be a chemically related species of glucose, e.g., glucosamine. In various embodiments, it may be advantageous for the ligand(s) to have a different chemical structure from glucose, e.g., in order to fine tune the glucose response of the conjugate. For example, in particular embodiments, one might use a ligand that includes glucose, mannose, L-fucose or derivatives of these (e.g., alpha-L-fucopyranoside, mannosamine, beta-linked N-acetyl mannosamine, methylglucose, methylmannose, ethylglucose, ethylmannose, propylglucose, propylmannose, etc.) and/or higher order combinations of these (e.g., a bimannose, linear and/or branched trimannose, etc.).

In particular embodiments, the ligand(s) include(s) a monosaccharide. In particular embodiments, the ligand(s) include(s) a disaccharide. In particular embodiments, the ligand(s) include(s) a trisaccharide. In some embodiments, the ligand(s) comprise a saccharide and one or more amine groups. In some embodiments, the ligand(s) comprise a saccharide and ethyl group. In particular embodiments, the saccharide and amine group are separated by a $C_1$-$C_6$ alkyl group, e.g., a $C_1$-$C_3$ alkyl group. In some embodiments, the ligand is aminoethylglucose (AEG). In some embodiments, the ligand is aminoethylmannose (AEM). In some embodiments, the ligand is aminoethylbimannose (AEBM). In some embodiments, the ligand is aminoethyltrimannose (AETM). In some embodiments, the ligand is β-aminoethyl-N-acetylglucosamine (AEGA). In some embodiments, the ligand is aminoethylfucose (AEF). In particular embodiments, the saccharide is of the "D" configuration and in other embodiments, the saccharide is of the "L" configuration. Below are the structures of exemplary saccharides having an amine group separated from the saccharide by a $C_2$ ethyl group wherein R may be hydrogen or a carbonyl group of the linker. Other exemplary ligands will be recognized by those skilled in the art.

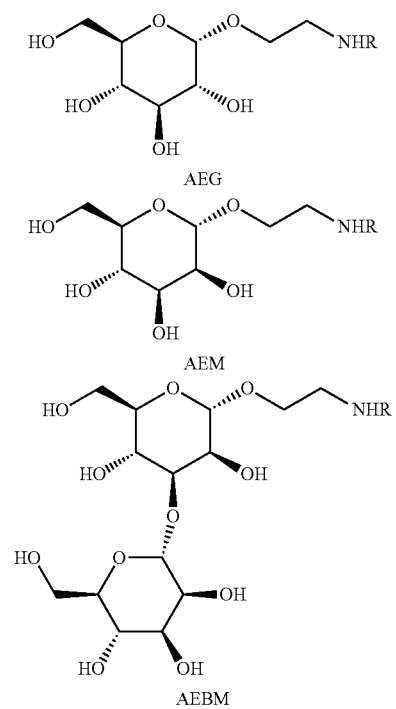

AEG

AEM

AEBM

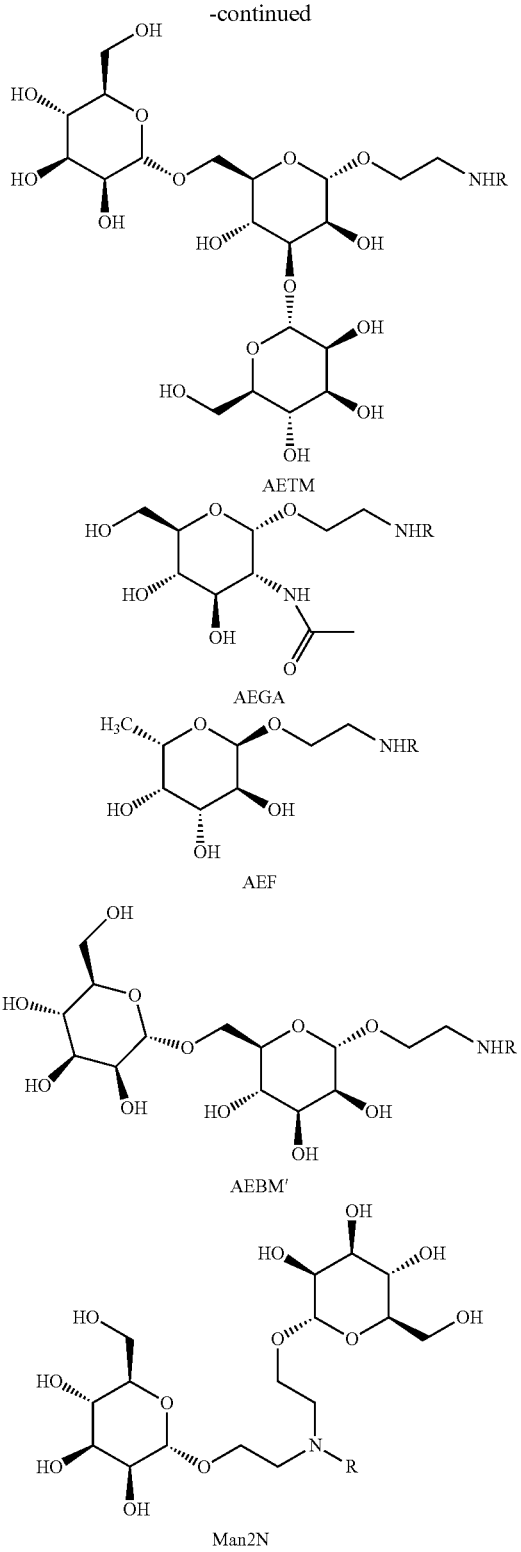

Insulin

As used herein, the term "insulin conjugate" includes insulin conjugates comprising an insulin analog molecule wherein the insulin analog comprises an amino acid sequence that differs from the native or wild-type human insulin amino acid sequence by at least one amino acid substitution, deletion, rearrangement, or addition. The wild-type sequence of human insulin (A-chain and B-chain) is shown below.

```
A-Chain polypeptide:
                                    (SEQ ID NO: 1)
GIVEQCCTSICSLYQLENYCN B-Chain polypeptide:
                                    (SEQ ID NO: 2)
FVNQHLCGSHLVEALYLVCGERGFFYTPKT
```

In particular aspects of the conjugate, the insulin analog comprise an A chain polypeptide sequence comprising a sequence of $X_1 I X_2 E X_3 CCX_4 X_5 X_6 CS X_7 X_8 X_9 LE X_{10} YC X_{11} X_{12}$ (SEQ ID NO: 3); and a B chain polypeptide sequence comprising a sequence of $X_{13} V X_{14} X_{15} HLCGS HLVEALX_{16} X_{17} VCGERGFX_{18} YTX_{19} X_2 X_2 X_{22} X_{23} X_{24} X_{25} X_{26}$ (SEQ ID NO: 4) wherein $X_1$ is glycine (G) or lysine (K);
$X_2$ is valine (V), glycine (G), or lysine (K);
$X_3$ is glutamine (Q) or lysine (K);
$X_4$ is threonine (T), histidine (H), or lysine (K);
$X_5$ is serine (S) or lysine (K);
$X_6$ is isoleucine (I) or lysine (K);
$X_7$ is leucine (L) or lysine (K);
$X_8$ is tyrosine (Y) or lysine (K);
$X_9$ is glutamine (Q) or lysine (K);
$X_{10}$ is asparagine (N) or lysine (K);
$X_{11}$ is asparagine (N), glycine (G), or lysine (K);
$X_{12}$ is arginine (R), lysine (K), or absent;
$X_{13}$ is phenylalanine (F) or lysine (K);
$X_{14}$ is asparagine (N) or lysine (K);
$X_{15}$ is glutamine (Q) or lysine (K);
$X_{16}$ is tyrosine (Y) or lysine (K);
$X_{17}$ is leucine (L) or lysine (K);
$X_{19}$ is phenylalanine (F) or lysine (K);
$X_{19}$ is proline (P) or lysine (K):
$X_{20}$ is lysine (K), proline (P), arginine (R), or is absent;
$X_{21}$ is threonine (T) or absent;
$X_{22}$ is arginine (R) if $X_{21}$ is threonine (T), or absent;
$X_{23}$ is proline (P) if $X_{22}$ is arginine (R), or absent;
$X_{24}$ is arginine (R) if $X_{23}$ is proline (P), or absent;
$X_{25}$ is proline (P) if $X_{24}$ is arginine (R), or absent; and
$X_{26}$ is arginine (R) if $X_{25}$ is proline (P), or absent,
with the proviso that at least one of $X_1$, $X_3$, $X_5$, $X_6$, $X_7$, $X_8$, $X_9$, $X_{10}$, $X_{12}$, $X_{13}$, $X_{14}$, $X_{15}$, $X_{16}$, $X_{17}$, $X_{18}$, and $X_{19}$ is a lysine (K) and when $X_{19}$ is lysine (K) then $X_{20}$ is absent or if $X_{20}$ is present then at least one of $X_1$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, and $X_{17}$ is lysine (K), or $X_4$ is histidine (H), or $X_{11}$ is glycine (G); or at least one of $X_{12}$ or $X_{21}$ is present.

In particular aspects of the conjugate, the insulin analog is GlyA21 human insulin; GlyA3 human insulin; LysA22 human insulin; LysB3 human insulin; HisA8 human insulin; GlyA21 ArgA22 human insulin; DesB30 human insulin; LysA9 DesB30 human insulin; GlyA21 DesB30 human insulin; LysA22 DesB30 human insulin; LysB3 DesB30 human insulin; LysA1 ArgB29 DesB30 human insulin; LysA5 ArgB29 DesB30 human insulin; LysA9 ArgB29 DesB30 human insulin; LysA10 ArgB29 DesB30 human insulin; LysA13 ArgB29 DesB30 human insulin; LysA14 ArgB29 DesB30 human insulin; LysA15 ArgB29 DesB30 human insulin; LysA18 ArgB29 DesB30 human insulin; LysA22 ArgB29 DesB30 human insulin; LysA1 GlyA21 ArgB29 DesB30 human insulin; GlyA21 ArgB29 DesB30 human insulin; LysB1 ArgB29 DesB30 human insulin;

LysB3 ArgB29 DesB30 human insulin; LysB4 ArgB29 DesB30 human insulin; LysB16 ArgB29 DesB30 human insulin; LysB17 ArgB29 DesB30 human insulin; LysB25 ArgB29 DesB30 human insulin; GlyA21 ArgB31 ProB32 ArgB33 ProB34 ArgB35 human insulin; or GlyA21 ArgA22 ArgB31 ProB32 ArgB33 human insulin.

Methods for Conjugating Insulin Analog Molecules are Described Below.

In particular embodiments, an insulin analog molecule is conjugated to a linker via the A1 amino acid residue. In particular embodiments, the A1 amino acid residue is glycine. It is to be understood however, that the present disclosure is not limited to N-terminal conjugation and that in particular embodiments an insulin analog molecule may be conjugated via a non-terminal A-chain amino acid residue. In particular, the present disclosure encompasses conjugation via the epsilon-amine group of a lysine residue present at any position in the A-chain, including at position A1. It will be appreciated that different conjugation positions on the A-chain may lead to different reductions in insulin activity.

In particular embodiments, an insulin analog molecule is conjugated to the linker via the B1 amino acid residue. In particular embodiments, the B1 amino acid residue is phenylalanine. It is to be understood however, that the present disclosure is not limited to N-terminal conjugation and that in particular embodiments an insulin analog molecule may be conjugated via a non-terminal B-chain amino acid residue. In particular, the present disclosure encompasses conjugation via the epsilon-amine group of a lysine residue present at any position in the B-chain, including position B1. It will be appreciated that different conjugation positions on the B-chain may lead to different reductions in insulin activity.

In particular embodiments, an insulin analog molecule is conjugated to the linker via the B29 amino acid residue. In particular embodiments, the B29 amino acid residue is lysine. It is to be understood however, that the present disclosure is not limited to N-terminal conjugation and that in particular embodiments an insulin analog molecule may be conjugated via a non-terminal B-chain amino acid residue. In particular, the present disclosure encompasses conjugation via the epsilon-amine group of a lysine residue present at any position in the B-chain, including position B29. It will be appreciated that different conjugation positions on the B-chain may lead to different reductions in insulin activity.

In particular embodiments, an insulin analog molecule is conjugated to the linker via acylation of the epsilon-amine group of lysine. In particular, the present disclosure encompasses conjugation via the epsilon-amine group of a lysine residue present at any position on the insulin or insulin analog molecule. It will be appreciated that different conjugation positions may lead to different reductions in insulin activity.

In particular embodiments, the ligands are conjugated to more than one conjugation point on the insulin analog molecule. For example, an insulin analog molecule can be conjugated at both the A1 N-terminus and the epsilon amino group of a lysine at position A5, A9, A10, A13, A14, A15, A18, A22, B1, B3, B4, B16, B17, B25, B28, or B29. In some embodiments, an insulin molecule can be conjugated at the A1 N-terminus, the B1 N-terminus, and the epsilon amino group of lysine. In yet other embodiments, protecting groups are used such that conjugation takes place at the B1 and epsilon amino group of lysine or B1 and A1 positions. It will be appreciated that any combination of conjugation points on an insulin molecule may be employed.

Insulin Conjugates

In particular embodiments, provided are insulin and insulin analog conjugates wherein the conjugate is characterized as having a ratio of EC50 or IP as determined by a functional insulin receptor phosphorylation assay as opposed to the IC50 or IP as determined by a competition binding assay at the macrophage mannose receptor is about 0.5:1 to about 1:100; about 1:1 to about 1:50; about 1:1 to about 1:20; or about 1:1 to about 1:10. In further aspects, the above conjugate is characterized as having a ratio of EC50 or IP as determined by a functional insulin receptor phosphorylation assay as opposed to the IC50 or IP as determined by a competition binding assay at the macrophage mannose receptor is about 0.5:1 to about 1:100; about 1:1 to about 1:50; about 1:1 to about 1:20; or about 1:1 to about 1:10.

The term "IP" refers to the inflection point, which is a point on a curve at which the curvature or concavity changes sign from plus to minus or from minus to plus. In general, IP is usually equivalent to the EC50 or IC50.

In particular aspects, the IC50 or IP as determined by a competition binding assay at the macrophage mannose receptor may be less than about 100 nM and greater than about 0.5 nM. In particular aspects, the IC50 or IP is less than about 50 nM and greater than about 1 nM; less than about 25 nM and greater than about 1 nM; or less than about 20 nM and greater than about 1 nM. In particular aspects, the IC50 or IP as determined by a functional insulin receptor phosphorylation assay may be less than about 100 nM and greater than about 0.5 nM. In particular aspects, the IC50 or IP is less than about 50 nM and greater than about 1 nM; less than about 25 nM and greater than about 1 nM; or less than about 20 nM and greater than about 1 nM.

The instant disclosure relates to glucose-responsive insulin conjugates having general formula (I):

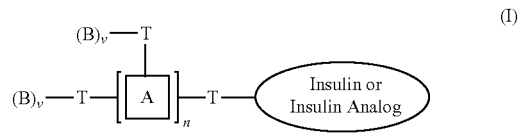

wherein
(a) the insulin or insulin analog is selected from human insulin, porcine insulin, insulin lispro, insulin aspart, insulin glulisine, insulin glargine, and insulin detemir;
(b) the spacer T is covalently linked to the amino group at position A1 of the insulin or insulin analog molecule; position B1 of the insulin or insulin analog molecule; position B29 of the insulin or insulin analog molecule; or other lysine residue of the insulin or insulin analog molecule;
(c) each occurrence of spacer T is selected independently from the group consisting of a covalent bond or a bivalent, straight or branched, saturated or unsaturated, optionally substituted $C_{1-30}$ hydrocarbon chain, wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;
(d) each occurrence of R is independently hydrogen, a suitable protecting group, or an acyl moiety, arylalkyl moiety, aliphatic moiety, aryl moiety, heteroaryl moiety, or heteroaliphatic moiety;

(e) each occurrence of [A] is independently an optionally substituted monomeric amino acid unit selected from the group consisting of aspartic acid and glutamic acid, where either α-carboxylic acid or side chain carboxylic acid group or both carboxylic acids are conjugated to a sugar, or lysine, where either α-amino group or ε-amino group or both amino groups are conjugated to a sugar;

(f) each occurrence of B is a sugar-containing moiety having a valence v that is independently 0, 1, 2, 3, or 4;

(h) n is the number of individual, independently selected monomeric units [A] and is selected from 0, 1, 2, 3, or 4.

In embodiments of the conjugate, each sugar-containing moiety B independently comprises or consists of a saccharide selected from the group consisting of fucose, mannose, glucosamine, glucose, bimannose, trimannose, tetramannose, or branched trimannose.

In particular embodiments, each sugar-containing moiety B comprises or consists of a saccharide and aminoethyl group. In particular embodiments, the saccharide and ethyl group are separated by a $C_1$-$C_6$ alkyl group, e.g., a $C_1$-$C_3$ alkyl group. In particular embodiments, the ligand comprises or consists of a saccharide selected from the group consisting of aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF). In particular embodiments, the saccharide is of the "D" configuration, and in other embodiments, the saccharide is of the "L" configuration.

In particular embodiments of the conjugate, the spacer T is covalently linked to the amino acid at position A1 of the insulin or insulin analog molecule; position B1 of the insulin or insulin analog molecule; or position B29 of the insulin or insulin molecule; or 8-amino group of lysine residue engineered into insulin analogs.

Description of Exemplary Groups

[A] (Monomeric Amino Acid Unit)

In particular embodiments, each occurrence of [A] is independently an optionally substituted monomeric amino acid unit selected from the group consisting of aspartic acid and glutamic acid, where either α-carboxylic acid or side chain carboxylic acid group or both carboxylic acids are conjugated to a sugar, or lysine, where either α-amino group or ε-amino group or both amino groups are conjugated to a sugar. In some embodiments, each occurrence of [A] is the same. In some embodiments, each occurrence of [A] is different from each other occurrences of [A].

T (Spacer)

In particular embodiments, each occurrence of T is independently a bivalent, straight or branched, saturated or unsaturated, optionally substituted $C_{1-20}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group. In particular embodiments, one, two, three, four, or five methylene units of T are optionally and independently replaced. In particular embodiments, T is constructed from a $C_{1-10}$, $C_{1-8}$, $C_{1-6}$, $C_{1-4}$, $C_{2-12}$, $C_{4-12}$, $C_{6-12}$, $C_{8-12}$, or $C_{10-12}$ hydrocarbon chain wherein one or more methylene units of T are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group. In some embodiments, one or more methylene units of T is replaced by a heterocyclic group. In some embodiments, one or more methylene units of T is replaced by a triazole moiety. In particular embodiments, one or more methylene units of T is replaced by —C(O)—. In particular embodiments, one or more methylene units of T is replaced by —C(O)N(R)—. In particular embodiments, one or more methylene units of T is replaced by —O—.

In particular embodiments, each individual T may be selected from structure

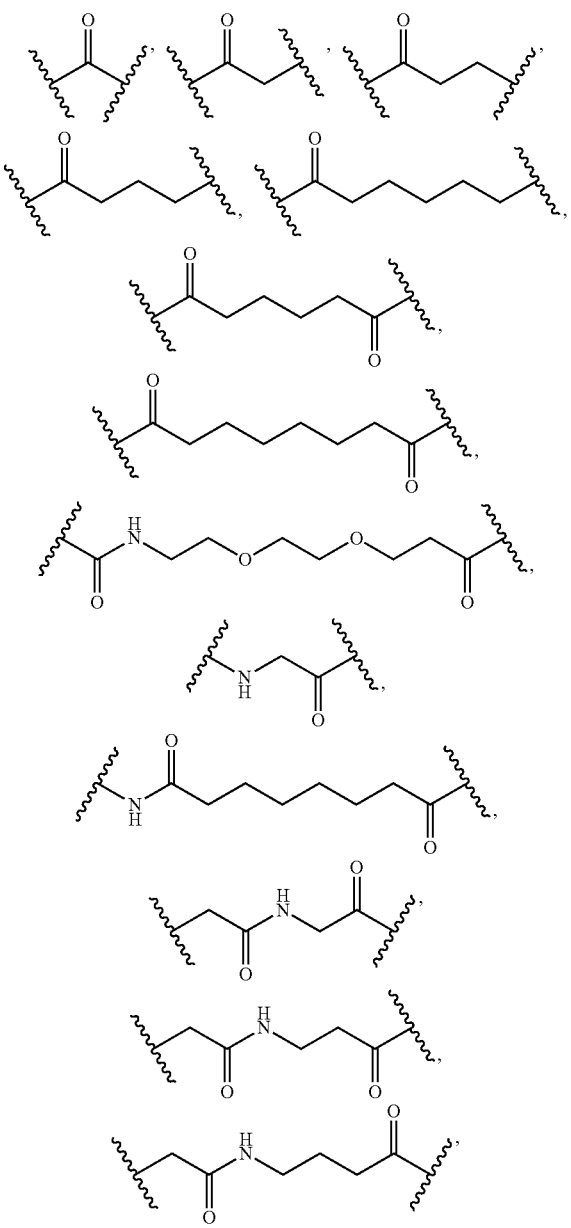

27
-continued
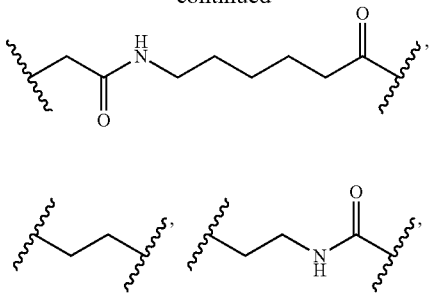
28
-continued
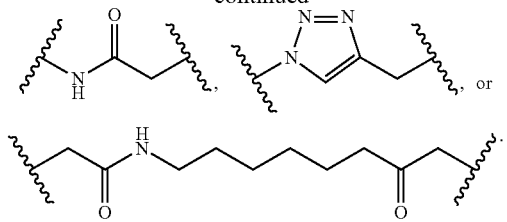
In particular embodiments, the present disclosure provides insulin analog conjugates comprising 1, 2, or 3 linkers, each independently selected from the group consisting of
A
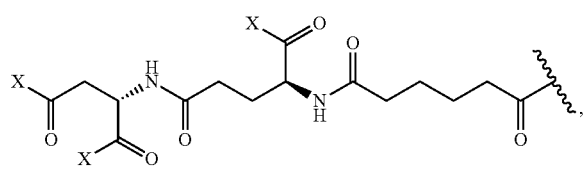
B
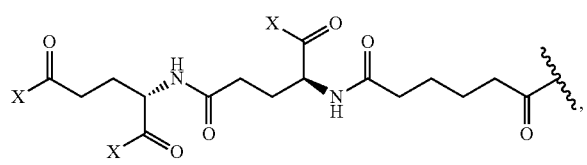
C
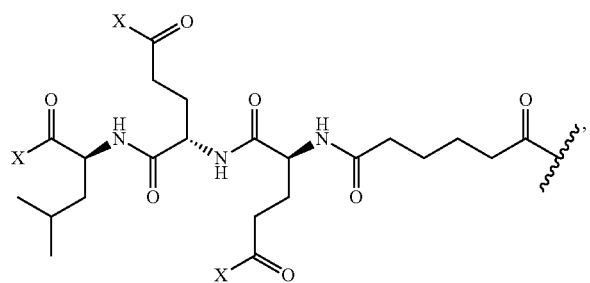
D
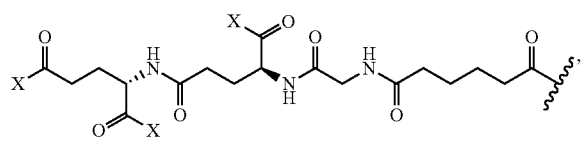
E
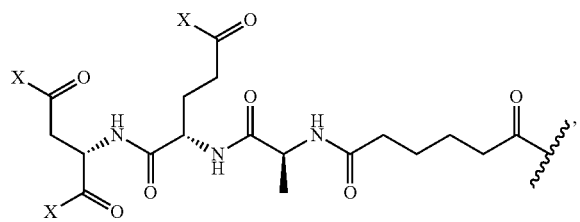
F
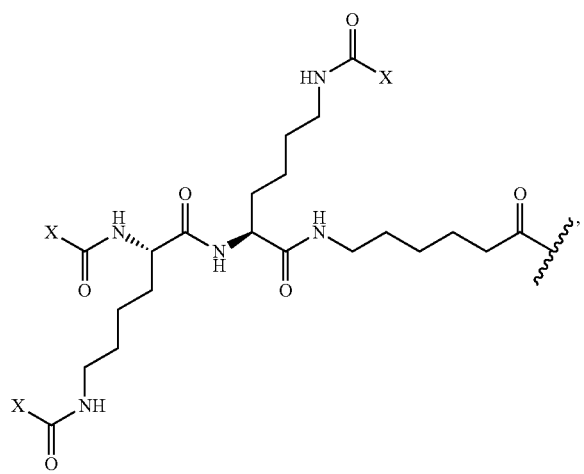
G
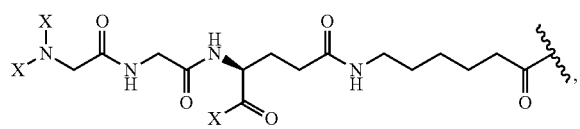
H
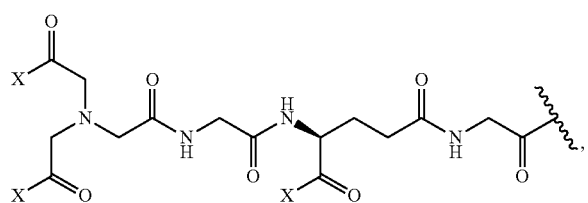

-continued
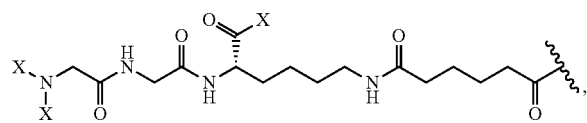
I
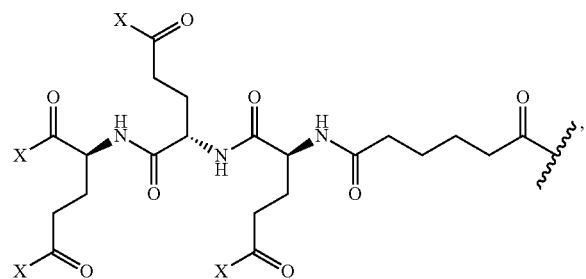
J
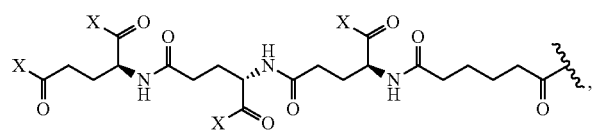
K
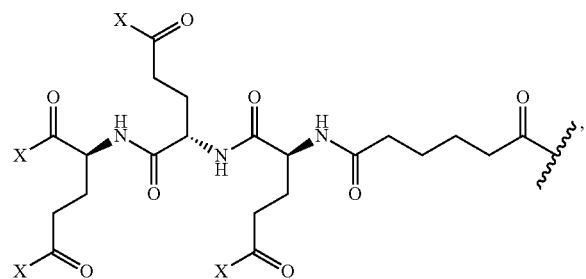
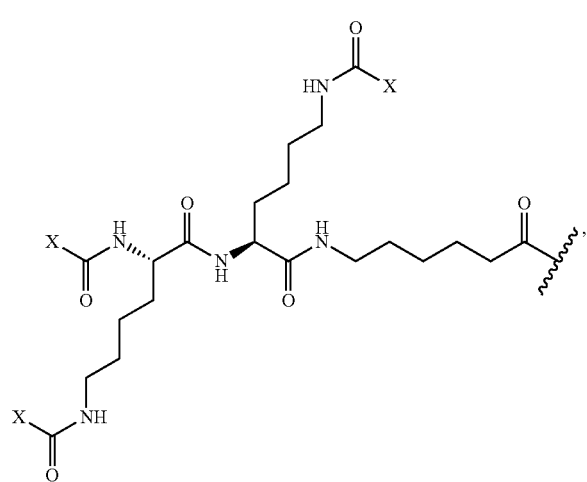
M
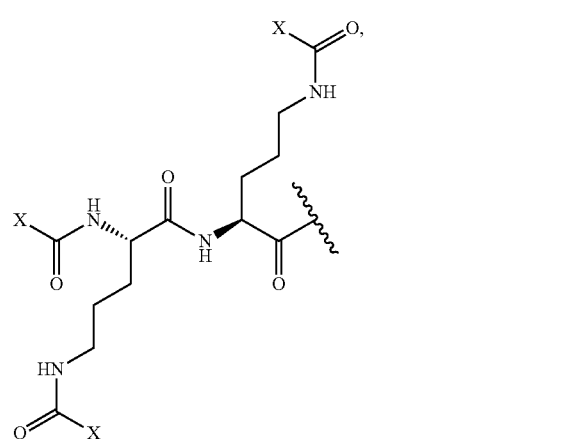
N
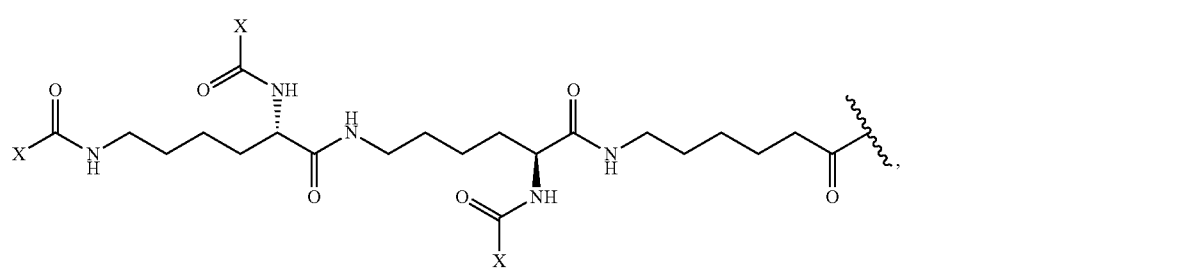
O
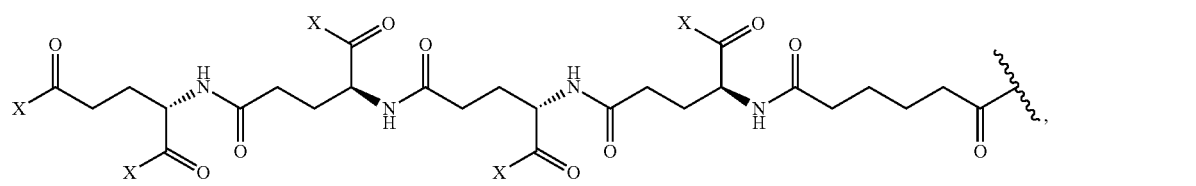
P
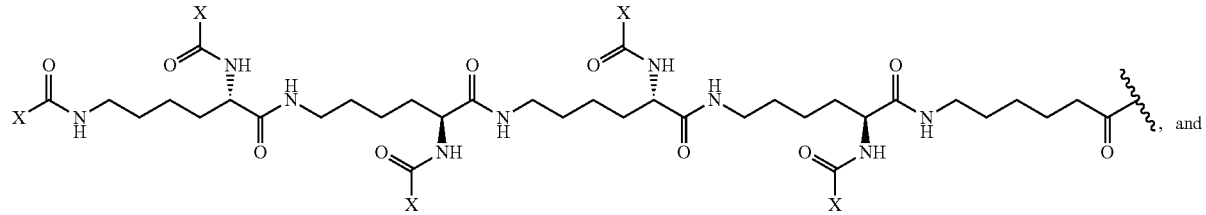
Q, and

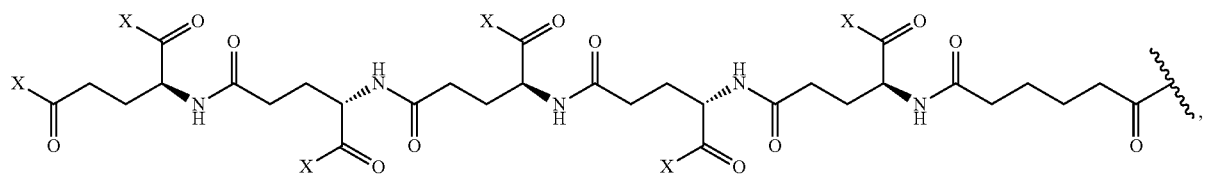
wherein each X is independently a ligand comprising a saccharide (B) and a spacer (T). The wavy line marks the bond between the linker and the amino group from the N-terminus or the epsilon amino group of lysine of the insulin analog. In particular embodiments, each B may independently be
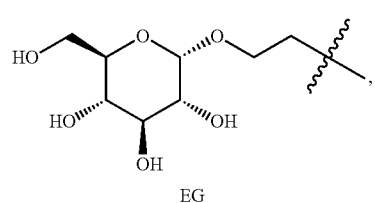
EG
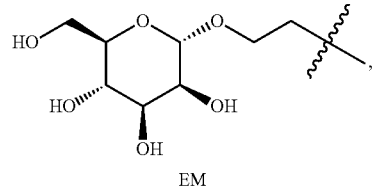
EM
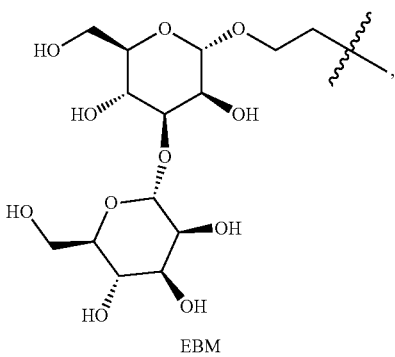
EBM
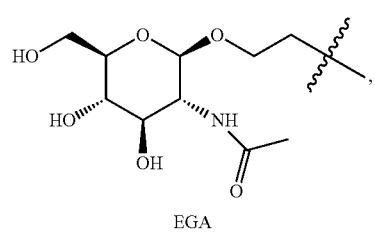
EGA
-continued
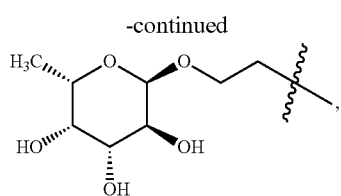
EF
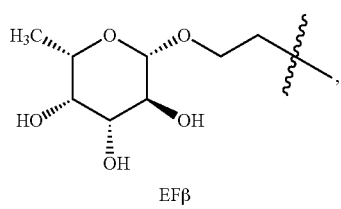
EFβ
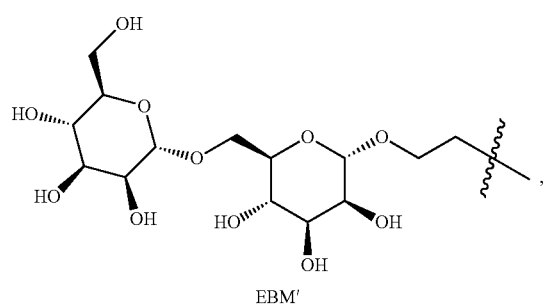
EBM'
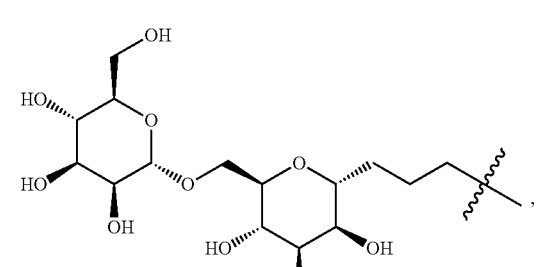
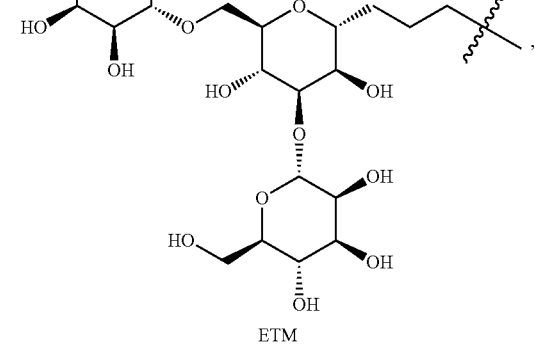
ETM

33

-continued

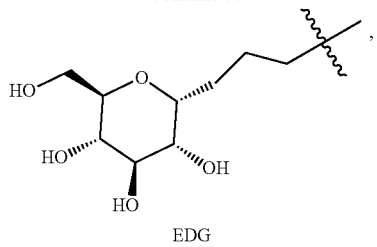

EDG

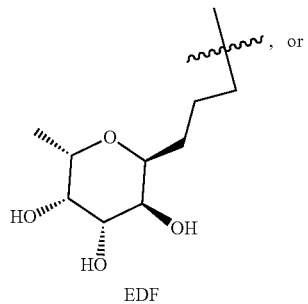

EDF

34

-continued

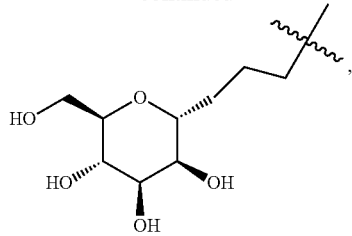

wherein the wavy line indicates the bond is linked to an atom comprising the linker. EG is ethylglucose, EM is ethylmannose, EF is ethylfucose, ETM is ethyltrimannose, EBM is ethyldimannose, EGA is ethylgluccosamine, EDG is ethyldeoxyglucose, EDF is ethyldeoxyfucose, and EDM is ethyldeoxymannose.

Examples of multivalent (B), groups are shown below wherein the wavy line indicates the bond linked to an atom comprising the spacer T:

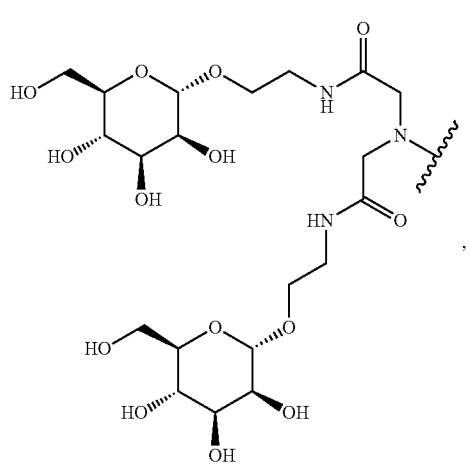

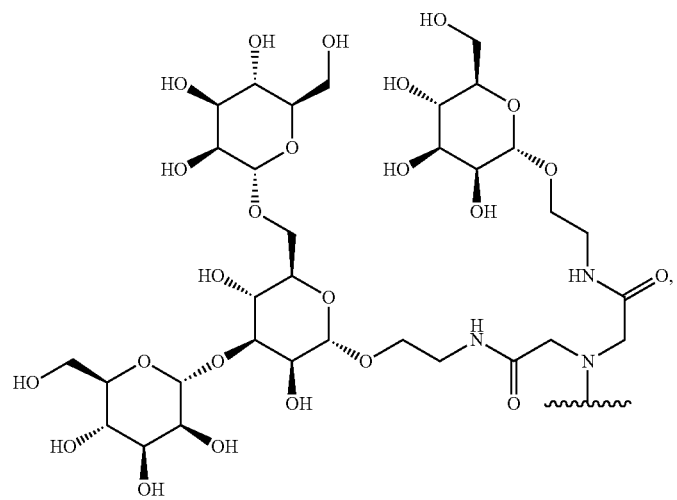

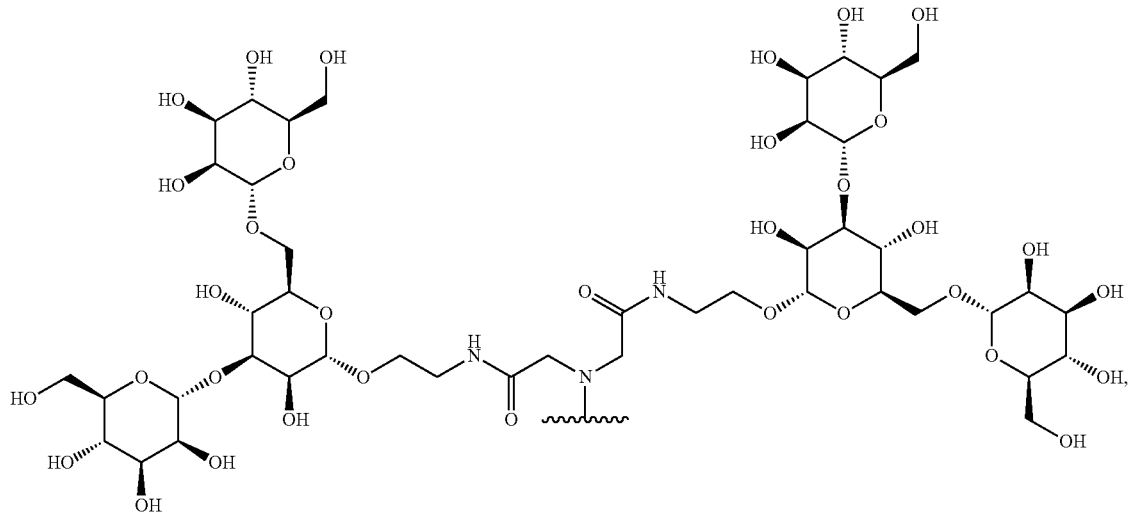

35
36
-continued
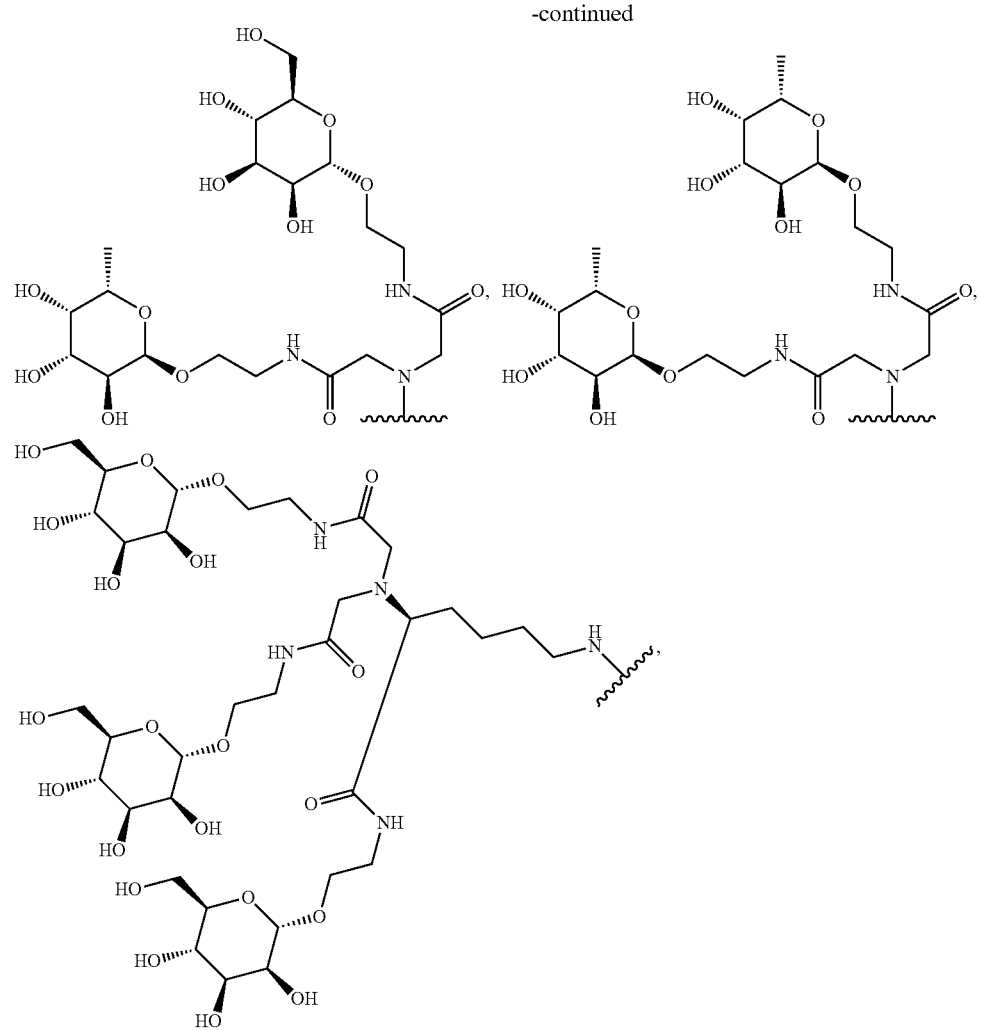
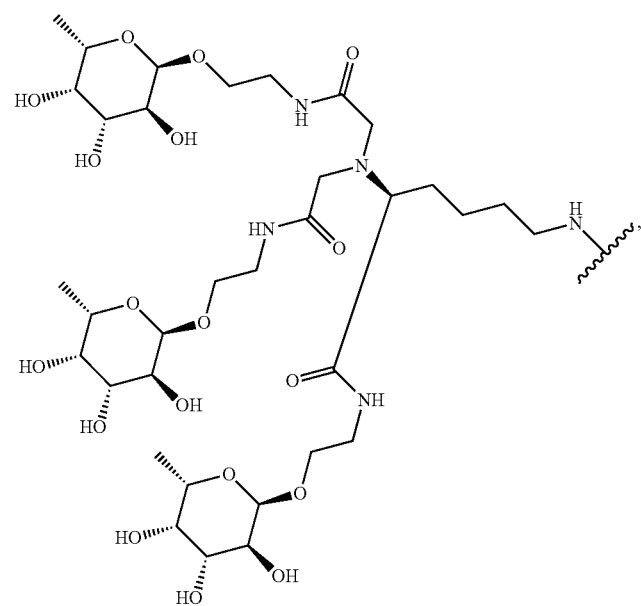

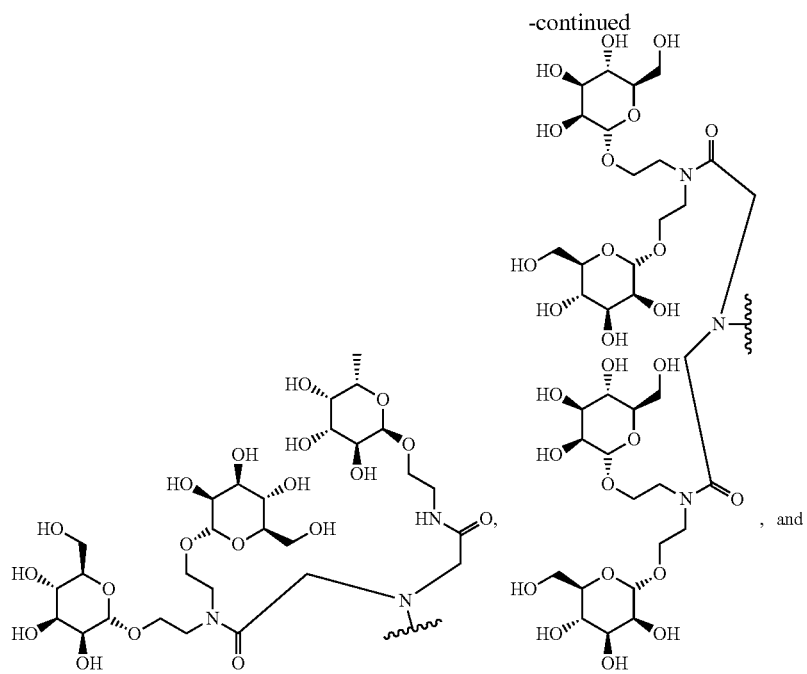

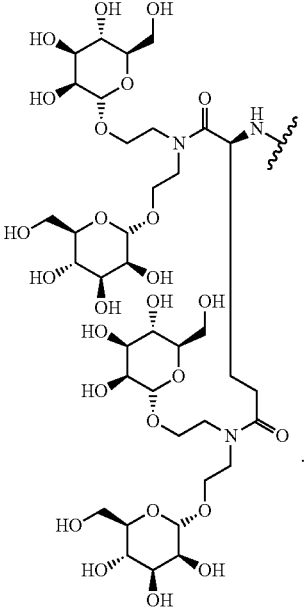

One of ordinary skill will appreciate that a variety of conjugation chemistries may be used to covalently conjugate an X with a linker. Such techniques are widely known in the art, and exemplary techniques are discussed below. Components can be directly bonded (i.e., with no intervening chemical groups) or indirectly bonded through a spacer (e.g., a coupling agent or covalent chain that provides some physical separation between X and the linker). It is to be understood that X may be covalently bound to a linker through any number of chemical bonds, including but not limited to amide, amine, ester, ether, thioether, isourea, imine, etc. bonds.

Particular components may naturally possess more than one of the same chemically reactive moieties. In some examples, it is possible to choose the chemical reaction type and conditions to selectively react with the component at only one of those sites. For example, in the case where insulin is conjugated through reactive amines, in particular embodiments, the N-terminal α-Phe-B1 may be more desirable as a site of attachment over the N-terminal α-Gly-A1 and F-Lys-B29 to preserve insulin bioactivity (e.g., see Mei et al., *Pharm. Res.* 16: 1680-1686, 1999 and references cited therein as well as Tsai et al., *J. Pharm. Sci.* 86: 1264-1268, 1997). In an exemplary reaction between insulin with hexadecenal (an aldehyde-terminated molecule), researchers found that mixing the two components overnight in a 1.5M pH 6.8 sodium salicylate aqueous solution containing 54% isopropanol at a ratio of 1:6 (insulin:aldehyde mol/mol) in the presence of sodium cyanoborohydride resulted in over 80% conversion to the single-substituted Phe-B1 secondary amine-conjugated product (Mei et al., *Pharm. Res.* 16:1680-1686, 1999). Their studies showed that the choice of solvent, pH, and insulin:aldehyde ratio all affected the selectivity and yield of the reaction. In most cases, however, achieving selectivity through choice of chemical reaction conditions is difficult. Therefore, in particular embodiments, it may be advantageous to selectively protect the component (e.g., insulin) at all sites other than the one desired for reaction followed by a deprotection step after the material has been reacted and purified. For example, there are numerous examples of selective protection of insulin amine groups available in the literature including those that may be deprotected under acidic (BOC), slightly acidic (citraconic anhydride), and basic (MSC) conditions (e.g., see Tsai et al., *J. Pharm. Sci.* 86: 1264-1268, 1997; Dixon et al., *Biochem. J.* 109: 312-314, 1968; and Schuettler et al., *D. Brandenburg Hoppe Seyler's Z. Physiol. Chem.* 360: 1721, 1979). In one example, the Gly-A1 and Lys-B29 amines may be selectively protected with tert-butoxycarbonyl (BOC) groups which are then removed after conjugation by incubation for one hour at 4 C in a 90% trifluoroacetic acid (TFA)/10% anisole solution. In one embodiment, a dry powder of insulin is dissolved in anhydrous DMSO followed by an excess of triethylamine. To this solution, approximately two equivalents of di-tert-butyl dicarbonate solution in THF are added slowly and the solution allowed to mix for 30 to 60 minutes. After reaction, the crude solution is poured in an excess of acetone followed by dropwise addition of dilute HCl to precipitate the reacted insulin. The precipitated material is centrifuged, washed with acetone and dried completely under vacuum.

The desired di-BOC protected product may be separated from unreacted insulin analog, undesired di-BOC isomers, and mono-BOC and tri-BOC byproducts using preparative reverse phase HPLC or ion exchange chromatography (e.g., see Tsai et al., *J. Pharm. Sci.* 86: 1264-1268, 1997). In the case of reverse phase HPLC, a solution of the crude product in 70% water/30% acetonitrile containing 0.1% TFA is loaded onto a C8 column and eluted with an increasing acetonitrile gradient. The desired di-BOC peak is collected, the acetonitrile removed and lyophilized to obtain the product.

In particular embodiments, the linker may have formula A, B, C, D, E, F, G, H, I, J, K, L, M, N, O, P, Q, and R, as shown supra wherein X is a saccharide; with the proviso that for at least one linker the X on at least one arm of the at least one linker is fucose. In particular embodiments, X has the formula EG, EM, EBM, EGA, EF, EFP, EBM, ETM, EDG, EDF, or EDM as shown supra.

In particular aspects of the conjugate, the insulin analog is conjugated to at least one linker selected from ML-1, ML-2, ML-3, ML-4, ML-5, ML-6, ML-7, ML-8, ML-9, ML-10, ML-11, ML-12, ML-13, ML-14, ML-15, ML-16, ML-17, ML-18, ML-19, ML-20, ML-21, ML-22, ML-23, ML-24, ML-25, ML-26, ML-27, ML-28, ML-29, ML-30, ML-31, ML-32, ML-33, ML-34, ML-35, ML-36, ML-37, ML-38, ML-39, ML-40, ML-41, ML-42, ML-43, ML-44, ML-45, and ML-46. Each conjugation may independently be an amide linkage between the linker and the N-terminal amino group of the A chain polypeptide or B chain polypeptide or the epsilon amino group of a lysine residue within the A chain polypeptide or B chain polypeptide.

In particular embodiments, at least one N-terminal amino acid is conjugated via the N2 nitrogen to a substituent comprising an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides, which in particular aspects RC(O)— may be acetyl, phenylacetyl, carbamoyl, N-alkyl carbamoyl, or alkoxycarbonyl. In particular aspects, the substituent is a carbamoyl group, acetyl group, glycine, methyl group, methoxy group, dimethyl group, isobutyl group, PEG1 group, or PEG2 group.

Exemplary substituents conjugated to the N-terminal amino group may be

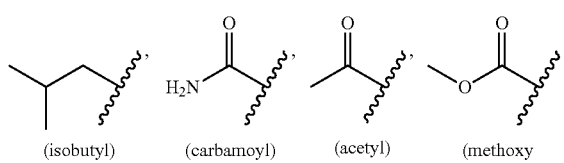

(isobutyl) (carbamoyl) (acetyl) (methoxy acetyl)

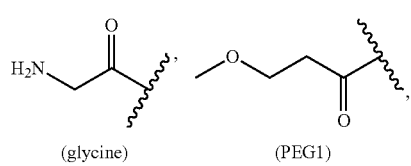

(glycine) (PEG1)

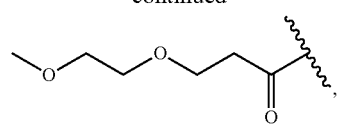

(PEG2)

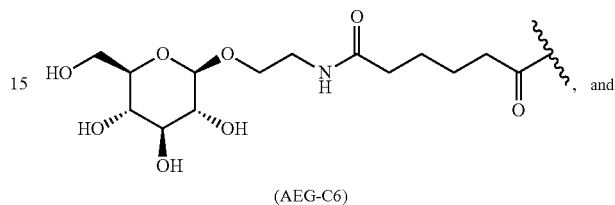

(AEG-C6)

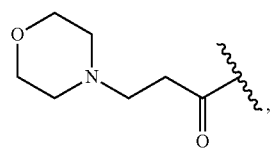

(3-morpholinoproprionate)

wherein the wavy line indicates the bond between the substituent and the N-terminal amino group. The substituent may also be

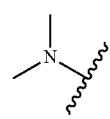

(Me$_2$N; N-dimethyl)

wherein the wavy line indicates the bond between Me$_2$N and the alpha carbon of the N-terminal amino acid.

Embodiments of this disclosure provide conjugates having the formula as set forth in Table 1 for IOC-1, 1° C.-2, IOC-3, IOC-4, IOC-5, IOC-6, IOC-7, IOC-8, IOC-9, IOC-10, IOC-11, IOC-12, IOC-13, IOC-14, IOC-15, IOC-16, IOC-17, IOC-18, IOC-19, IOC-20, IOC-21, IOC-22, IOC-23, IOC-24, IOC-25, IOC-26, IOC-27, IOC-28, IOC-29, IOC-30, IOC-31, IOC-32, IOC-33, IOC-34, IOC-35, IOC-36, IOC-37, IOC-38, IOC-39, IOC-40, IOC-41, IOC-42, IOC-43, IOC-44, IOC-45, IOC-46, IOC-47, IOC-48, IOC-49, IOC-50, IOC-51, IOC-52, IOC-53, IOC-54, IOC-55, IOC-56, IOC-57, IOC-58, IOC-59, IOC-60, IOC-61, and IOC-62.

| Conjugate | Compound Formula & Structure |
|---|---|
| IOC-1 | 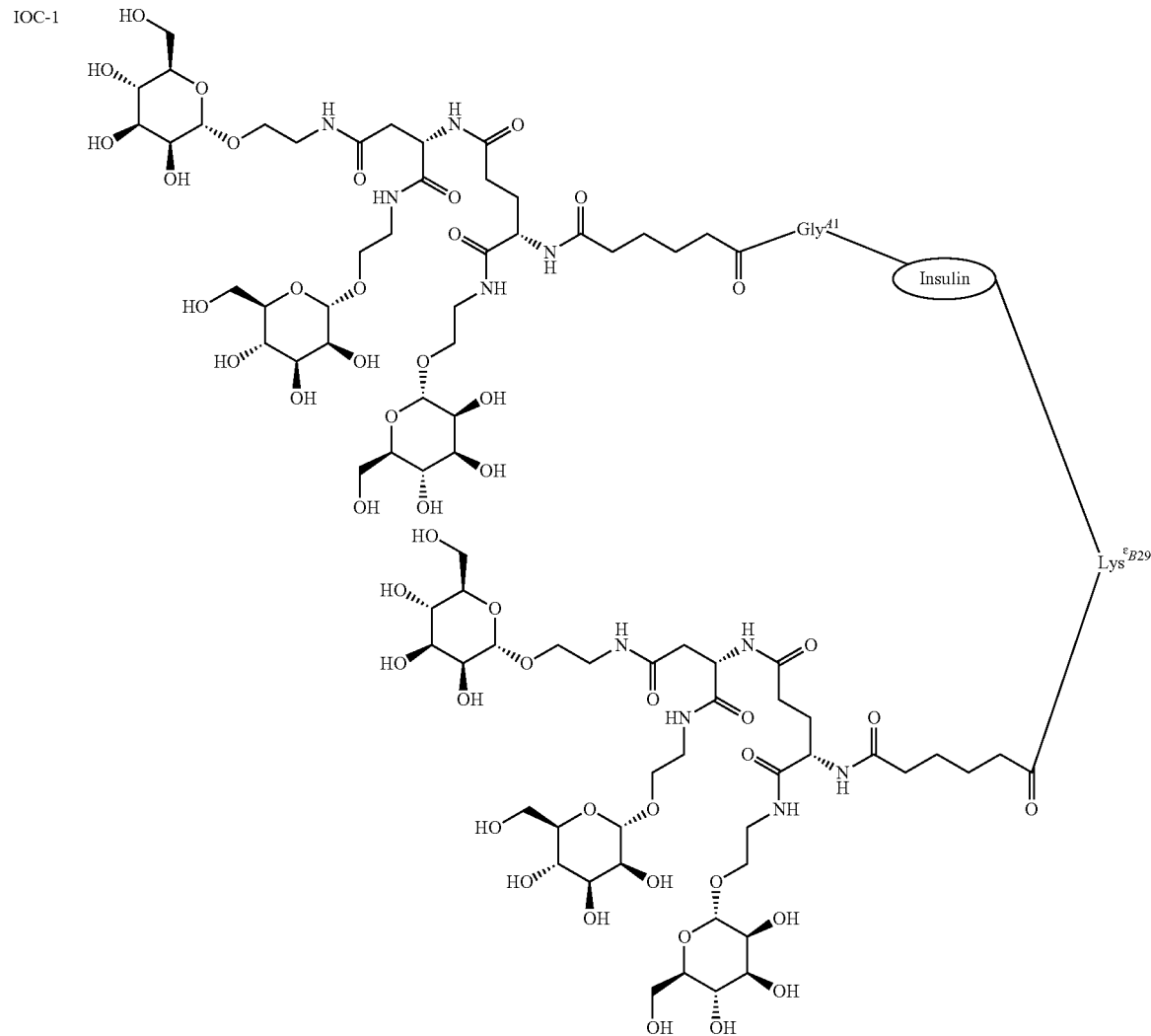 |

| Conjugate | Compound Formula & Structure |
|---|---|
| IOC-2 | 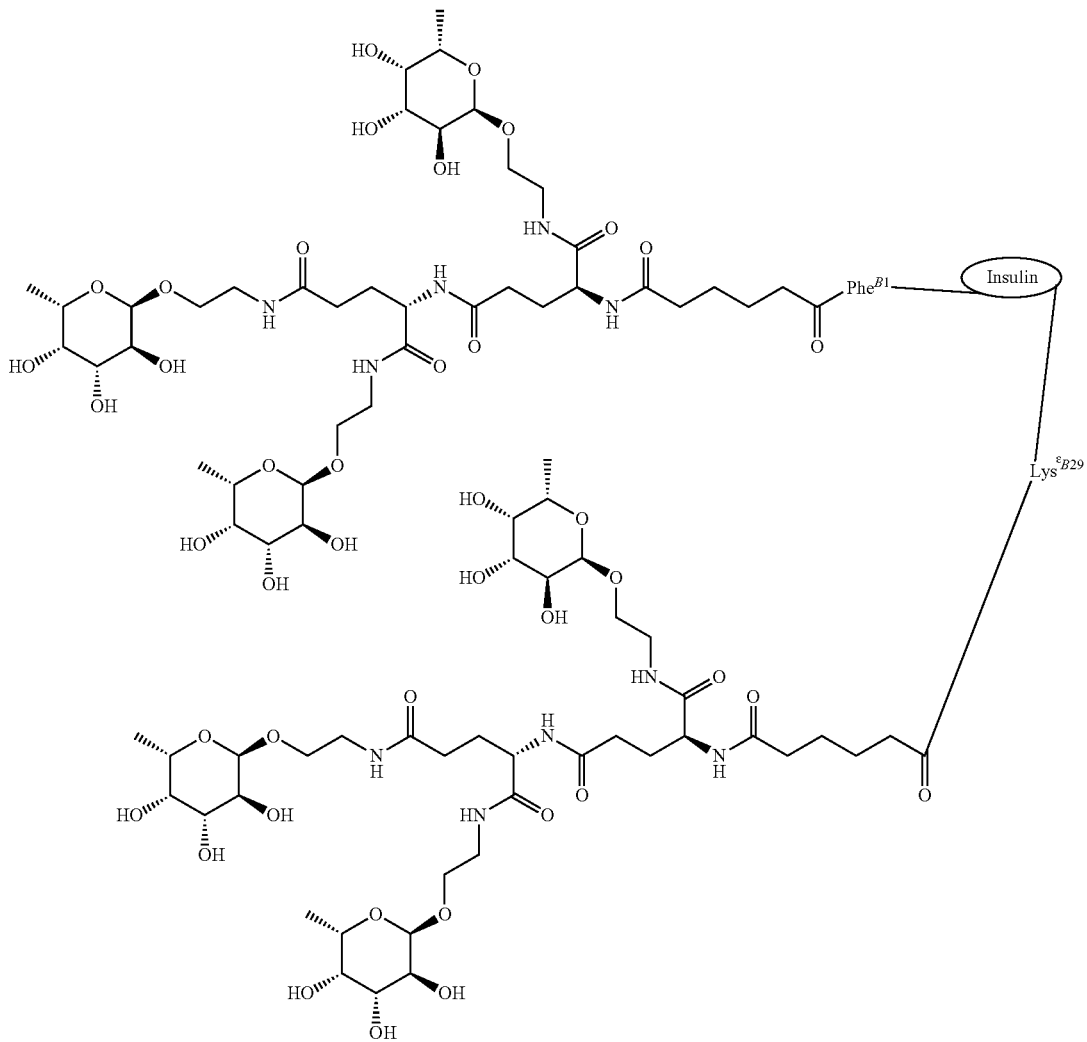 |

-continued
| Conjugate | Compound Formula & Structure |
|---|---|
| IOC-3 | 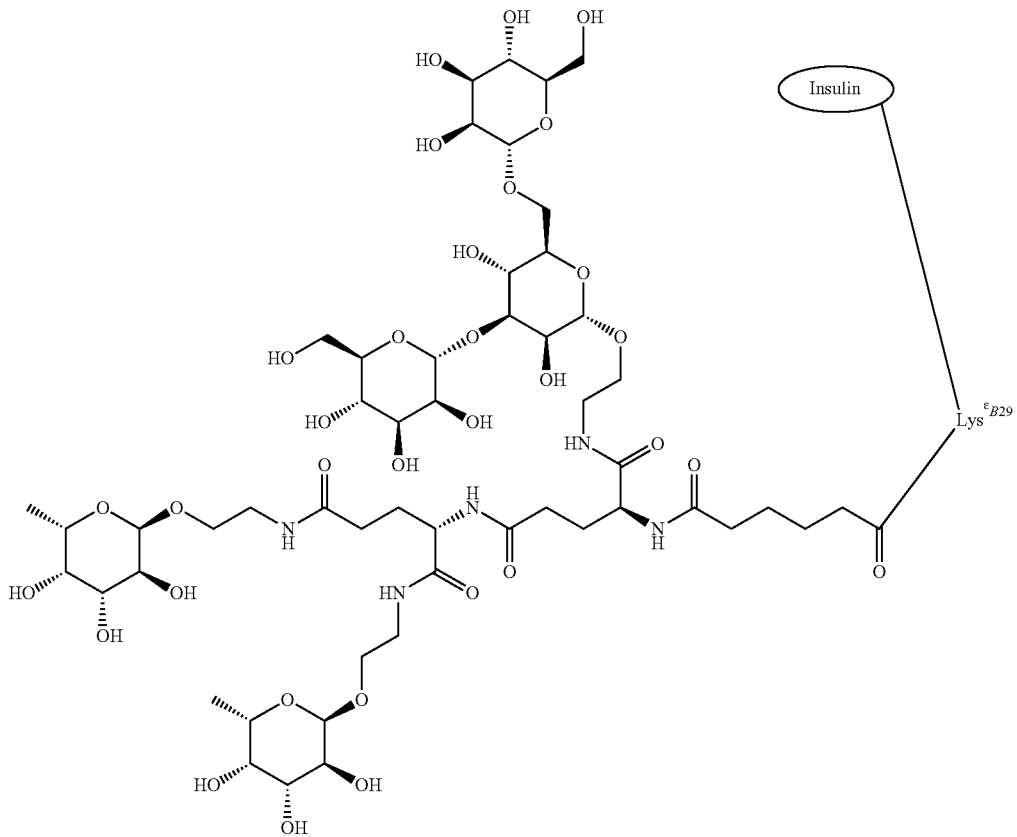 |

| Con- jugate | Compound Formula & Structure |
|---|---|
| IOC-4 | 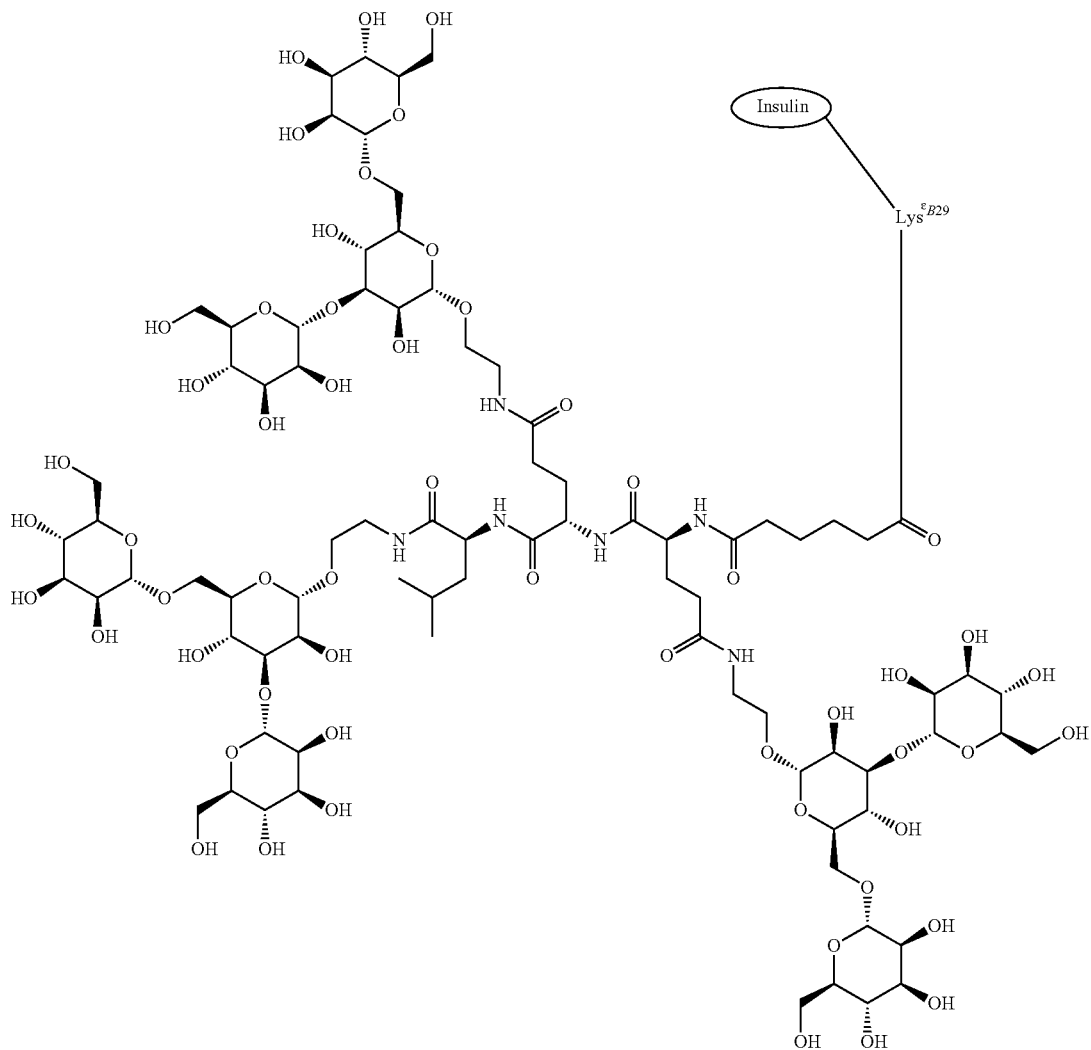 |

| Con-jugate | Compound Formula & Structure |
|---|---|
| IOC-5 | 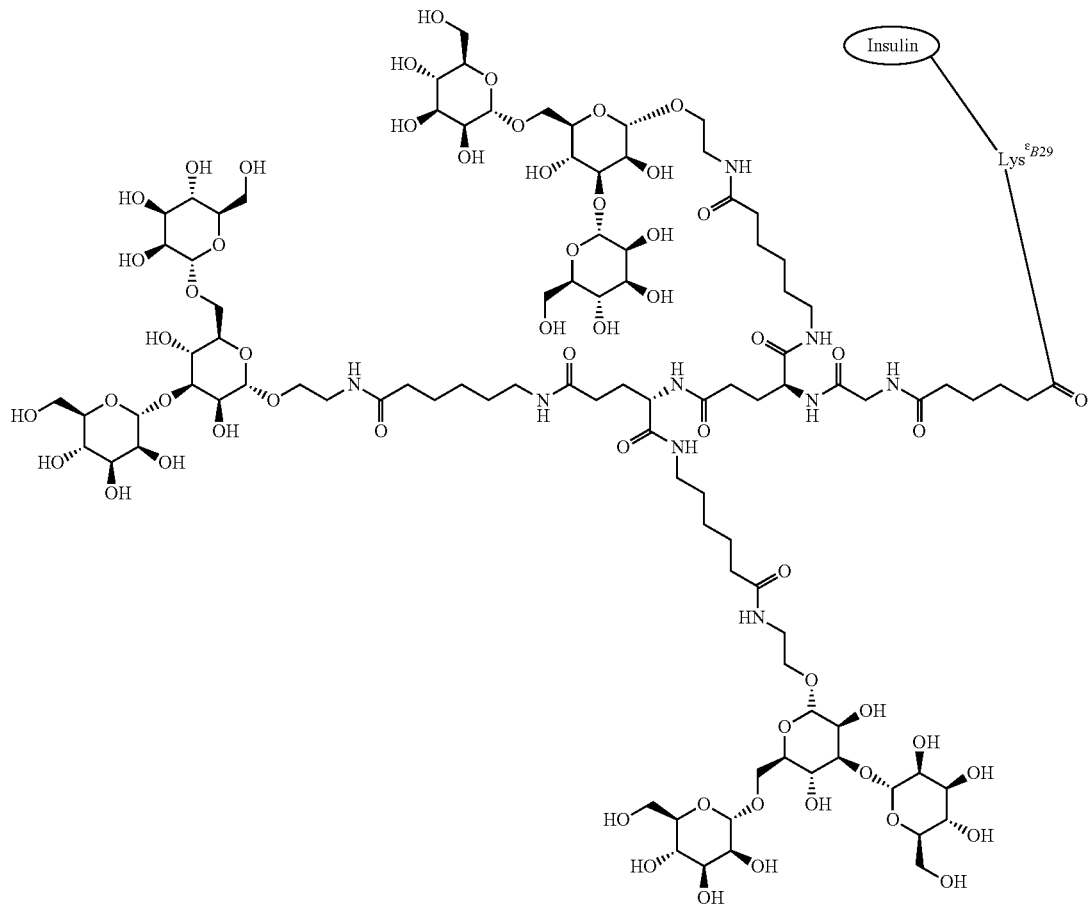 |

-continued
| Con-jugate | Compound Formula & Structure |
|---|---|
| IOC-6 | 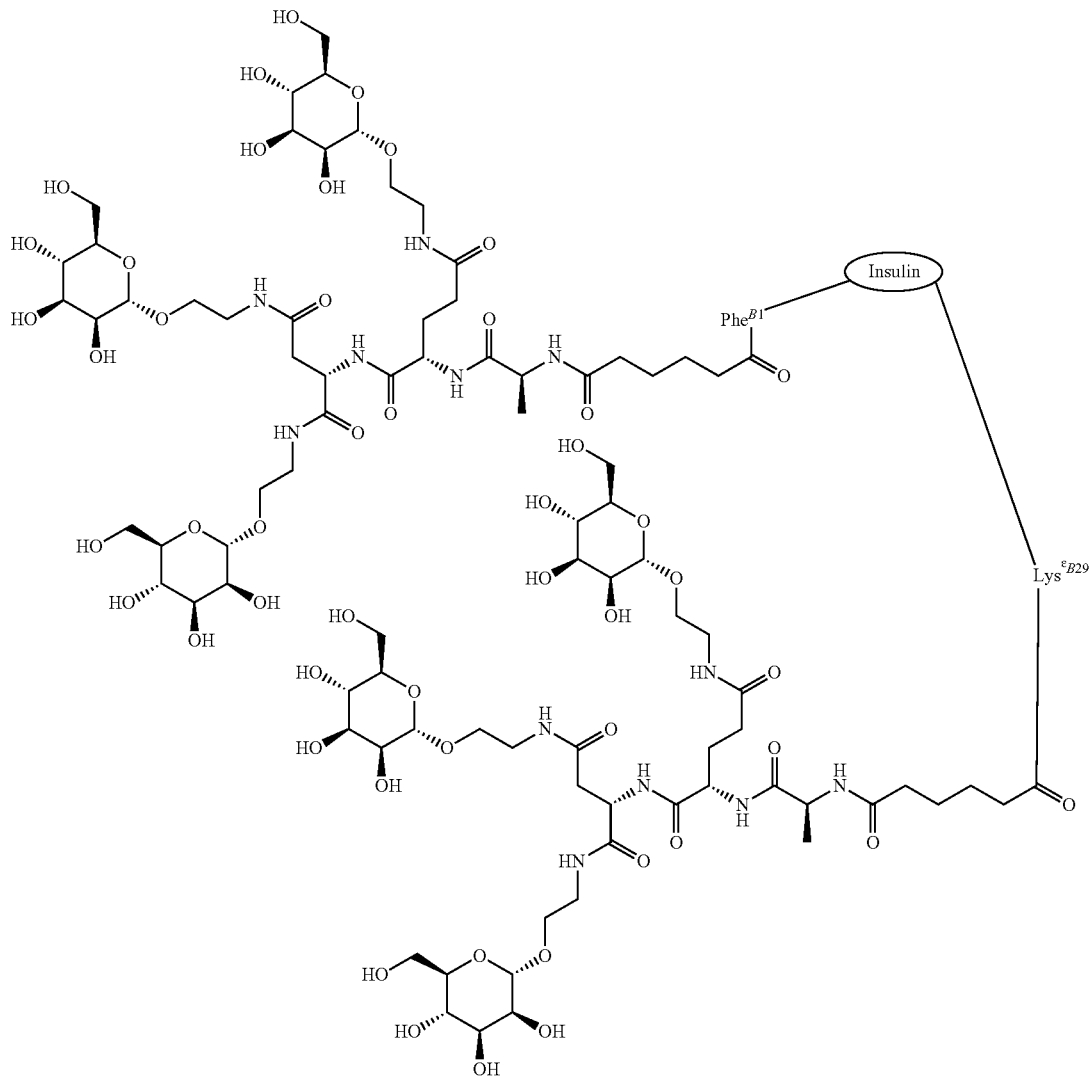 |

| Conjugate | Compound Formula & Structure |
|---|---|
| IOC-7 | 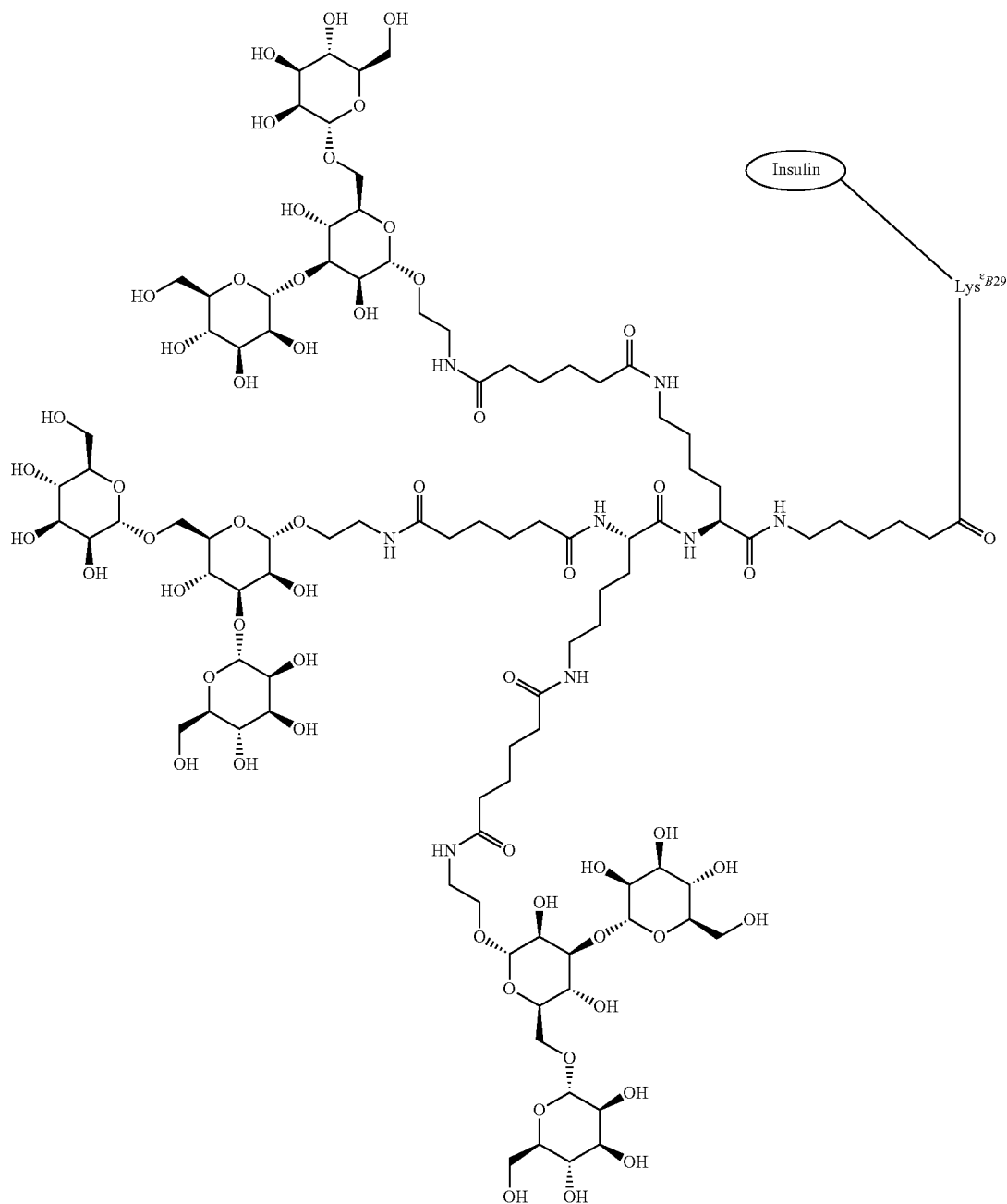 |

| Conjugate | Compound Formula & Structure |
|---|---|
| IOC-8 | 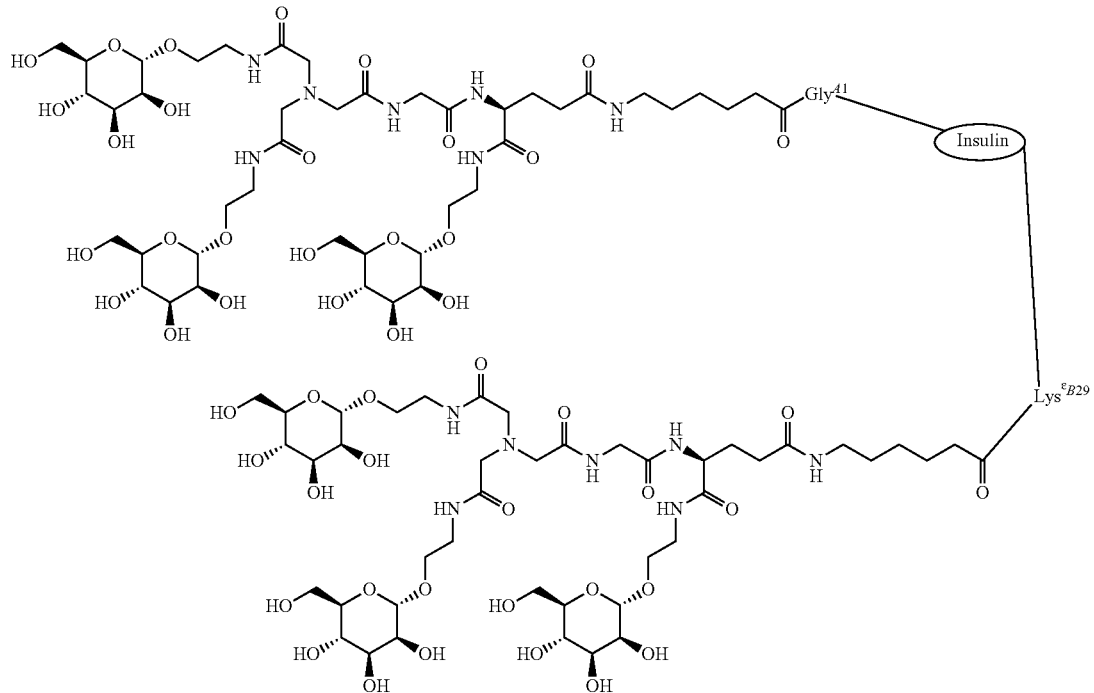 |
| IOC-9 | 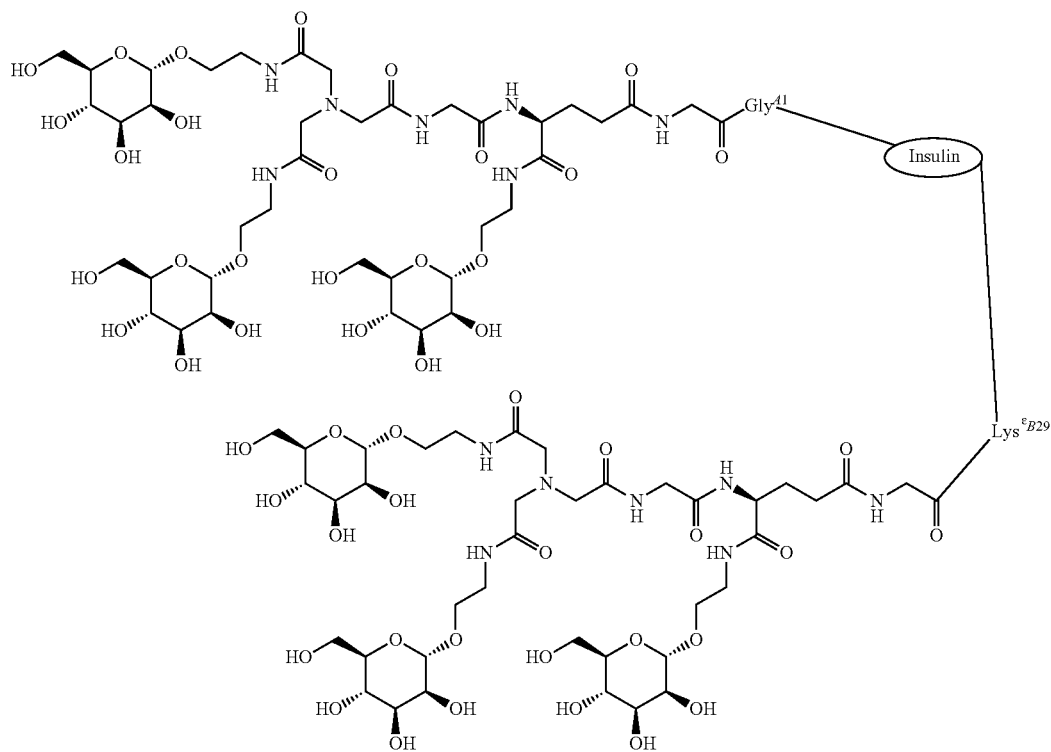 |

| Conjugate | Compound Formula & Structure |
|---|---|
| IOC-10 | 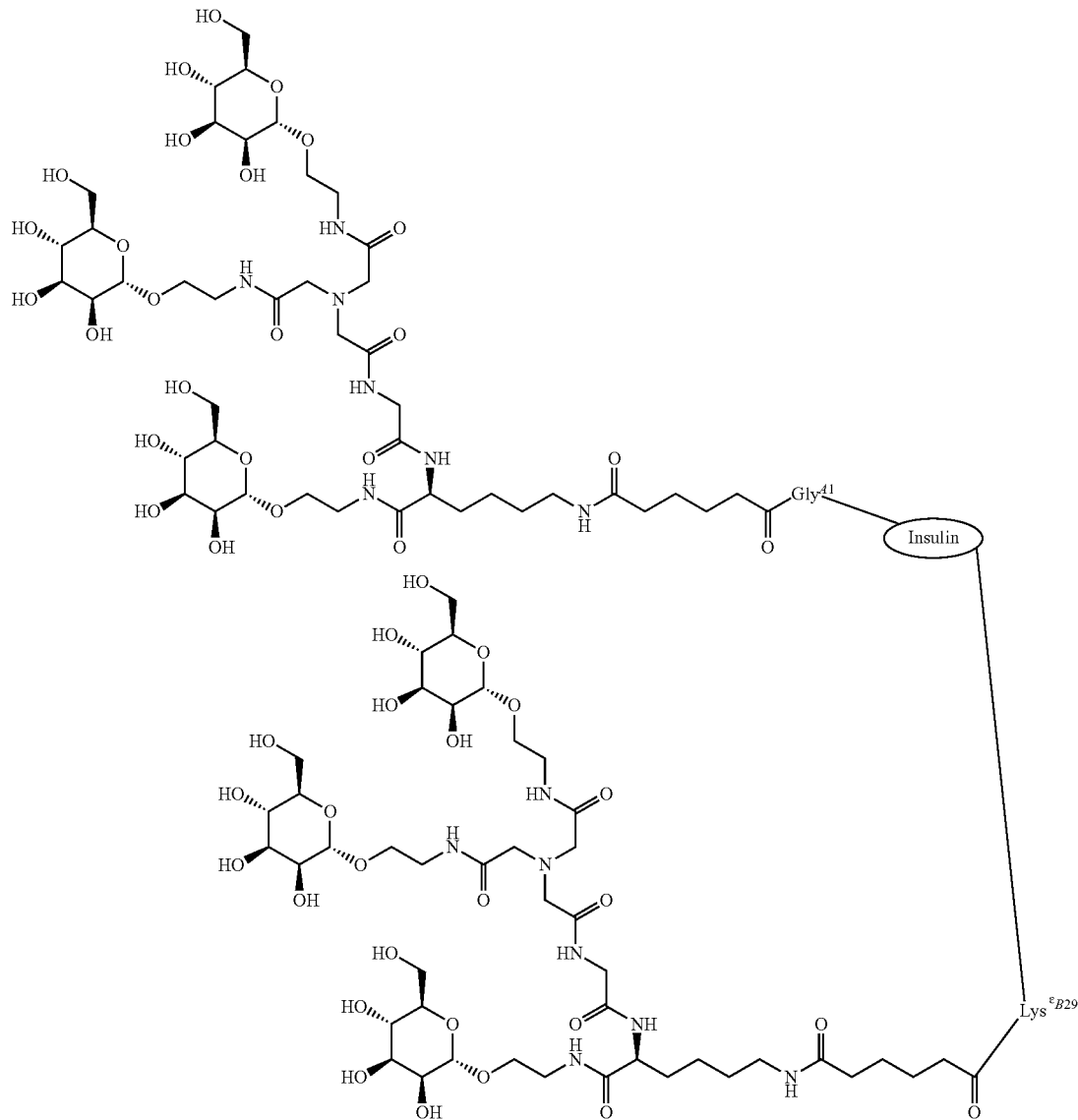 |

| Con-jugate | Compound Formula & Structure |
|---|---|
| IOC-11 | 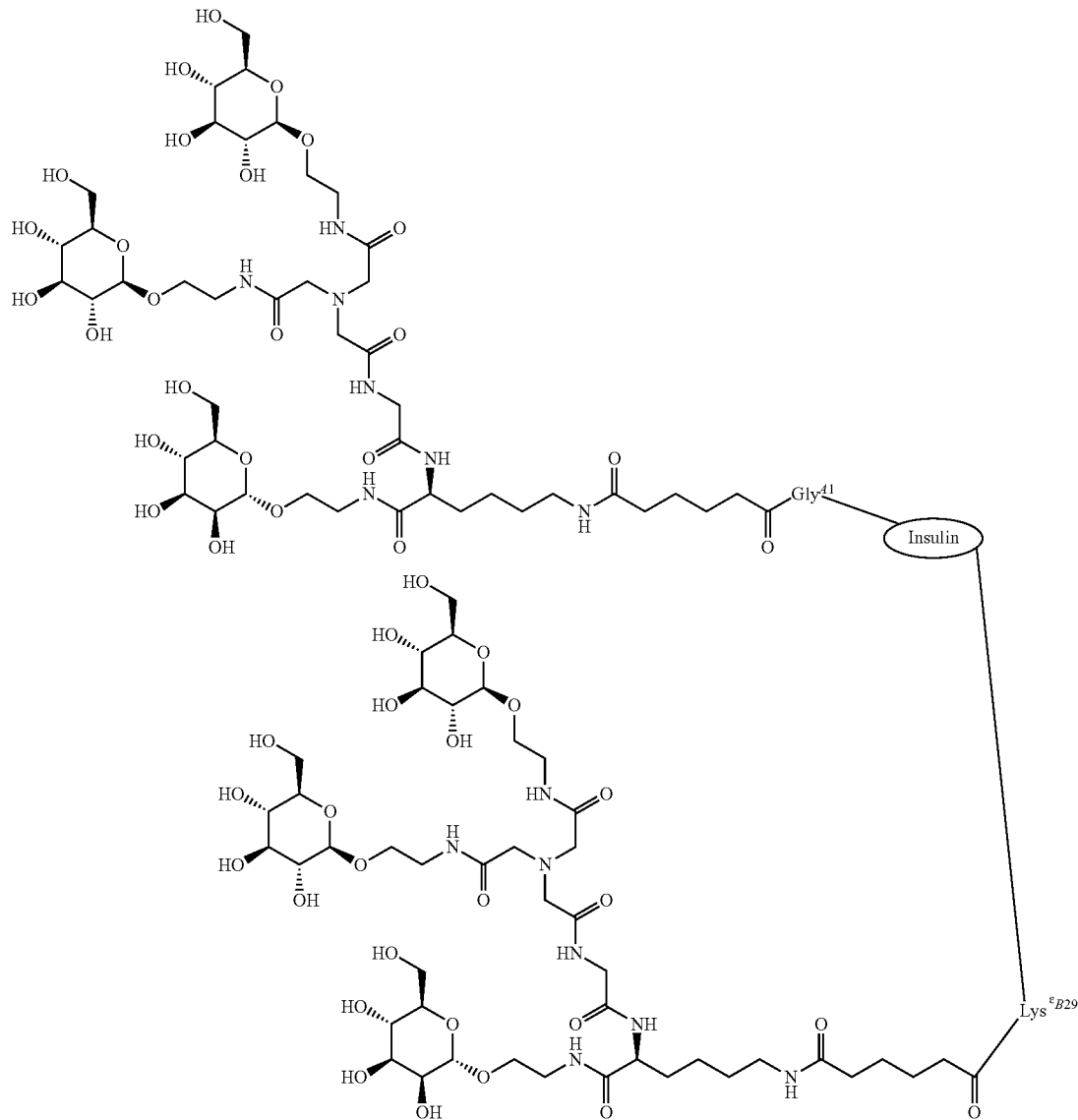 |

-continued
| Con-jugate | Compound Formula & Structure |
|---|---|
| IOC-12 | 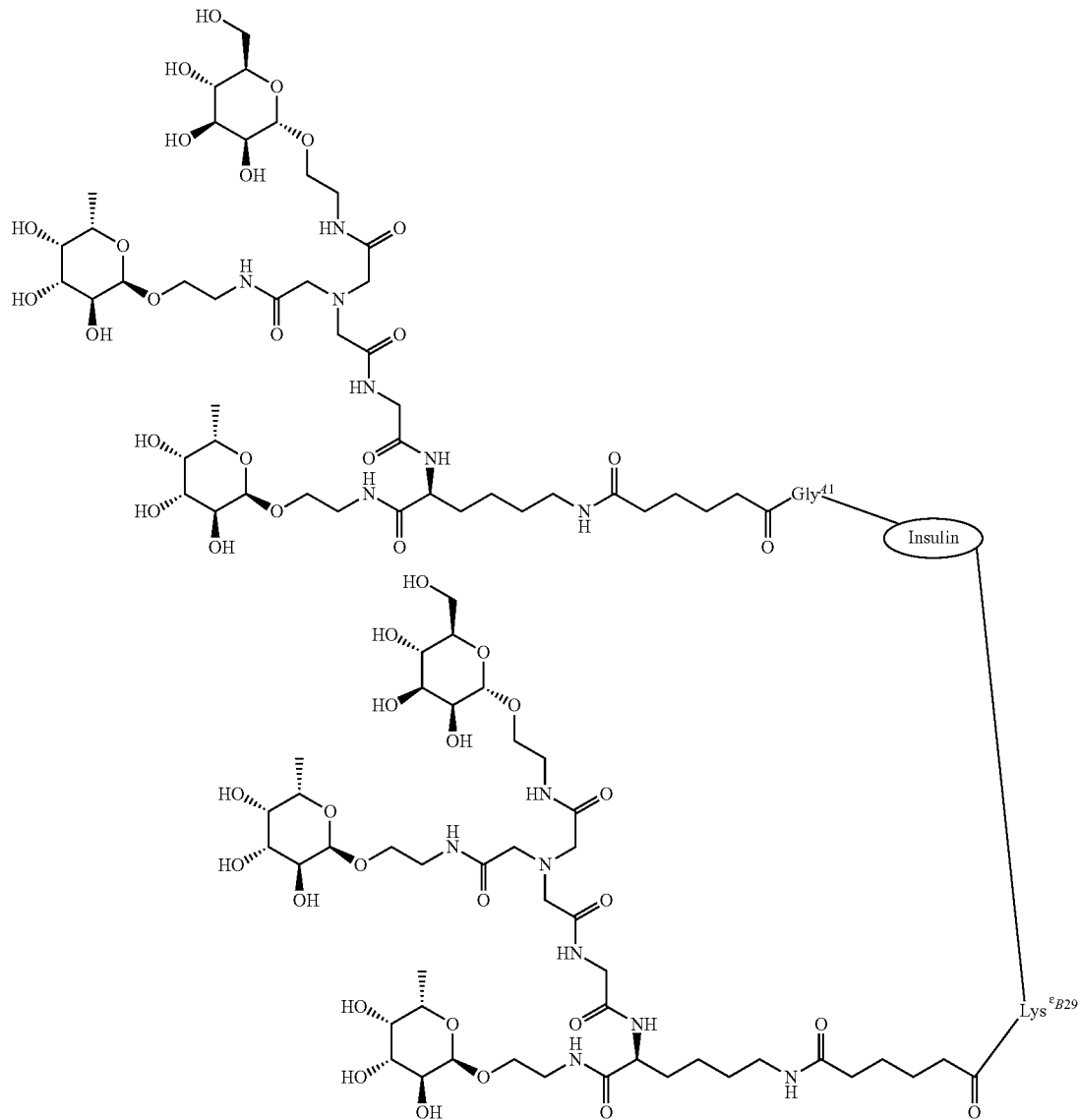 |

| Con-jugate | Compound Formula & Structure |
|---|---|
| IOC-13 | 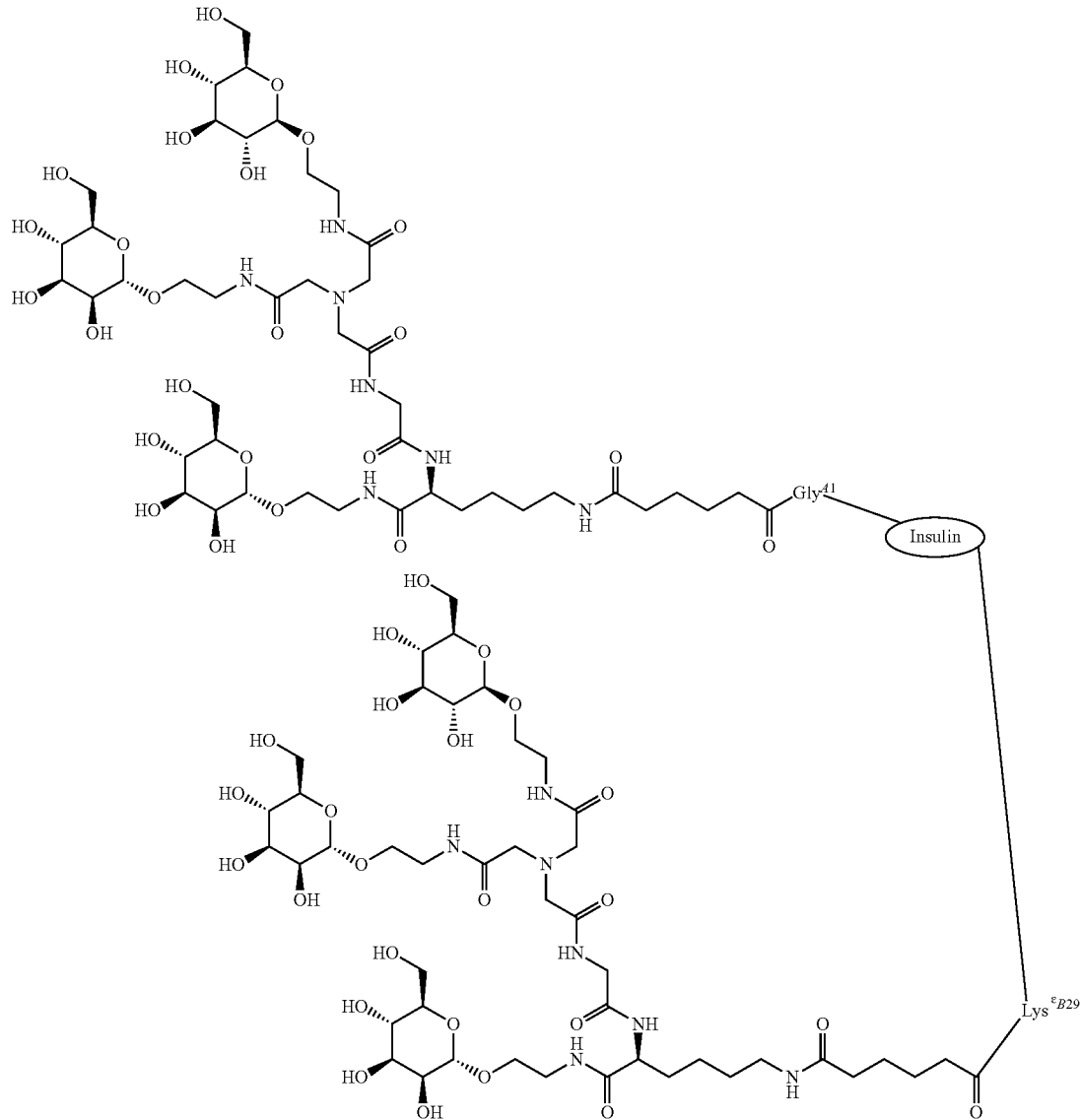 |

| Conjugate | Compound Formula & Structure |
|---|---|
| IOC-14 | 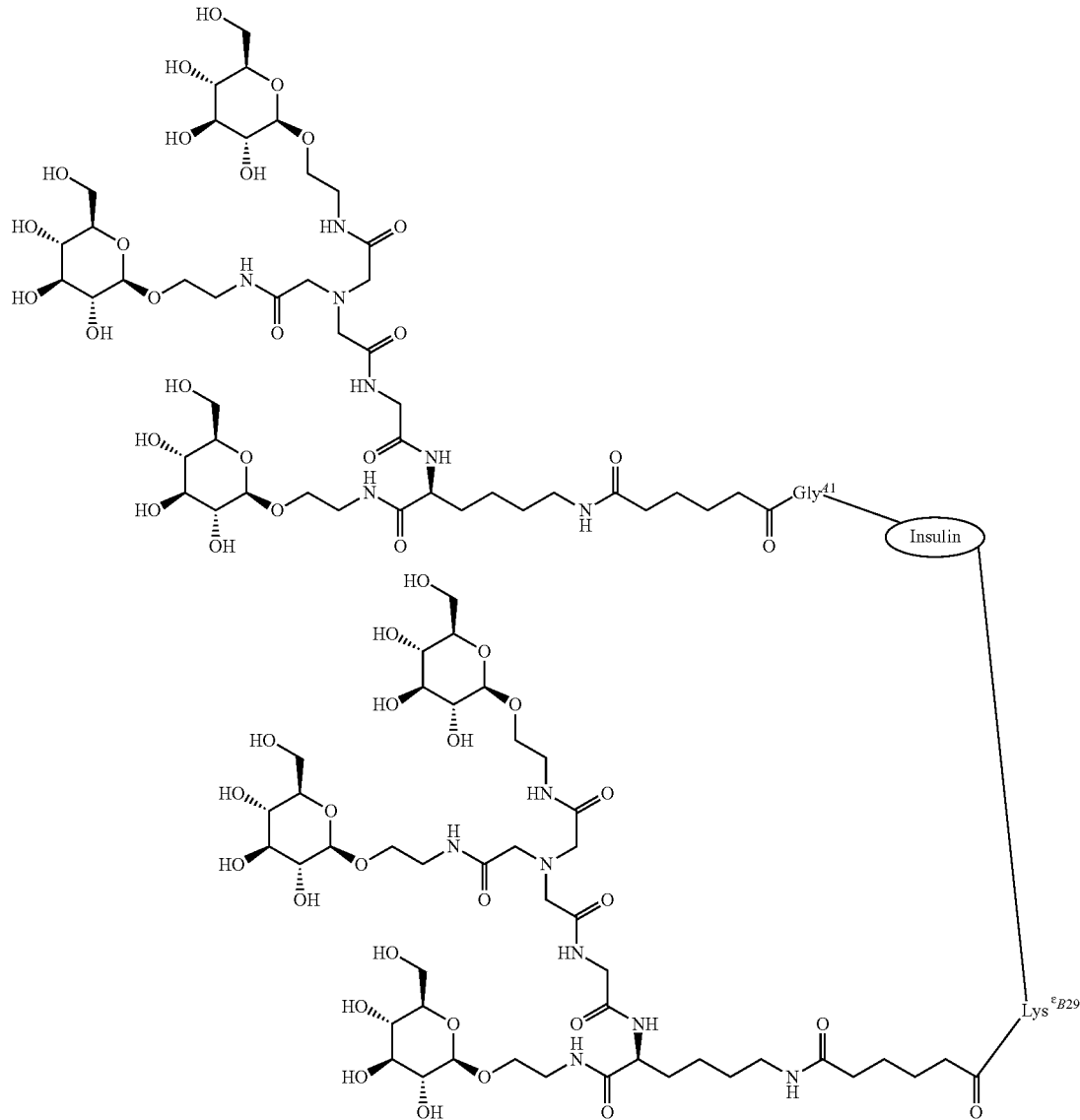 |

| Con-jugate | Compound Formula & Structure |
|---|---|
| IOC-15 | 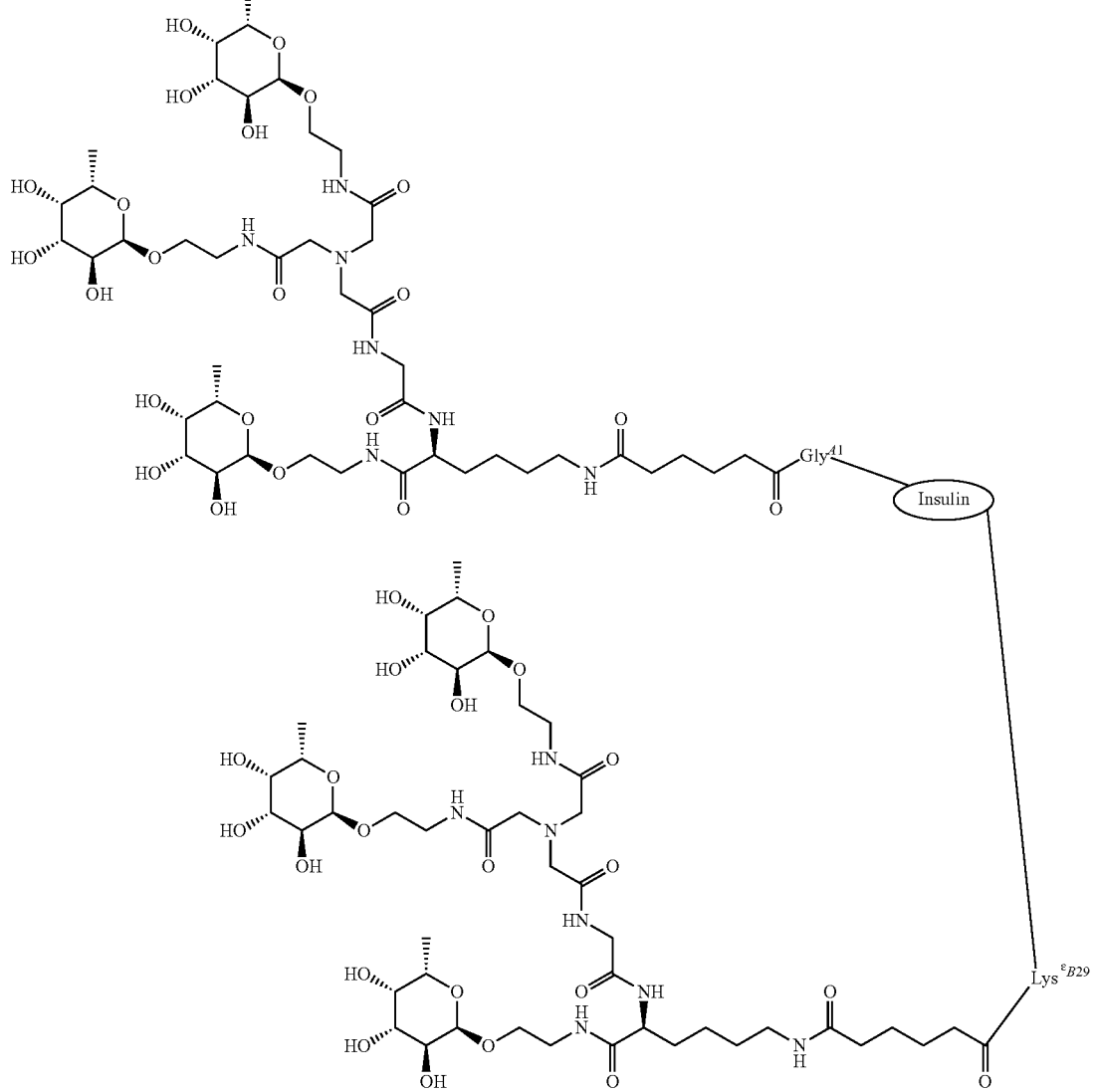 |

-continued
| Con-jugate | Compound Formula & Structure |
|---|---|
| IOC-16 | 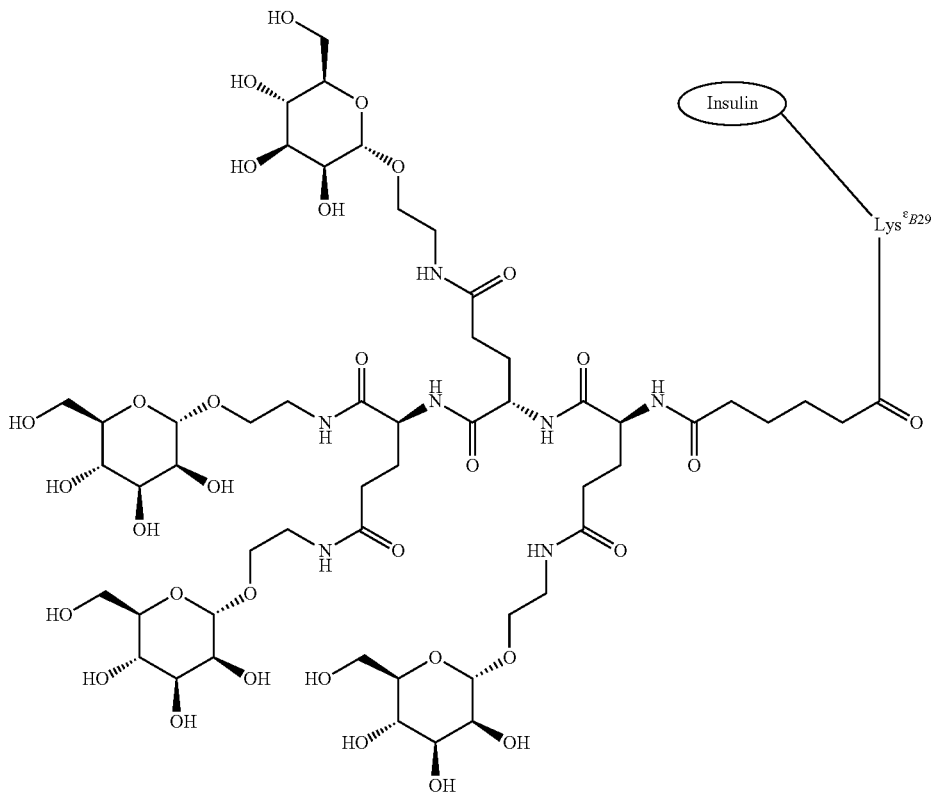 |

| Con-jugate | Compound Formula & Structure |
|---|---|
| IOC-17 | 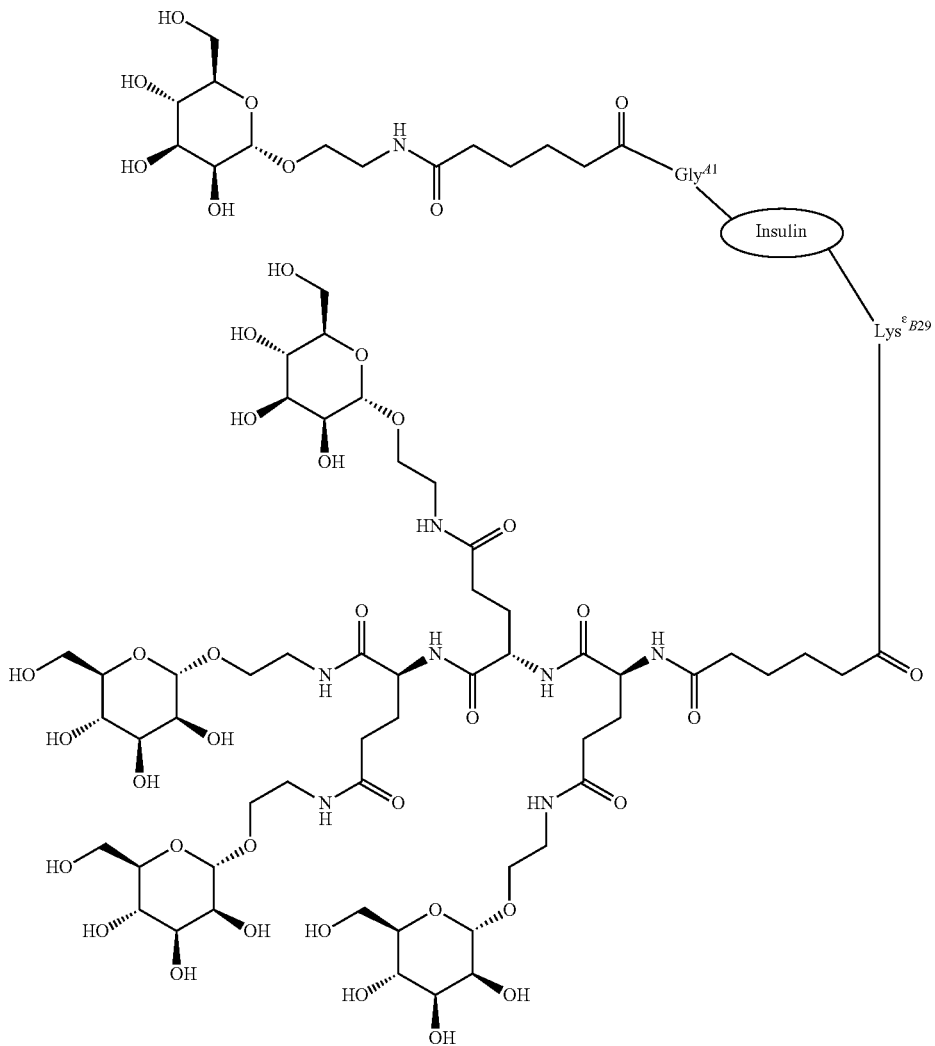 |

-continued
| Con-jugate | Compound Formula & Structure |
|---|---|
| IOC-18 | 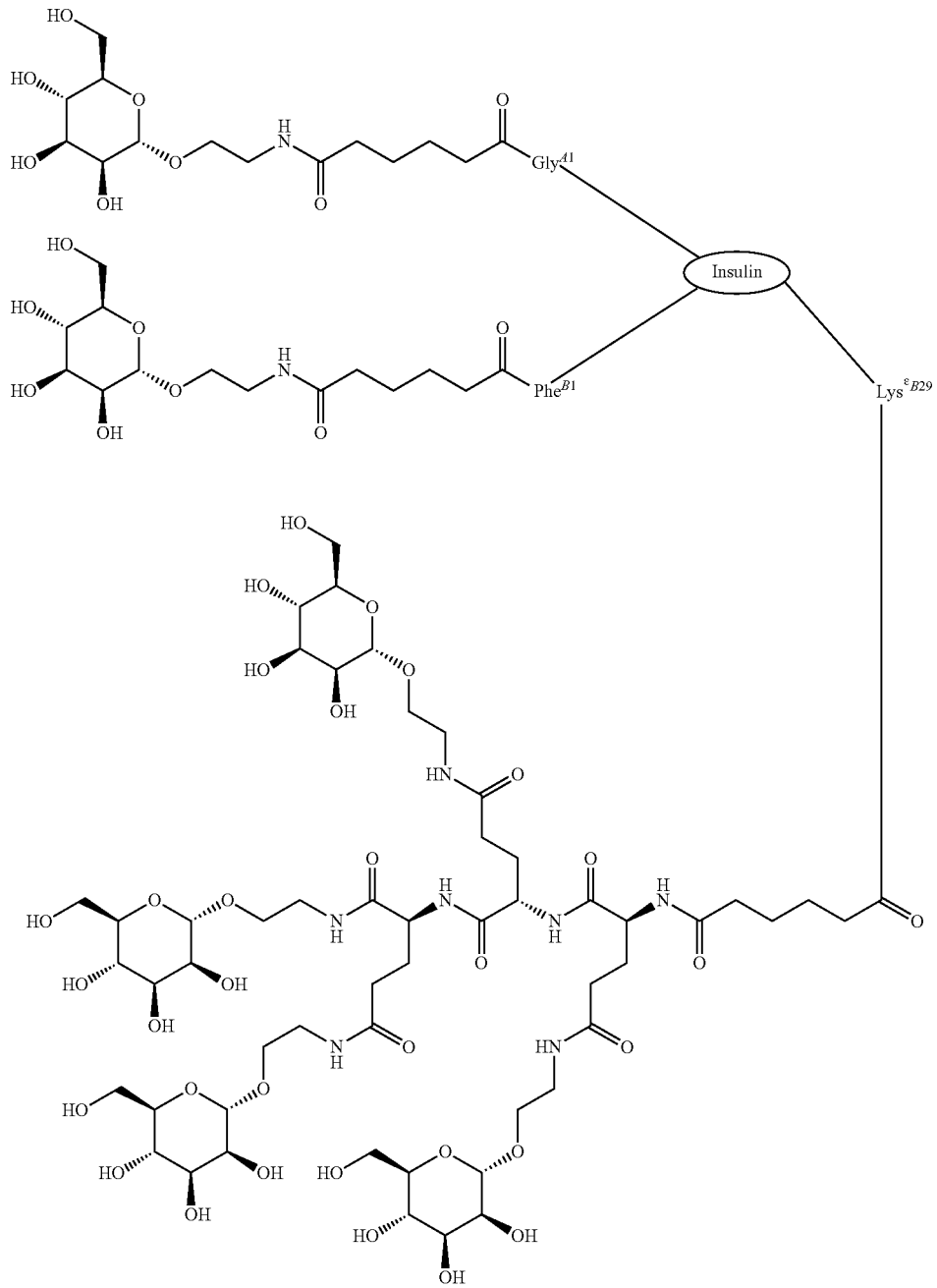 |

-continued
| Conjugate | Compound Formula & Structure |
|---|---|
| IOC-19 | 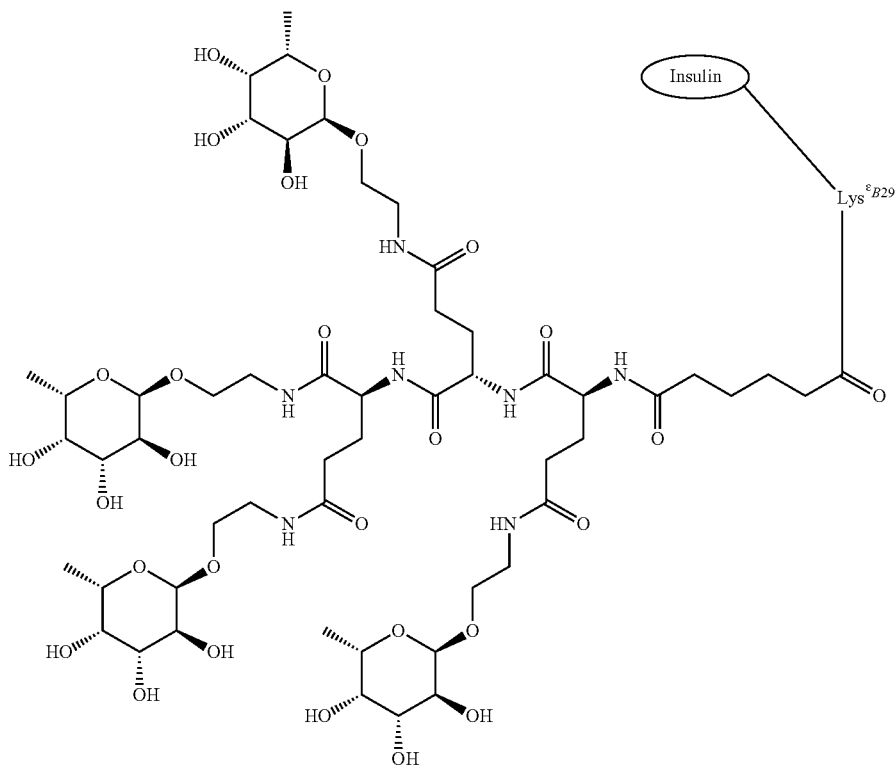 |

| Conjugate | Compound Formula & Structure |
|---|---|
| IOC-20 | 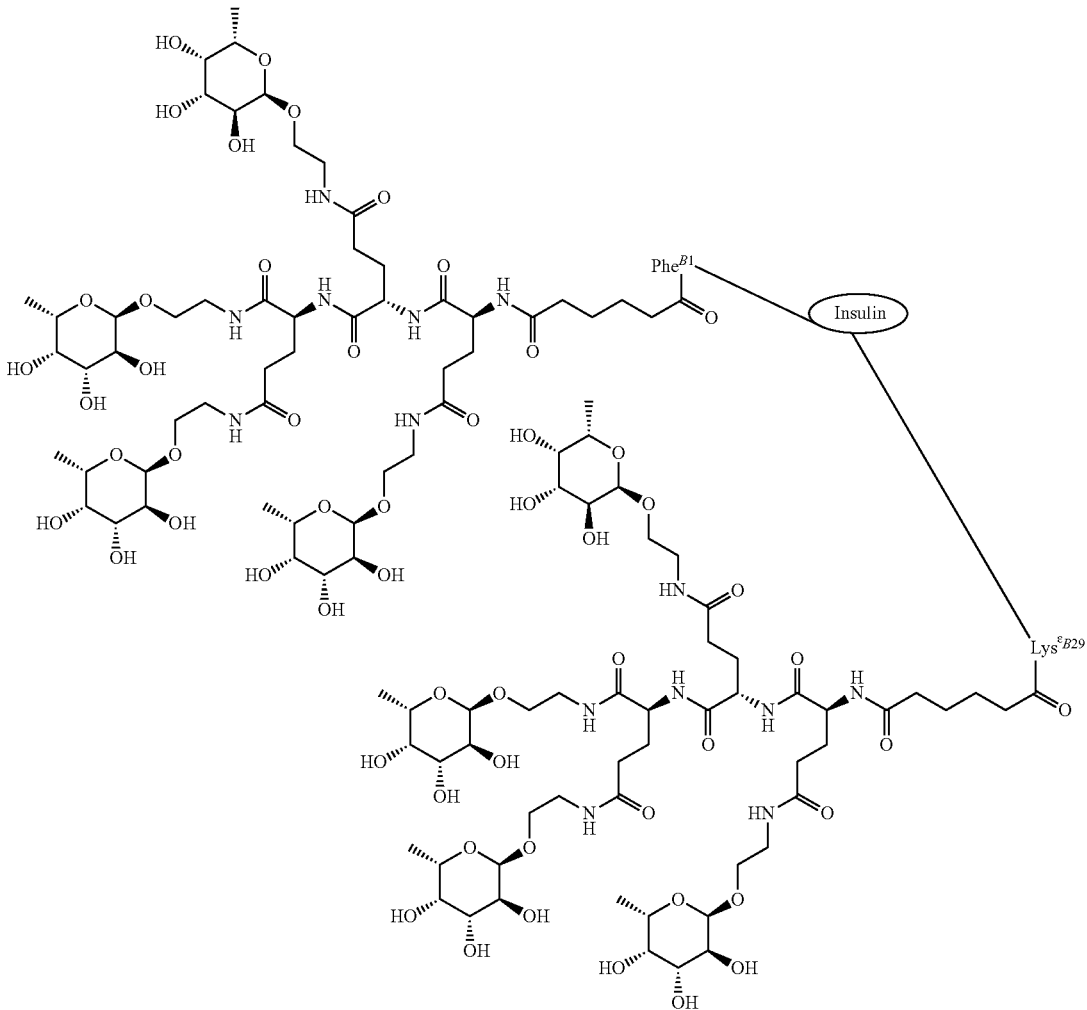 |

| Conjugate | Compound Formula & Structure |
|---|---|
| IOC-21 | 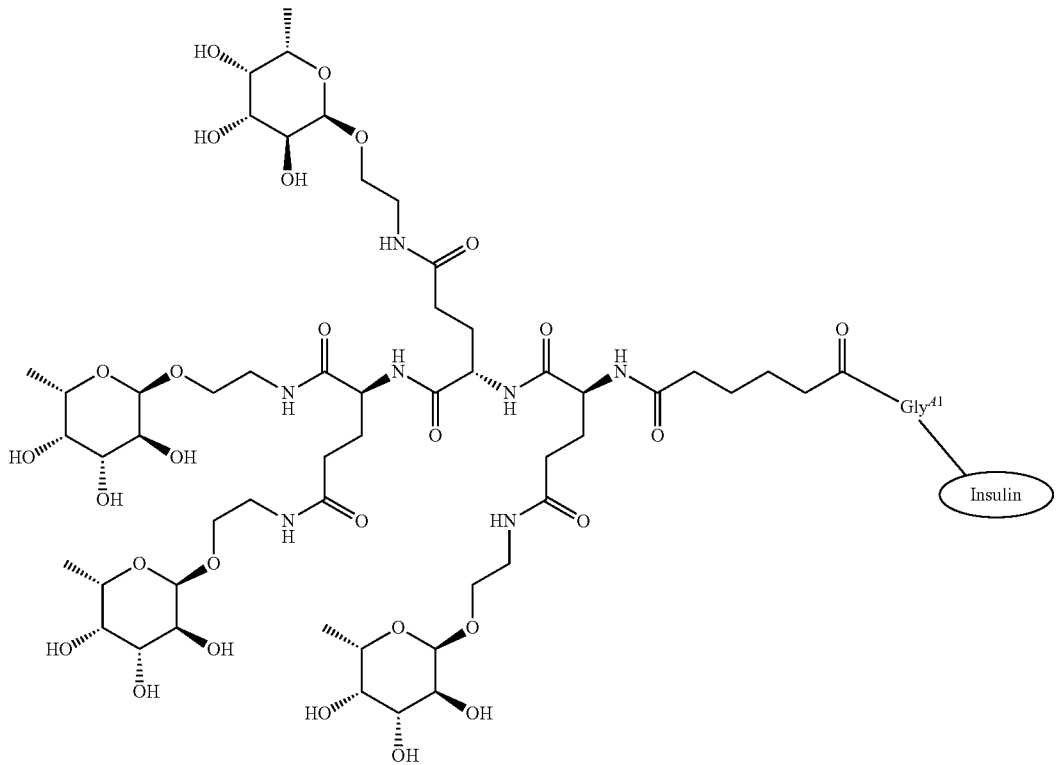 |

| Conjugate | Compound Formula & Structure |
|---|---|
| IOC-22 | 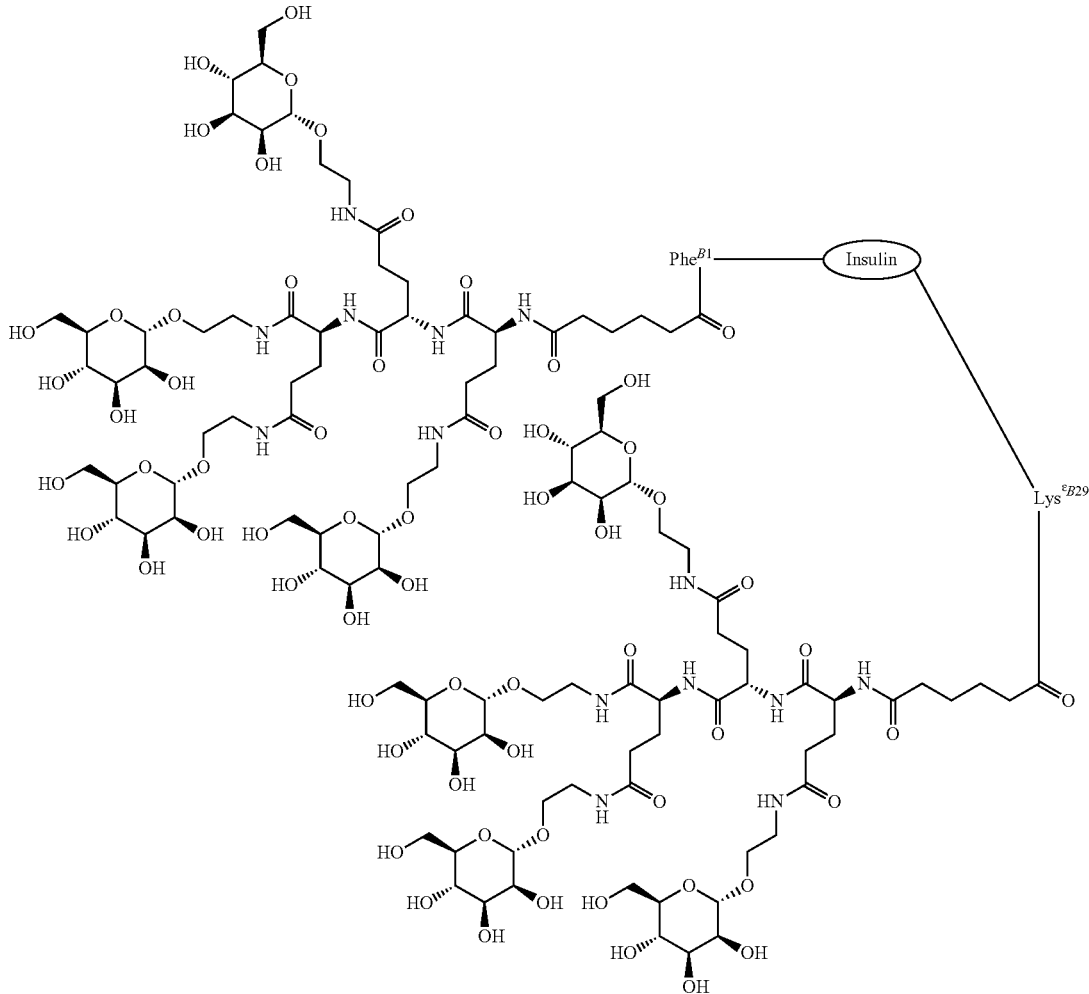 |

| Conjugate | Compound Formula & Structure |
|---|---|
| IOC-23 | 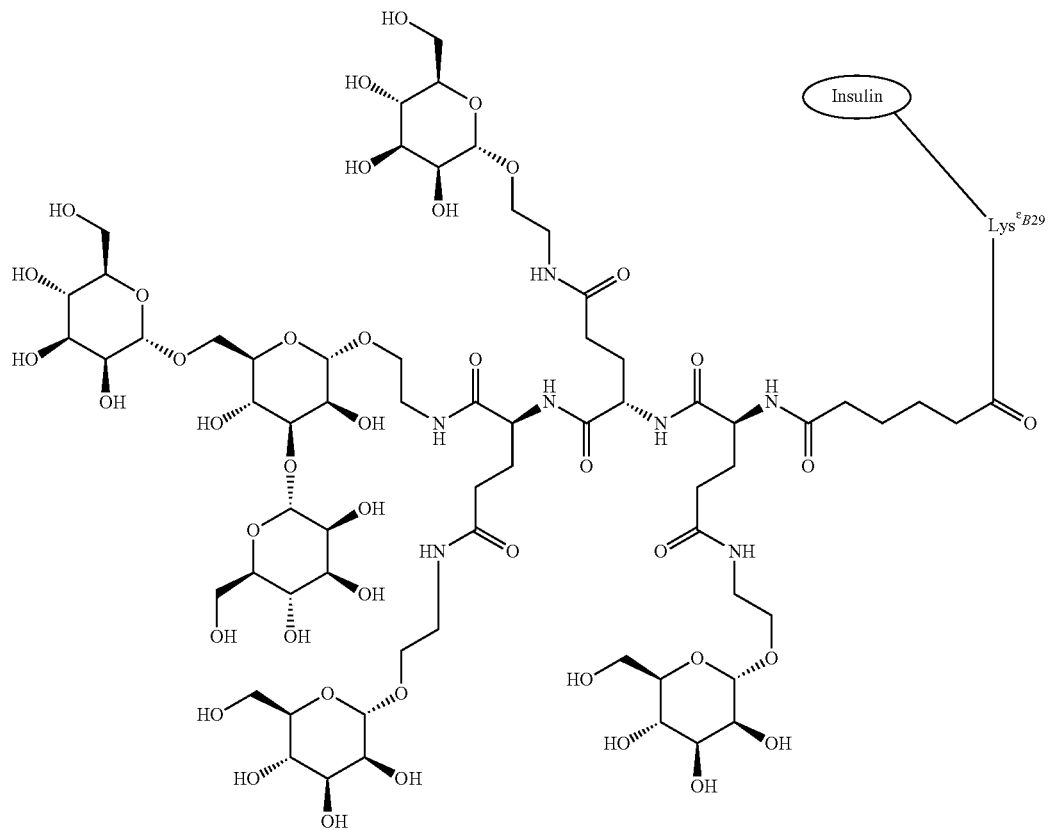 |

| Conjugate | Compound Formula & Structure |
|---|---|
| IOC-24 | 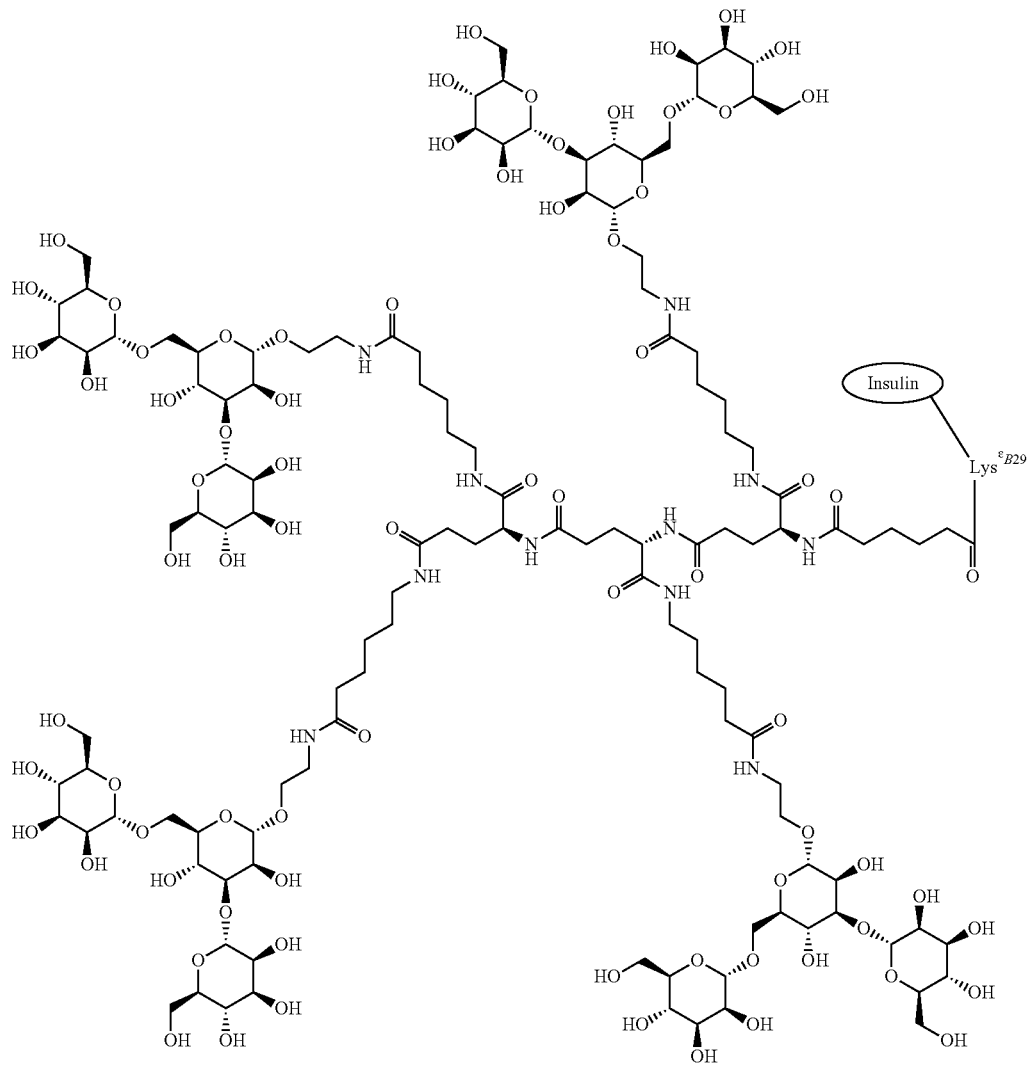 |
| IOC-25 | 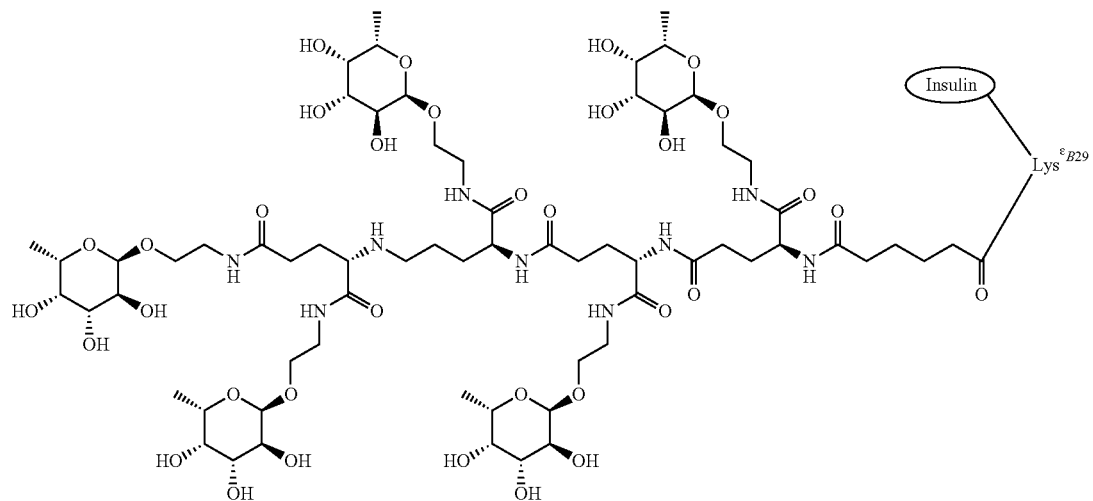 |

| Conjugate | Compound Formula & Structure |
|---|---|
| IOC-26 | 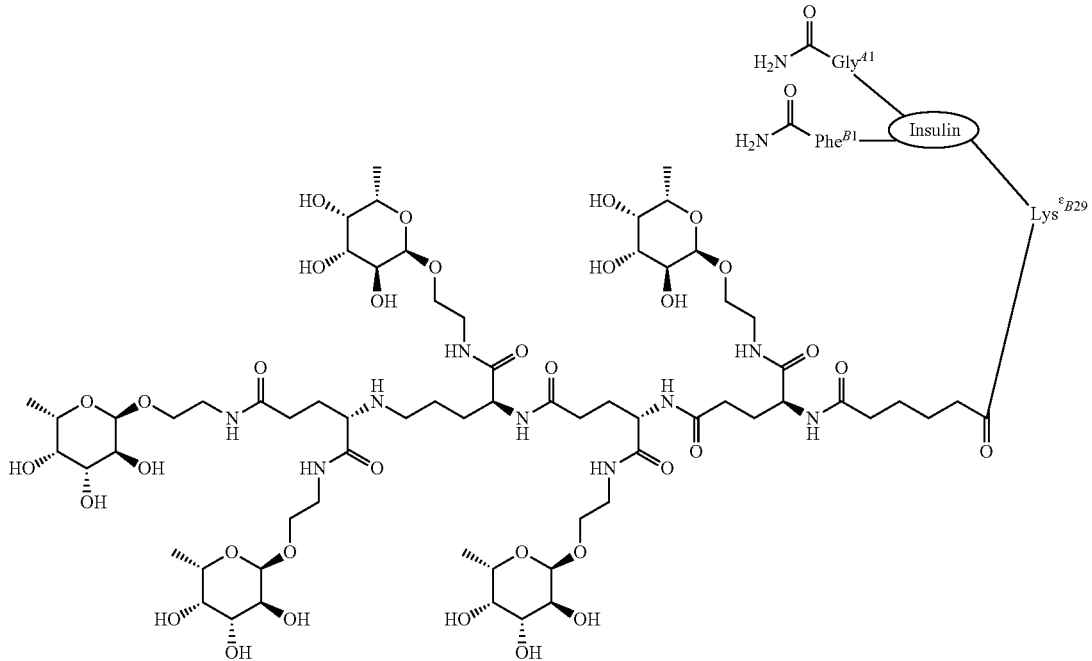 |

| Con-jugate | Compound Formula & Structure |
|---|---|
| IOC-27 | 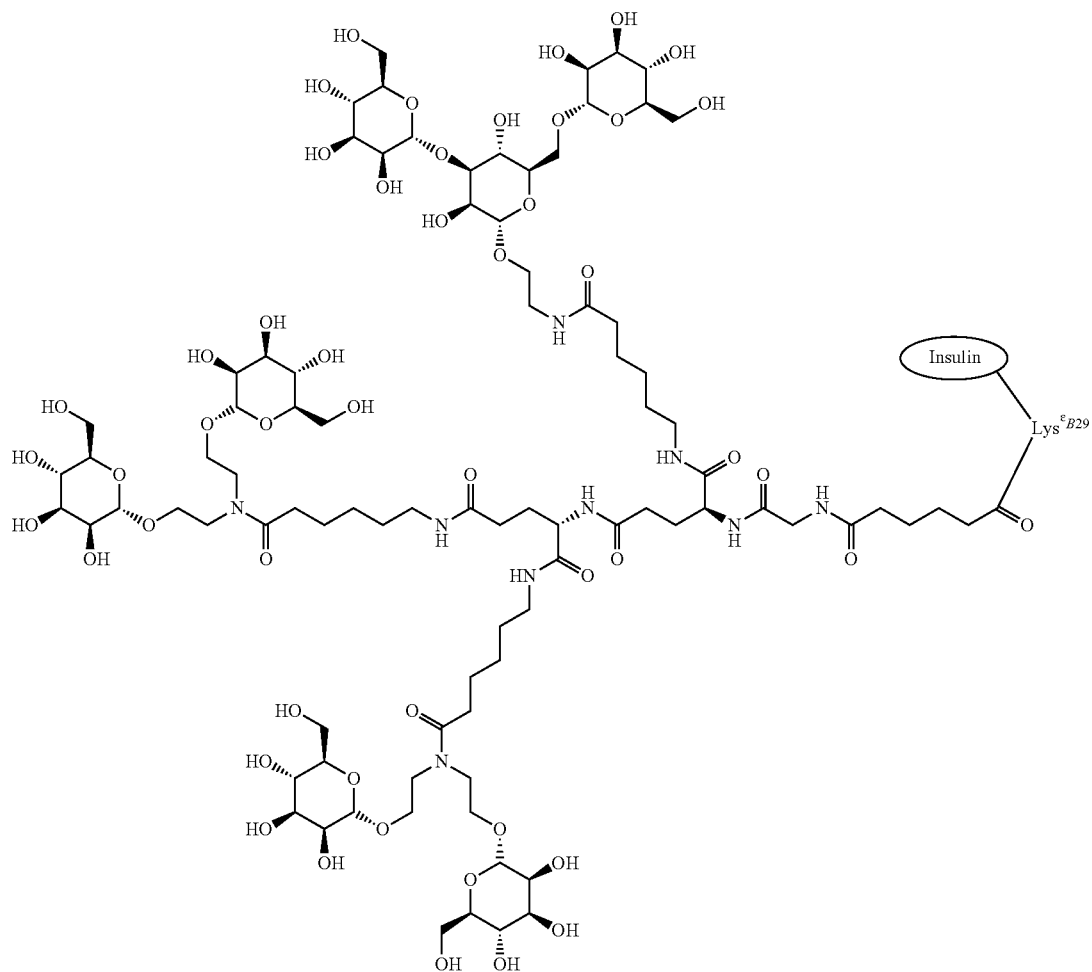 |

| Con-jugate | Compound Formula & Structure |
|---|---|
| IOC-28 | 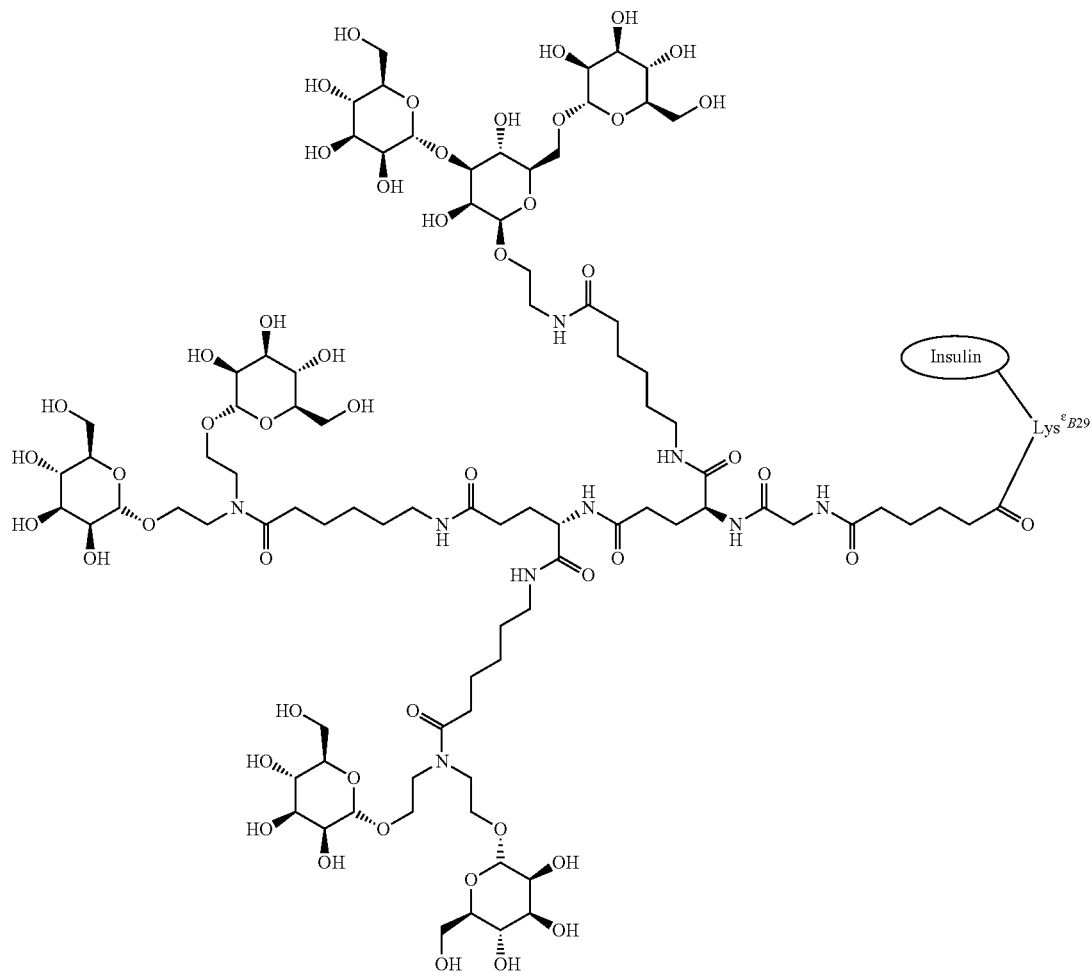 |

| Con-jugate | Compound Formula & Structure |
|---|---|
| IOC-29 | 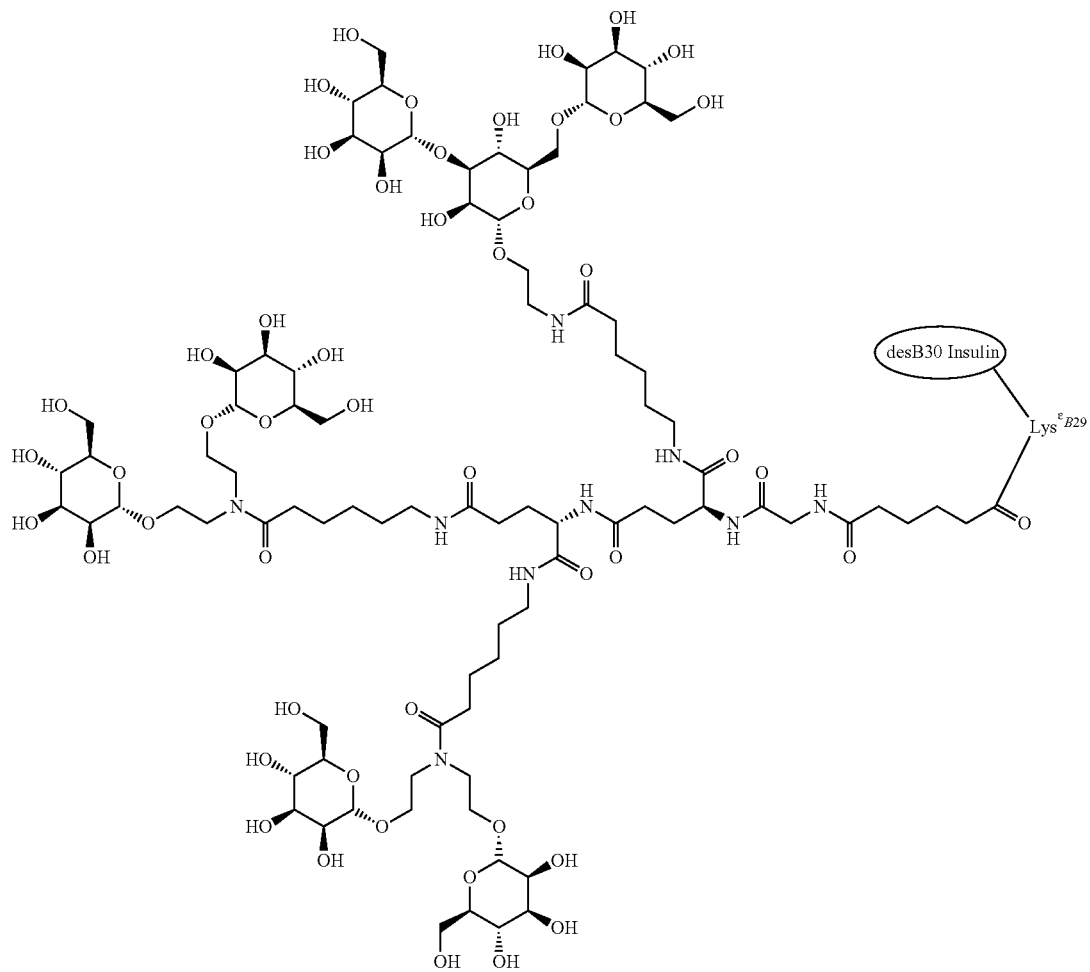 |

| Conjugate | Compound Formula & Structure |
|---|---|
| IOC-30 | 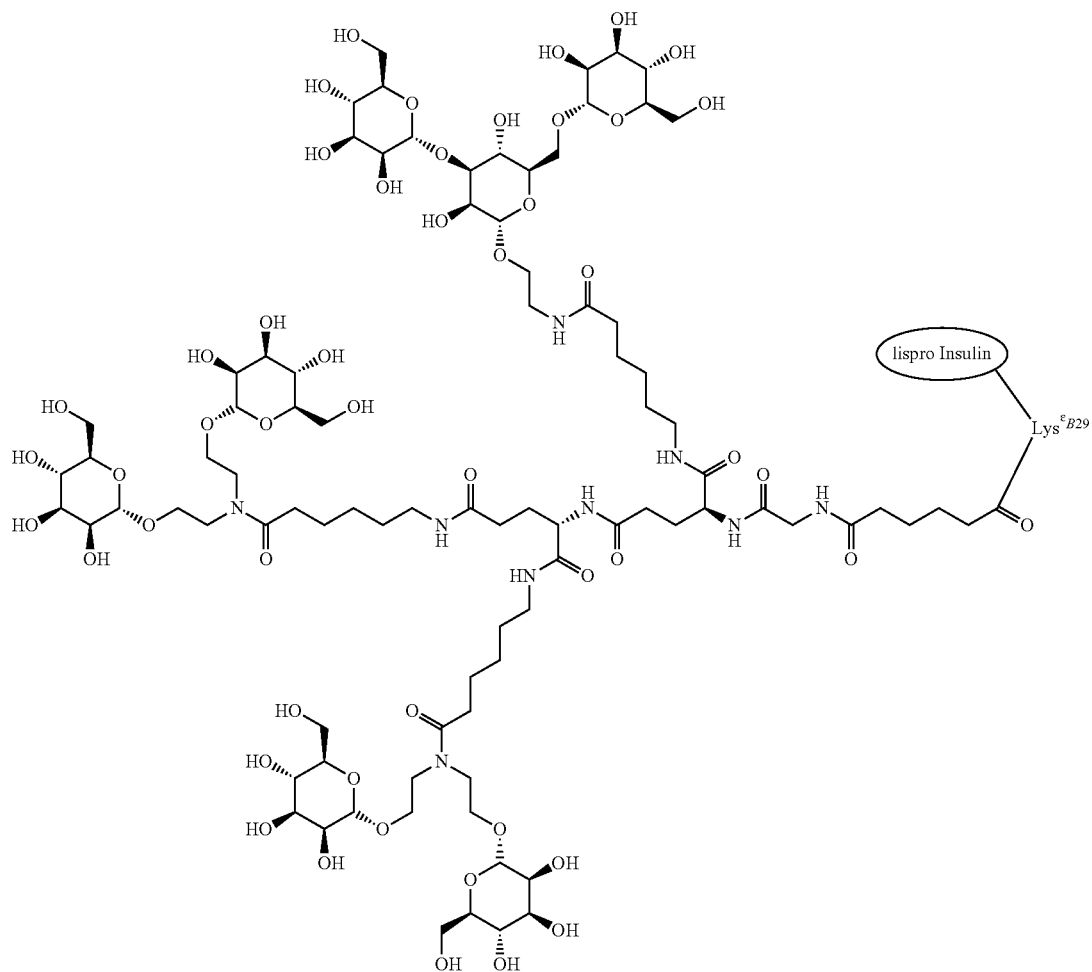 |

| Conjugate | Compound Formula & Structure |
|---|---|
| IOC-31 | 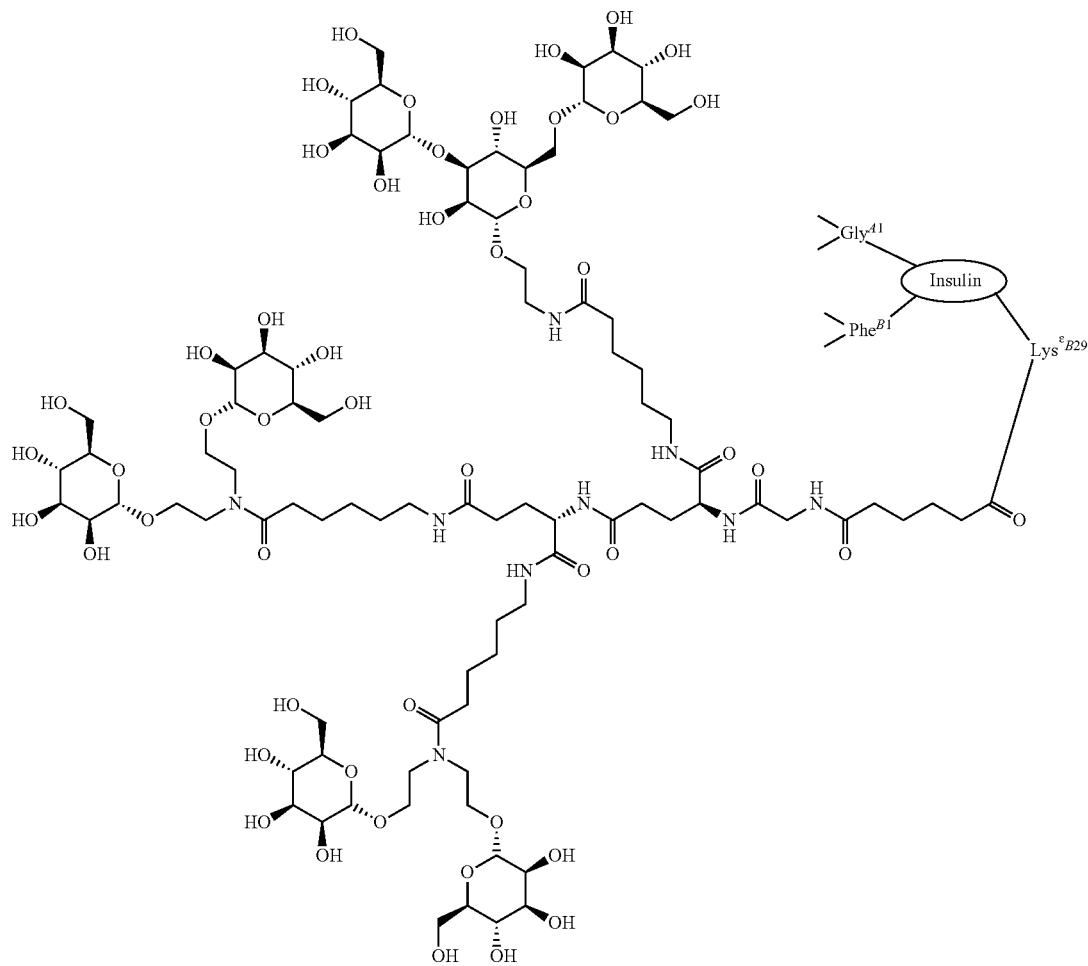 |

| Conjugate | Compound Formula & Structure |
|---|---|
| IOC-32 | 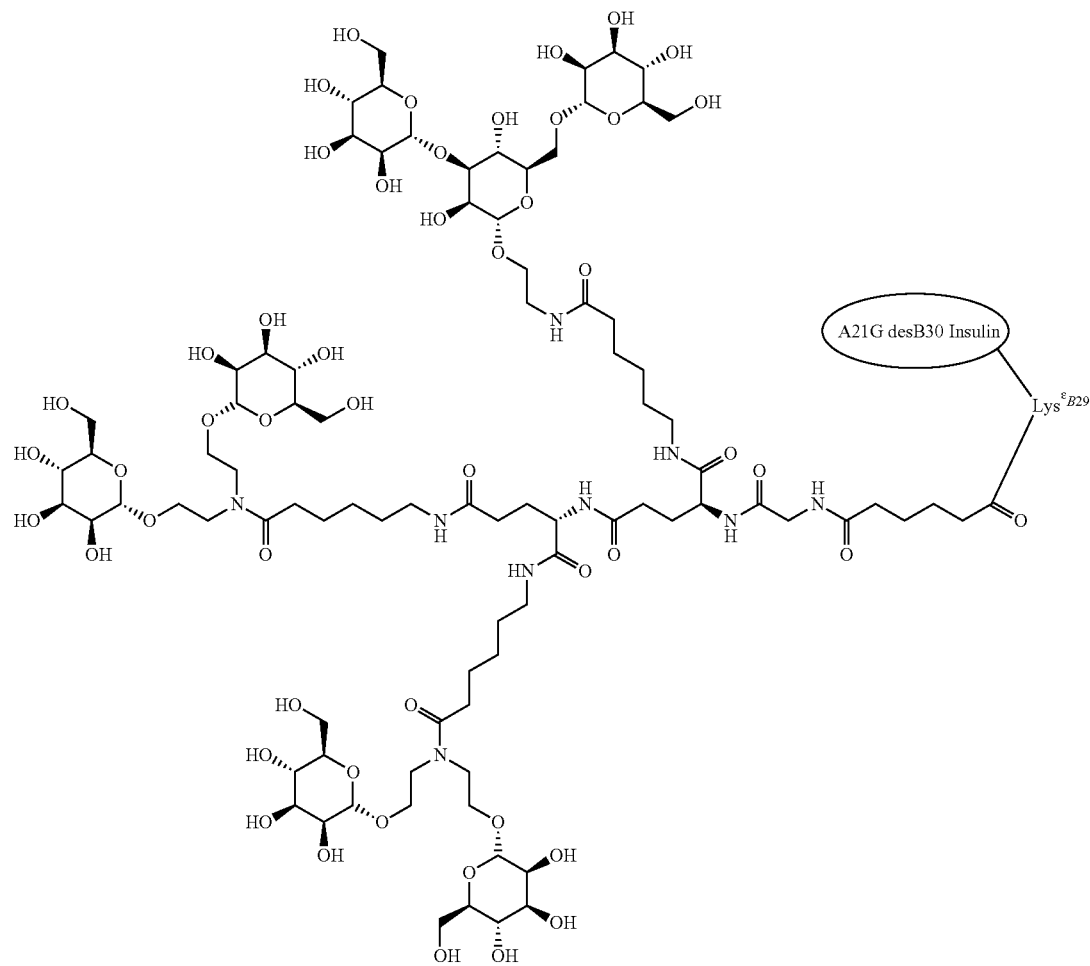 |

-continued
| Con-jugate | Compound Formula & Structure |
|---|---|
| IOC-33 | 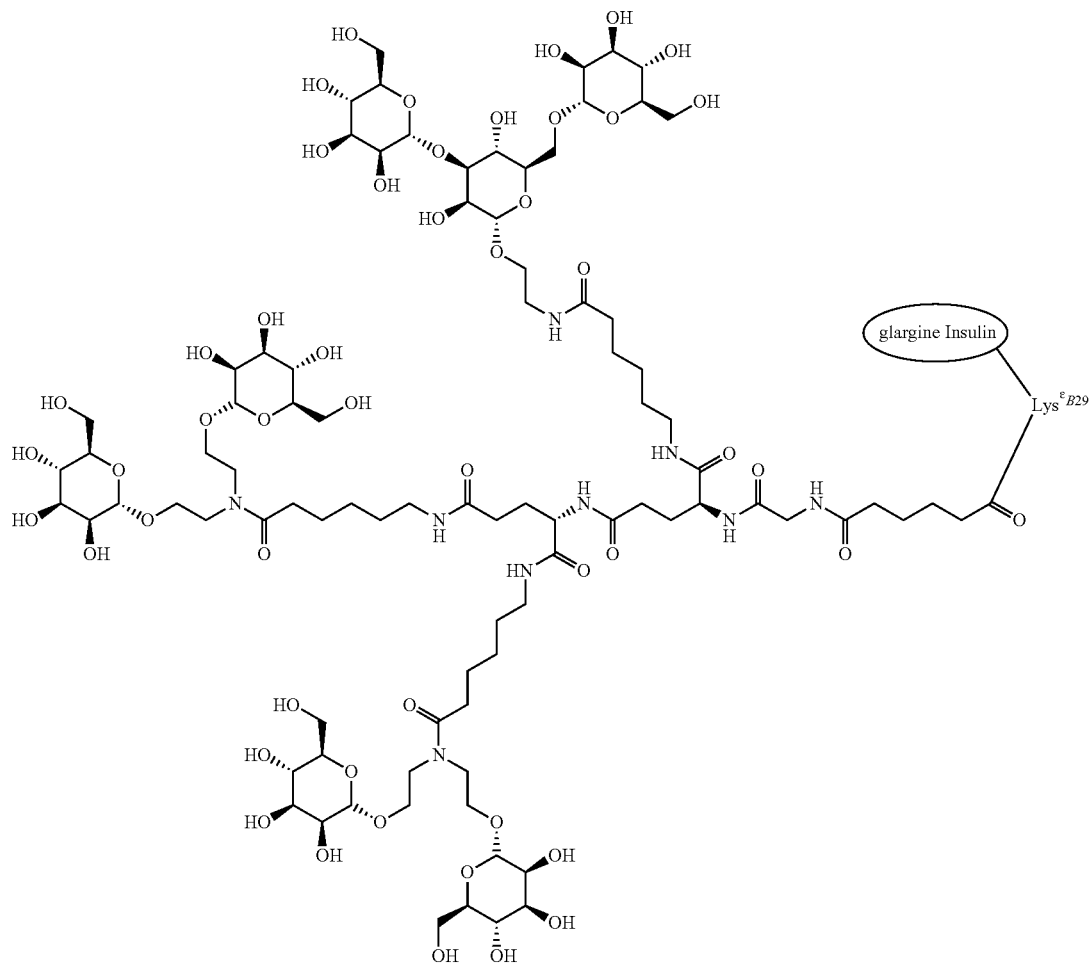 |

| Conjugate | Compound Formula & Structure |
|---|---|
| IOC-34 | 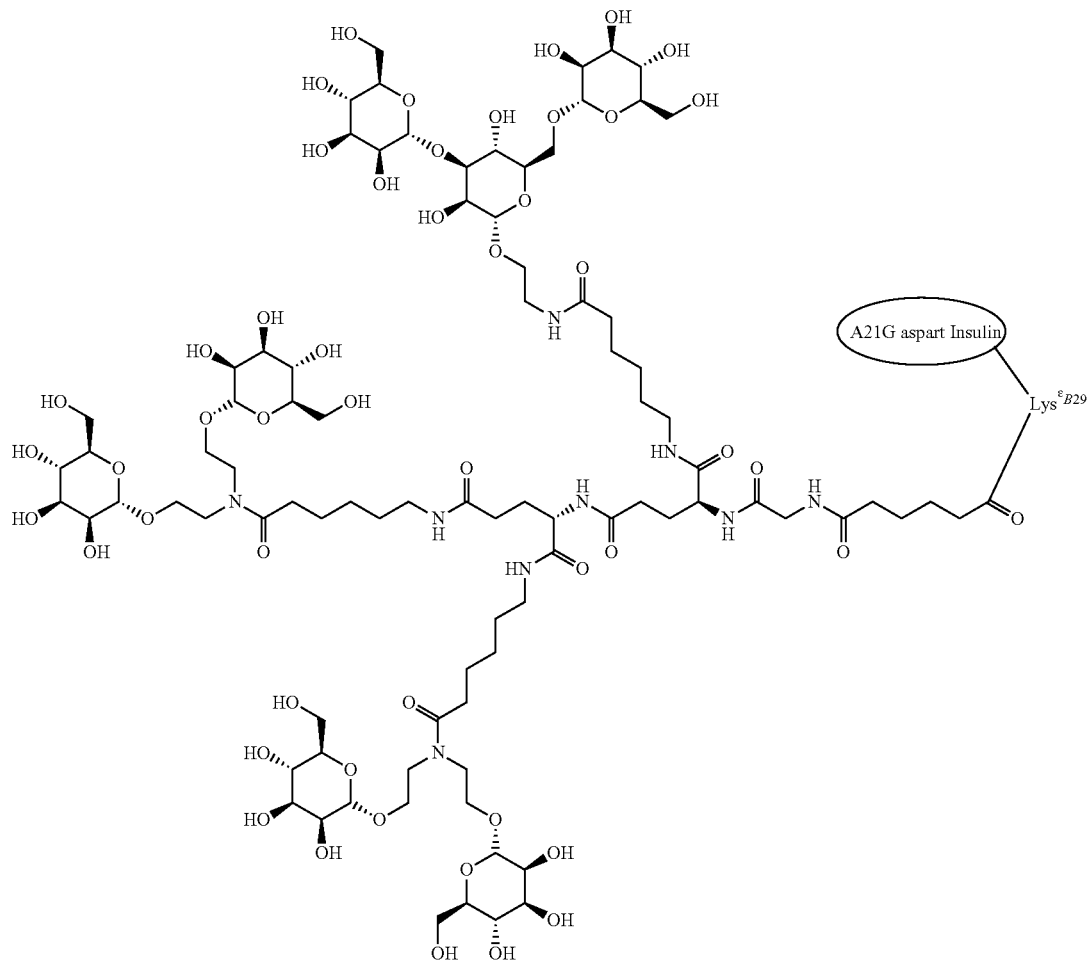 |

-continued
| Con-jugate | Compound Formula & Structure |
|---|---|
| IOC-35 | 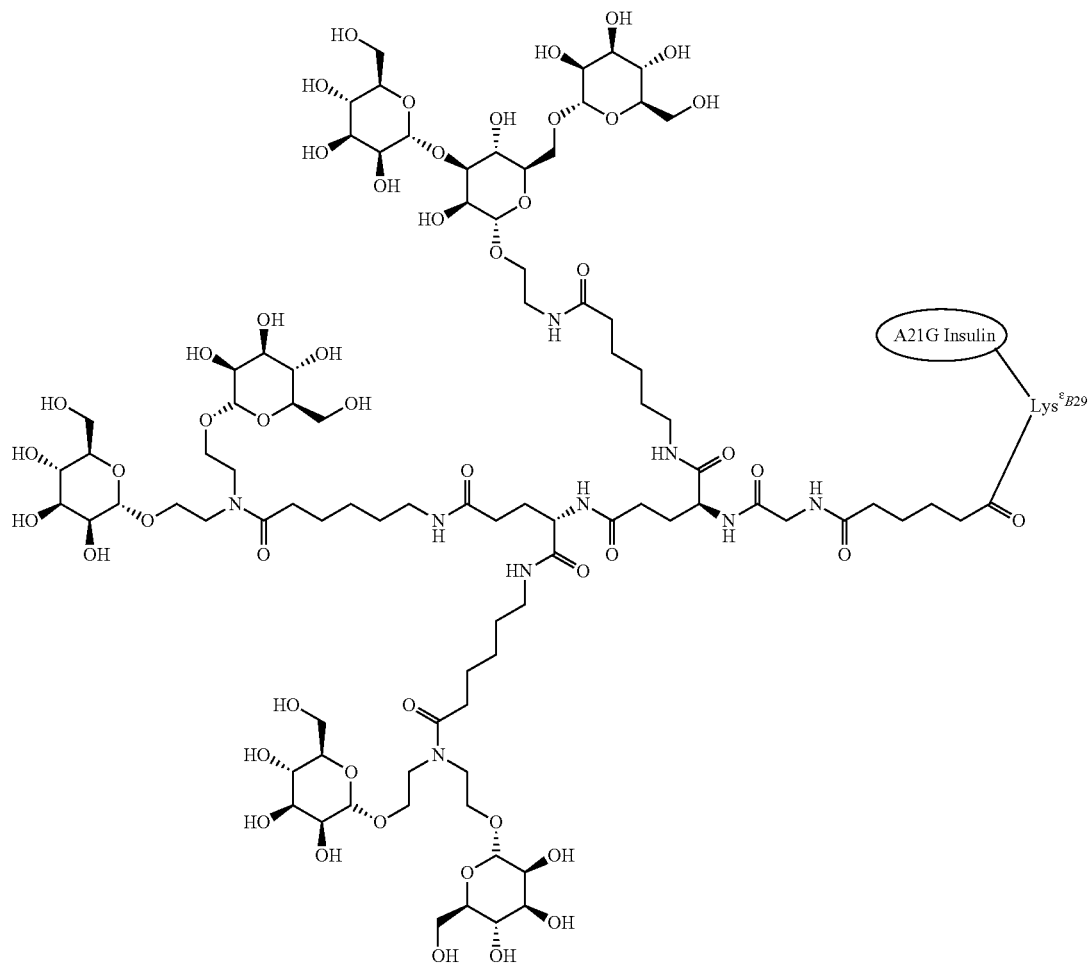 |

-continued
| Conjugate | Compound Formula & Structure |
|---|---|
| IOC-36 | 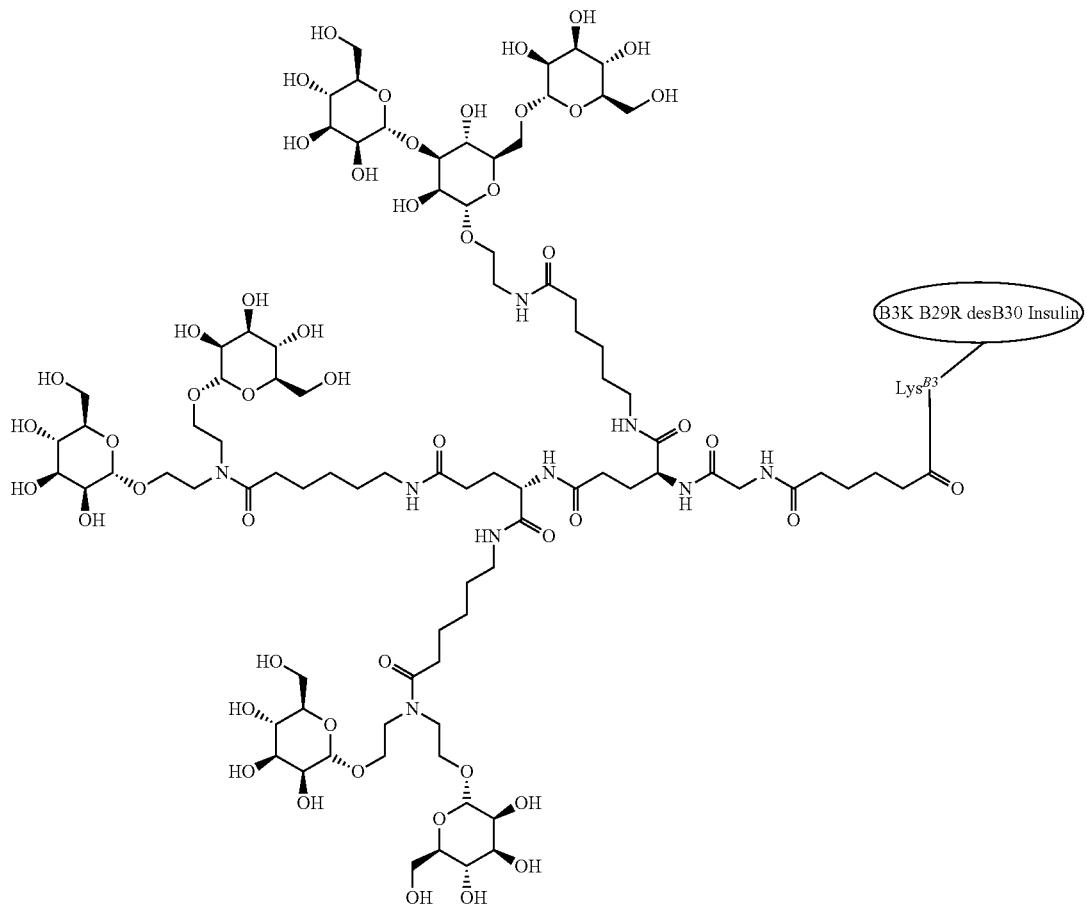 |

| Conjugate | Compound Formula & Structure |
|---|---|
| IOC-37 | 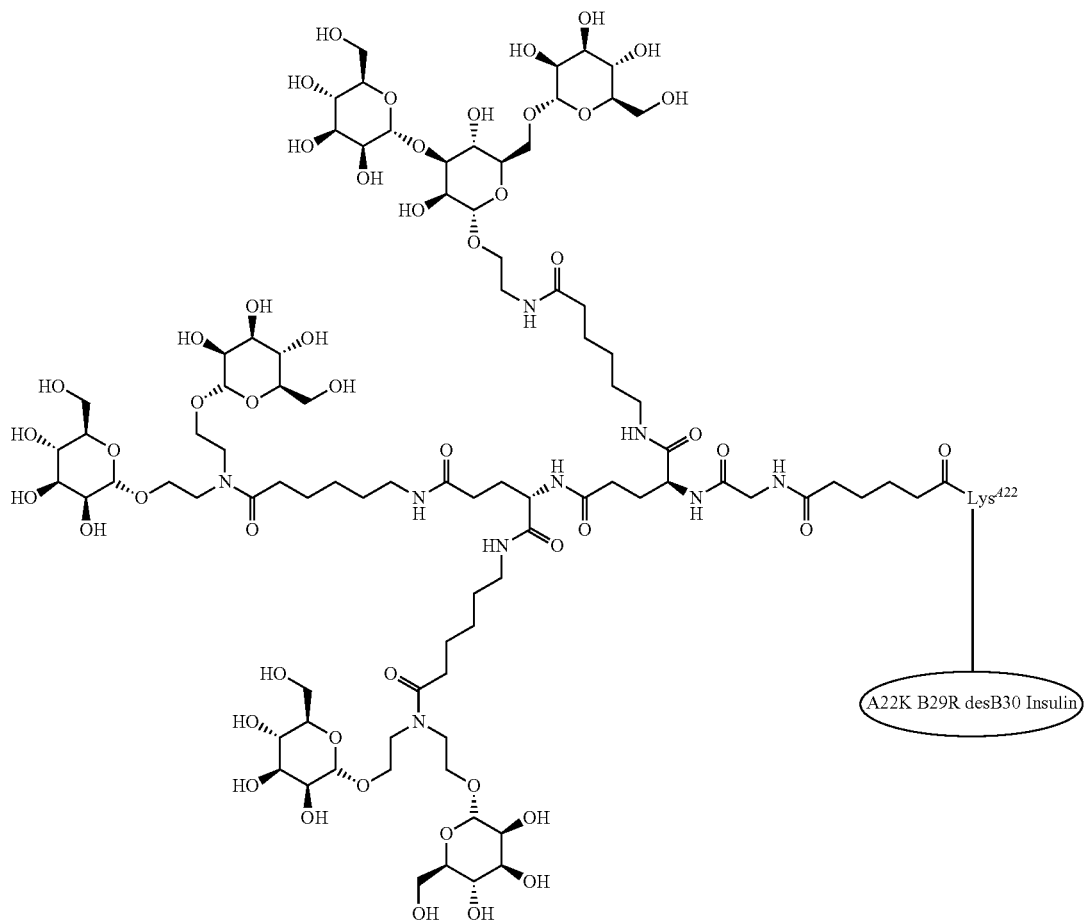 |

| Conjugate | Compound Formula & Structure |
|---|---|
| IOC-38 | 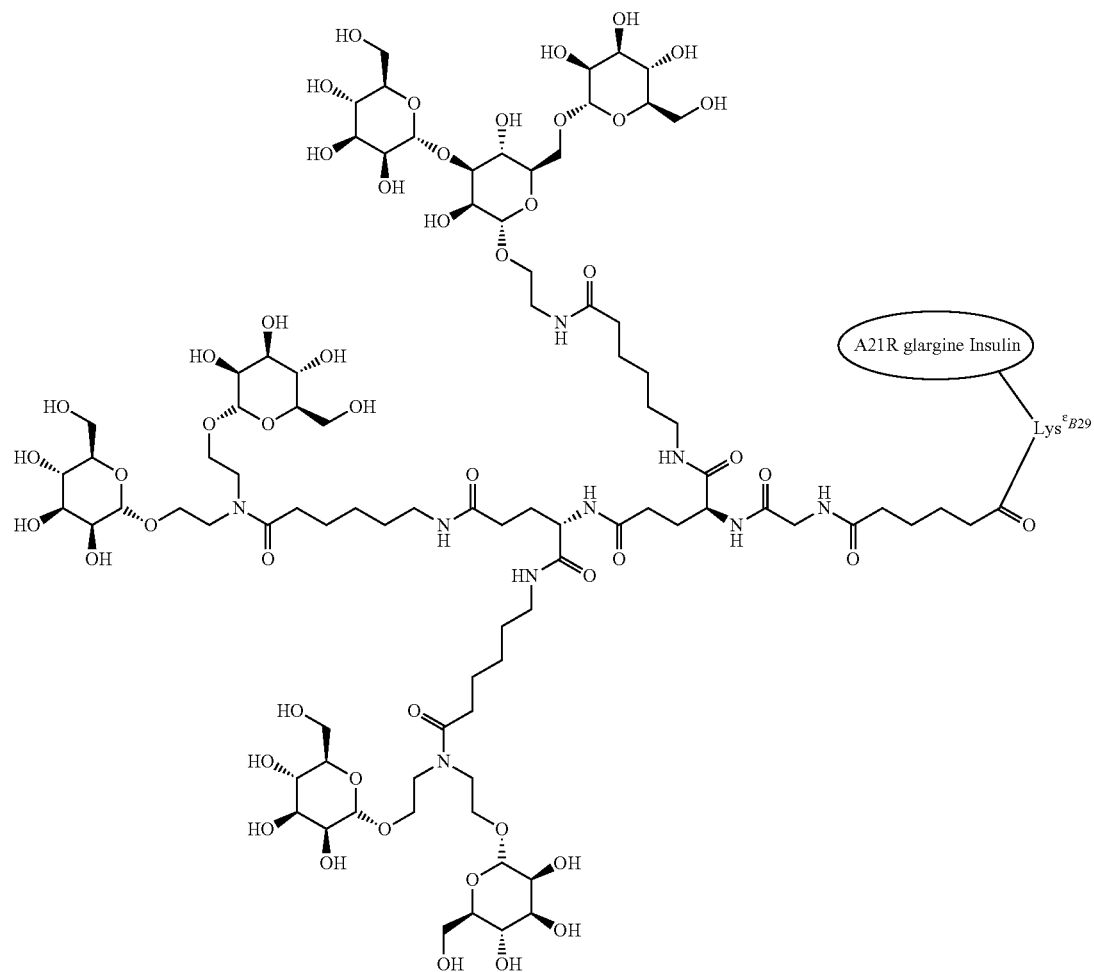 |

| Con-jugate | Compound Formula & Structure |
|---|---|
| IOC-39 | 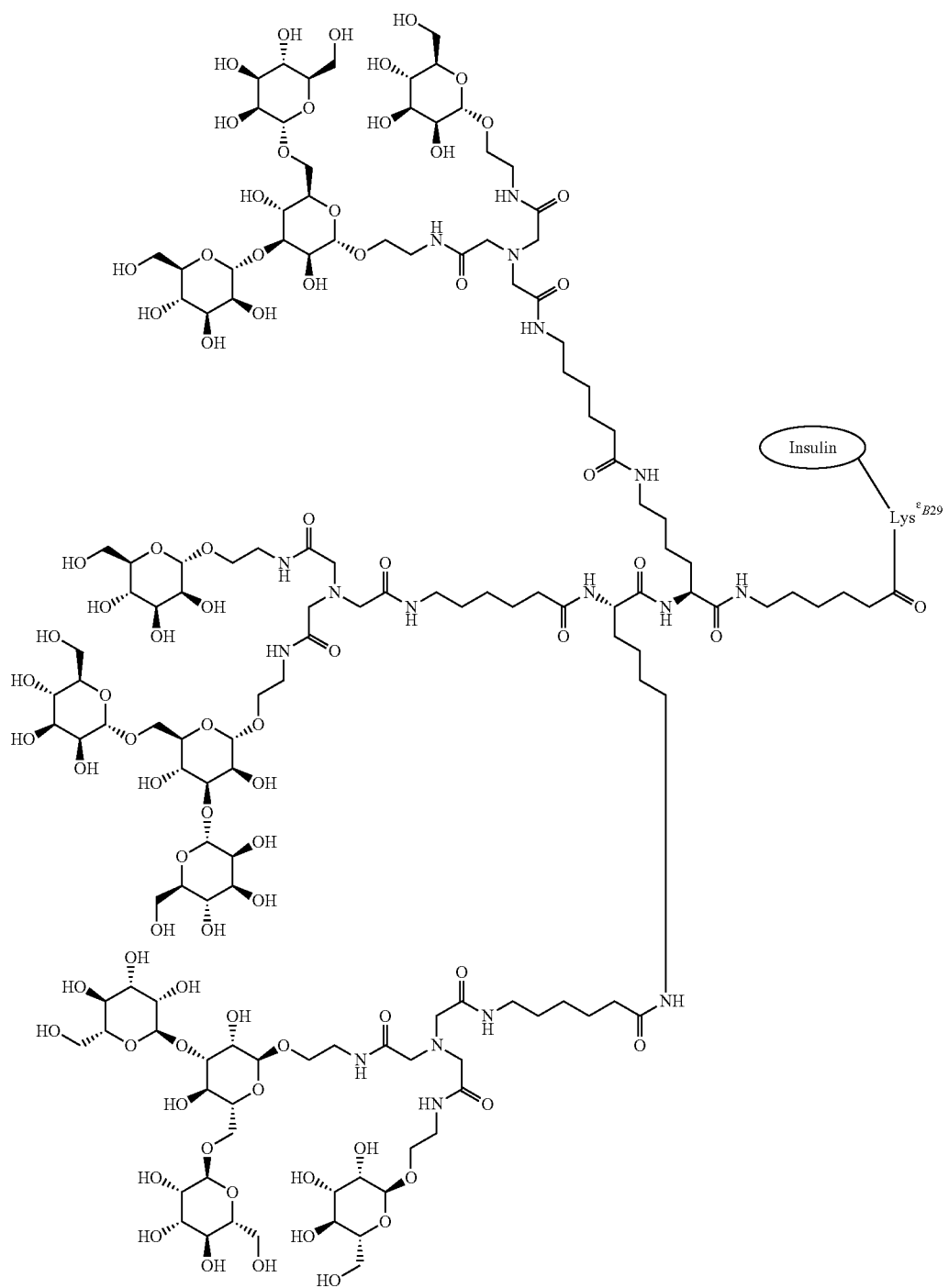 |

| Conjugate | Compound Formula & Structure |
|---|---|
| IOC-40 | 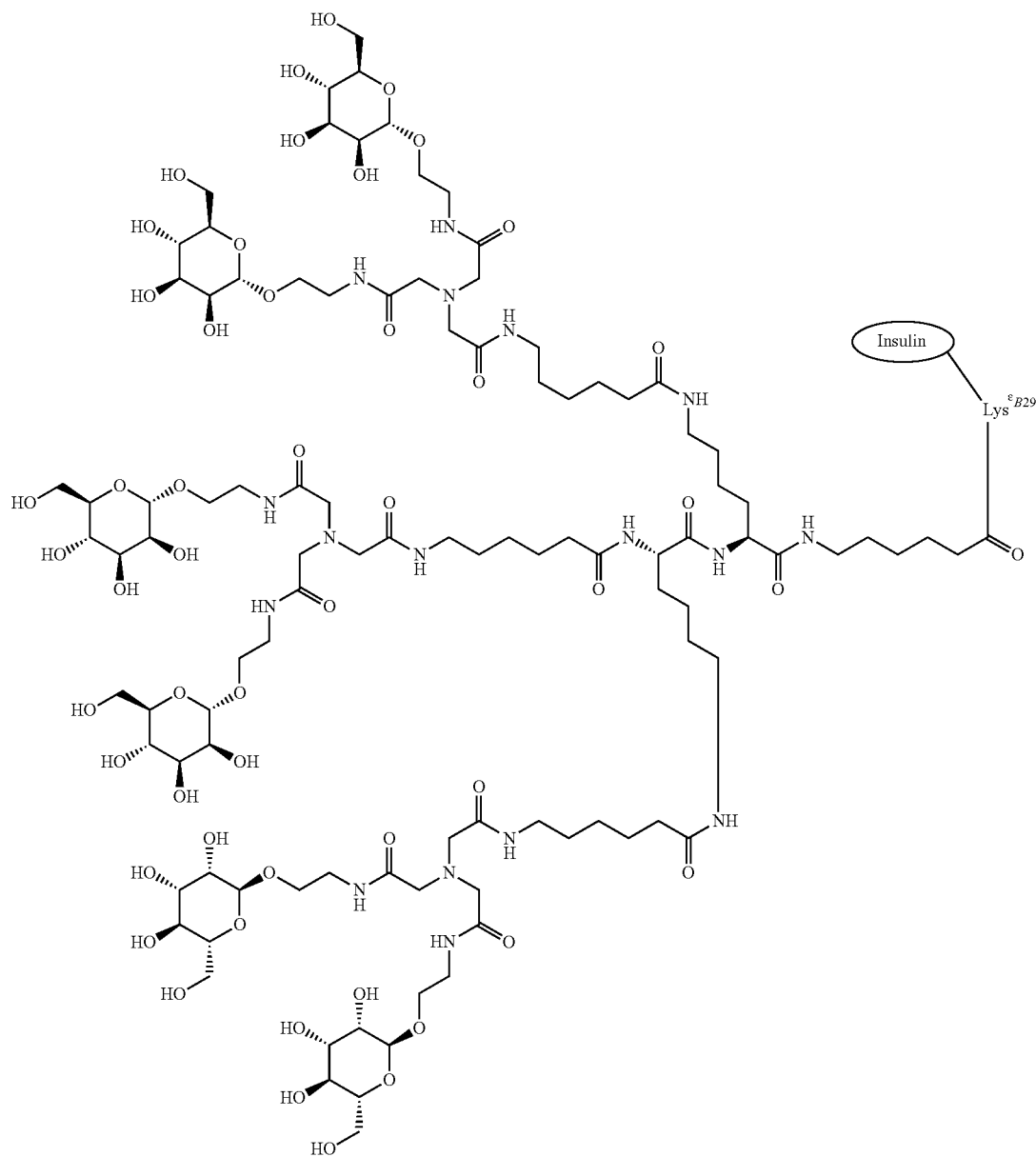 |

| Conjugate | Compound Formula & Structure |
|---|---|
| IOC-41 | 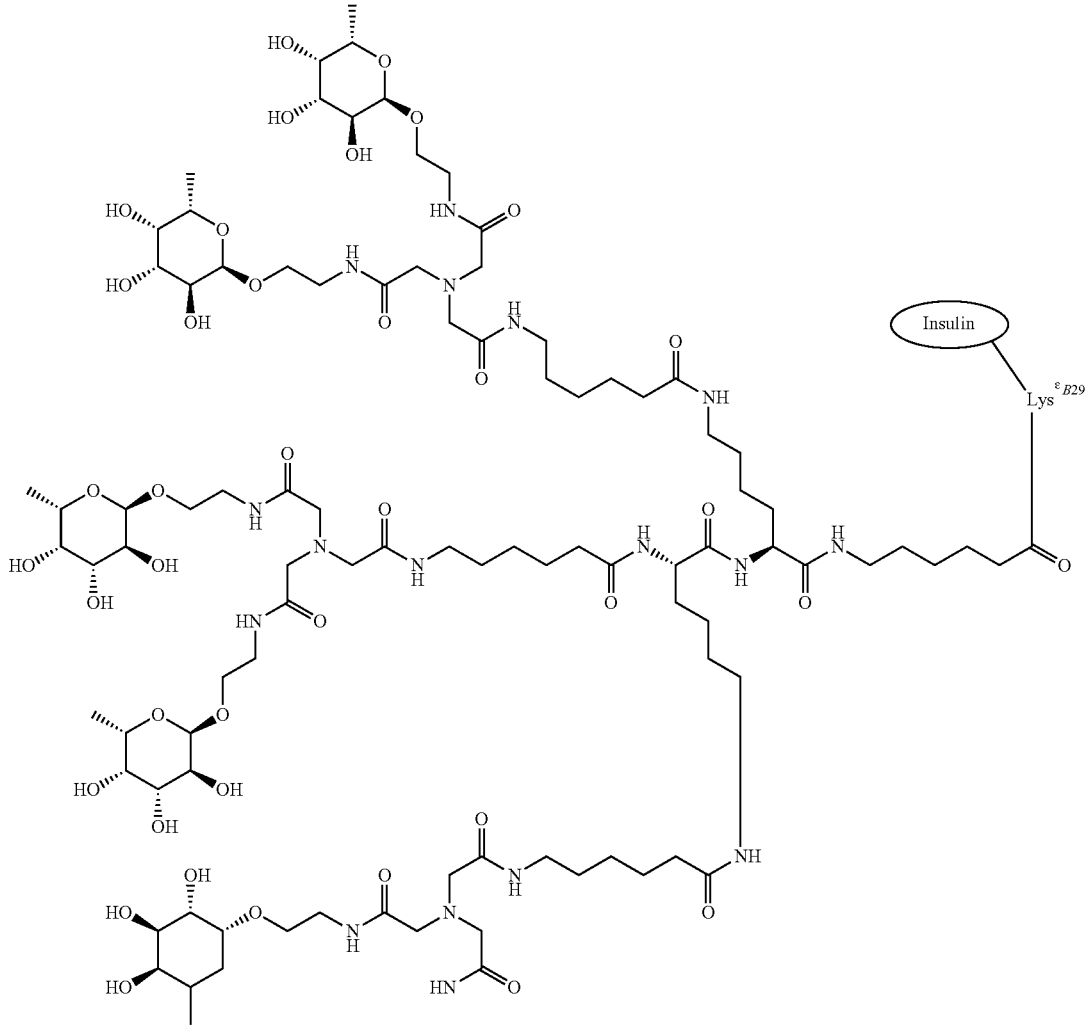 |

| Con- jugate | Compound Formula & Structure |
|---|---|
| IOC-42 | 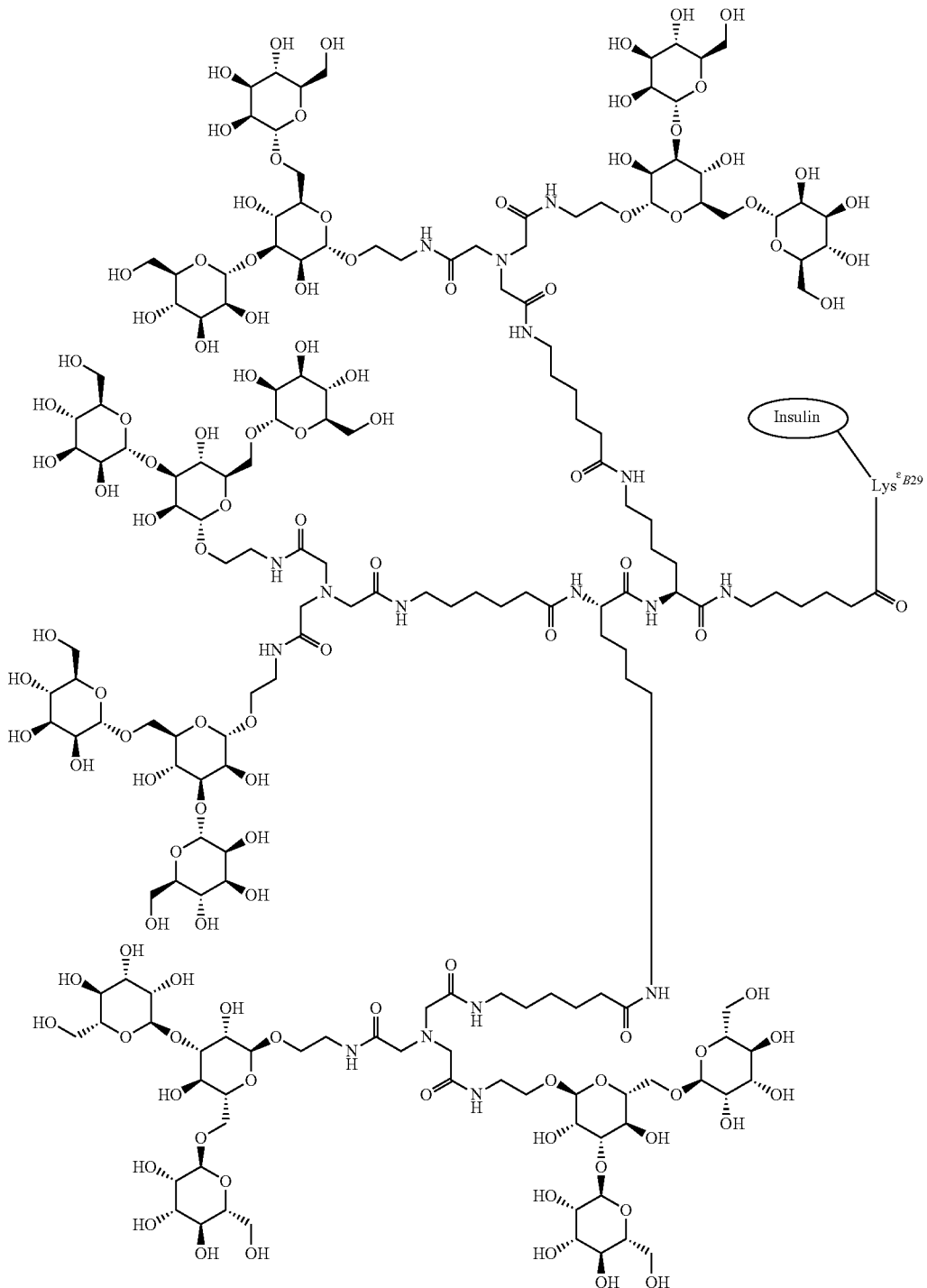 |

| Con- jugate | Compound Formula & Structure |
|---|---|
| IOC-43 | 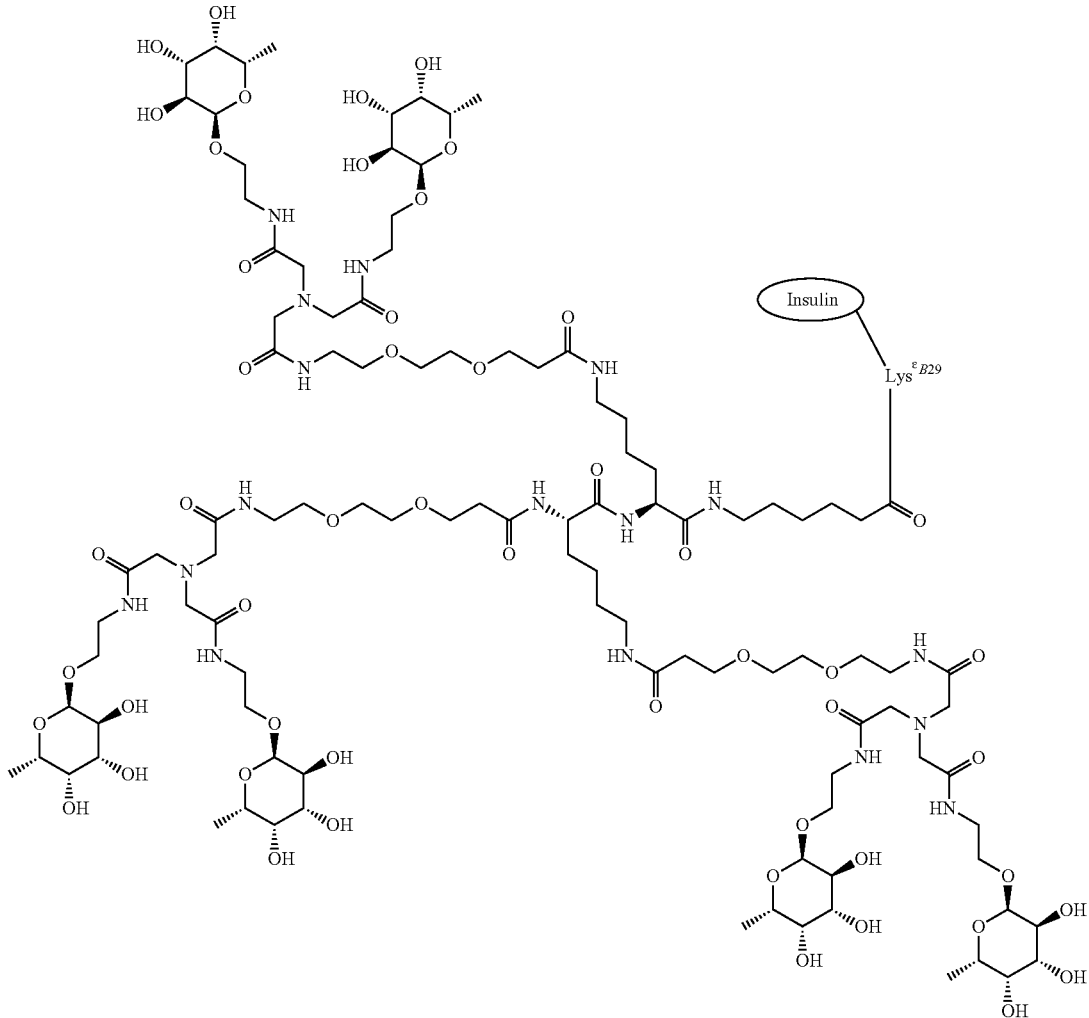 |

| Conjugate | Compound Formula & Structure |
|---|---|
| IOC-44 | 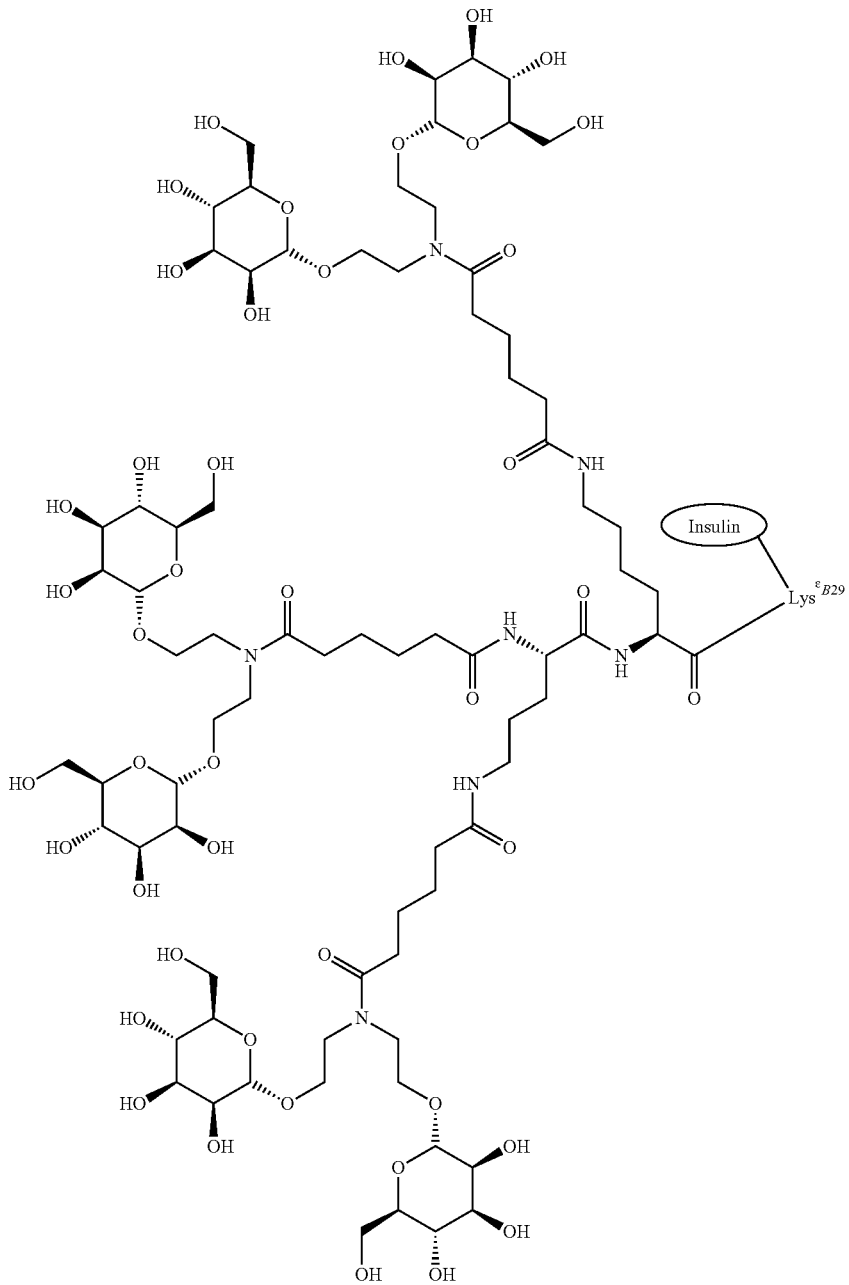 |

| Con-jugate | Compound Formula & Structure |
|---|---|
| IOC-45 | 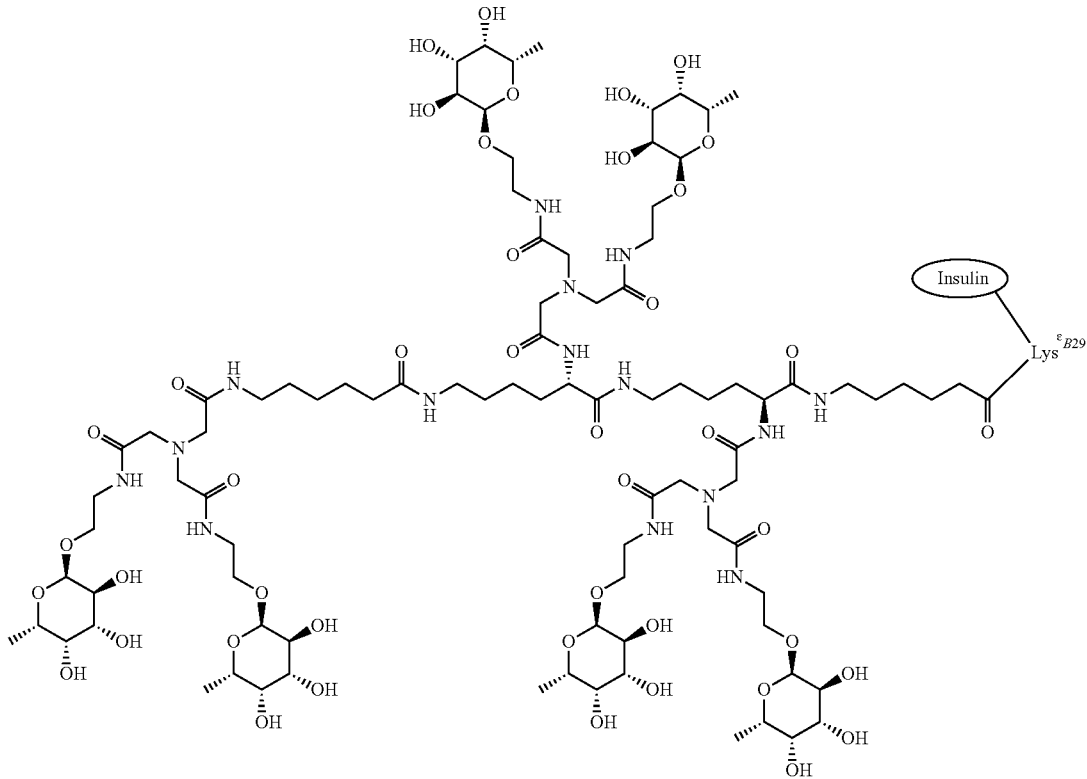 |
| IOC-46 | 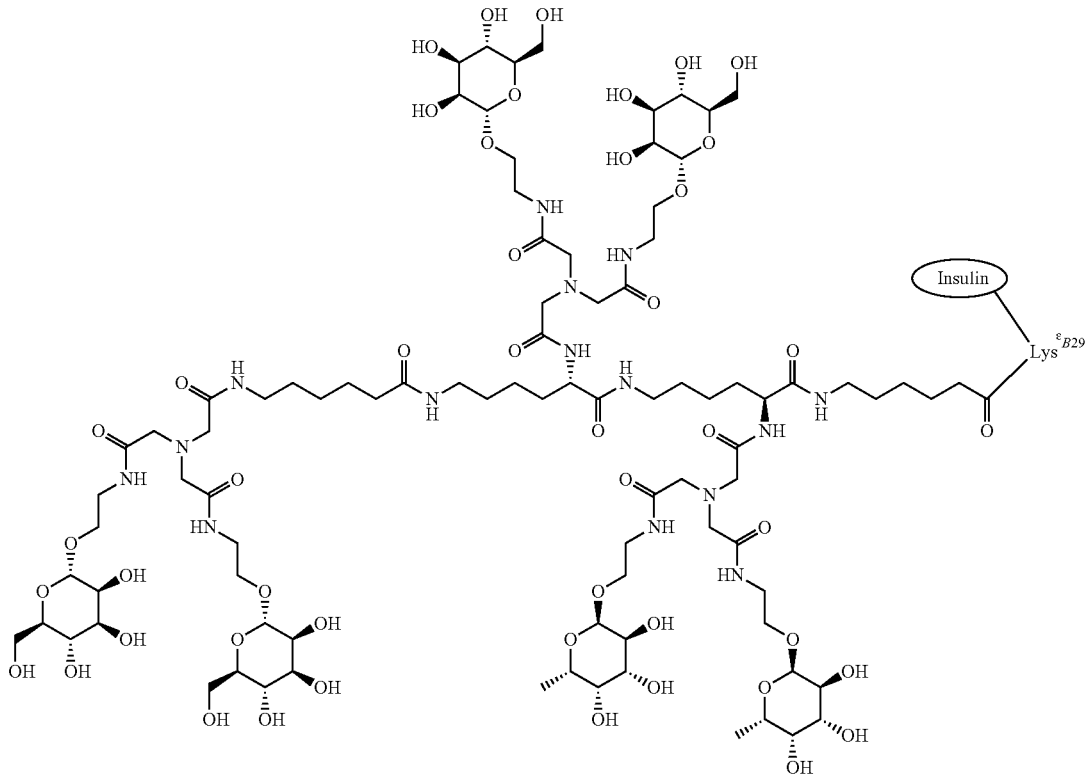 |

| Con-jugate | Compound Formula & Structure |
|---|---|
| IOC-47 | 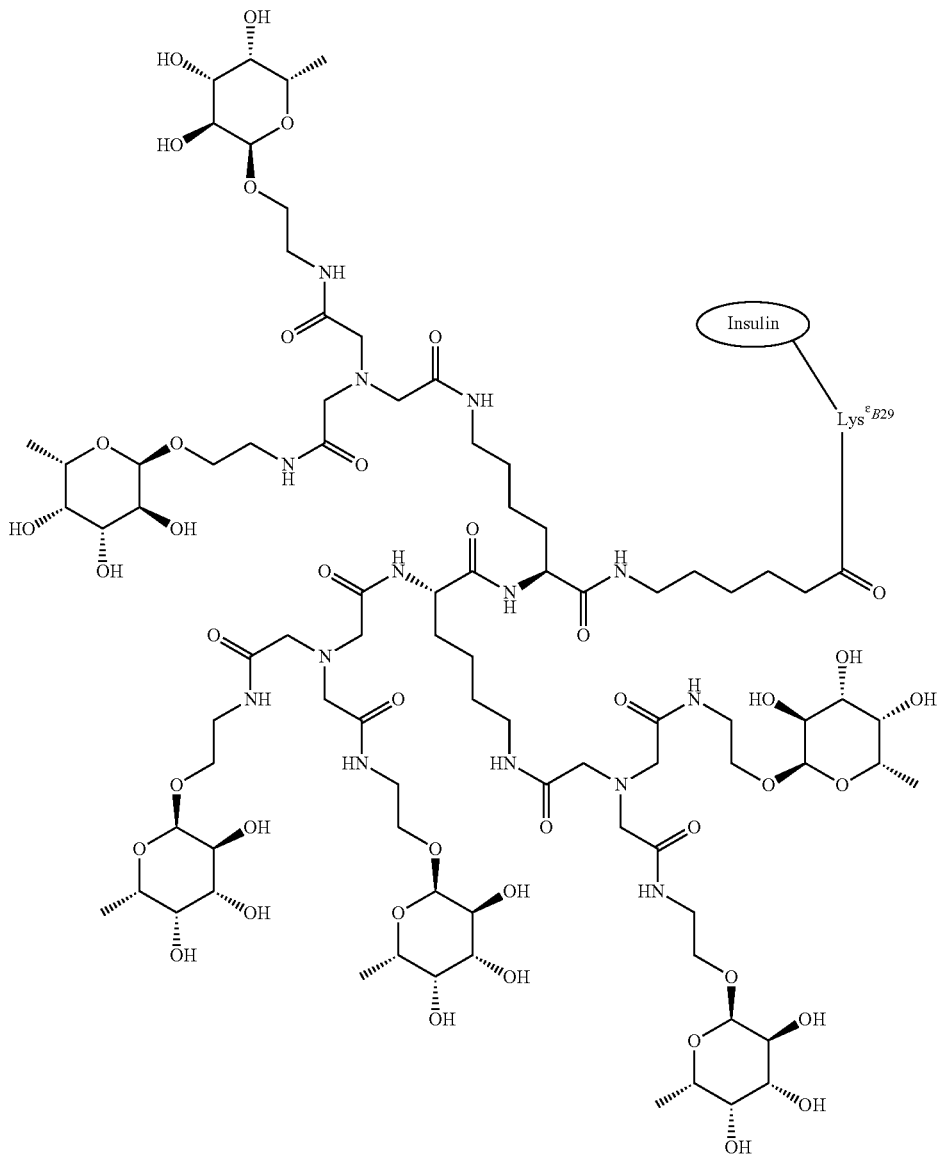 |

| Conjugate | Compound Formula & Structure |
|---|---|
| IOC-48 | 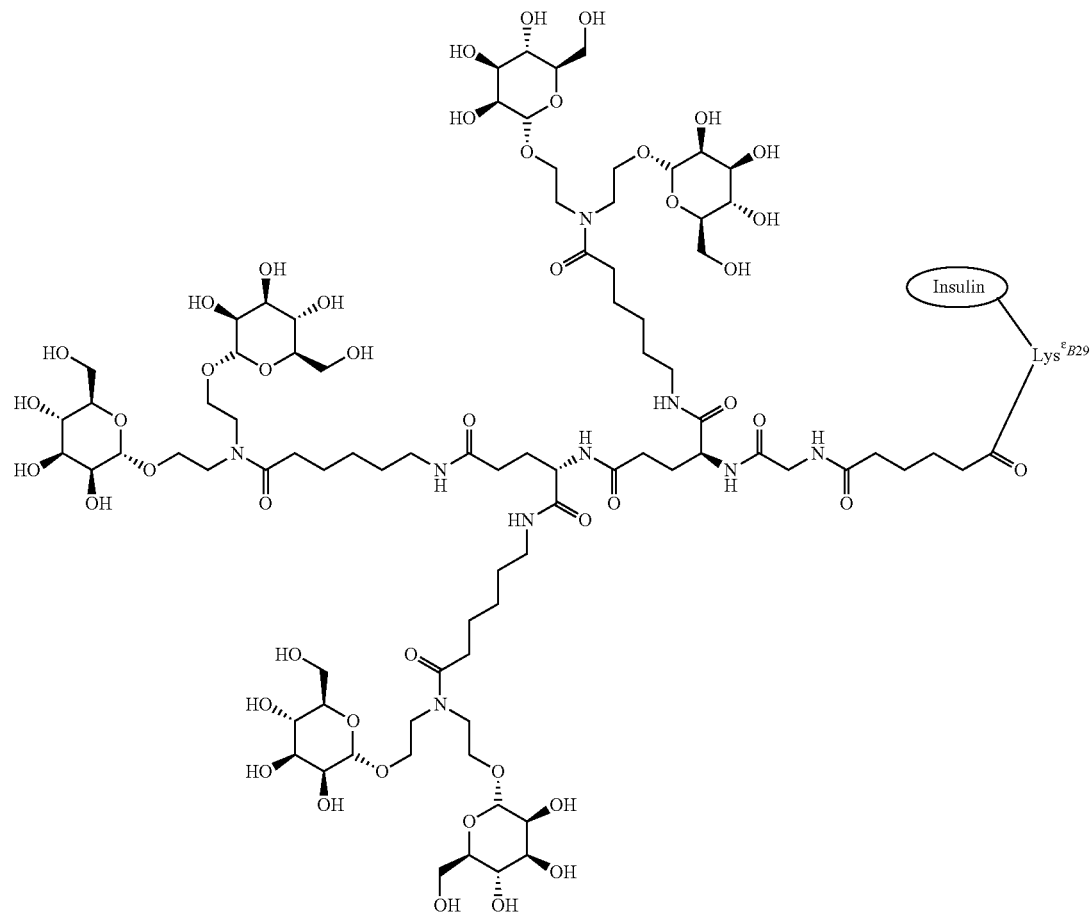 |

| Conjugate | Compound Formula & Structure |
|---|---|
| IOC-49 | 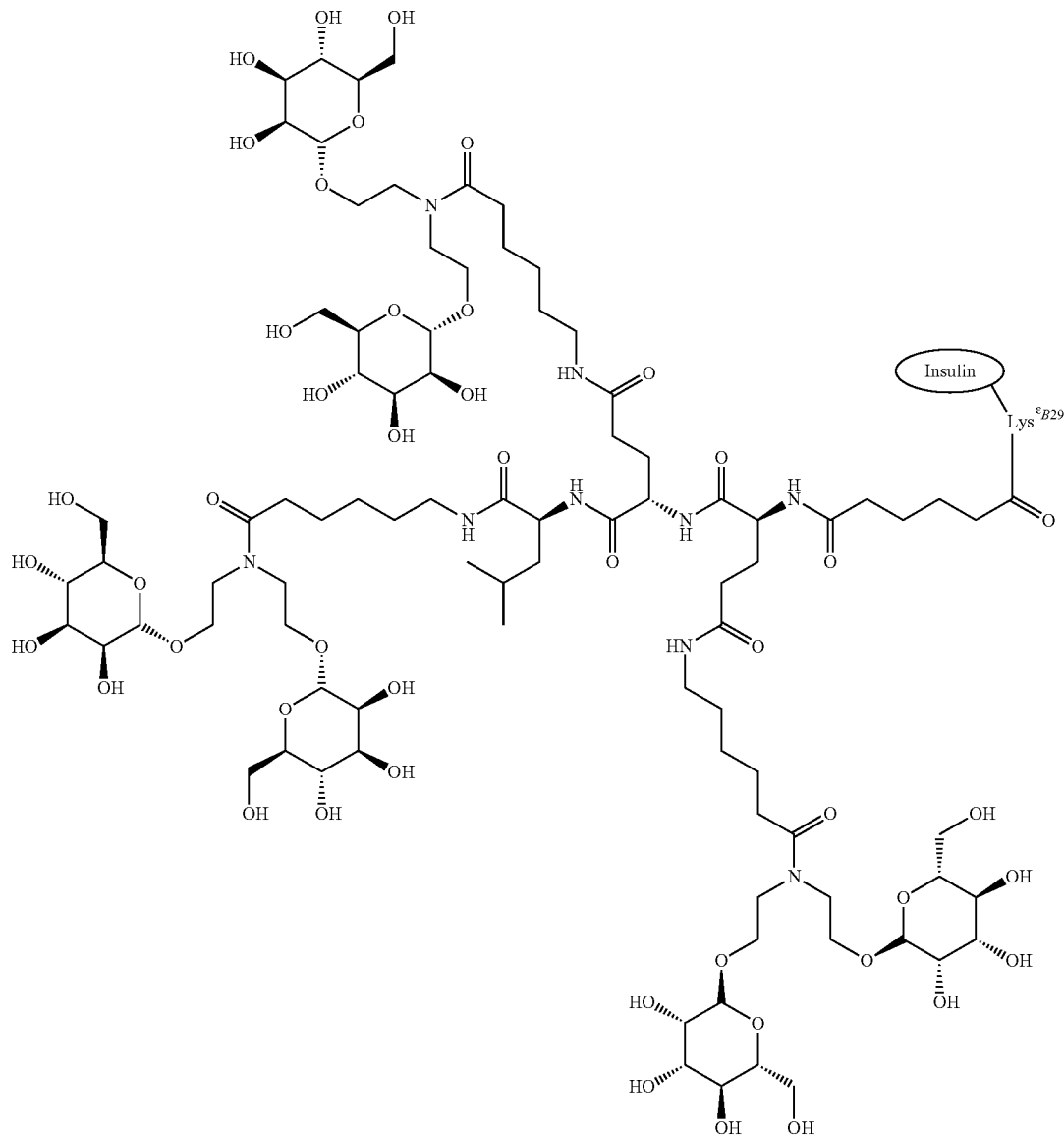 |

| Conjugate | Compound Formula & Structure |
|---|---|
| IOC-50 | 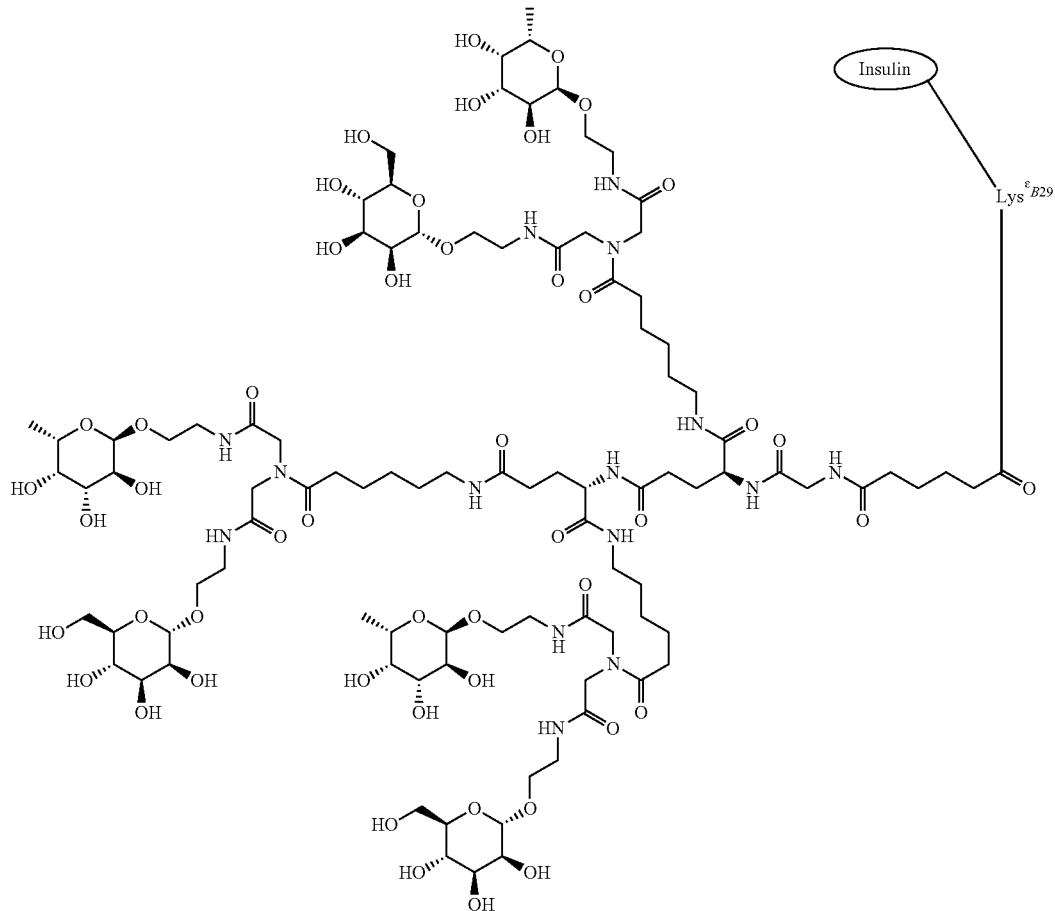 |

| Con- jugate | Compound Formula & Structure |
|---|---|
| IOC-51 | 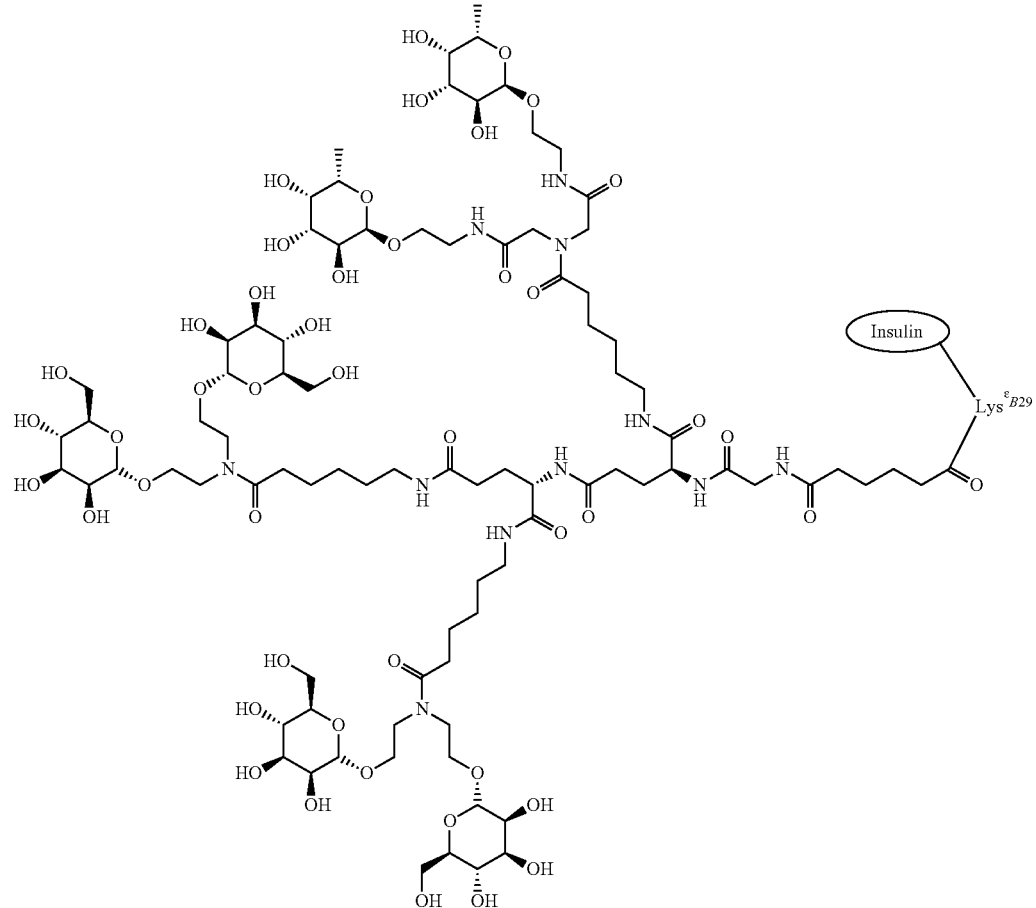 |

-continued
| Con-jugate | Compound Formula & Structure |
|---|---|
| IOC-52 | 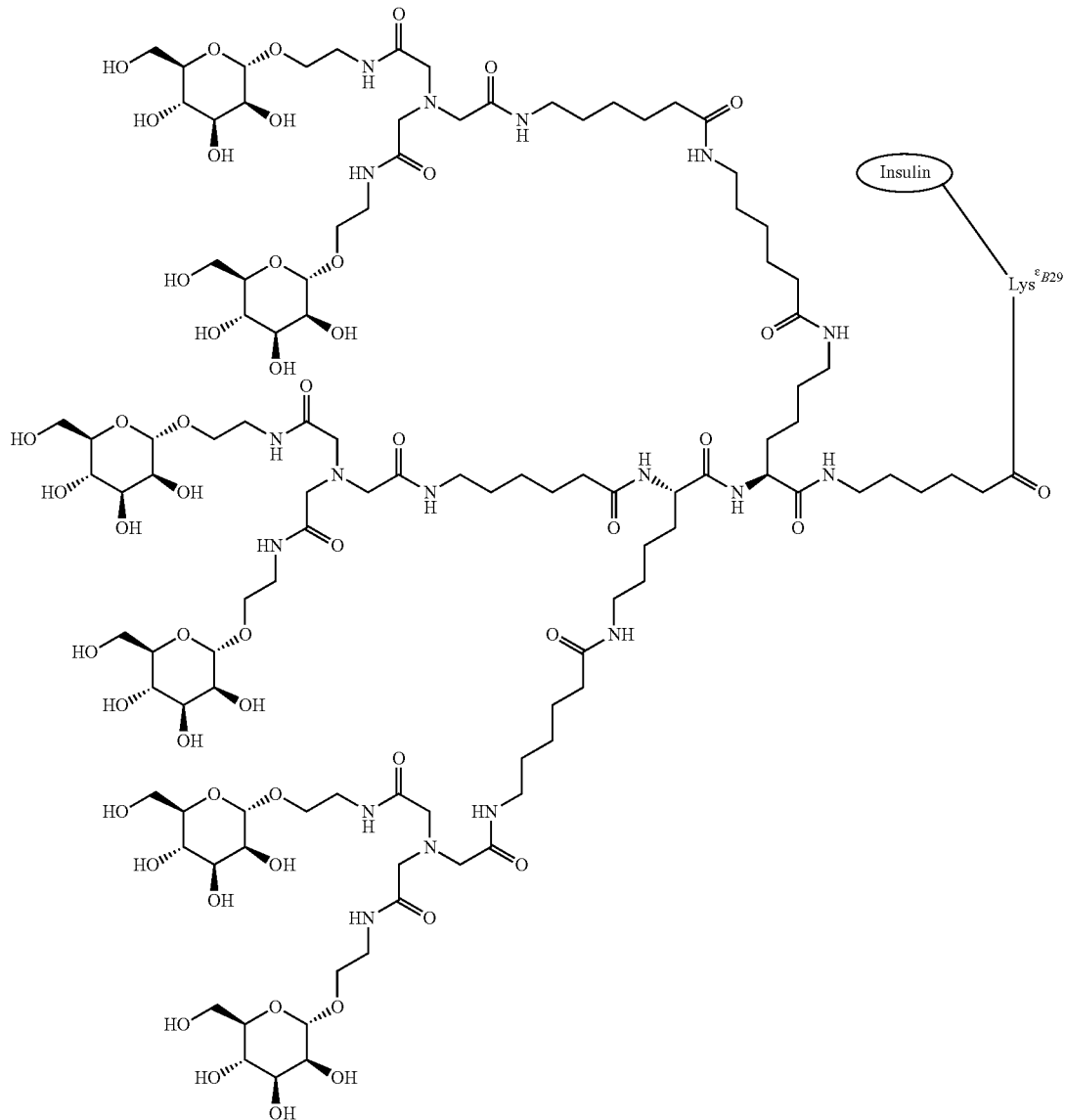 |

| Con- jugate | Compound Formula & Structure |
|---|---|
| IOC-53 | 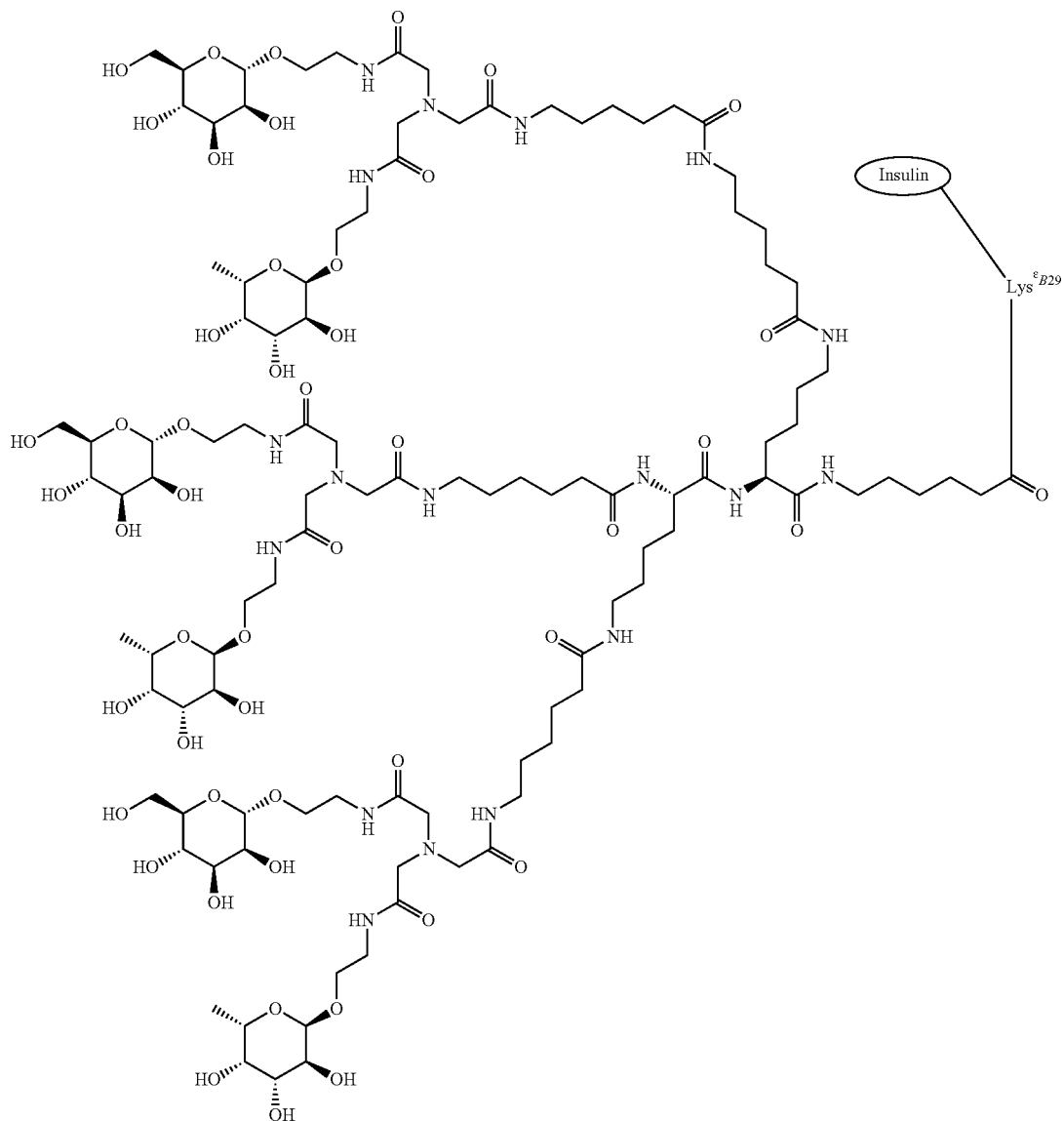 |

-continued
| Con-jugate | Compound Formula & Structure |
|---|---|
| IOC-54 | 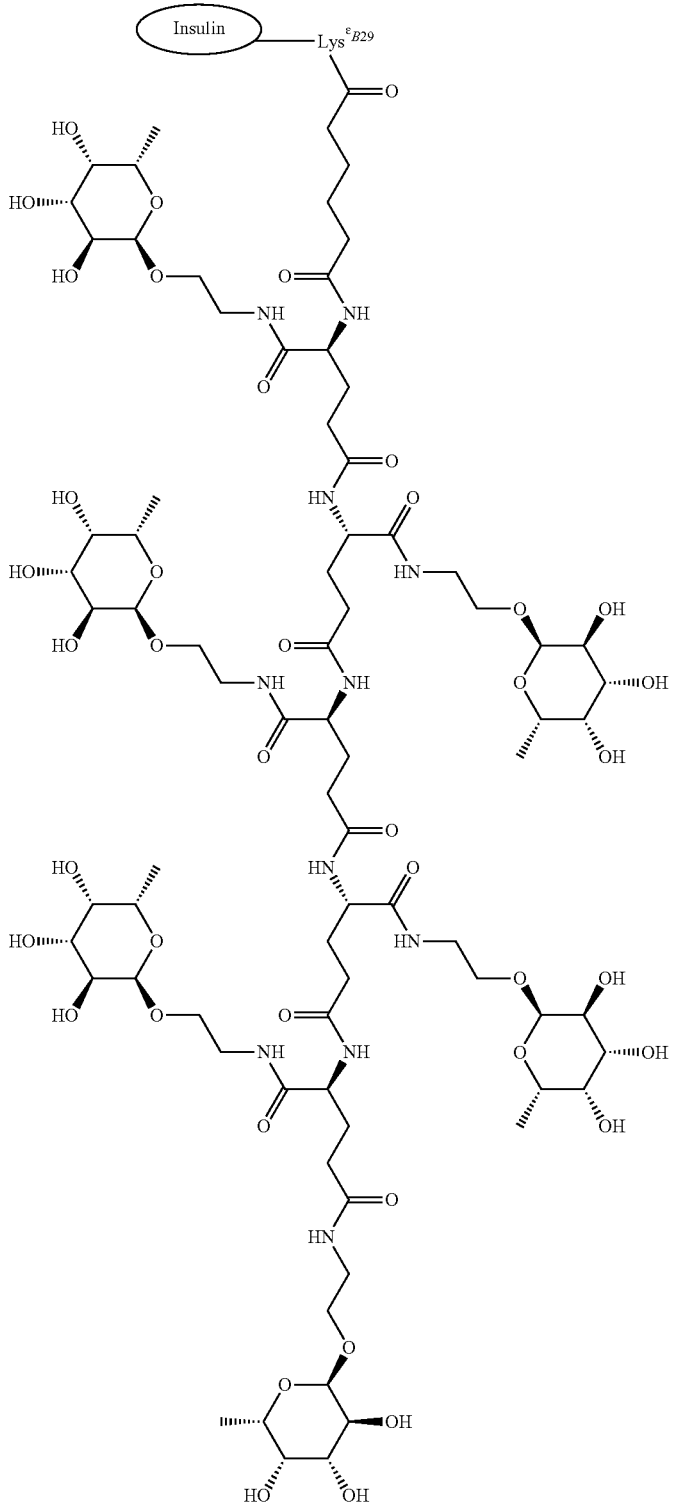 |

-continued
| Conjugate | Compound Formula & Structure |
|---|---|
| IOC-55 | 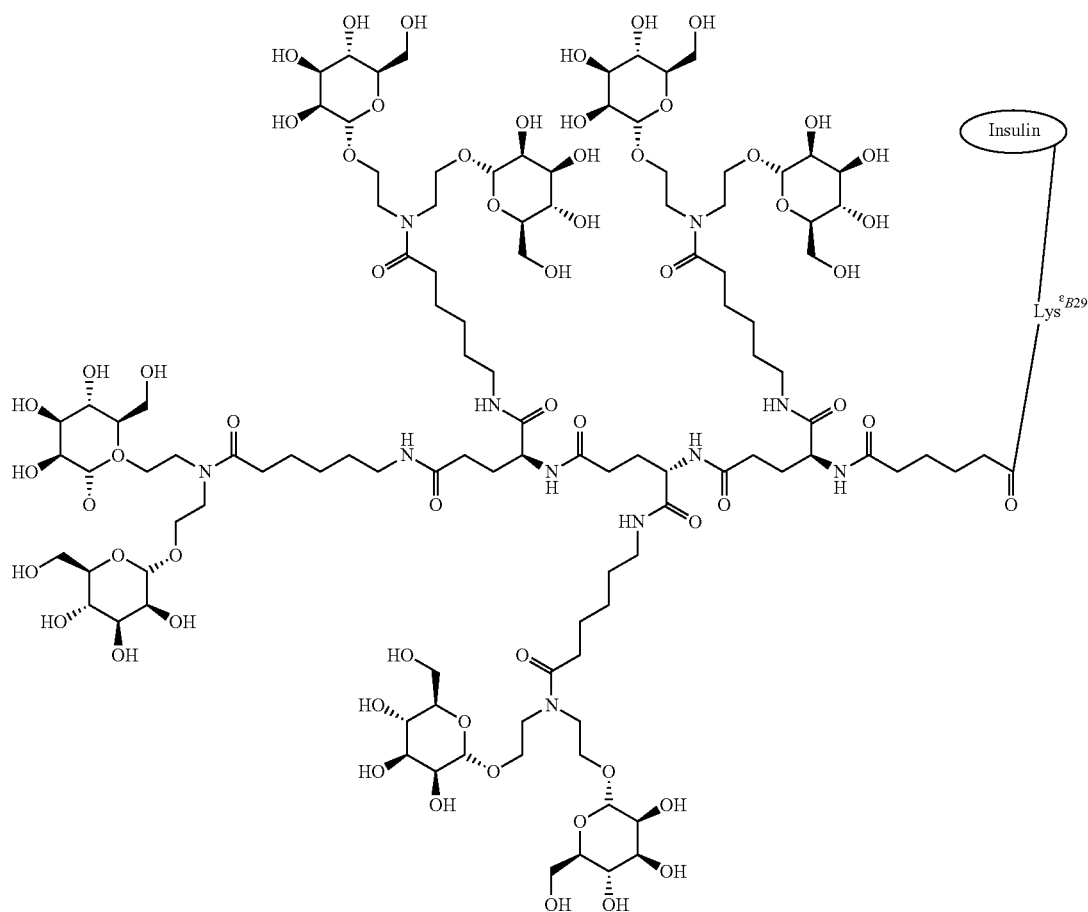 |

-continued
| Con-jugate | Compound Formula & Structure |
|---|---|
| IOC-56 | 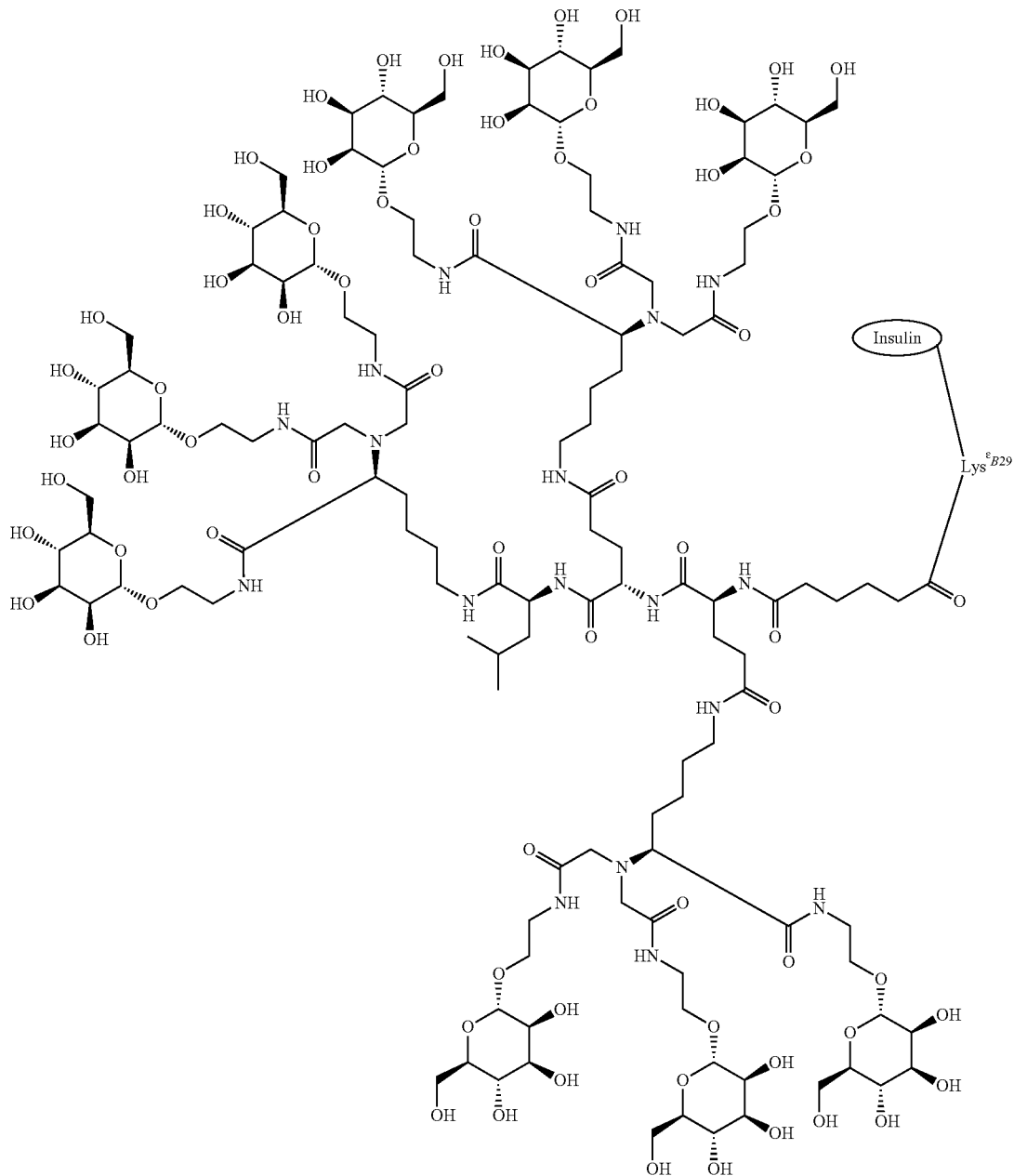 |

| Conjugate | Compound Formula & Structure |
|---|---|
| IOC-57 | 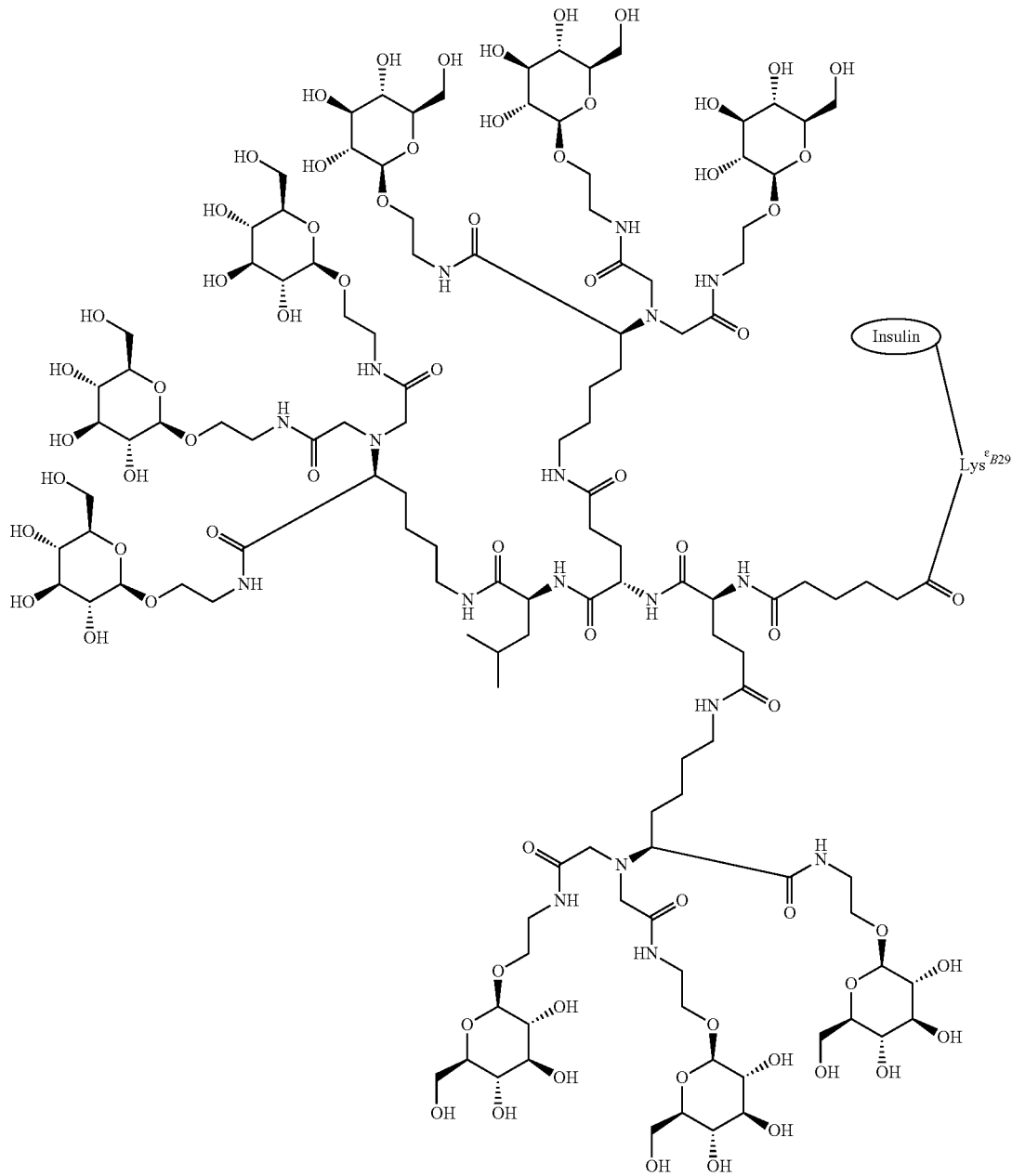 |

| Conjugate | Compound Formula & Structure |
|---|---|
| IOC-58 | 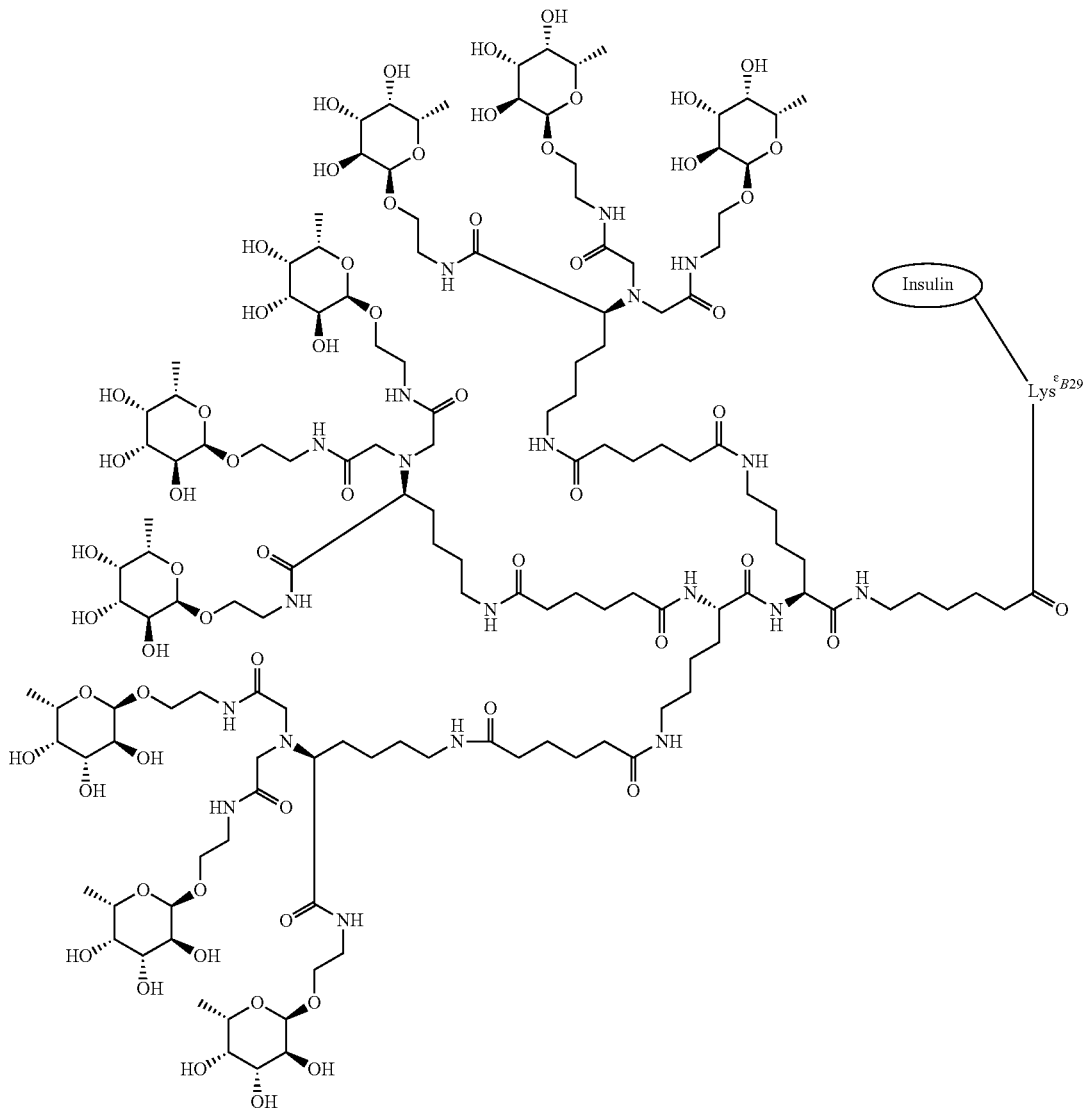 |

| Con-jugate | Compound Formula & Structure |
|---|---|
| IOC-59 | 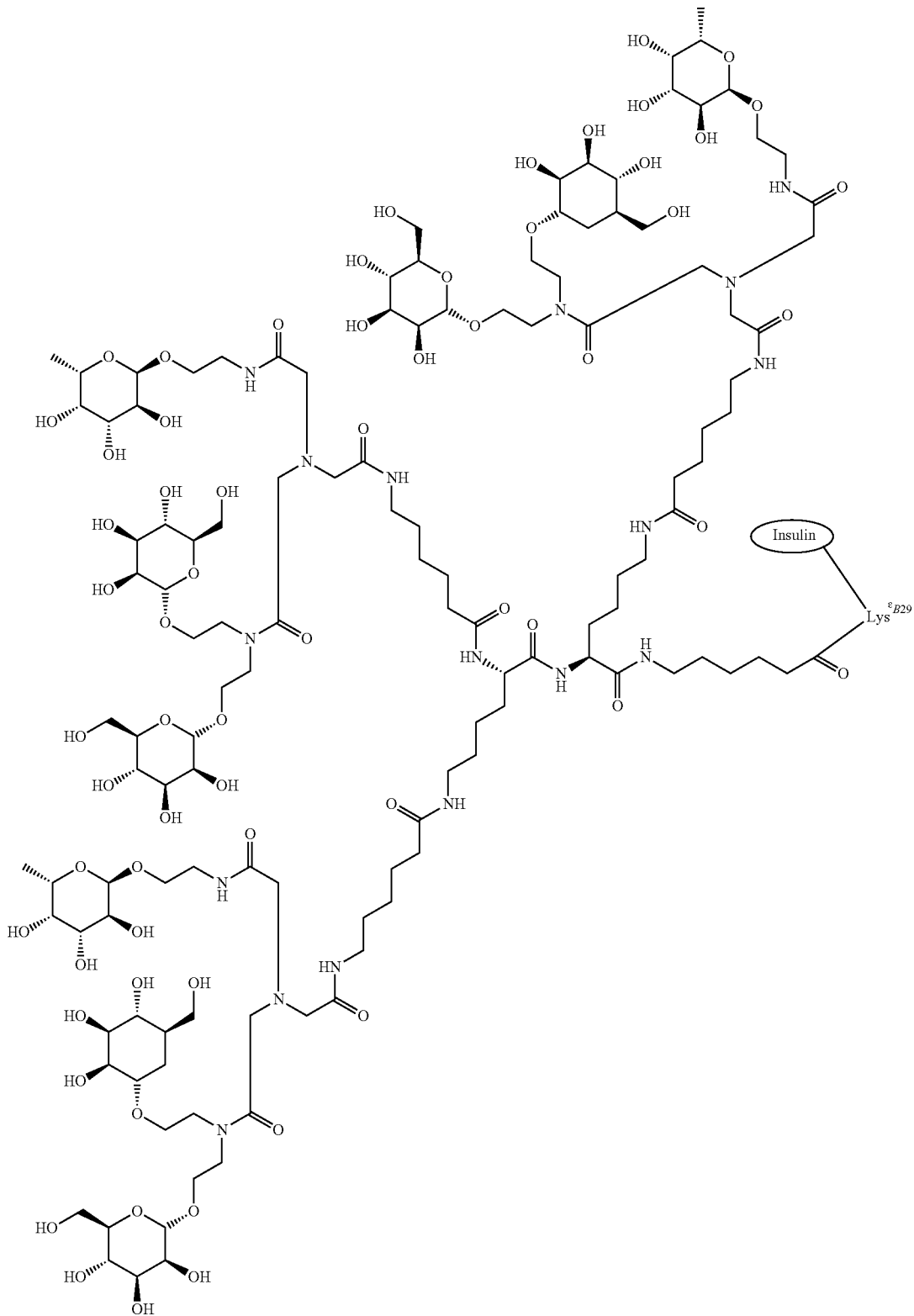 |

| Conjugate | Compound Formula & Structure |
|---|---|
| IOC-60 | 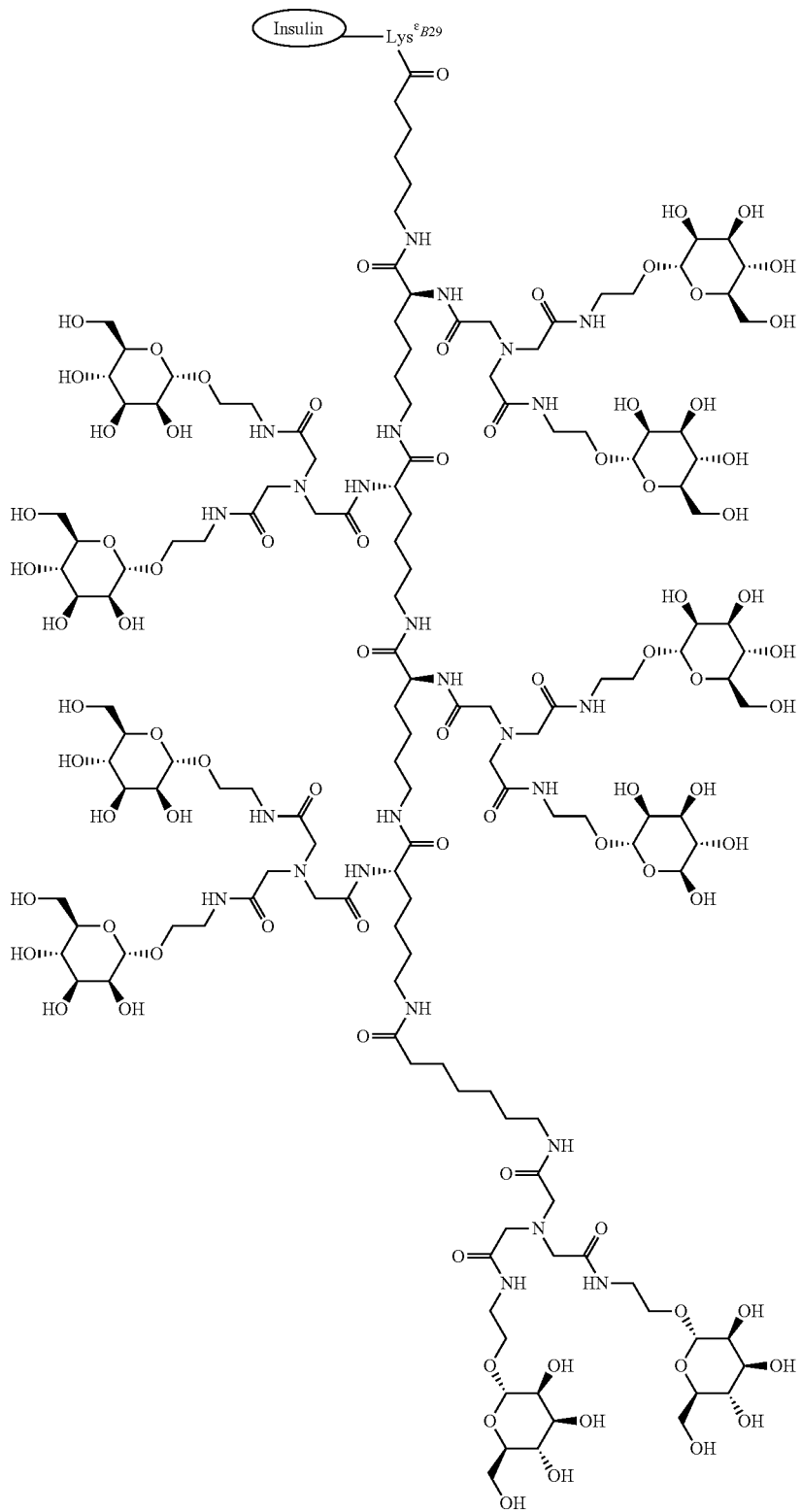 |

| Con- jugate | Compound Formula & Structure |
|---|---|
| IOC-61 | 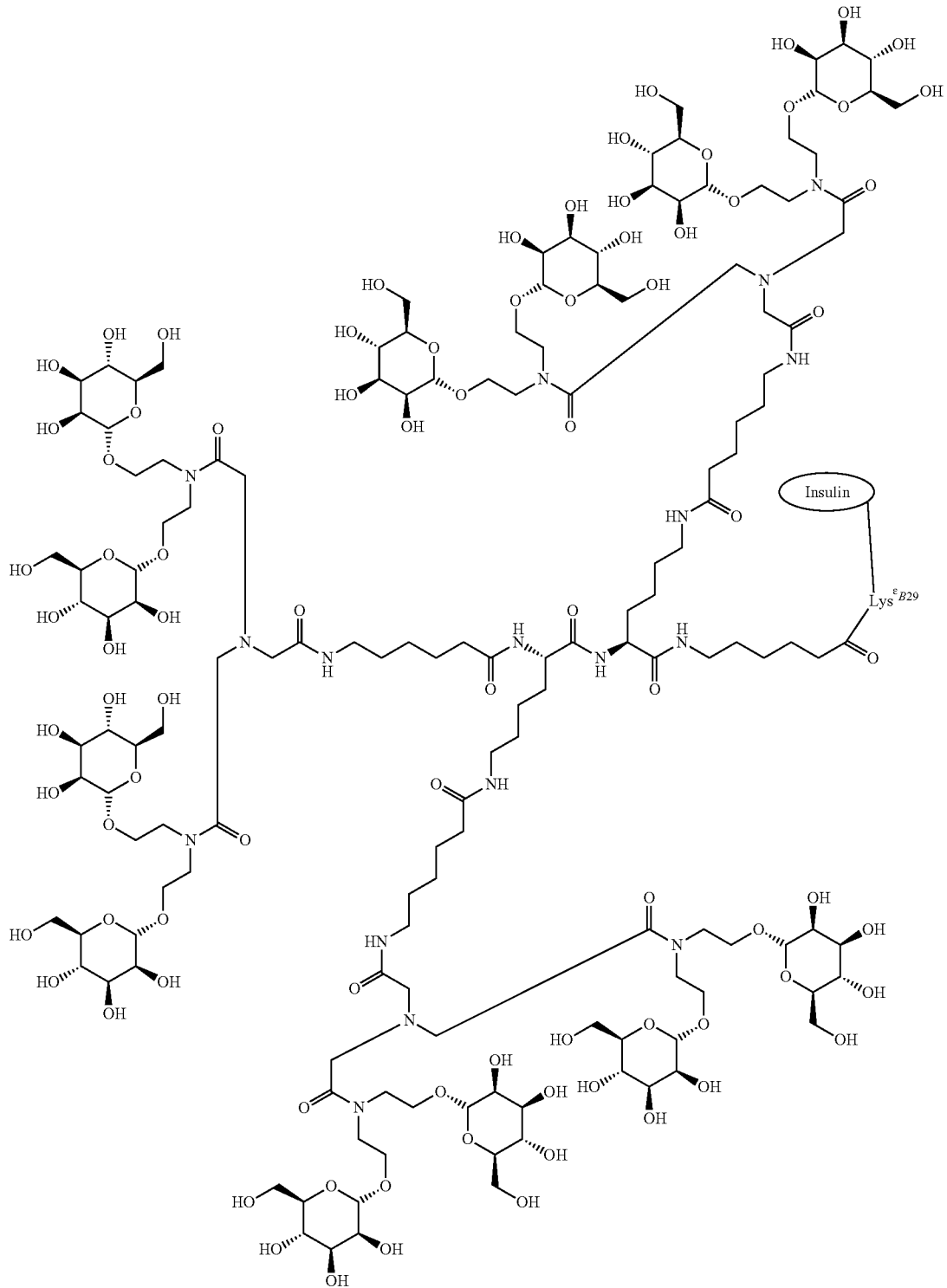 |

| Conjugate | Compound Formula & Structure |
|---|---|
| IOC-62 | 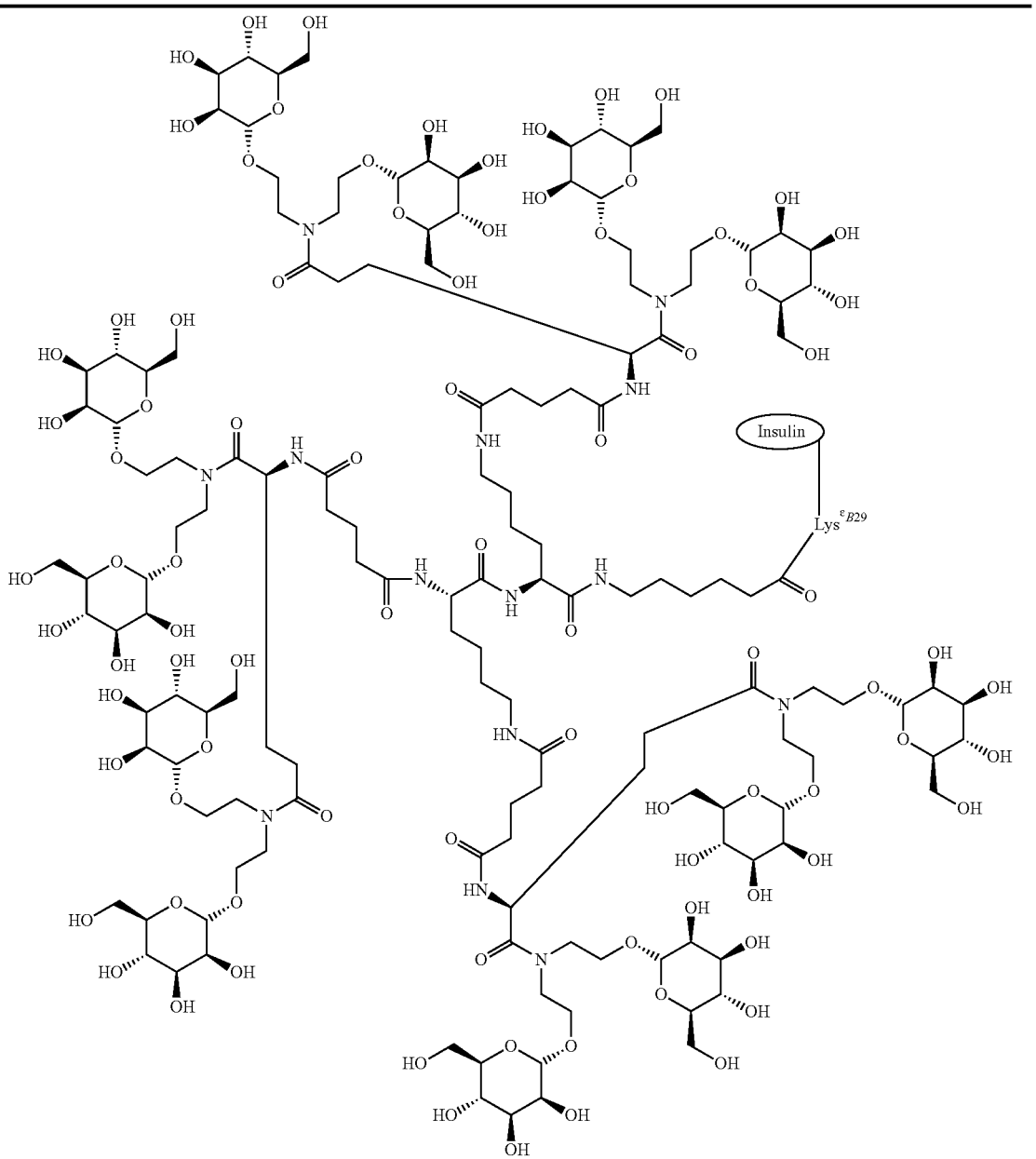 |

Additional embodiments of the disclosure provide for the use of any one of the conjugates disclosed herein for the manufacture of a medicament to treat diabetes.

Additional embodiments of the disclosure provide for the use of any one of the conjugates disclosed herein for the manufacture of a medicament to treat a Type I diabetes, Type II diabetes, gestational diabetes, impaired glucose tolerance, or prediabetes.

Additional embodiments of the disclosure provide a composition comprising of any one of the conjugates disclosed herein and a pharmaceutically acceptable carrier.

Additional embodiments of the disclosure provide for use of the composition comprising of any one of the conjugates disclosed herein and a pharmaceutically acceptable carrier for the treatment of diabetes. In particular aspects, the diabetes is Type I diabetes, Type II diabetes, or gestational diabetes.

The disclosure further provides embodiments of a method for treating a subject who has diabetes, comprising administering to the subject an effective amount of the composition comprising of any one of the conjugates disclosed herein and a pharmaceutically acceptable carrier for treating the diabetes, wherein said administering treats the diabetes. In particular aspects, the diabetes is Type I diabetes, Type II diabetes, or gestational diabetes.

The disclosure further provides embodiments of a composition comprising any one of the conjugates disclosed herein, wherein the conjugate is characterized as having a ratio of EC50 or IP as determined by a functional insulin receptor phosphorylation assay to the IC50 or IP as determined by a competition binding assay at the macrophage mannose receptor that is about 0.5:1 to about 1:100; about 1:1 to about 1:50; about 1:1 to about 1:20; or about 1:1 to about 1:10; and a pharmaceutically acceptable carrier.

The disclosure still further provides embodiments of a method for treating a subject who has diabetes, comprising administering to the subject a composition comprising any one of the conjugates disclosed herein, wherein the conjugate is characterized as having a ratio of EC50 or IP as determined by a functional insulin receptor phosphorylation assay to the IC50 or IP as determined by a competition binding assay at the macrophage mannose receptor that is about 0.5:1 to about 1:100; about 1:1 to about 1:50; about 1:1 to about 1:20; or about 1:1 to about 1:10; and a pharmaceutically acceptable carrier, wherein the administering treats the diabetes. In particular aspects, the diabetes is Type I diabetes, Type II diabetes, or gestational diabetes.

Sustained Release Formulations

In particular embodiments, it may be advantageous to administer an insulin conjugate in a sustained fashion (i.e., in a form that exhibits an absorption profile that is more sustained than soluble recombinant human insulin). This will provide a sustained level of conjugate that can respond to fluctuations in glucose on a timescale that is more closely related to the typical glucose fluctuation timescale (i.e., hours rather than minutes). In particular embodiments, the sustained release formulation may exhibit a zero-order release of the conjugate when administered to a mammal under non-hyperglycemic conditions (i.e., fasted conditions). It will be appreciated that any formulation that provides a sustained absorption profile may be used. In particular embodiments this may be achieved by combining the conjugate with other ingredients that slow its release properties into systemic circulation.

For example, PZI (protamine zinc insulin) formulations may be used for this purpose. The present disclosure encompasses amorphous and crystalline forms of these PZI formulations.

Thus, in particular embodiments, a formulation of the present disclosure includes from about 0.05 to about 10 mg protamine/mg conjugate. For example, from about 0.2 to about 10 mg protamine/mg conjugate, e.g., about 1 to about 5 mg protamine/mg conjugate.

In particular embodiments, a formulation of the present disclosure includes from about 0.006 to about 0.5 mg zinc/mg conjugate. For example, from about 0.05 to about 0.5 mg zinc/mg conjugate, e.g., about 0.1 to about 0.25 mg zinc/mg conjugate.

In particular embodiments, a formulation of the present disclosure includes protamine and zinc in a ratio (w/w) in the range of about 100:1 to about 5:1, for example, from about 50:1 to about 5:1, e.g., about 40:1 to about 10:1. In particular embodiments, a PZI formulation of the present disclosure includes protamine and zinc in a ratio (w/w) in the range of about 20:1 to about 5:1, for example, about 20:1 to about 10:1, about 20:1 to about 15:1, about 15:1 to about 5:1, about 10:1 to about 5:1, about 10:1 to about 15:1.

One or more of the following components may be included in the PZI formulation: an antimicrobial preservative, an isotonic agent, and/or an unconjugated insulin molecule.

In particular embodiments, a formulation of the present disclosure includes an antimicrobial preservative (e.g., m-cresol, phenol, methylparaben, or propylparaben). In particular embodiments, the antimicrobial preservative is m-cresol. For example, in particular embodiments, a formulation may include from about 0.1 to about 1.0% v/v m-cresol. For example, from about 0.1 to about 0.5% v/v m-cresol, e.g., about 0.15 to about 0.35% v/v m-cresol.

In particular embodiments, a formulation of the present disclosure includes a polyol as isotonic agent (e.g., mannitol, propylene glycol or glycerol). In particular embodiments the isotonic agent is glycerol. In particular embodiments, the isotonic agent is a salt, e.g., NaCl. For example, a formulation may comprise from about 0.05 to about 0.5M NaCl, e.g., from about 0.05 to about 0.25M NaCl or from about 0.1 to about 0.2M NaCl.

In particular embodiments, a formulation of the present disclosure includes an amount of unconjugated insulin molecule. In particular embodiments, a formulation includes a molar ratio of conjugated insulin molecule to unconjugated insulin molecule in the range of about 100:1 to 1:1, e.g., about 50:1 to 2:1 or about 25:1 to 2:1.

The present disclosure also encompasses the use of standard sustained (also called extended) release formulations that are well known in the art of small molecule formulation (e.g., see Remington's Pharmaceutical Sciences, 19th ed., Mack Publishing Co., Easton, Pa., 1995). The present disclosure also encompasses the use of devices that rely on pumps or hindered diffusion to deliver a conjugate on a gradual basis. In particular embodiments, a long acting formulation may (additionally or alternatively) be provided by using a modified insulin molecule. For example, one could use insulin glargine (LANTUS®) or insulin detemir (LEVEMIR®) instead of wild-type human insulin in preparing the conjugate. Insulin glargine is an exemplary long acting insulin analog in which Asn at position A21 of the A-chain has been replaced by glycine and two arginine residues are at the C-terminus of the B-chain. The effect of these changes is to shift the isoelectric point, producing an insulin that is insoluble at physiological pH but is soluble at pH 4. Insulin detemir is another long acting insulin analog in which Thr at position B30 of the B-chain has been deleted and a C14 fatty acid chain has been attached to the Lys at position B29.

Uses of Conjugates

In another aspect, the present disclosure provides methods of using the insulin conjugates. In general, the insulin conjugates can be used to controllably provide insulin to an individual in need in response to a saccharide (e.g., glucose or an exogenous saccharide such as mannose, alpha-methyl mannose, L-fucose, etc.). The disclosure encompasses treating diabetes by administering an insulin conjugate of the present disclosure. Although the insulin conjugates can be used to treat any patient (e.g., dogs, cats, cows, horses, sheep, pigs, mice, etc.), they are most preferably used in the treatment of humans. An insulin conjugate may be administered to a patient by any route. In general, the present disclosure encompasses administration by oral, intravenous, intramuscular, intra-arterial, subcutaneous, intraventricular, transdermal, rectal, intravaginal, intraperitoneal, topical (as by powders, ointments, or drops), buccal, or as an oral or nasal spray or aerosol. General considerations in the formulation and manufacture of pharmaceutical compositions for these different routes may be found, for example, in Remington's Pharmaceutical Sciences, 19th ed., Mack Publishing Co., Easton, Pa., 1995. In various embodiments, the conjugate may be administered subcutaneously, e.g., by injection. The insulin conjugate may be dissolved in a carrier for ease of delivery. For example, the carrier can be an aqueous solution including, but not limited to, sterile water, saline or buffered saline.

In general, a therapeutically effective amount of the insulin conjugate will be administered. The term "therapeutically effective amount" means a sufficient amount of the insulin conjugate to treat diabetes at a reasonable benefit/risk ratio, which involves a balancing of the efficacy and toxicity of the insulin conjugate. In various embodiments, the average daily dose of insulin is in the range of 10 to 200 U, e.g., 25 to 100 U (where 1 Unit of insulin is 0.04 mg). In particular embodiments, an amount of conjugate with these insulin doses is administered on a daily basis. In particular embodiments, an amount of conjugate with 5 to 10 times these insulin doses is administered on a weekly basis. In particular embodiments, an amount of conjugate with 10 to 20 times these insulin doses is administered on a bi-weekly basis. In particular embodiments, an amount of conjugate with 20 to 40 times these insulin doses is administered on a monthly basis.

In particular embodiments, a conjugate of the present disclosure may be used to treat hyperglycemia in a patient (e.g., a mammalian or human patient). In particular embodiments, the patient is diabetic. However, the present methods are not limited to treating diabetic patients. For example, in particular embodiments, a conjugate may be used to treat hyperglycemia in a patient with an infection associated with impaired glycemic control. In particular embodiments, a conjugate may be used to treat diabetes.

In particular embodiments, when an insulin conjugate or formulation of the present disclosure is administered to a patient (e.g., a mammalian patient) it induces less hypoglycemia than an unconjugated version of the insulin molecule. In particular embodiments, a formulation of the present disclosure induces a lower HbA1c value in a patient (e.g., a mammalian or human patient) than a formulation comprising an unconjugated version of the insulin molecule. In particular embodiments, the formulation leads to an HbA1c value that is at least 10% lower (e.g., at least 20% lower, at least 30% lower, at least 40% lower, at least 50% lower) than a formulation comprising an unconjugated version of the insulin molecule. In particular embodiments, the formulation leads to an HbA1c value of less than 7%, e.g., in the range of about 4 to about 6%. In particular embodiments, a formulation comprising an unconjugated version of the insulin molecule leads to an HbA1c value in excess of 7%, e.g., about 8 to about 12%.

Exogenous Trigger

As mentioned previously, the methods, conjugates and compositions that are described herein are not limited to glucose responsive-conjugates. As demonstrated in the Examples, several exemplary insulin conjugates were also responsive to exogenous saccharides such as alpha-methyl mannose. It will therefore be appreciated that, in particular embodiments, an insulin conjugate may be triggered by exogenous administration of a saccharide other than glucose such as alpha-methyl mannose or any other saccharide that can alter the PK or PD properties of the conjugate.

Once a conjugate has been administered as described above (e.g., as a sustained release formulation), it can be triggered by administration of a suitable exogenous saccharide. In a particular embodiment, a triggering amount of the exogenous saccharide is administered. As used herein, a "triggering amount" of exogenous saccharide is an amount sufficient to cause a change in at least one PK and/or PD property of the conjugate (e.g., $C_{max}$, AUC, half-life, etc. as discussed previously). It is to be understood that any of the aforementioned methods of administration for the conjugate apply equally to the exogenous saccharide. It is also to be understood that the methods of administration for the conjugate and exogenous saccharide may be the same or different. In various embodiments, the methods of administration are different (e.g., for purposes of illustration the conjugate may be administered by subcutaneous injection on a weekly basis while the exogenous saccharide is administered orally on a daily basis). The oral administration of an exogenous saccharide is of particular value because it facilitates patient compliance. In general, it will be appreciated that the PK and PD properties of the conjugate will be related to the PK profile of the exogenous saccharide. Thus, the conjugate PK and PD properties can be tailored by controlling the PK profile of the exogenous saccharide. As is well known in the art, the PK profile of the exogenous saccharide can be tailored based on the dose, route, frequency and formulation used. For example, if a short and intense activation of the conjugate is desired then an oral immediate release formulation might be used. In contrast, if a longer less intense activation of conjugate is desired then an oral extended release formulation might be used instead. General considerations in the formulation and manufacture of immediate and extended release formulation may be found, for example, in Remington's Pharmaceutical Sciences, 19th ed., Mack Publishing Co., Easton, Pa., 1995.

It will also be appreciated that the relative frequency of administration of a conjugate of the present disclosure and an exogenous saccharide may be the same or different. In particular embodiments, the exogenous saccharide is administered more frequently than the conjugate. For example, in particular embodiment, the conjugate may be administered daily while the exogenous saccharide is administered more than once a day. In particular embodiment, the conjugate may be administered twice weekly, weekly, biweekly or monthly while the exogenous saccharide is administered daily. In particular embodiments, the conjugate is administered monthly and the exogenous saccharide is administered twice weekly, weekly, or biweekly. Other variations on these schemes will be recognized by those skilled in the art and will vary depending on the nature of the conjugate and formulation used.

The following examples are intended to promote a further understanding of the present invention.

EXAMPLES

General Procedures

All chemicals were purchased from commercial sources, unless otherwise noted. Reactions sensitive to moisture or air were performed under nitrogen or argon using anhydrous solvents and reagents. The progress of reactions was monitored by analytical thin layer chromatography (TLC), high performance liquid chromatography-mass spectrometry (HPLC-MS), or ultra performance liquid chromatography-mass spectrometry (UPLC-MS). TLC was performed on E. Merck TLC plates precoated with silica gel 60F-254, layer thickness 0.25 mm. The plates were visualized using 254 nm UV and/or by exposure to cerium ammonium molybdate (CAM) or p-anisaldehyde staining solutions followed by charring. High performance liquid chromatography (HPLC) was conducted on a Waters Acquity™ UPLC® using BEH C18, 1.7 µm, 1.0×50 mm column with gradient 10:90-99:1 v/v $CH_3CN/H_2O$+v 0.05% TFA over 2.0 min; flow rate 0.3 mL/min, UV range 215 nm (LC-MS Method A). Mass analysis was performed on a Waters Micromass® ZQ™ with electrospray ionization in positive ion detection mode and the scan range of the mass-to-charge ratio was either 170-900 or 500-1500. Ultra performance liquid chromatography (UPLC) was performed on a Waters Acquity™ UPLC® system using the following methods:

UPLC-MS Method A: Waters Acquity™ UPLC® BEH C18 1.7 m 2.1×100 mm column with gradient 10:90-70:30 v/v $CH_3CN/H_2O$+v 0.1% TFA over 4.0 min and 70:30-95:5 v/v $CH_3CN/H_2O$+v 0.1% TFA over 0.4 min; flow rate 0.3 mL/min, UV wavelength 200-300 nm.

UPLC-MS Method B: Waters Acquity™ UPLC® BEH C18 1.7 m 2.1×100 mm column with gradient 60:40-100:0 v/v $CH_3CN/H_2O$+v 0.1% TFA over 4.0 min and 100:0-95:5 v/v $CH_3CN/H_2O$+v 0.1% TFA over 0.4 min; flow rate 0.3 mL/min, UV wavelength 200-300 nm.

UPLC-MS Method C: Waters Acquity™ UPLC® HSS T3 1.7 µm 2.1×100 mm column with gradient 0:100-40:60 v/v $CH_3CN/H_2O$+v 0.05% TFA over 8.0 min and 40:60-10:90 v/v $CH_3CN/H_2O$+v 0.05% TFA over 2.0 min; flow rate 0.3 mL/min, UV wavelength 200-300 nm.

UPLC-MS Method D: Waters Acquity™ UPLC® BEH C18 1.7 m 2.1×100 mm column with gradient 0:100-60:40 v/v $CH_3CN/H_2O$+v 0.1% TFA over 8.0 min and 60:40-90:10 v/v $CH_3CN/H_2O$+v 0.1% TFA over 3.0 min and hold at 100:0 v/v $CH_3CN/H_2O$+v 0.1% TFA for 2 min; flow rate 0.3 mL/min, UV wavelength 200-300 nm.

UPLC-MS Method E: Waters Acquity™ UPLC® BEH C8 1.7 m 2.1×100 mm column with gradient 10:90-55:45 v/v $CH_3CN/H_2O$+v 0.1% TFA over 4.2 min and 100:0-95:5 v/v $CH_3CN/H_2O$+v 0.1% TFA over 0.4 min; flow rate 0.3 mL/min, UV wavelength 200-300 nm.

UPLC-MS Method F: Waters Acquity™ UPLC® BEH C8 1.7 m 2.1×100 mm column with gradient 10:90-90:10 v/v $CH_3CN/H_2O$+v 0.1% TFA over 4.2 min and 90:10-95:5 v/v $CH_3CN/H_2O$+v 0.1% TFA over 0.4 min; flow rate 0.3 mL/min, UV wavelength 200-300 nm.

UPLC-MS Method G: Waters Acquity™ UPLC® BEH300 C4 1.7 m 2.1×100 mm column with gradient 10:90-90:10 v/v $CH_3CN/H_2O$+v 0.1% TFA over 4.0 min and 90:10-95:5 v/v $CH_3CN/H_2O$+v 0.1% TFA over 0.4 min; flow rate 0.3 mL/min, UV wavelength 200-300 nm.

Mass analysis was performed on a Waters Micromass® LCT Premier™ XE with electrospray ionization in positive ion detection mode and the scan range of the mass-to-charge ratio was 300-2000. The identification of the produced insulin conjugates was confirmed by comparing the theoretical molecular weight to the experimental value that was measured using UPLC-MS. For the determination of the position of sugar modification(s), specifically, insulin conjugates were subjected to DTT treatment (for a/b chain) or Glu-C digestion (with reduction and alkylation), and then the resulting peptides were analyzed by LC-MS. Based on the measured masses, the sugar positions were deduced.

Flash chromatography was performed using either a Biotage Flash Chromatography apparatus (Dyax Corp.) or a CombiFlash® Rf instrument (Teledyne Isco). Normal-phase chromatography was carried out on silica gel (20-70 µm, 60 Å pore size) in pre-packed cartridges of the size noted. Concentration of organic solutions was carried out on a rotary evaporator under reduced pressure. Reverse-phase chromatography was carried out on C18-bonded silica gel (20-60 µm, 60-100 Å pore size) in pre-packed cartridges of the size noted. Preparative scale HPLC was performed on Gilson GX-281 Liquid Handler powered by Gilson 333-334 binary system using Waters Delta Pak C4 15 µm, 300 Å, 50×250 mm column or Kromasil® C8 10 µm, 100 Å, 50×250 mm column, flow rate 85 mL/min, with gradient noted. Ion exchange chromatography was carried out on Gilson 215 Liquid Handler powered by Gilson 332 binary system using PolyLC PolySULFOEthyl A 9.4×250 mm column, with gradient 5-25% Mobile Phase B in Mobile Phase A (Mobile Phase A: 0.1% (v/v) $H_3PO_4$/25% AcCN in water, mobile phase B: 0.1% (v/v) $H_3PO_4$/25% AcCN/0.5M NaCl in water, over 30 min, flow rate 15 mL/min). Concentration and diafiltration of aqueous solutions or HPLC fractions were carried out using Amicon Ultra-15 Centrifugal Filter Units (Millipore) with 10K MWCO, unless noted otherwise, on a Hettich Rotina 380R Benchtop Centrifuge at 3500 RPM and 4° C., or freeze-dried on a VirTis Freezemobile Freeze Dryer (SP Scientific).

$^1$H-NMR spectra were acquired at 500 MHz (or otherwise specified) spectrometers in deuterated solvents noted. Chemical shifts were reported in parts per million (ppm). Tetramethylsilane (TMS) or residual proton peak of deuterated solvents was used as an internal reference. Coupling constants (J) were reported in hertz (Hz).

Abbreviations: acetic acid (AcOH), acetonitrile (AcCN or MeCN), aqueous (aq), tert-butoxycarbonyl protecting group (Boc), O-(7-azabenzotriazol-1-yl)-N,N,N',N'-tetramethyluronium hexafluorophosphate) (HATU), column volume (CV), N,N'-Dicyclohexylcarbodiimide (DCC), dichloromethane (DCM), diethyl ether (ether or $Et_2O$), N,N-diisopropylethylamine or Hünig's base (DIPEA), N,N-dimethylacetamide (DMA), (4-dimethylamino)pyridine (DMAP), N,N-dimethylformamide (DMF), dimethylsulfoxide (DMSO), ethyl acetate (EtOAc), N-(3-dimethylaminopropyl)-N'-ethylcarbodiimide hydrochloride (EDC), gram(s) (g), 1-hydroxy-benzotriazole hydrate (HOBt), hour(s) (h or hr), isopropyl alcohol (IPA), liquid chromatography-mass spectrometry (LC-MS), mass spectrum (ms or MS), N-methylmorpholine (NMM), microliter(s) (µL), milligram(s) (mg), milliliter(s) (mL), millimole (mmol), minute(s) (min), tert-butyl ester (OtBu), pentafluorphenoltetramethyluronium hexafluorophosphate (PFTU), petroleum ether (PE), silicon dioxide ($SiO_2$), retention time ($t_R$), room temperature (rt), saturated (sat.), saturated aq sodium chloride solution (brine), triethylamine (TEA), trifluoroacetic acid (TFA), trifluoroacetic anhydride (TFAA), tetrahydrofuran (THF), N,N,N',N'-tetramethyl-O—(N-succinimidyl)uronium tetrafluoroborate (TSTU), and weight (wt).

Example 1: 2,5-dioxopyrrolidin-1-yl 6-{[(S)-5-{[(S)-1,5-dioxo-1,5-bis({2-[(α-D-mannopyranosyl)oxy]ethyl}amino)pentan-2-yl]amino}-1,5-dioxo-1-({2-[(α-D-mannopyranosyl)oxy]ethyl}amino)pentan-2-yl]amino}-6-oxohexanoate (ML-1)

ML-1

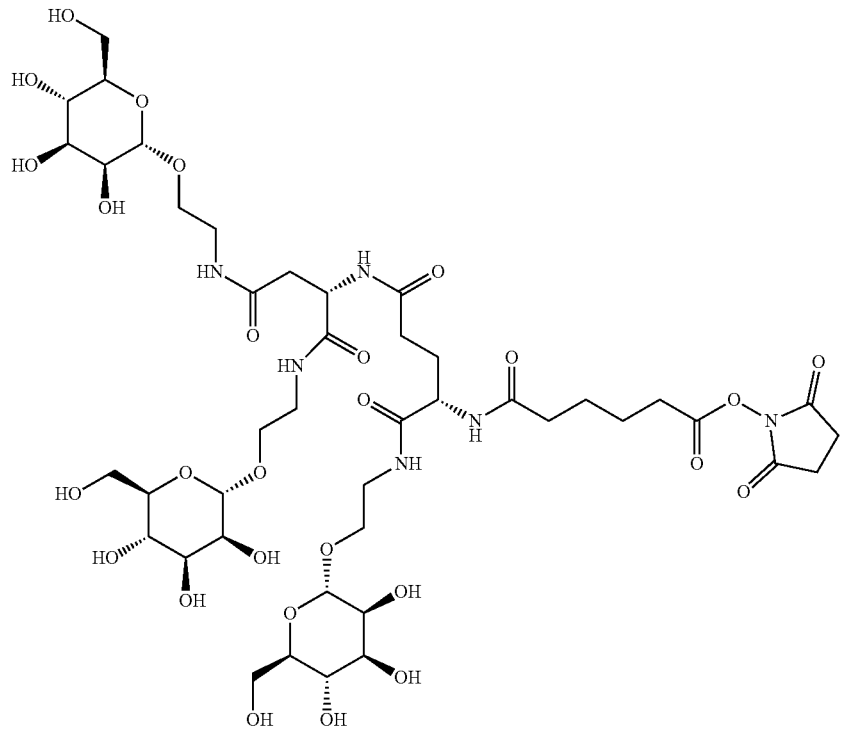

Step 1. {(S)-4-[6-(benzyloxy)-6-oxohexanamido]-4-carboxybutanoyl}-L-glutamic Acid To a solution of H-Glu-Asp-OH (1.0 g, 3.81 mmol) in DMF (26 mL) at 0° C. was added benzyl (2,5-dioxopyrrolidin-1-yl) adipate (1.34 g, 4.00 mmol) in DMF (3 mL) portionwise over 15 min and then TEA (585 µL, 4.20 mmol) dropwise over a period of 10 min. After stirring at rt overnight, to the resulting suspension was added more benzyl (2,5-dioxopyrrolidin-1-yl) adipate (70 mg) in DMF (18 mL). After overnight, insoluble material was removed by filtration, and the filtrate was concentrated. The residue was purified by reverse phase prep HPLC (C-4 column, 50×250 cm, 85 mL/min, gradient from 11% to 19% in 20 min) (Water with 0.1% TFA and MeCN with 0.1% TFA) to give the title compound. $^1$H-NMR (CD$_3$OD) δ: 7.28-7.36 (m, 5H), 5.12 (s, 2H), 4.74 (t, J=5.7, 1H), 4.43 (t, J=5.7, 1H), 2.84 (d, J=5.7, 2H), 2.38-2.45 (m, 4H), 2.26 (t, J=7.0, 2H), 2.12 (m, 1H), 1.91 (m, 1H), 1.60-1.70 (m, 2H).

Step 2. Benzyl 6-{[(S)-5-{[(S)-1,5-dioxo-1,5-bis({2-[(α-D-mannopyranosyl)oxy]ethyl}amino)pentan-2-yl]amino}-1,5-dioxo-]-({2-[(α-D-mannopyranosyl)oxy]ethyl}amino)pentan-2-yl]amino}-6-oxohexanoate To a solution of {(S)-4-[6-(benzyloxy)-6-oxohexanamido]-4-carboxybutanoyl}-L-glutamic acid (1.114 g, 2.319 mmol) in DMF (40 mL) at 0° C. was added EDC (2.22 g, 11.59 mmol) and HOBt (1.78 g, 11.59 mmol). After stirring at 0° C. for 30 min to the resulting suspension was added 2-aminoethyl α-D-mannopyranoside (2.588 g, 11.59 mmol) in DMF (15 mL). The mixture was allowed to gradually warm to rt and stirred at rt. After overnight, the reaction mixture was concentrated. The residue was purified by column chromatography on silica gel (120 g), eluting with EtOAC/MeOH/MeCN/H$_2$O (60:15:15:15), to give the title compound. UPLC-MS Method A: m/z=1096.4 (z=1); t$_R$=2.32 min.

Step 3. 6-{[(S)-5-{[(S)-1,5-dioxo-1,5-bis({2-[(α-D-mannopyranosyl)oxy]ethyl}amino)pentan-2-yl]amino}-1,5-dioxo-]-({2-[(α-D-mannopyranosyl)oxy]ethyl}amino)pentan-2-yl]amino}-6-oxohexanoic Acid To a solution of benzyl 6-{[(S)-5-{[(S)-1,5-dioxo-1,5-bis({2-[(α-D-mannopyranosyl)oxy]ethyl}amino)pentan-2-yl]amino}-1,5-dioxo-1-({2-[(α-D-mannopyranosyl)oxy]ethyl}amino) pentan-2-yl]amino}-6-oxohexanoate (1.84 g, 1.679 mmol) in H$_2$O (30 mL) was added Pd/C (268 mg, 0.252 mmol). The resulting mixture was stirred under H$_2$ at rt overnight. The catalyst was filtered off through a cake of diatomaceous earth (e.g. CELITE®) and washed with MeOH. The filtrate was concentrated, redissolved in water and freeze-dried to give the title compound. UPLC-MS Method A: m/z=1006.4 (z=1); t$_R$=1.20 min.

Step 4. 2,5-dioxopyrrolidin-1-yl 6-{[(S)-5-{[(S)-1,5-dioxo-1,5-bis({2-[(α-D-mannopyranosyl)oxy]ethyl}amino)pentan-2-yl]amino}-1,5-dioxo-]-({2-[(α-D-mannopyranosyl)oxy]ethyl}amino) pentan-2-yl]amino}-6-oxohexanoate To a solution of 6-{[(S)-5-{[(S)-1,5-dioxo-1,5-bis({2-[(α-D-mannopyranosyl)oxy]ethyl}amino)pentan-2-yl]amino}-1,5-dioxo-1-({2-[(α-D-mannopyranosyl)oxy]ethyl}amino) pentan-2-yl]amino}-6-oxohexanoic acid (1.735 g, 1.725 mmol) in DMF (62 mL) at 0° C. was added TSTU (701 mg, 2.328 mmol) and DIPEA (467 µL, 2.67 mmol). After stirring at 0° C. for 1 hr and then at rt for 1 hr, UPLC-MS analysis showed that still some starting material left. To the reaction mixture was added TSTU (70 mg) and DIPEA (45 µL). After stirring at rt for 1 hr, the reaction mixture was concentrated, and the residue was added dropwise to AcCN (100 mL). The resulting precipitate was collected through centrifugation to give the title compound. UPLC-MS Method A: m/z=1103.4 (z=1); $t_R$=1.32 min.

Example 2: 2,5-dioxopyrrolidin-1-yl 6{[(S)-5-{[(S)-1,5-dioxo-1,5-bis({2-[(α-L-fucopyranosyl)oxy]ethyl}amino)pentan-2-yl]amino}-1,5-dioxo-1-({2-[(α-L-fucopyranosyl)oxy]ethyl}amino)pentan-2-yl]amino}-6-oxohexanoate (ML-2)

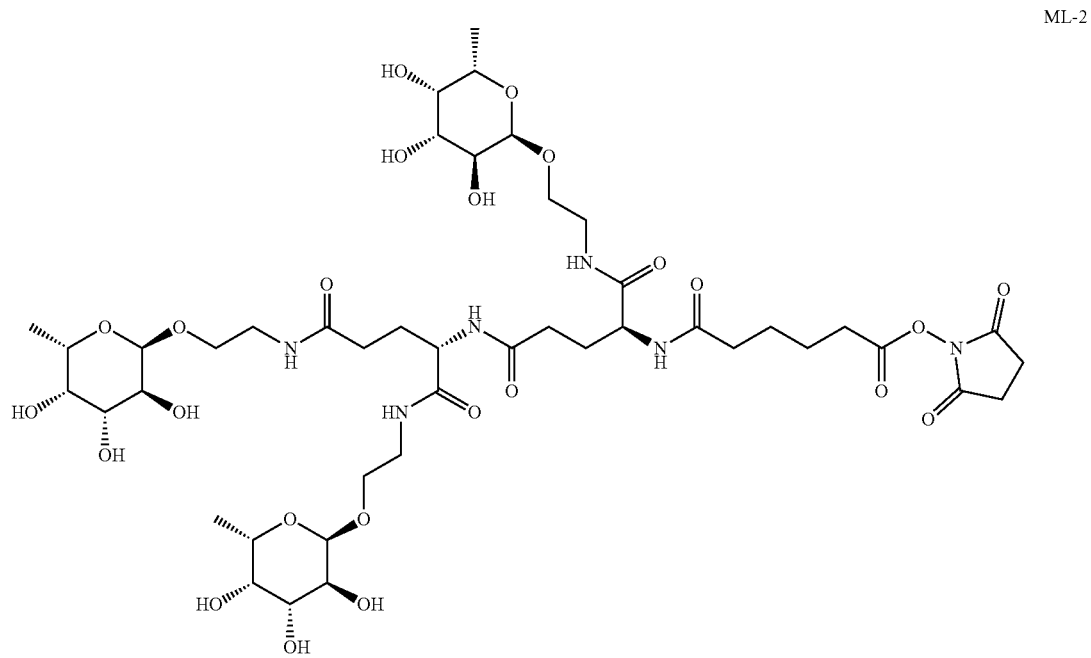 [SMILES: C[C@@H]1O[C@@H](OCCNC(=O)CC[C@H](NC(=O)CC[C@H](NC(=O)CCCCC(=O)ON2C(=O)CCC2=O)C(=O)NCCO[C@@H]2O[C@@H](C)[C@@H](O)[C@@H](O)[C@@H]2O)C(=O)NCCO[C@@H]2O[C@@H](C)[C@@H](O)[C@@H](O)[C@@H]2O)[C@@H](O)[C@H](O)[C@@H]1O]

ML-2

The title compound was prepared using procedures analogous to those described for ML-1 substituting H-g-Glu-Glu-OH for H-Glu-Asp-OH in Step 1 and 2-aminoethyl α-L-fucopyranoside for 2-aminoethyl α-D-mannopyranoside in Step 2, respectively. UPLC-MS Method A: m/z=1069.526 (z=1); $t_R$=2.03 min.

Example 3: 2,5-dioxopyrrolidin-1-yl 6-{[(S)-5-{[(S)-1,5-dioxo-1,5-bis({2-[(α-L-fucopyranosyl)oxy]ethyl}amino)pentan-2-yl]amino}-1,5-dioxo-1-{[2-({α-D-mannopyranosyl-(1→3)-[α-D-mannopyranosyl-(1→6)]-α-D-mannopyranosyl}oxy) ethyl]amino}pentan-2-yl]amino}6-oxohexanoate (ML-3)
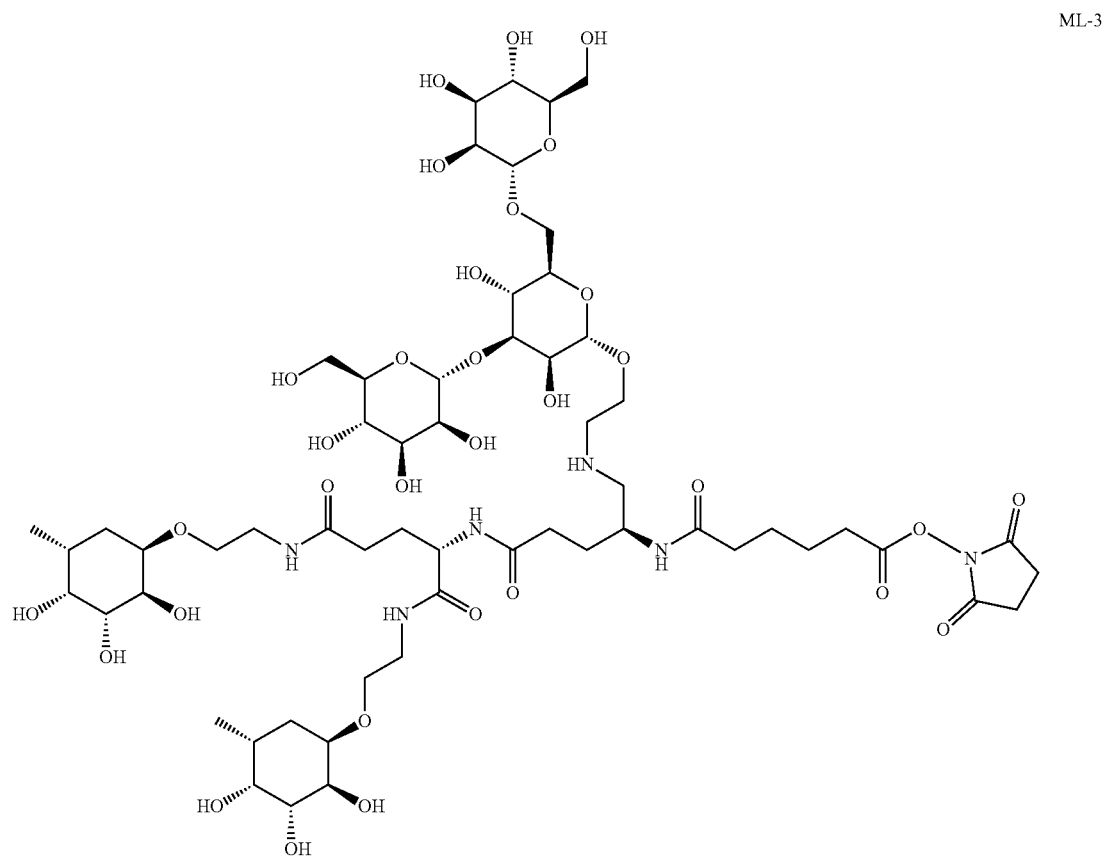 [SMILES: C[C@@H]1C[C@@H](OCCNC(=O)CC[C@H](NC(=O)CC[C@@H](CNCCO[C@H]2O[C@H](CO[C@H]3O[C@H](CO)[C@@H](O)[C@H](O)[C@@H]3O)[C@@H](O)[C@H](O[C@H]3O[C@H](CO)[C@@H](O)[C@H](O)[C@@H]3O)[C@@H]2O)NC(=O)CCCCC(=O)ON2C(=O)CCC2=O)C(=O)NCCO[C@@H]2C[C@@H](C)[C@@H](O)[C@@H](O)[C@@H]2O)[C@@H](O)[C@H](O)[C@@H]1O]
ML-3

Step 1. Benzyl (S)-4-{[(benzyloxy)carbonyl]amino}-5-oxo-5-{[2-({α-D-mannopyranosyl-(1→3)-[α-D-mannopyranosyl-(1→6)]-α-D-mannopyranosyl}oxy)ethyl]amino}pentanoate To a solution of Z-Glu-α-Bn (1.0 g, 2.69 mmol) and 2-({α-D-mannopyranosyl-(1→3)-[α-D-mannopyranosyl-(1-6)]-α-D-mannopyranosyl}oxy)ethan-1-amine (2.21 g, 4.04 mmol) in DMF (10 mL) was added HOBt (41 mg, 0.269 mmol), EDC (1.29 g, 6.73 mmol) and TEA (38 μL, 0.269 mmol). The mixture was stirred at rt. After overnight, the mixture was diluted with H$_2$O (20 mL), and the resulting mixture was purified on HPLC (50×250 mm, C4, flow rate 85 mL/min, gradient 25-35% AcCN in H$_2$O with 0.1% TFA over 30 min). The desired fractions were combined and freeze-dried to give the title compound. UPLC-MS Method A: m/z=901.315 (z=1); t$_R$=3.49 min.

Step 2. (S)-4-amino-5-oxo-5-{[2-({α-D-mannopyranosyl-(1→3)-[α-D-mannopyranosyl-(1→6)]-α-D-mannopyranosyl}oxy)ethyl]amino}pentanoic Acid A mixture of benzyl (S)-4-{[(benzyloxy)carbonyl]amino}-5-oxo-5-{[2-({α-D-mannopyranosyl-(1→3)-[α-D-mannopyranosyl-(1→6)]-α-D-mannopyranosyl}oxy)ethyl]amino}pentanoate (1.41 g, 1.565 mmol) and Pd(OH)$_2$ (110 mg, 0.157 mmol) in H$_2$O (30 mL) was shaken under 344.74 kPa of H$_2$ on a Parr shaker overnight at rt. The mixture was diluted with 20 mL of CH$_3$OH, and the catalyst was filtered off through a fiberglass filter and washed with H$_2$O. The filtrate was concentrated to give the title compound. UPLC-MS Method A: m/z=677.25 (z=1); t$_R$=1.11 min.

Step 3. (S)-4-[6-(benzyloxy)-6-oxohexanamido]-5-oxo-5-{[2-({α-D-mannopyranosyl-(1→3)-[α-D-mannopyranosyl-(1→6)]-α-D-mannopyranosyl}oxy)ethyl]amino}pentanoic Acid To a suspension containing (S)-4-amino-5-oxo-5-{[2-({α-D-mannopyranosyl-(1→3)-[α-D-mannopyranosyl-(1-6)]-α-D-mannopyranosyl}oxy)ethyl]amino}pentanoic acid (1.06 g, 1.565 mmol) and TEA (436 μL, 3.13 mmol) in DMF (10 mL) at rt was added benzyl (2,5-dioxopyrrolidin-1-yl) adipate (574 mg, 1.72 mmol). The mixture was stirred at rt overnight. The mixture was diluted with H$_2$O (10 mL) and purified using HPLC (C4, 50×250 mm, 10-30% AcCN in H$_2$O with 0.1% TFA over 25 min, flow rate 85 mL/min). The desired fractions were combined and freeze-dried to give the title compound.

Step 4. Benzyl (S)-[1,5-dioxo-1,5-bis({2-[(α-L-fucopyranosyl)oxy]ethyl}amino)pentan-2-yl]carbamate To a solution of Z-Glu-OH (1.1 g, 3.91 mmol) and 2-aminoethyl α-L-fucopyranoside (2.03 g, 9.78 mmol) in DMF (20 mL) was added EDC (3.00 g, 15.64 mmol) and HOBt (60 mg, 0.391 mmol). The mixture was stirred at rt. After overnight, the reaction mixture was diluted with H$_2$O (20 mL) and purified using HPLC (C4, 50×250 mm, gradient 5-30% AcCN with 0.1% TFA in H$_2$O with 0.1% TFA over 20 min, flow rate 85 mL/min). The desired fractions were combined and freeze-dried to give the title compound. UPLC-MS Method A: m/z=660.29 (z=1); t$_R$=2.78 min.

Step 5. (S)-2-amino-N1,N5-bis{2-[(α-L-fucopyranosyl)oxy]ethyl}pentanediamide A suspension of benzyl (S)-[1,5-dioxo-1,5-bis({2-[(α-L-fucopyranosyl)oxy]ethyl}amino) pentan-2-yl]carbamate (660 mg, 1.000 mmol) and Pd(OH)$_2$ (70 mg, 0.100 mmol) in H$_2$O (20 mL) was stirred under H$_2$ at rt. After stirring overnight, the reaction mixture was diluted with H$_2$O (20 mL), and the catalyst was filtered off through a pad of CELITE®. The filtrate was freeze-dried to give the title compound. UPLC-MS Method A: m/z=526.25 (z=1); t$_R$=1.09 min.

Step 6. Benzyl 6-{[(S)-5-{[(S)-1,5-dioxo-1,5-bis({2-[(α-L-fucopyranosyl)oxy]ethyl}amino)pentan-2-yl]amino}-1,5-dioxo-]-{[2-({α-D-mannopyranosyl-(1→3)-[α-D-mannopyranosyl-(1→6)]-α-D-mannopyranosyl}oxy)ethyl]amino}pentan-2-yl]amino}6-oxohexanoate To a solution of (S)-4-[6-(benzyloxy)-6-oxohexanamido]-5-oxo-5-{[2-({α-D-mannopyranosyl-(1→3)-[α-D-mannopyranosyl-(1→6)]-α-D-mannopyranosyl}oxy)ethyl]amino}pentanoic acid (158.4 mg, 0.177 mmol) and (S)-2-amino-N1,N5-bis{2-[(α-L-fucopyranosyl)oxy]ethyl}pentanediamide (93 mg, 0.177 mmol) in DMF (10 mL) at rt was added EDC (51 mg, 0.266 mmol). The mixture was stirred at rt overnight. The mixture was diluted with H$_2$O (10 mL) and purified using HPLC (C4, 50×250 mm, 10-30% AcCN in H$_2$O with 0.1% TFA over 25 min, flow rate 85 mL/min). The desired fractions were combined and freeze-dried to give the title compound. UPLC-MS Method A: m/z=1050.373 (z=1); t$_R$=3.01 min.

Step 7. 2,5-dioxopyrrolidin-1-yl 6-{[(S)-5-{[(S)-1,5-dioxo-1,5-bis({2-[(α-L-fucopyranosyl)oxy]ethyl}amino)pentan-2-yl]amino}-1,5-dioxo-1-{[2-({α-D-mannopyranosyl-(1→3)-[α-D-mannopyranosyl-(1→6)]-α-D-mannopyranosyl}oxy)ethyl]amino}pentan-2-yl]amino}6-oxohexanoate The title compound was prepared using procedures analogous to those described for ML-1 substituting benzyl 6-{[(S)-5-{[(S)-1,5-dioxo-1,5-bis({2-[(α-L-fucopyranosyl)oxy]ethyl}amino)pentan-2-yl]amino}-1,5-dioxo-1-{[2-({α-D-mannopyranosyl-(1→3)-[α-D-mannopyranosyl-(1→6)]-α-D-mannopyranosyl}oxy)ethyl]amino}pentan-2-yl]amino}6-oxohexanoate for benzyl 6-{[(S)-5-{[(S)-1,5-dioxo-1,5-bis({2-[(α-D-mannopyranosyl)oxy]ethyl}amino)pentan-2-yl]amino}-1,5-dioxo-1-({2-[(α-D-mannopyranosyl)oxy]ethyl}amino) pentan-2-yl]amino}-6-oxohexanoate in Step 3. UPLC-MS Method A: m/z=1409.56 (z=1); t$_R$=1.96 min.

Example 4: 2,5-dioxopyrrolidin-1-yl (5S,8S,11S)-5-isobutyl-4,7,10,13-tetraoxo-8,11-bis(3-oxo-3-{[2-({α-D-mannopyranosyl-(1→3)-[α-D-mannopyranosyl-(1→6)]-α-D-mannopyranosyl}oxy)ethyl]amino}propyl)-1-({α-D-mannopyranosyl-(1→3)-[α-D-mannopyranosyl-(1→6)]-α-D-mannopyranosyl}oxy)-3,6,9,12-tetraazaoctadecan-18-oate (ML-4)

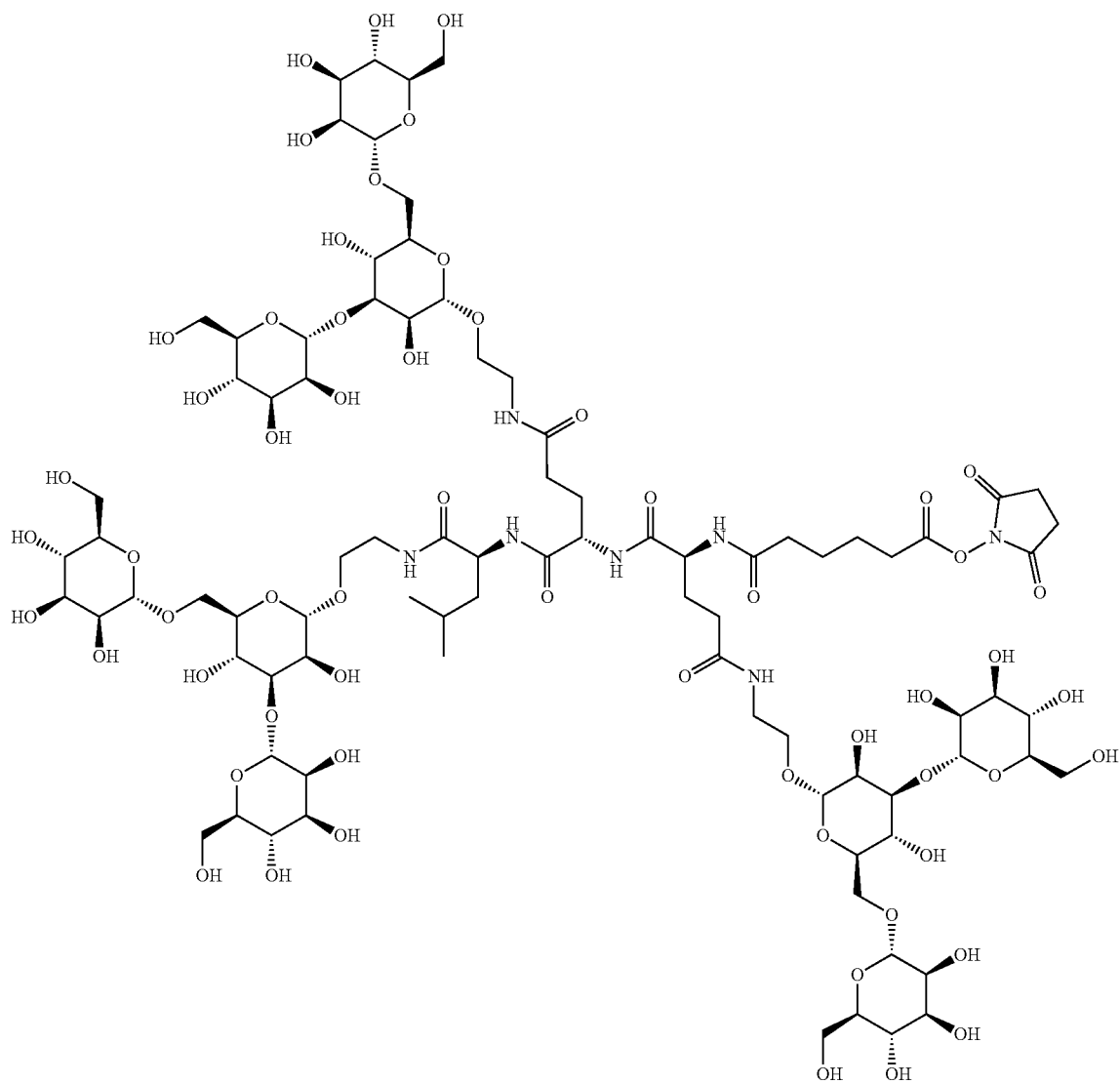

ML-4

Step 1. (10S,13S,16S)-10,13-bis(2-carboxyethyl)-16-isobutyl-3,8,11,14-tetraoxo-1-phenyl-2-oxa-9,12,15-triazaheptadecan-17-oic Acid To a solution of H-Glu-Glu-Leu-OH (1.0 g, 2.57 mmol) in DMF (20 mL) at 0° C. was added 1-benzyl 8-(2,5-dioxopyrrolidin-1-yl) octanedioate (899 mg, 2.70 mmol) in DMF (3 mL) portionwise over 15 min and then TEA (394 µL, 2.82 mmol) over 10 min. The resulting suspension was stirred at rt overnight and then concentrated. The residue was purified by column chromatography on 100 g C18 reverse phase silica gel, eluting with AcCN/H$_2$O (gradient from 5% to 60% in 24 CV), to give the title compound. UPLC-MS Method B: m/z=608.2 (z=1); t$_R$=3.91 min.

Step 2. benzyl (5S,8S,1S)-5-isobutyl-4,7,10,13-tetraoxo-8,11-bis(3-oxo-3-{[2-({α-D-mannopyranosyl-(1→3)-[α-D-mannopyranosyl-(1→6)]-α-D-mannopyranosyl}oxy)ethyl]amino}propyl)-1-({α-D-mannopyranosyl-(1→3)-[α-D-mannopyranosyl-(1→6)]-α-D-mannopyranosyl}oxy)-3,6,9,12-tetraazaoctadecan-18-oate To a solution of (10S,13S,16S)-10,13-bis(2-carboxyethyl)-16-isobutyl-3,8,11,14-tetraoxo-1-phenyl-2-oxa-9,12,15-triazaheptadecan-17-oic acid (220 mg, 0.362 mmol) in DMF (10 mL) at 0° C. were added EDC (312 mg, 1.629 mmol) and HOBt (55.4 mg, 0.362 mmol). After stirring at 0°

C. for 30 min, to the resulting mixture was added 2-({α-D-mannopyranosyl-(1→3)-[α-D-mannopyranosyl-(1→6)]-α-D-mannopyranosyl}oxy)ethan-1-amine (837 mg, 1.267 mmol) in DMF (8 mL). The mixture was gradually warmed up to rt. After stirring at rt overnight, the mixture was concentrated. The residue was purified by column chromatography on 130 g C18 reverse phase silica gel, eluting with AcCN/H$_2$O (gradient from 5% to 40% in 15 CV), to give the title compound. UPLC-MS Method A: m/z=1268.468 (z=2); $t_R$=4.12 min.

Step 3. 2,5-dioxopyrrolidin-1-yl (5S,8S,11S)-5-isobutyl-4,7,10,13-tetraoxo-8,11-bis(3-oxo-3-{[2-({α-D-mannopyranosyl-(1→3)-[α-D-mannopyrano-syl-(1→6)]-α-D-mannopyranosyl}oxy)ethyl]amino}propyl)-1-({α-D-mannopyranosyl-(1→3)-[α-D-mannopyranosyl-(1→6)]-α-D-mannopyranosyl}oxy)-3,6,9,12-tetraazaoctadecan-18-oate The title compound was prepared using procedures analogous to those described for ML-1 substituting benzyl (5S,8S,11S)-5-isobutyl-4,7,10,13-tetraoxo-8,11-bis(3-oxo-3-{[2-({α-D-mannopyranosyl-(1→3)-[α-D-mannopyranosyl-(1→6)]-α-D-mannopyranosyl}oxy)ethyl]amino}propyl)-1-({α-D-mannopyranosyl-(1→3)-[α-D-mannopyranosyl-(1→6)]-α-D-mannopyranosyl}oxy)-3,6,9,12-tetraazaoctadecan-18-oate for benzyl 6-{[(S)-5-{[(S)-1,5-dioxo-1,5-bis({2-[(α-D-mannopyranosyl)oxy]ethyl}amino)pentan-2-yl]amino}-1,5-dioxo-1-({2-[(α-D-mannopyranosyl)oxy]ethyl}amino)pentan-2-yl]amino}-6-oxohexanoate in Step 3. UPLC-MS Method A m/z=1223.472 (z=2); $t_R$=3.72 min.

Example 5: 2,5-dioxopyrrolidin-1-yl (14S,19S)-14-{[6-(bis{2-[(α-D-mannopyranosyl)oxy]ethyl}amino)-6-oxohexyl]carbamoyl}-4,11,16,21,24-pentaoxo-19-[(6-oxo-6-{[2-({α-D-mannopyrano-syl-(1→3)-[α-D-mannopyranosyl-(1→6)]-α-D-mannopyranosyl}oxy)ethyl]amino}hexyl)carbamoyl]-1-[(α-D-mannopyranosyl)oxy]-3-{2-[(α-D-mannopyranosyl)oxy]ethyl}-3,10,15,20,23-pentaazanonacosan-29-oate (ML-5)

ML-5

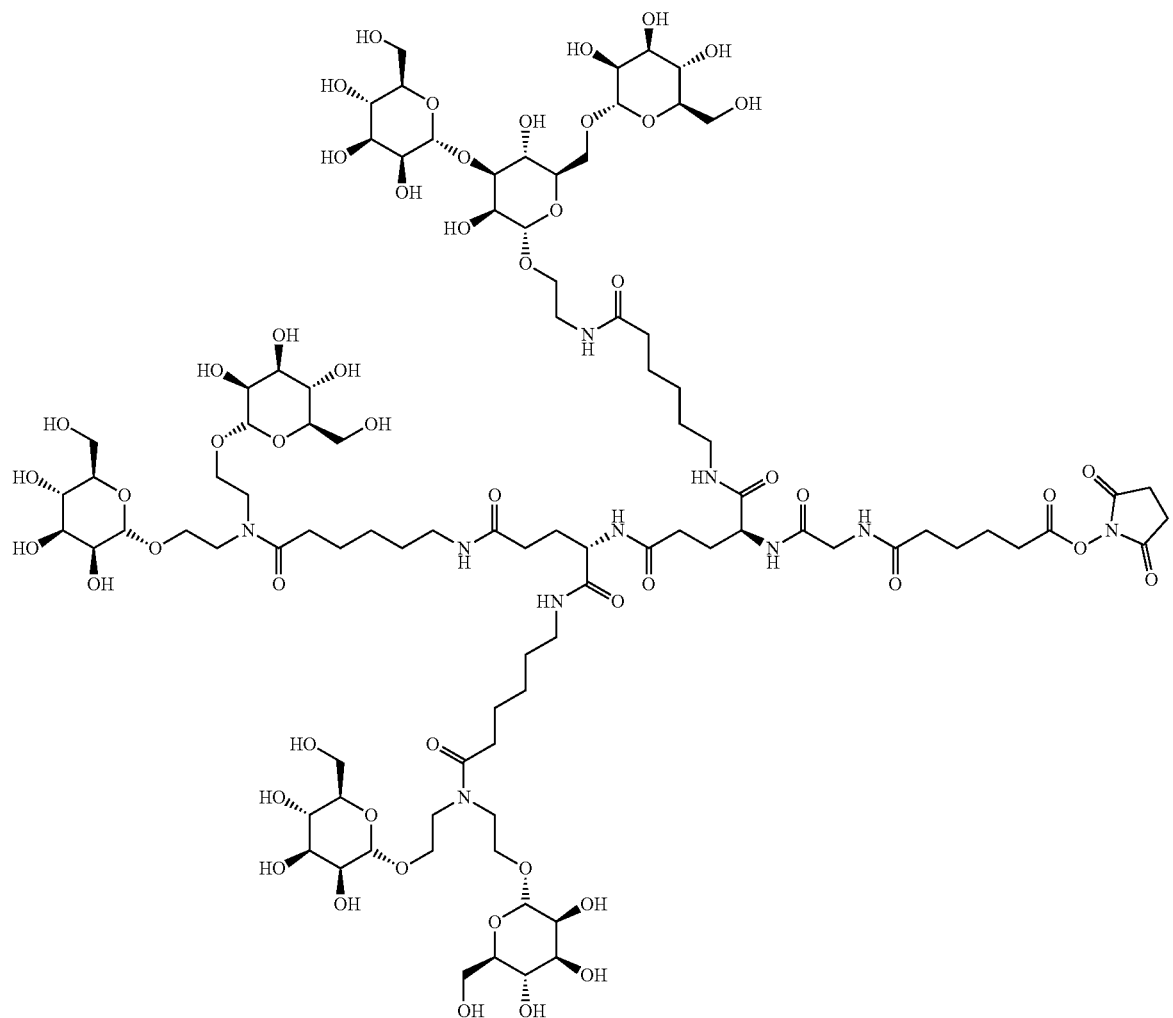

Step 1. [(S)-4-{2-[8-(benzyloxy)-8-oxooctanamido] acetamido}-5-(tert-butoxy)-5-oxopentanoyl]-L-glutamic Acid To a solution of H-Gly-γGlu(OtBu)-Glu-OH (503 mg, 1.292 mmol) in DMF (10 mL) at 0° C. was added 1-benzyl 8-(2,5-dioxopyrrolidin-1-yl) octanedioate (490 mg, 1.356 mmol) in DMF (2 mL) portionwise over 15 min and then TEA (360 μL, 2.58 mmol) dropwise over 10 min. The resulting suspension was stirred at rt overnight and concentrated. The residue was purified by column chromatography on 100 g C18 reverse phase silica gel, eluting with AcCN/H$_2$O (gradient from 5% to 60% in 24 CV), to give the title compound. UPLC-MS Method B: m/z=636.367 (z=1); t$_R$=4.63 min.

Step 2. Benzyl (14S,19S)-14-[(6-{bis(2-[(α-D-mannopyranosyl)oxy]ethyl}amino)-6-oxohexyl) carbamoyl]-19-(tert-butoxycarbonyl)-4,11,16,21,24-pentaoxo-1-[(α-D-mannopyranosyl)oxy]-3-{2-[(α-D-mannopyranosyl)oxy]ethyl}-3,10,15,20,23-pentaazahentriacontan-31-oate To a solution of [(S)-4-{2-[8-(benzyloxy)-8-oxooctanamido]acetamido}-5-(tert-butoxy)-5-oxopentanoyl]-L-glutamic acid (1.0 g, 1.646 mmol) in DMF (40 mL) was added EDC (946 mg, 4.94 mmol) and HOBt (252 mg, 1.646 mmol) at 0° C. After stirring at 0° C. for 30 min, to the mixture was added 6-amino-N,N-bis{2-[(α-D-mannopyranosyl)oxy]ethyl}hexanamide (2.054 g, 3.79 mmol). The mixture was allowed to gradually warm up to rt and to stir overnight. The resulting mixture was concentrated, and the residue was purified by column chromatography on 150 g C18 reverse phase silica gel, eluting with AcCN/H$_2$O (gradient from 0% to 50% in 20 CV), to give the title compound. UPLC-MS Method B: m/z=1657.862 (z=1); t$_R$=4.60 min.

Step 3. N2-{[8-(benzyloxy)-8-oxooctanoyl]glycyl}-N5-[(S)-4,11,15,22-tetraoxo-1,25-di[(α-D-mannopyranosyl)oxy]-3,23-bis{2-[(α-D-mannopyranosyl)oxy]ethyl}-3,10,16,23-tetraazapentacosan-12-yl]-L-glutamine To a flask containing benzyl (14S,19S)-14-[(6-{bis(2-[(α-D-mannopyranosyl)oxy]ethyl}amino)-6-oxohexyl)carbamoyl]-19-(tert-butoxycarbonyl)-4,11,16,21,24-pentaoxo-1-[(α-D-mannopyranosyl)oxy]-3-{2-[(α-D-mannopyranosyl)oxy]ethyl}-3,10,15,20,23-pentaaza-hentriacontan-31-oate (1.967 g, 1.187 mmol) at 0° C. was added TFA (14 mL, 182 mmol). The mixture was stirred at 0° C. for 2 hr and then concentrated. The residue was purified by column chromatography on 100 g C18 reverse phase silica gel, eluting with AcCN/H$_2$O (gradient from 0% to 55% in 26 min), to give the title compound. UPLC-MS Method B: m/z=1601.839 (z=1); t$_R$=4.08 min.

Step 4. benzyl (14S,19S)-14-{[6-(bis{2-[(α-D-mannopyranosyl)oxy]ethyl}amino)-6-oxohexyl]carbamoyl}-4,11,16,21,24-pentaoxo-19-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-1-[(α-D-mannopyranosyl)oxy]-3-{2-[(α-D-mannopyranosyl)oxy]ethyl}-3,10,15,20,23-pentaazanonacosan-29-oate To a solution of N2-{[8-(benzyloxy)-8-oxooctanoyl]glycyl}-N5-[(S)-4,11,15,22-tetraoxo-1,25-di[(α-D-mannopyranosyl)oxy]-3,23-bis{2-[(α-D-mannopyranosyl)oxy]ethyl}-3,10,16,23-tetraazapentacosan-12-yl]-L-glutamine (820 mg, 0.512 mmol) in DMF (40 mL) at 0° C. was added EDC (196 mg, 1.025 mmol) and HOBt (39.2 mg, 0.256 mmol). After stirring at 0° C. for 30 min, to the resulting mixture was added 6-amino-N-[2-({α-D-mannopyranosyl-(1-3)-[α-D-mannopyranosyl-(1-6)]-α-D-mannopyranosyl}oxy)ethyl]hexanamide (406 mg, 0.615 mmol). The mixture was allowed to gradually warm to rt and to stir at rt overnight. The mixture was concentrated, and the residue was purified by column chromatography on 100 g C18 reverse phase silica gel, eluting with AcCN/H$_2$O (gradient from 0% to 45% in 2 CV), to give the title compound. UPLC-MS Method B: m/z=1122.705 (z=2); t$_R$=2.19 min.

Step 5. 2,5-dioxopyrrolidin-1-yl (14S,19S)-14-{[6-(bis{2-[(α-D-mannopyranosyl)oxy]ethyl}amino)-6-oxohexyl]carbamoyl}-4,11,16,21,24-pentaoxo-19-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-1-[(α-D-mannopyranosyl)oxy]-3-{2-[(α-D-mannopyranosyl)oxy]ethyl}-3,10,15,20,23-pentaazanonacosan-29-oate The title compound was prepared using procedures analogous to those described for ML-1 substituting benzyl (14S,19S)-14-{[6-(bis{2-[(α-D-mannopyranosyl)oxy]ethyl}amino)-6-oxohexyl]carbamoyl}-4,11,16,21,24-pentaoxo-19-[(6-oxo-6-{[2-({α-D-mannopyranosyl-(1→3)-[α-D-mannopyranosyl-(1→6)]-α-D-mannopyranosyl}oxy)ethyl]amino} hexyl) carbamoyl]-1-[(α-D-mannopyranosyl)oxy]-3-{2-[(α-D-mannopyranosyl)oxy]ethyl}-3,10,15,20,23-penta-azanonacosan-29-oate for benzyl 6-{[(S)-5-{[(S)-1,5-dioxo-1,5-bis({2-[(α-D-mannopyranosyl) oxy]ethyl}amino)pentan-2-yl]amino}-1,5-dioxo-1-({2-[(α-D-mannopyranosyl)oxy]ethyl}amino) pentan-2-yl]amino}-6-oxohexanoate in Step 3. UPLC-MS Method A: m/z=1125.669 (z=2); t$_R$=1.63 min.

Example 6: 2,5-dioxopyrrolidin-1-yl (6S,9S,12S)-12-methyl-4,8,11,14-tetraoxo-9-[3-oxo-3-({2-[(α-D-mannopyranosyl)oxy]ethyl} amino)propyl]-1-[(α-D-mannopyranosyl)oxy]-6-({2-[(α-D-mannopyranosyl)oxy]ethyl} carbamoyl)-3,7,10,13-tetraazanonadecan-19-oate (ML-6)

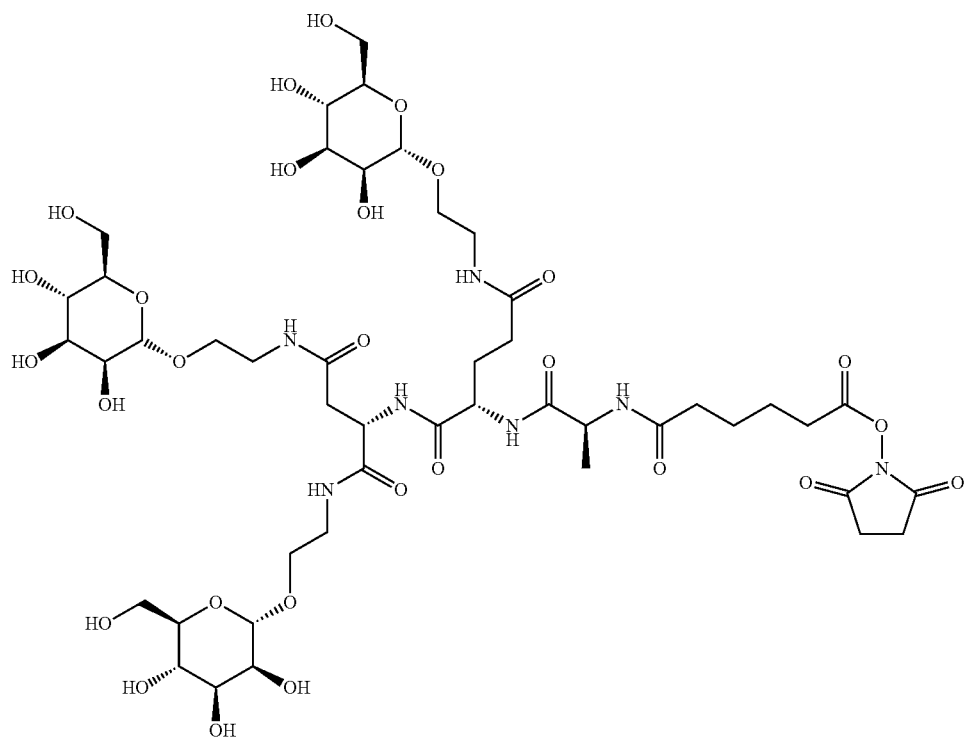

ML-6

The title compound was prepared using procedures analogous to those described for ML-1 substituting [6-(benzyloxy)-6-oxohexanoyl]-L-alanyl-L-glutamyl-L-aspartic acid for {(S)-4-[6-(benzyloxy)-6-oxohexanamido]-4-carboxybutanoyl}-L-glutamic acid in Step 2. UPLC-MS Method A: m/z=1231.5653 (z=2); $t_R$=1.50 min.

Example 7: 2,5-dioxopyrrolidin-1-yl (15S,18S)-4,9,16,19-tetraoxo-15-(6-oxo-6-{[2-({α-D-mannopyranosyl-(1→3)-[α-D-mannopyranosyl-(1→6)]-α-D-mannopyranosyl}oxy)ethyl]amino}hexanamido)-18-[4-(6-oxo-6-{[2-({α-D-mannopyranosyl-(1→3)-[α-D-mannopyranosyl-(1→6)]-α-D-mannopyranosyl}oxy)ethyl]amino}hexanamido)butyl]-1-({α-D-mannopyranosyl-(1→3)-[α-D-mannopyranosyl-(1→6)]-α-D-mannopyranosyl} oxy)-3,10,17,20-tetraazahexacosan-26-oate (ML-7)
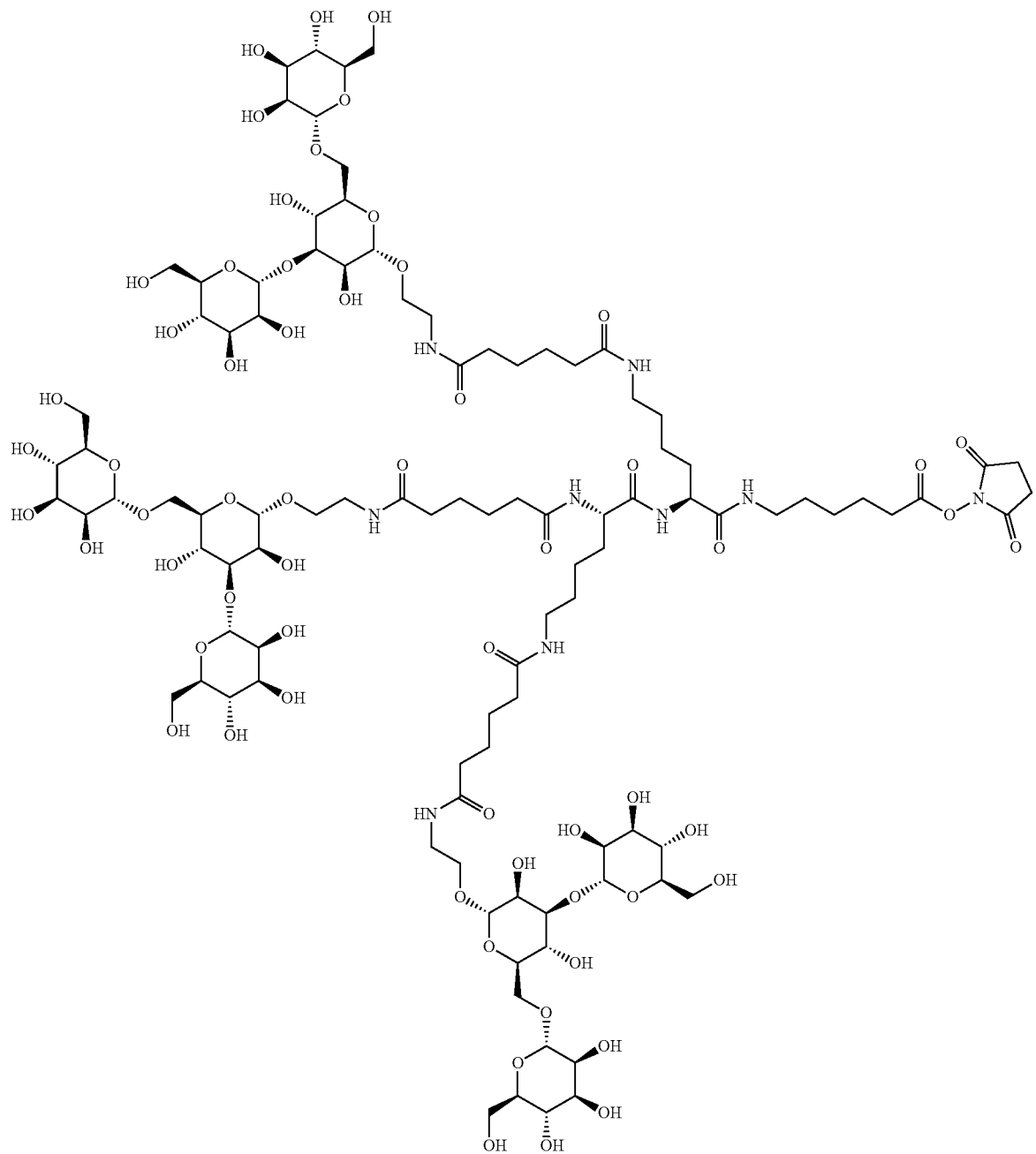
ML-7

Step 1. N6-[(benzyloxy)carbonyl]-N2-{N2,N6-bis[(benzyloxy)carbonyl]-L-lysyl}-L-lysine To a solution of L-lysyl-L-lysine dihydrochloride (1.00 g, 2.88 mmol) in a mixture of 1M NaOH (8.64 mL, 8.64 mmol) and dioxane (19.2 mL) at rt was added dibenzyl dicarbonate (3.30 g, 11.52 mmol). After stirring overnight, the mixture was diluted with $H_2O$ and acidified with 1M HCl to pH~2. The resulting mixture was extracted with EtOAc. The organic phase was separated, washed with brine, and concentrated. The title material was isolated by chromatography (120 g $SiO_2$ column, flow 100 mL/min, gradient A-B of 0-50% B in 30 min followed by hold, where solvent A was EtOAc and solvent B was EtOAc/MeOH/AcCN/$H_2O$ (v/v/v/v=6/1/1/1). UPLC-MS Method D: m/z=677.34 (z=1); $t_R$=4.44 min.

Step 2. Benzyl (9S,12S)-9-{[(benzyloxy)carbonyl]amino}-12-(4-{[(benzyloxy)carbonyl]amino}butyl)-3,10,13-trioxo-1-phenyl-2-oxa-4,11,14-triazaicosan-20-oate To a solution of 6-(benzyloxy)-6-oxohexan-1-aminium 4-methylbenzenesulfonate (704 mg, 1.788 mmol) and N6-[(benzyloxy)carbonyl]-N2-{N2,N6-bis[(benzyloxy)carbonyl]-L-lysyl}-L-lysine (931 mg, 1.376 mmol) in DMF (13.8 mL) was added HOBt (316 mg, 2.064 mmol), DIPEA (312 μl, 1.788 mmol), and EDC (343 mg, 1.788 mmol). After stirring overnight, the mixture was diluted with EtOAc (100 mL) and washed with 1M HCl (2×50 mL), NaHCO$_3$ (2×50 mL), and brine (50 mL). The organic phase was separated, dried over Na$_2$SO$_4$, and concentrated. The residue was purified by chromatography (SiO$_2$ column, solvent A=DCM, Solvent B=80% EtOAc/20% DCM, gradient 0-100% A-B in 30 min followed by hold) to give the title material. LC-MS Method A: m/z=880.60 (z=1); $t_R$=1.42 min.

Step 3. 6-{(S)-6-amino-2-[(S)-2,6-diaminohexanamido]hexanamido}hexanoic Acid A mixture of benzyl (9S,12S)-9-{[(benzyloxy)carbonyl]amino}-12-(4-{[(benzyloxy) carbonyl]amino}butyl)-3,10,13-trioxo-1-phenyl-2-oxa-4,11,14-triazaicosan-20-oate (810 mg, 0.920 mmol) in MeOH (180 mL) and Pd(OH)$_2$ (129 mg, 0.184 mmol) was shaken on a Parr shaker under 344.74 kPa of H$_2$ overnight. The catalyst was filtered off, and the filtrate was concentrated to give the title compound. UPLC-MS Method A: m/z=388.3 (z=1); $t_R$=1.74 min.

Step 4. (15S,18S)-4,9,16,19-tetraoxo-15-(6-oxo-6-{[2-({α-D-mannopyranosyl-(1→3)-[α-D-mannopyranosyl-(1→6)]-α-D-mannopyranosyl}oxy)ethyl]amino}hexanamido)-18-[4-(6-oxo-6-{[2-({α-D-mannopyranosyl-(1→3)-[α-D-mannopyranosyl-(1→6)]-α-D-mannopyranosyl}oxy) ethyl]amino}hexanamido)butyl]-1-({α-D-mannopyranosyl-(1→3)-[α-D-mannopyranosyl-(1→6)]-α-D-mannopyranosyl}oxy)-3,10,17,20-tetraazahexacosan-26-oic Acid To a solution of 6-[(2,5-Dioxopyrrolidin-1-yl)oxy]-N-(2-{[α-D-mannopyranosyl-(1-3)-[α-D-mannopyranosyl-(1-6)]-α-D-mannopyranosyl]oxy}ethyl)-6-oxohexanamide (598 mg, 0.774 mmol, WO 2015/051052 A2) and 6-{(S)-6-amino-2-[(S)-2,6-diaminohexanamido]hexanamido}hexanoic acid (100 mg, 0.258 mmol) in DMF (5 mL) was added TEA (106 μL, 0.774 mmol). After 1 hr, the mixture was purified by chromatography (240 g reverse phase C18 silica gel column, 0 to 50% AcCN in H$_2$O over 60 min), and the desired fractions were combined and dried, which was further purified on 40 g silica column (flow rate 40 mL/min, gradient 0-100% Solvent B in Solvent A over 30 min; hold at 100% B for 5 min; Solvent A: EtOAc/MeOH/AcCN/H$_2$O (v/v/v/v=6/1/1/1) and Solvent B: EtOAc/MeOH/AcCN/H$_2$O (v/v/v/v=2/1/1/1) to give the title compound. UPLC-MS Method A: m/z=1181.0841 (z=2); $t_R$=4.20 min.

Step 4. 2,5-dioxopyrrolidin-1-yl (15S,18S)-4,9,16,19-tetraoxo-15-(6-oxo-6-{[2-({α-D-mannopyranosyl-(1→3)-[α-D-mannopyranosyl-(1→6)]-α-D-mannopyranosyl}oxy)ethyl]amino}hexanamido)-18 [4-(6-oxo-6-{[2-({α-D-mannopyranosyl-(1→3)-[α-D-mannopyranosyl-(1→6)]-α-D-mannopyranosyl}oxy)ethyl]amino}hexanamido) butyl]-1-({α-D-mannopyranosyl-(1→3)-[α-D-mannopyranosyl-(1→6)]-α-D-mannopyranosyl}oxy)-3,10,17,20-tetraazahexacosan-26-oate The title compound was prepared using procedures analogous to those described for ML-1 substituting (15S,18S)-4,9,16,19-tetraoxo-15-(6-oxo-6-{[2-({α-D-mannopyranosyl-(1→3)-[α-D-mannopyranosyl-(1→6)]-α-D-mannopyranosyl}oxy)ethyl]amino}hexanamido)-18-[4-(6-oxo-6-{[2-({α-D-mannopyranosyl-(1→3)-[α-D-mannopyranosyl-(1→6)]-α-D-mannopyranosyl}oxy) ethyl]amino}hexanamido)butyl]-1-({α-D-mannopyranosyl-(1→3)-[α-D-mannopyranosyl-(1→6)]-α-D-mannopyranosyl}oxy)-3,10,17,20-tetraazahexacosan-26-oic acid for 6-{[(S)-5-{[(S)-1,5-dioxo-1,5-bis({2-[(α-D-mannopyranosyl)oxy]ethyl}amino)pentan-2-yl]amino}-1,5-dioxo-1-({2-[(α-D-mannopyranosyl)oxy]ethyl}amino)pentan-2-yl]amino}-6-oxohexanoic acid in Step 4.

Example 8: 2,5-dioxopyrrolidin-1-yl (S)-1-[(α-D-mannopyranosyl)oxy]-6-[2-({2-[(α-D-mannopyranosyl)oxy]ethyl}amino)-2-oxoethyl]-13-({2-[(α-D-mannopyranosyl)oxy]ethyl}arbamoyl)-4,8,11,16-tetraoxo-3,6,9,12,17-pentaazatricosan-23-oate (ML-8)

ML-8

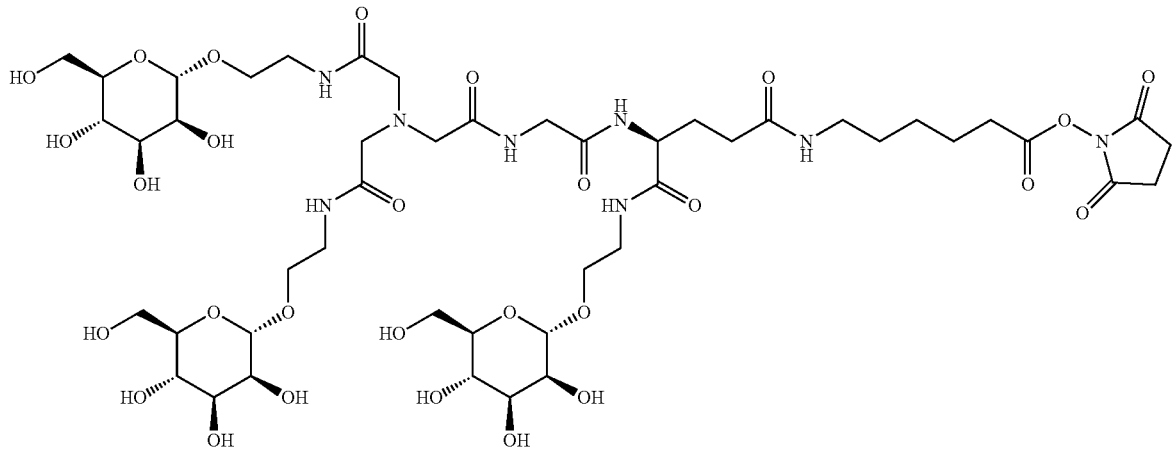

Step 1. 2,2'-[(2-{[2-(benzyloxy)-2-oxoethyl]amino}-2-oxoethyl)azanediyl]diacetic Acid To a solution of 2-(benzyloxy)-2-oxoethanaminium chloride (4.0 g, 19.84 mmol) in DMF (29 mL) was added DIPEA (3.46 mL, 19.84 mmol) at 0° C. The mixture was stirred at 0° C. for 2 hr and then transferred via a cannula to a stirred solution of 2-(2,6-dioxomorpholino)acetic acid (3.434 g, 19.84 mmol) in DMF (29.0 mL) at 0° C. The resulting mixture was stirred at 0° C. for 30 min, then at rt for 2 hr. The reaction was quenched at 0° C. by adding $H_2O$ (29 mL). The resulting mixture was concentrated, and the residue was resuspended in $H_2O$ (29 mL). The mixture was stirred at 0° C. for 3 hr, and the precipitate was collected by filtration, washed with $H_2O$ (25×2 mL), and dried to give the title compound. UPLC-MS Method A: m/z=339.13 (z=1); $t_R$=2.72 min.

Step 2. Benzyl bis[2-({2-[(α-D-mannopyranosyl)oxy]ethyl}amino)-2-oxoethyl]glycylglycinate To a solution of 2,2'-[(2-{[2-(benzyloxy)-2-oxoethyl]amino}-2-oxoethyl)azanediyl]diacetic acid (3.4 g, 10.05 mmol) in DMF (10 mL) at 0° C. was added EDC (5.78 g, 30.1 mmol) HOBt (4.62 g, 30.1 mmol), and 30 min later, 2-aminoethyl α-D-mannopyranoside (5.61 g, 25.1 mmol). The resulting mixture was allowed to gradually warm to rt, stirred overnight, and concentrated. The residue was purified by column chromatography on 130 g C18 reverse phase silica gel (3×), eluting with AcCN/$H_2O$ (gradient from 5% to 30% in 15 CV), to give the title compound. UPLC-MS Method A: m/z=749.3 (z=1); $t_R$=2.19 min.

Step 3. Bis[2-({2-[(α-D-mannopyranosyl)oxy]ethyl}amino)-2-oxoethyl]glycylglycine To a degassed solution of benzyl bis[2-({2-[(α-D-mannopyranosyl)oxy]ethyl} amino)-2-oxoethyl]glycyl glycinate (4.1 g, 5.48 mmol) in $H_2O$ (50 mL) was added Pd/C (1.07 g, 1.005 mmol). The mixture was stirred at rt under $H_2$ for 15 hr. The mixture was diluted with MeOH (50 mL), filtered through a pad of CELITE®, washed with MeOH/water (v/v=1:1, 15 mL). The filtrate was concentrated and freeze-dried to give the title compound. UPLC-MS Method A: m/z=659.3 (z=1); $t_R$=0.91 min.

Step 4. Benzyl (S)-4-amino-5-({2-[(α-D-mannopyranosyl)oxy]ethyl}amino)-5-oxopentanoate In a 250 mL round bottom flask were added L-glutamic acid γ-benzyl ester (1.0 g, 4.21 mmol), EDC (808 mg, 4.21 mmol), HOBt (645 mg, 4.21 mmol) and 2-aminoethyl α-D-mannopyranoside (941 mg, 4.21 mmol). To the flask was added DMF (30 mL). The mixture was stirred at rt for 48 hr and concentrated. The residue was purified by C18 reverse phase chromatography (eluted with 0-40% AcCN/$H_2O$ in 30 min) to give the title product. UPLC-MS Method A: m/z=443.2 (z=1); $t_R$=2.18 min.

Step 5. (S)-4,8,11-trioxo-6-[2-oxo-2-({2-[(α-D-mannopyranosyl)oxy]ethyl}amino)ethyl]-1-[(α-D-mannopyranosyl)oxy]-13-({2-[(α-D-mannopyranosyl)oxy]ethyl}carbamoyl)-3,6,9,12-tetraazahexadecan-16-oic Acid In a solution of bis[2-({2-[(α-D-mannopyranosyl)oxy]ethyl}amino)-2-oxoethyl]glycyl glycine (476 mg, 0.723 mmol) in DMF (6 mL) was added EDC (208 mg, 1.085 mmol) HOBt (166 mg, 1.085 mmol), and 20 min later, benzyl (S)-4-amino-5-({2-[(α-D-mannopyranosyl)oxy]ethyl}amino)-5-oxopentanoate (320 mg, 0.723 mmol) in DMF (3 mL) dropwise. After stirring at 25° C. for 18 hr, the reaction mixture was concentrated, and the residue was purified by C18 (eluted with 5-40% AcCN/$H_2O$) and C8 reverse phase chromatography (eluted with 5-32% AcCN/

H₂O with 0.1% TFA) to give the title compound. UPLC-MS Method A: m/z=1083.4 (z=1); $t_R$=2.17 min.

To a solution of the resulting product in H₂O (20 mL) was added Pd/C (7.7 mg, 0.072 mmol). The flask was degassed and filled with N₂ (3×), then stirred under H₂ for 2 hr. The mixture was filtered through a pad of CELITE®, and the filtrate was freeze-dried to give the title compound. UPLC-MS Method A: m/z=993.4 (z=1); $t_R$=1.36 min.

Step 6. Benzyl (S)-4,8,11,16-tetraoxo-6-[2-oxo-2-({2-[(α-D-mannopyranosyl)oxy]ethyl}amino) ethyl]-1-[(α-D-mannopyranosyl)oxy]-13-({2-[(α-D-mannopyranosyl)oxy]ethyl}carbamoyl)-3,6,9,12,17-pentaazatricosan-23-oate The title compound was prepared using the procedure analogous to that described for ML-7 substituting (S)-4,8,11-trioxo-6-[2-oxo-2-({2-[(α-D-mannopyranosyl)oxy]ethyl}amino) ethyl]-1-[(α-D-mannopyranosyl)oxy]-13-({2-[(α-D-mannopyranosyl)oxy]ethyl}carbamoyl)-3,6,9,12-tetraazahexadecan-16-oic acid for 6-(benzyloxy)-6-oxohexan-1-aminium 4-methylbenzenesulfonate in Step 2. UPLC-MS Method A: m/z=1106.5 (z=1); $t_R$=1.52 min.

Step 7. 2,5-dioxopyrrolidin-1-yl (S)-1-[(α-D-mannopyranosyl)oxy]-6-[2-({2-[(α-D-mannopyranosyl)oxy]ethyl}amino)-2-oxoethyl]-13-({2-[(α-D-mannopyranosyl)oxy]ethyl}arbamoyl)-4,8,11,16-tetraoxo-3,6,9,12,17-pentaazatricosan-23-oate The title compound was prepared using procedures analogous to those described for ML-1 substituting benzyl (S)-4,8,11,16-tetraoxo-6-[2-oxo-2-({2-[(α-D-mannopyranosyl)oxy]ethyl}amino)ethyl]-1-[(α-D-mannopyranosyl)oxy]-13-({2-[(α-D-mannopyranosyl)oxy]ethyl}carbamoyl)-3,6,9,12,17-pentaazatricosan-23-oate for benzyl 6-{[(S)-5-{[(S)-1,5-dioxo-1,5-bis({2-[(α-D-mannopyranosyl)oxy]ethyl}amino)pentan-2-yl]amino}-1,5-dioxo-1-({2-[(α-D-mannopyranosyl)oxy]ethyl}amino)pentan-2-yl]amino}-6-oxohexanoate in Step 3. UPLC-MS Method A: m/z=1203.52 (z=1); $t_R$=1.99 min.

Example 9: 2,5-dioxopyrrolidin-1-yl (S)-{4-[2-(2-{bis-[2-oxo-2-({2-[(α-D-mannopyranosyl)oxy]ethyl}amino)ethyl]amino}acetamido)acetamido]-5-oxo-5-({2-[(α-D-mannopyranosyl)oxy]ethyl}amino)pentanoyl}glycinate (ML-9)

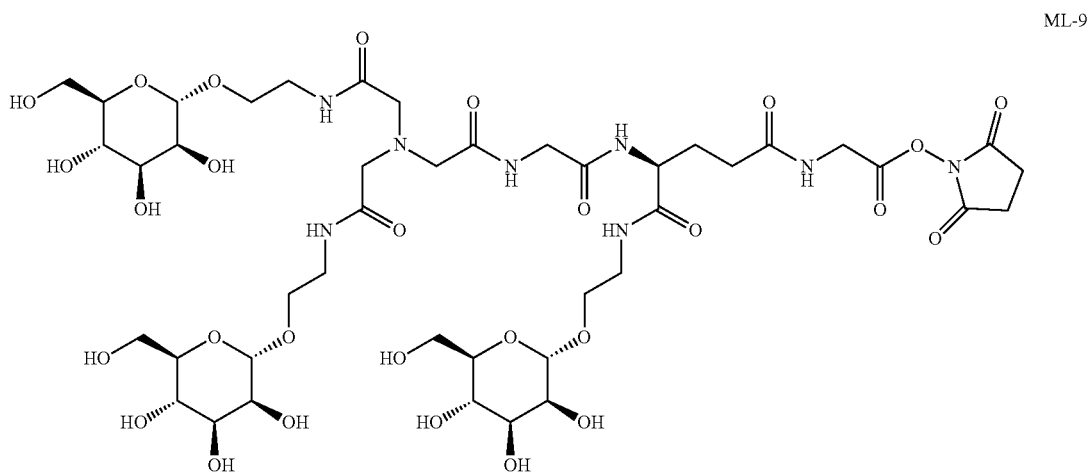 [SMILES: O=C(CC[C@H](NC(=O)CNC(=O)CN(CC(=O)NCCO[C@H]1O[C@H](CO)[C@@H](O)[C@H](O)[C@@H]1O)CC(=O)NCCO[C@H]1O[C@H](CO)[C@@H](O)[C@H](O)[C@@H]1O)C(=O)NCCO[C@H]1O[C@H](CO)[C@@H](O)[C@H](O)[C@@H]1O)NCC(=O)ON1C(=O)CCC1=O]

ML-9

The title compound was prepared using procedures analogous to those described for ML-8 substituting benzyl glycinate p-toluenesulfonate for 6-(benzyloxy)-6-oxohexan-1-aminium 4-methylbenzenesulfonate in Step 6.

Example 10: 2,5-dioxopyrrolidin-1-yl (S)-4,8,11,19-tetraoxo-6-[2-oxo-2-({2-[(α-D-glucopyranosyl)oxy]ethyl}amino)ethyl]-13-({2-[(α-D-mannopyranosyl)oxy]ethyl}carbamoyl)-1-[(α-D-glucopyranosyl)oxy]-3,6,9,12,18-pentaazatetracosan-24-oate (ML-10)

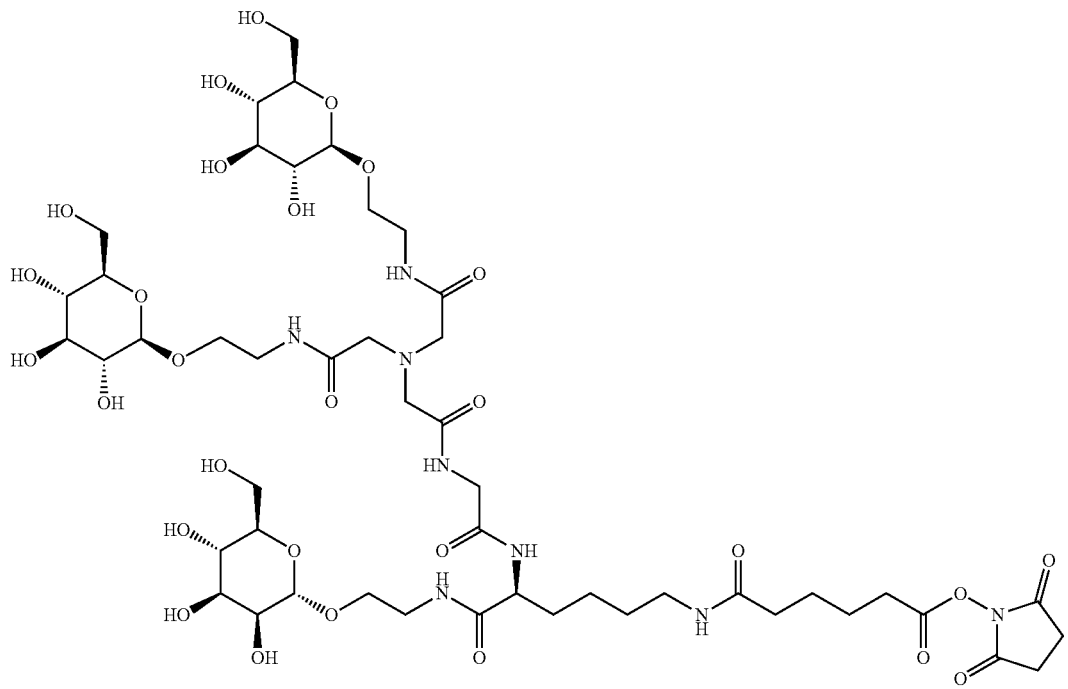

ML-10

Step 1. Bis[2-({2-[(α-D-glucopyranosyl)oxy]ethyl}amino)-2-oxoethyl]glycylglycine The title compound was prepared using procedures analogous to those (Step 1-3) described for ML-8 substituting 2-aminoethyl α-D-glucopyranoside for 2-aminoethyl α-D-mannopyranoside in Step 2. UPLC-MS Method A: m/z=659.2562 (z=1); $t_R$=0.91 min.

Step 2. Benzyl (S)-[5-amino-6-oxo-6-({2-[(α-D-mannopyranosyl)oxy]ethyl}amino)hexyl]carbamate To a solution of (S)-6-(((benzyloxy)carbonyl)amino)-2-((tert-butoxycarbonyl) amino) hexanoic acid (2.0 g, 5.26 mmol) in DMF (30 mL) at 0° C. was added EDC (1.51 mg, 7.89 mmol) and HOBt (242 mg, 1.577 mmol). After stirring at rt for 20 min, to the resulting mixture was added 2-aminoethyl α-D-mannopyranoside (1.174 g, 5.26 mmol). After stirring at rt overnight, the reaction mixture was concentrated, and the residue was purified by flash column (40 g, eluted with 0-17% MeOH/DCM in 16 CV). UPLC-MS Method A: m/z=586.3254 (z=1); $t_R$=2.74 min.

The resulting intermediate (1.24 g, 2.117 mmol) was dissolved in DCM/TFA (1/1 20 mL) at rt. After stirring for 2 hr, the reaction mixture was concentrated, and the residue was purified by C18 reverse phase column (eluted with 0-30% AcCN/H₂O) to give the title compound. LC-MS Method A: m/z=5486.33 (z=1); $t_R$=1.22 min.

Step 3. (S)-2,2'-({2-[(2-{[6-amino-1-oxo-]-({2-[(α-D-mannopyranosyl)oxy]ethyl}amino)hexan-2-yl]amino)-2-oxoethyl}amino)-2-oxoethyl]azanediyl}bis(N-{2-[(α-D-glucopyranosyl)oxy]ethyl}acetamide)

To a solution of bis[2-({2-[(α-D-glucopyranosyl)oxy]ethyl}amino)-2-oxoethyl]glycylglycine (75 mg, 0.114 mmol) in DMF (6 mL) at rt was added DCC (28.2 mg, 0.137 mmol) and, 20 min later, benzyl (S)-[5-amino-6-oxo-6-({2-[(α-D-mannopyranosyl)oxy]ethyl}amino) hexyl]carbamate (39 mg, 0.080 mmol) in DMF (3 mL) dropwise. After stirring at rt for 4 hr, the reaction mixture was concentrated, and the residue was purified by reverse phase C18 chromatography (5-40% AcCN/water) and reverse phase C8 chromatography (gradient 5-32% AcCN/water) to give the benzyl ester intermediate. UPLC-MS Method A: m/z=1126.4677 (z=1); $t_R$=2.43 min.

To a solution of the resulting benzyl ester intermediate in water (10 mL) was added Pd/C (12 mg, 0.114 mmol). The mixture was degassed and filled with N₂ (3×), and then stirred under H₂ for 2 hr. The mixture filtered through a pad of CELITE®, and the filtrate was freeze-dried to give the title compound. UPLC-MS Method A: m/z=992.4921 (z=1); $t_R$=1.35 min.

Step 4. Benzyl (S)-4,8,11,19-tetraoxo-6-[2-oxo-2-({2-[(α-D-glucopyranosyl)oxy]ethyl}amino) ethyl]-13-({2-[(α-D-mannopyranosyl)oxy]ethyl}carbamoyl)-1-[(α-D-glucopyranosyl)oxy]-3,6,9,12,18-pentaazatetracosan-24-oate To a solution of (S)-2,2'-({2-[(2-{[6-amino-1-oxo-1-({2-[(α-D-mannopyranosyl)oxy]ethyl}amino)hexan-2-yl]

amino)-2-oxoethyl}amino)-2-oxoethyl]azanediyl}bis(N-{2-[(α-D-glucopyranosyl)oxy]ethyl}acetamide) (115 mg, 0.116 mmol) in DMF (1 mL) and 1,4-dioxane (4 mL) was added benzyl (2,5-dioxopyrrolidin-1-yl) adipate (43 mg, 0.128 mmol) and TEA (18 μL, 0.128 mmol). The reaction mixture was stirred at rt for 5 hr and concentrated. The residue was purified by C18 reverse phase column chromatography to give the title compound. UPLC-MS Method A: m/z=1210.5599 (z=1); $t_R$=2.75 min.

Step 5. 2,5-dioxopyrrolidin-1-yl (S)-4,8,11,19-tetraoxo-6-[2-oxo-2-({2-[(α-D-glucopyranosyl) oxy]ethyl}amino)ethyl]-13-({2-[(α-D-mannopyranosyl)oxy]ethyl}carbamoyl)-1-[(α-D-glucopyranosyl) oxy]-3,6,9,12,18-pentaazatetracosan-24-oate The title compound was prepared using procedures analogous to those described for ML-1 substituting benzyl (S)-4,8,11,19-tetraoxo-6-[2-oxo-2-({2-[(α-D-glucopyranosyl)oxy]ethyl}amino)ethyl]-13-({2-[(α-D-mannopyranosyl)oxy]ethyl}carbamoyl)-1-[(α-D-glucopyranosyl) oxy]-3,6,9,12,18-pentaazatetracosan-24-oate for benzyl 6-{[(S)-5-{[(S)-1,5-dioxo-1,5-bis({2-[(α-D-mannopyranosyl)oxy]ethyl}amino)pentan-2-yl]amino}-1,5-dioxo-1-({2-[(α-D-mannopyranosyl)oxy]ethyl}amino)pentan-2-yl]amino}-6-oxohexanoate in Step 3.

Example 11: 2,5-dioxopyrrolidin-1-yl (S)-4,8,11,19-tetraoxo-6-[2-oxo-2-({2-[(α-D-mannopyranosyl)oxy]ethyl}amino)ethyl]-1-[(α-D-mannopyranosyl)oxy]-13-({2-[(α-D-mannopyranosyl)oxy]ethyl}carbamoyl)-3,6,9,12,18-pentaazatetracosan-24-oate (ML-11)

ML-11

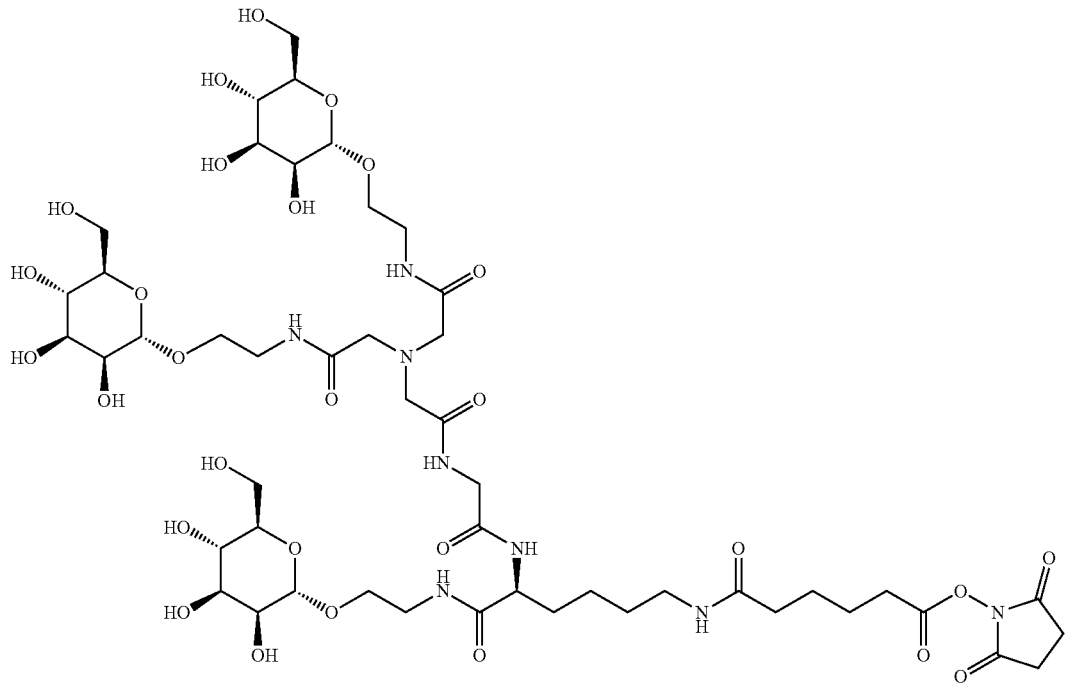

The title compound was prepared using procedures analogous to those described for ML-10 substituting 2-aminoethyl α-D-mannopyranoside for 2-aminoethyl α-D-glucopyranoside in Step 1. UPLC-MS Method A: m/z=1217.5698 (z=1); $t_R$=1.90 min.

Example 12: 2,5-dioxopyrrolidin-1-yl (S)-4,8,11,19-tetraoxo-6-[2-oxo-2-({2-[(α-L-fucoyranosyl)oxy]ethyl}amino)ethyl]-1-[(α-D-mannopyranosyl) oxy]-13-({2-[(α-L-fucopyranosyl)oxy]ethyl}carbamoyl)-3,6,9,12,18-pentaazatetracosan-24-oate (ML-12)

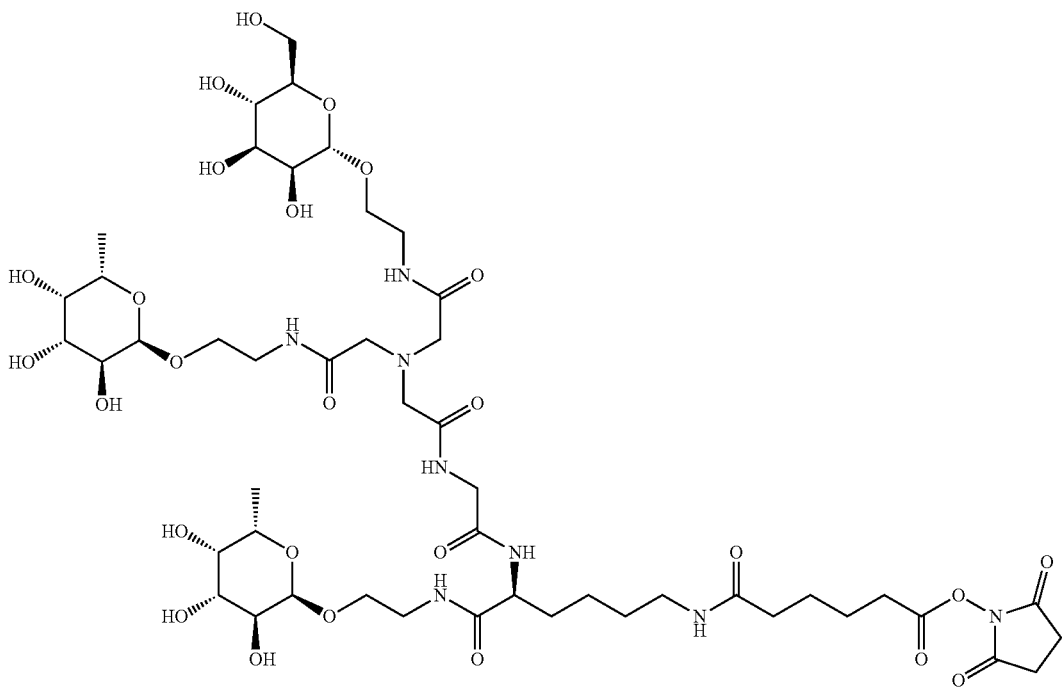

ML-12

The title compound was prepared using procedures analogous to those described for ML-10 substituting 2-aminoethyl α-L-fucopyranoside for 2-aminoethyl α-D-glucopyranoside in Step 1. UPLC-MS Method A: m/z=1185.5710 (z=1); $t_R$=2.08 min.

Example 13: 2,5-dioxopyrrolidin-1-yl (S)-4,8,11,19-tetraoxo-6-[2-oxo-2-({2-[(α-D-mannoyranosyl)oxy]ethyl}amino)ethyl]-1-[(α-D-glucopyranosyl) oxy]-13-({2-[(α-D-mannopyranosyl)oxy]ethyl}carbamoyl)-3,6,9,12,18-pentaazatetracosan-24-oate (ML-13)

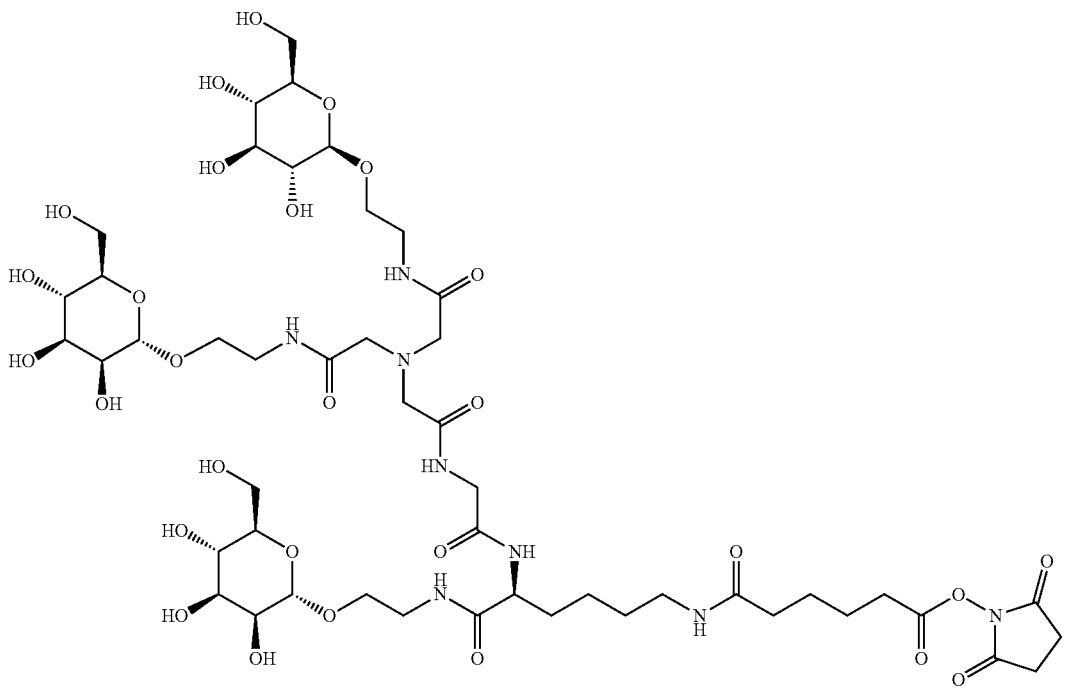

ML-13

The title compound was prepared using procedures analogous to those described for ML-10 substituting 2-aminoethyl α-D-mannopyranoside for 2-aminoethyl α-D-glucopyranoside in Step 1 and 2-aminoethyl α-D-glucopyranoside for 2-aminoethyl α-D-mannopyranoside in Step 2, respectively. UPLC-MS Method A: m/z=1217.5433 (z=1); $t_R$=1.89 min.

Example 14: 2,5-dioxopyrrolidin-1-yl (S)-4,8,11,19-tetraoxo-6-[2-oxo-2-({2-[(α-D-glucoyranosyl)oxy]ethyl}amino)ethyl]-1-[(α-D-glucopyranosyl) oxy]-13-({2-[(α-D-glucopyranosyl)oxy]ethyl}carbamoyl)-3,6,9,12,18-pentaazatetracosan-24-oate (ML-14)

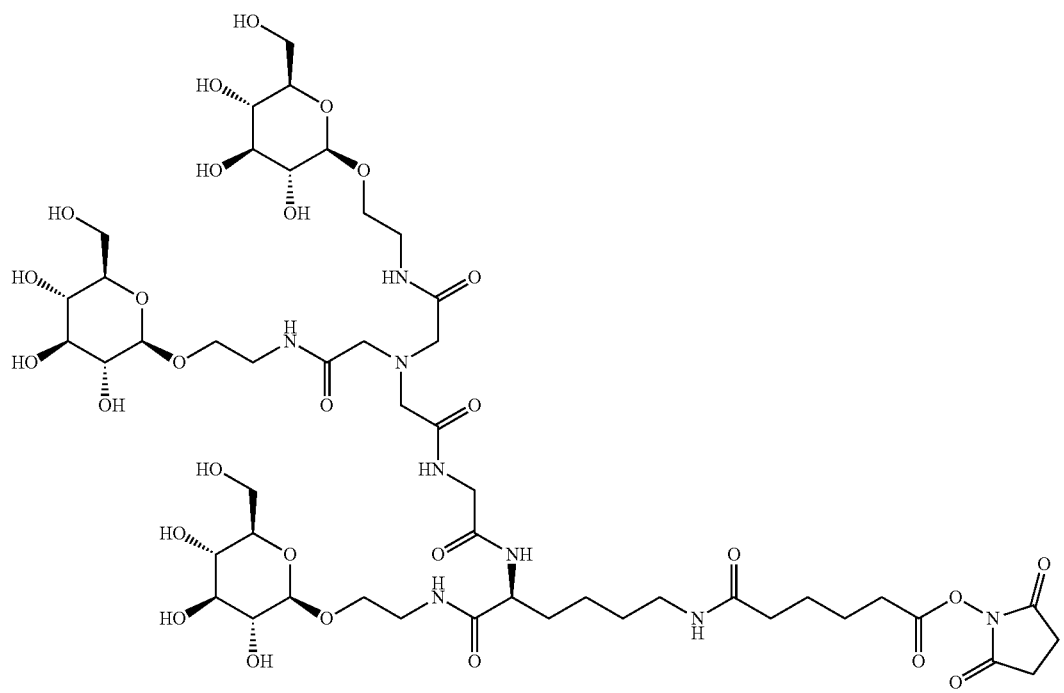

ML-14

The title compound was prepared using procedures analogous to those described for ML-10 substituting 2-aminoethyl α-D-glucopyranoside for 2-aminoethyl α-D-mannopyranoside in Step 2. UPLC-MS Method A: m/z=1217.5182 (z=1); $t_R$=1.88 min.

Example 15: 2,5-dioxopyrrolidin-1-yl (S)-4,8,11,19-tetraoxo-6-[2-oxo-2-({2-[(α-L-fucoyranosyl)oxy]ethyl}amino)ethyl]-1-[(α-L-fucopyranosyl) oxy]-13-({2-[(α-L-fucopyranosyl)oxy]ethyl}carbamoyl)-3,6,9,12,18-pentaazatetracosan-24-oate (ML-15)

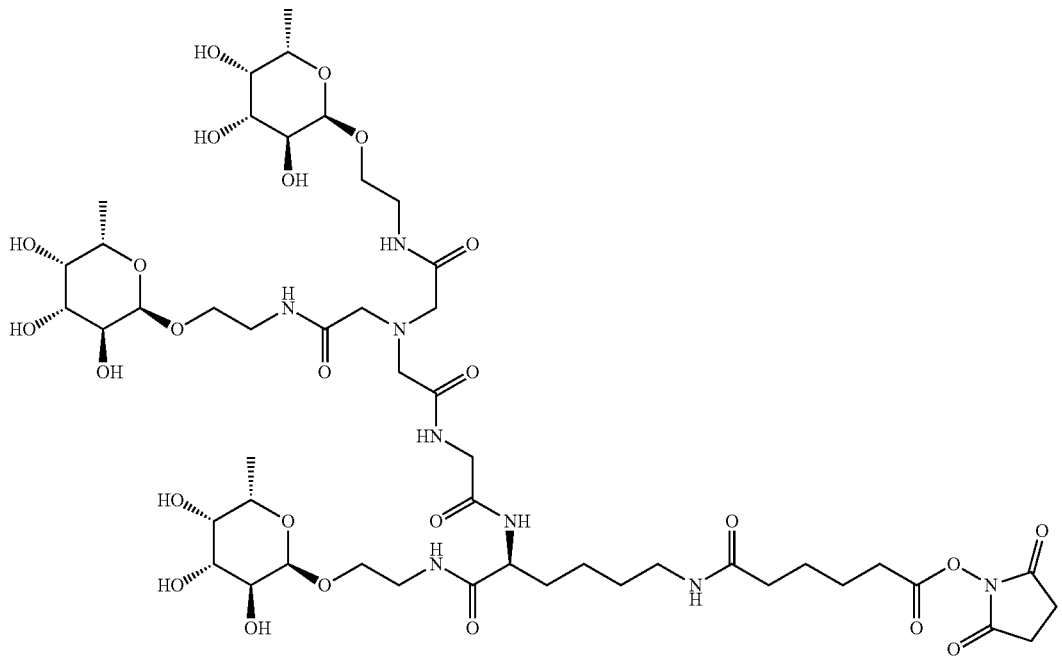

ML-15

The title compound was prepared using procedures analogous to those described for ML-10 substituting 2-aminoethyl α-L-fucopyranoside for 2-aminoethyl α-D-glucopyranoside in Step 1 and 2-aminoethyl α-L-fucopyranoside for 2-aminoethyl α-D-mannopyranoside in Step 2, respectively.
UPLC-MS Method A: m/z=1169.5745 (z=1); $t_R$=2.17 min.

Example 16: 2,5-dioxopyrrolidin-1-yl (7S,10S,13S)-4,9,12,15-tetraoxo-10,13-bis[3-oxo-3-({2-[(α-D-mannopyranosyl)oxy]ethyl} amino)propyl]-1-[(α-D-mannopyranosyl)oxy]-7-({2-[(α-D-mannopyranosyl)oxy]ethyl} carbamoyl)-3,8,11,14-tetraazaicosan-20-oate (ML-16)
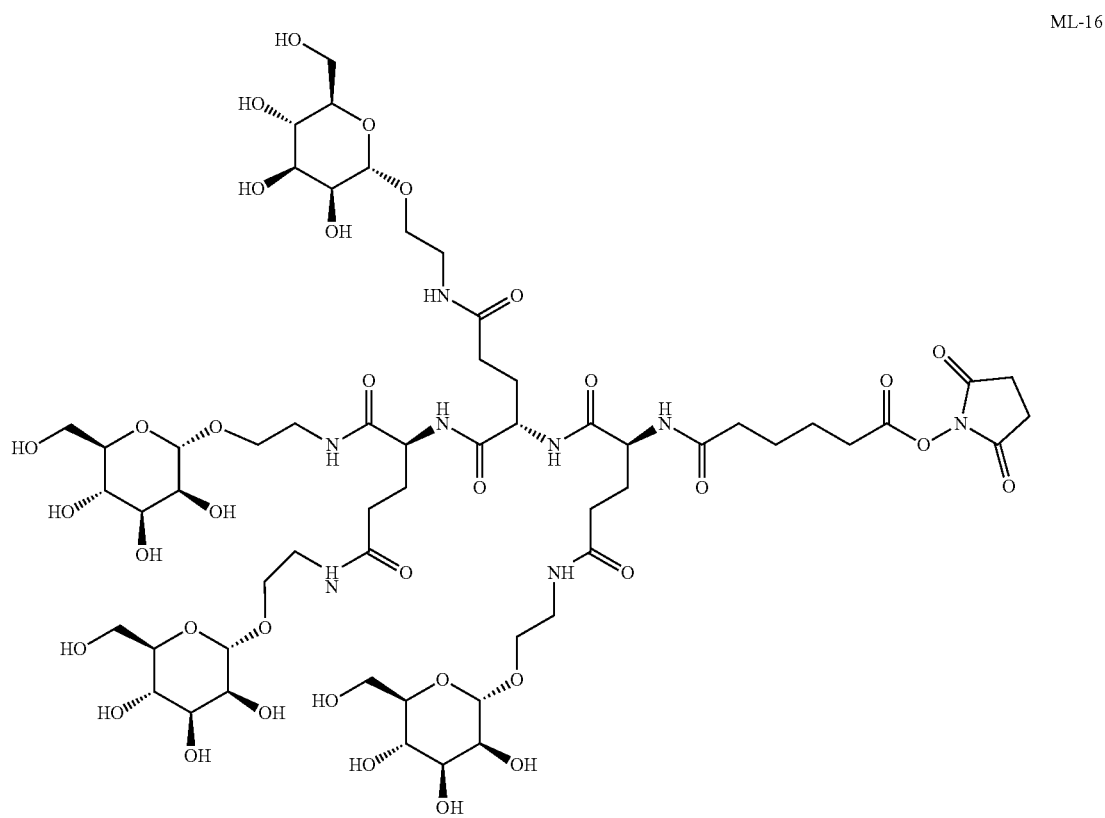 [SMILES: O=C(CC[C@H](NC(=O)CCCCC(=O)ON1C(=O)CCC1=O)C(=O)N[C@@H](CCC(=O)NCCO[C@H]1O[C@H](CO)[C@@H](O)[C@H](O)[C@@H]1O)C(=O)N[C@@H](CCC(=O)NCCO[C@H]1O[C@H](CO)[C@@H](O)[C@H](O)[C@@H]1O)C(=O)NCCO[C@H]1O[C@H](CO)[C@@H](O)[C@H](O)[C@@H]1O)NCCO[C@H]1O[C@H](CO)[C@@H](O)[C@H](O)[C@@H]1O]
ML-16
The title compound was prepared using procedures analogous to those described for ML-1 substituting H-Glu-Glu-Glu-OH for H-Glu-Asp-OH in Step 1. UPLC-MS Method A: m/z=1451.1 (z=1); $t_R$ 1.11 min.

Example 17: 2,5-dioxopyrrolidin-1-yl (7S,10S,13S)-4,9,12,15-tetraoxo-10,13-bis[3-oxo-3-({2-[(α-L-fucopyranosyl)oxy]ethyl}amino) propyl]-1-[(α-L-fucopyranosyl)oxy]-7-({2-[(α-L-fucopyranosyl)oxy]ethyl}carbamoyl)-3,8,11,14-tetraazaicosan-20-oate (ML-17)

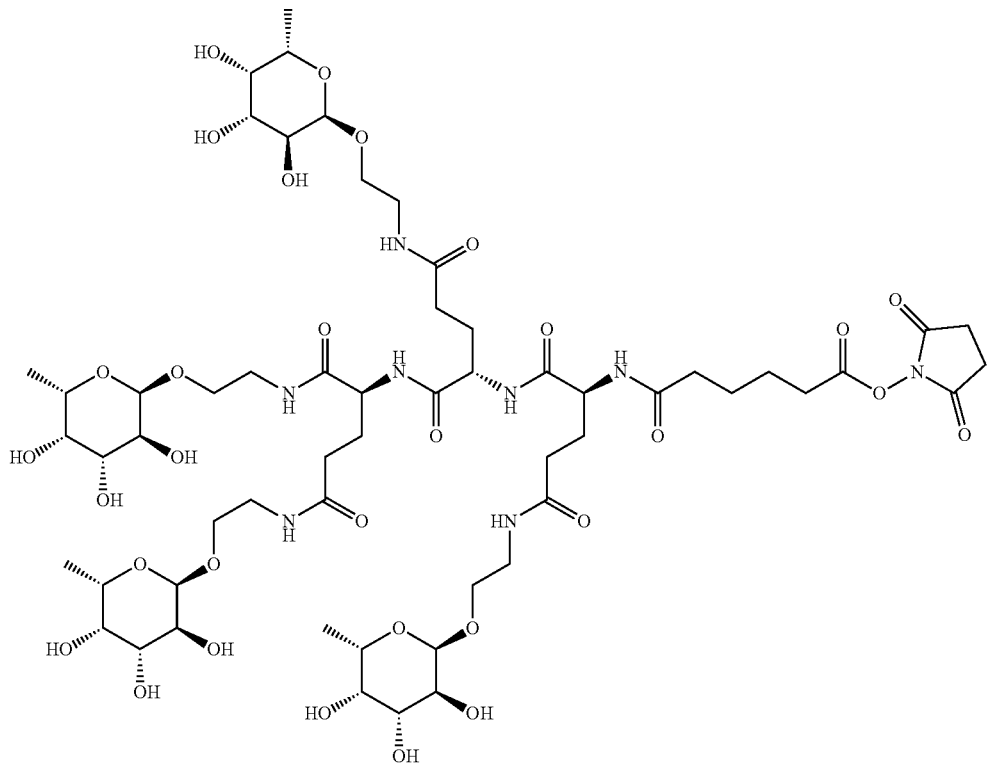

ML-17

The title compound was prepared using procedures analogous to those described for ML-1 substituting H-Glu-Glu-Glu-OH for H-Glu-Asp-OH in Step 1 and 2-aminoethyl α-L-fucopyranoside for 2-aminoethyl α-D-mannopyranoside in Step 2, respectively. UPLC-MS Method A: m/z=1387.4 (z=1); $t_R$=1.93 min.

Example 18: 2,5-dioxopyrrolidin-1-yl (7S,10S,13S)-4,9,12,15-tetraoxo-10,13-bis[3-oxo-3-({2-[(α-D-mannopyranosyl)oxy]ethyl}amino)propyl]-1-[(α-D-mannopyranosyl)oxy]-7-{[2-({α-D-mannopyranosyl-(1→3)-[α-D-mannopyranosyl-(1→6)]-α-D-mannopyranosyl}oxy) ethyl]carbamoyl}-3,8,11,14-tetraazaicosan-20-oate (ML-18)
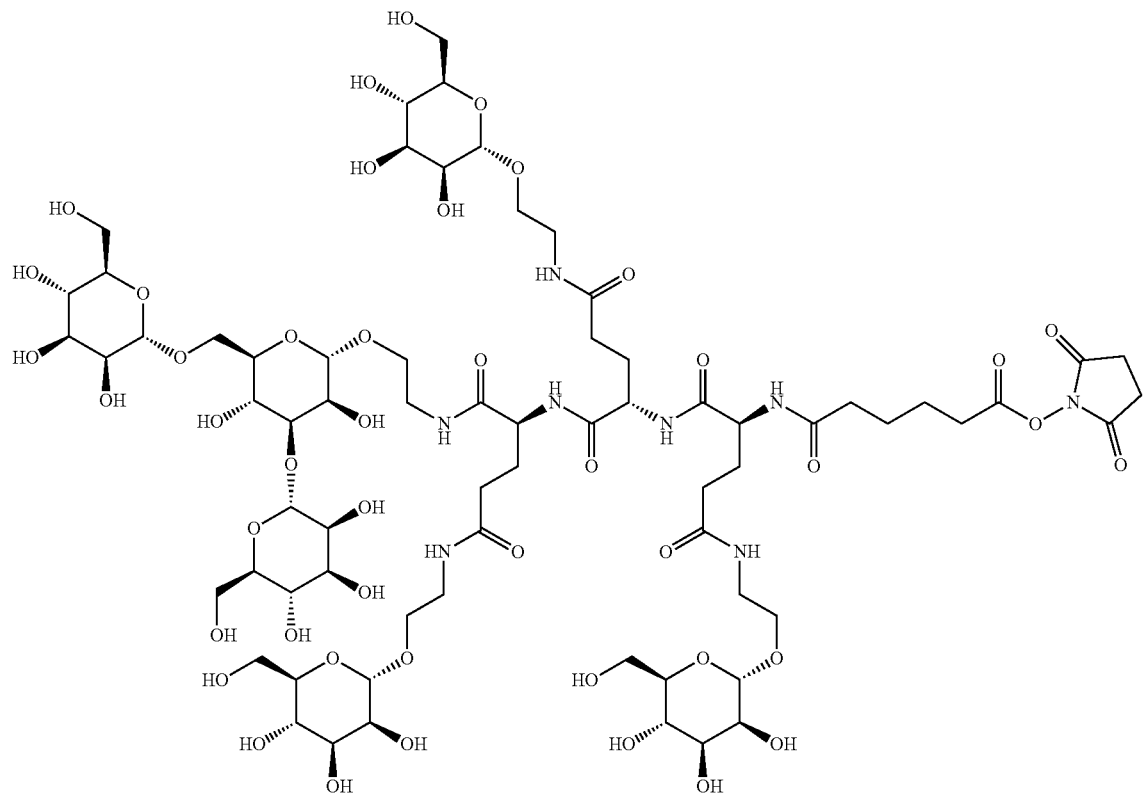
ML-18

Step 1. Tert-butyl (6S,9S,12S)-6,9-bis[3-(tert-butoxy)-3-oxopropyl]-2,2-dimethyl-4,7,10-trioxo-12-{[2-({α-D-mannopyranosyl-(1→3)-[α-D-mannopyranosyl-(1→6)]-α-D-mannopyranosyl}oxy)ethyl]carbamoyl}-3-oxa-5,8,11-triazapentadecan-15-oate To a solution of Boc-Glu(OtBu)-Glu(OtBu)-Glu(OtBu) (1.80 g, 2.67 mmol) in DMF (30 mL) at 0° C. was added EDC (1.02 g, 5.34 mmol) and HOBt (205 mg, 1.336 mmol) and, after 30 min, a suspension of 2-({α-D-mannopyranosyl-(1→3)-[α-D-mannopyranosyl-(1→6)]-α-D-mannopyranosyl}oxy)ethan-1-amine (3.06 g, 3.21 mmol). After stirring at rt overnight, the mixture was concentrated, and the residue was purification by reverse phase prep HPLC (C-4 column, 50×250 cm, 85 mL/min, gradient from 20% to 90% in 20 min) (Water with 0.1% TFA and MeCN with 0.1% TFA). UPLC-MS Method A: m/z=1203.393 (z=1); $t_R$=3.56 min.

Step 2. (S)-4-amino-5-{[(S)-4-carboxy-]-{[(S)-4-carboxy-]-oxo-1-{[2-({α-D-mannopyranosyl-(1→3)-[α-D-mannopyranosyl-(1→6)]-α-D-mannopyranosyl}oxy)ethyl]amino}butan-2-yl]amino}-1-oxobutan-2-yl]amino}-5-oxopentanoic Acid To a round bottom flask containing tert-butyl (6S,9S,12S)-6,9-bis[3-(tert-butoxy)-3-oxopropyl]-2,2-dimethyl-4,7,10-trioxo-12-{[2-({α-D-mannopyranosyl-(1→3)-[α-D-mannopyranosyl-(1→6)]-α-D-mannopyranosyl}oxy)ethyl]carbamoyl}-3-oxa-5,8,11-triazapentadecan-15-oate (1.20 g, 0.997 mmol) at 0° C. was added TFA (5 mL, 64.9 mmol). The mixture was stirred at 0° C. for 60 min and concentrated. The residue was dissolved in H₂O (10 mL), and the resulting mixture was freeze-dried to give the title compound. UPLC-MS Method A: m/z=935.249 (z=1); $t_R$=1.01 min.

Step 3. (10S,13S,16S)-10,13-bis(2-carboxyethyl)-3,8,11,14-tetraoxo-1-phenyl-16-{[2-({α-D-mannopyranosyl-(1→3)-[α-D-mannopyranosyl-(1→6)]-α-D-mannopyranosyl}oxy)ethyl]carbamoyl}-2-oxa-9,12,15-triazanonadecan-19-oic Acid To a solution of (S)-4-amino-5-{[(S)-4-carboxy-1-{[(S)-4-carboxy-1-oxo-1-{[2-({α-D-mannopyranosyl-(1→3)-[α-D-mannopyranosyl-(1→6)]-α-D-mannopyranosyl}oxy)ethyl]amino}butan-2-yl]amino}-1-oxobutan-2-yl]amino}-5-oxopentanoic acid (1.05 g, 1.119 mmol) in DMF (20 mL) at 0° C. was added benzyl (2,5-dioxopyrrolidin-1-yl) adipate (392 mg, 1.175 mmol) in DMF (3 mL) portionwise over 15 min and then TEA (312 μL, 2.238 mmol) dropwise over 10 min. The resulting mixture was stirred at rt over weekend. Insoluble material was removed by filtration, and the filtrate was concentrated. The residue was purified by reverse phase prep HPLC (C-4 column, 50×250 cm, 85 mL/min, gradient from 15% to 40% in 20 min) (Water with 0.1% TFA and MeCN with 0.1% TFA) to give the title compound. UPLC-MS Method: m/z=1153.385 (z=1); $t_R$=3.08 min. 5 min run.

Step 4. benzyl (7S,10S,13S)-4,9,12,15-tetraoxo-10,13-bis[3-oxo-3-({2-[(α-D-mannopyranosyl) oxy]ethyl}amino)propyl]-1-[(α-D-mannopyranosyl)oxy]-7-{[2-({α-D-mannopyranosyl-(1→3)-[α-D-mannopyranosyl-(1→6)]-α-D-mannopyranosyl}oxy)ethyl]carbamoyl}-3,8,11,14-tetraazaicosan-20-oate To a solution of (10S,13S,16S)-10,13-bis(2-carboxyethyl)-3,8,11,14-tetraoxo-1-phenyl-16-{[2-({α-D-mannopyranosyl-(1→3)-[α-D-mannopyranosyl-(1→6)]-α-D-mannopyranosyl}oxy)ethyl]carbamoyl}-2-oxa-9,12,15-triazanonadecan-19-oic acid (544 mg, 0.873 mmol) in DMF (5.0 mL) at 0° C. was added EDC (185 mg, 0.964 mmol), HOBt (74 mg, 0.482 mmol) and, after 30 min, a suspension of 2-aminoethyl α-D-mannopyranoside (215 mg, 0.964 mmol) in DMF (5.0 mL). After stirring at rt overnight, the mixture was concentrated, and the residue was purified by reverse phase prep HPLC (C-4 column, 50×250 cm, 85 mL/min, gradient from 10% to 17% in 17 min). (Water with 0.1% TFA and MeCN with 0.1% TFA) to give the title compound. UPLC-MS Method A: m/z/=1769.228 (z=1); $t_R$=2.42 min.

Step 5. 2,5-dioxopyrrolidin-1-yl (7S,10S,13S)-4,9,12,15-tetraoxo-10,13-bis[3-oxo-3-({2-[(α-D-mannopyranosyl)oxy]ethyl}amino)propyl]-1-[(α-D-mannopyranosyl)oxy]-7-{[2-({α-D-mannopyranosyl-(1→3)-[α-D-mannopyranosyl-(1-6)]-α-D-mannopyranosyl}oxy)ethyl]carbamoyl}-3,8,11,14-tetraazaicosan-20-oate The title compound was prepared using procedures analogous to those described for ML-1 substituting benzyl (7S,10S,13S)-4,9,12,15-tetraoxo-10,13-bis[3-oxo-3-({2-[(α-D-mannopyranosyl)oxy]ethyl}amino)propyl]-1-[(α-D-mannopyranosyl)oxy]-7-{[2-({α-D-mannopyranosyl-(1→3)-[α-D-mannopyranosyl-(1-6)]-α-D-mannopyranosyl}oxy)ethyl]carbamoyl}-3,8,11,14-tetraazaicosan-20-oate for benzyl 6-{[(S)-5-{[(S)-1,5-dioxo-1,5-bis({2-[(α-D-mannopyranosyl)oxy]ethyl}amino)pentan-2-yl]amino}-1,5-dioxo-1-({2-[(α-D-mannopyranosyl)oxy]ethyl}amino)pentan-2-yl]amino}-6-oxohexanoate in Step 3. UPLC-MS Method A: m/z=1776.461 (z=1); $t_R$=1.11 min.

Example 19: 2,5-dioxopyrrolidin-1-yl (14S,19S,24S)-4,11,16,21,26-pentaoxo-14,19,24-tris[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-1-({α-D-mannopyranosyl-(1→3)-[α-D-mannopyranosyl-(1→6)]-α-D-mannopyranosyl}oxy)-3,10,15,20,25-pentaazahentriacontan-31-oate (ML-19)

ML-19

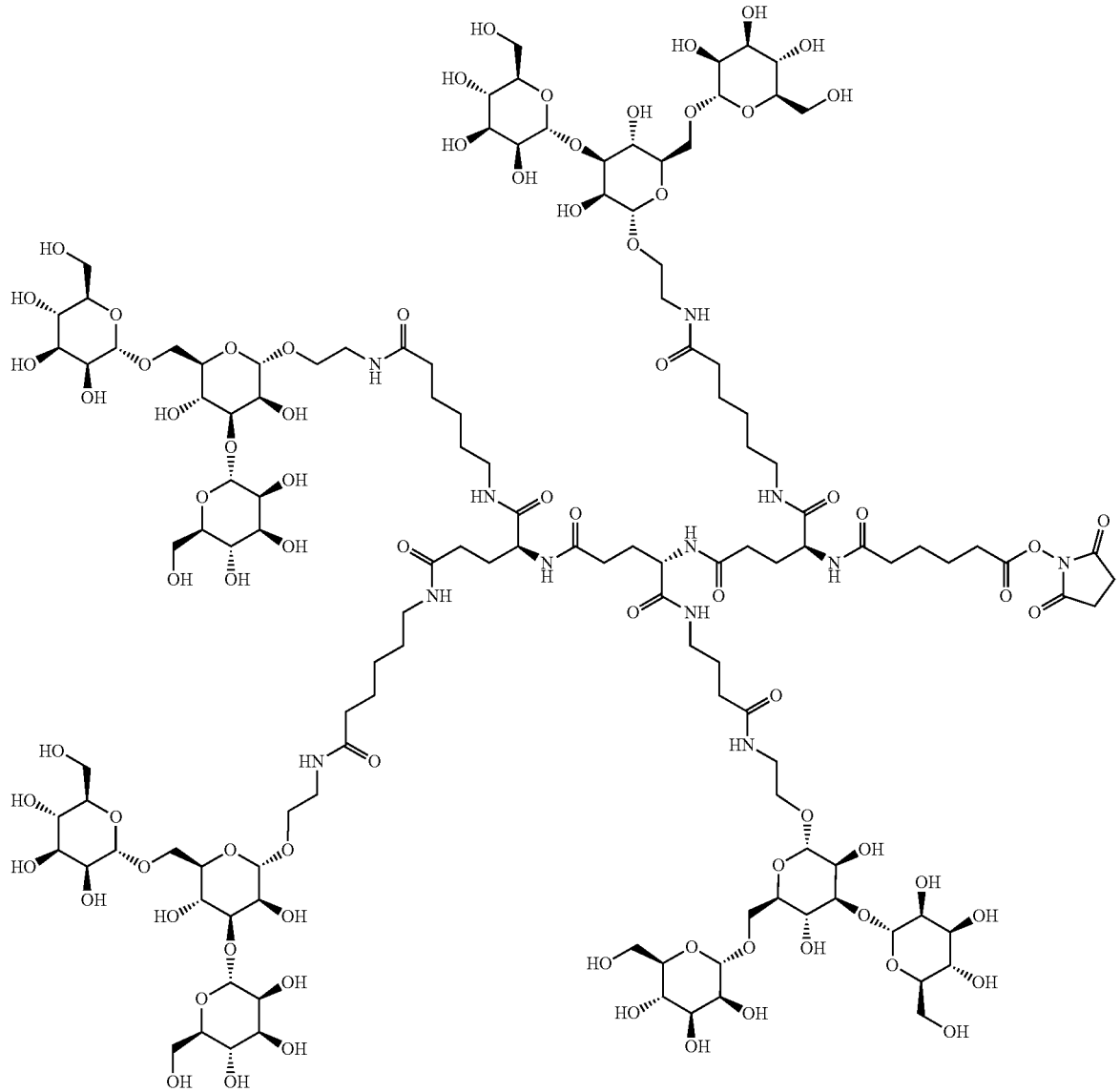

The title compound was prepared using procedures analogous to those described for ML-1 substituting {(S)-4-[(S)-4-amino-4-carboxybutanamido]-4-carboxybutanoyl}-L-glutamic acid for H-Glu-Asp-OH in Step 1 and 6-amino-N-[2-({α-D-mannopyranosyl-(1→3)-[α-D-mannopyranosyl-(1→6)]-α-D-mannopyranosyl}oxy)ethyl]hexanamide for 2-aminoethyl α-D-mannopyranoside in Step 2, respectively. UPLC-MS Method A: m/z=1601.445 (z=2); $t_R$=2.82 min.

Example 20: 2,5-dioxopyrrolidin-1-yl (7S,12S,17S, 22S)-4,9,14,19,24-pentaoxo-1-[(α-L-fucopyranosyl) oxy]-7,12,17,22-tetrakis({2-[(α-L-fucopyranosyl) oxy]ethyl}carbamoyl)-3,8,13,18,23-pentaazanona- cosan-29-oate (ML-20)

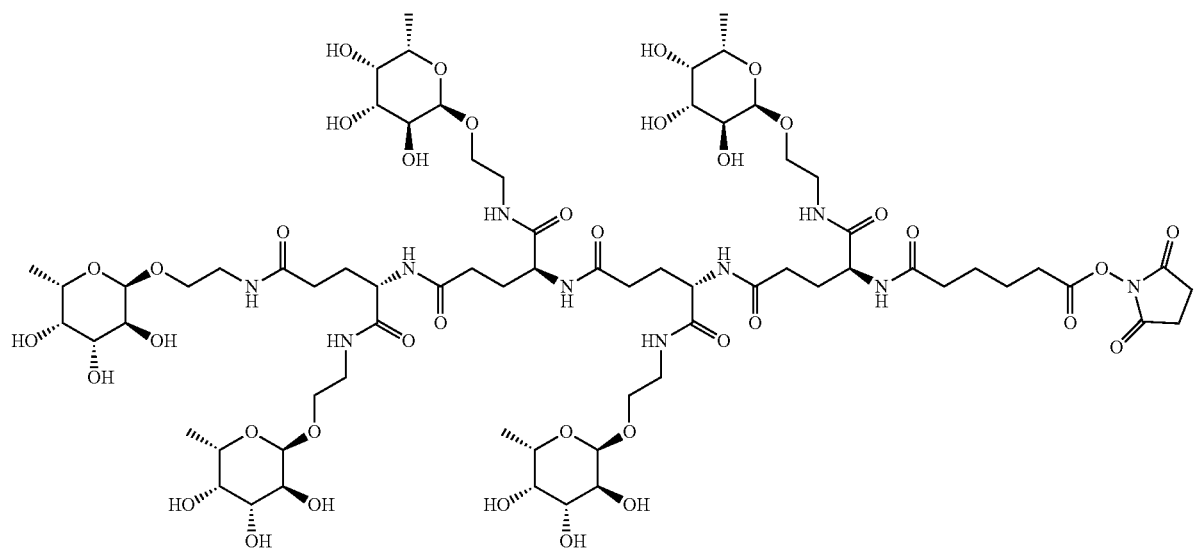

ML-20

The title compound was prepared using procedures analogous to those described for ML-1 substituting {(S)-4-[(S)-4-amino-4-carboxybutanamido]-4-carboxybutanoyl}-L-glutamic acid for H-Glu-Asp-OH in Step 1 and 2-aminoethyl α-L-fucopyranoside for 2-aminoethyl α-D-mannopyranoside in Step 2, respectively. UPLC-MS Method A: m/z=1705.785 (z=1); $t_R$=1.75 min.

Example 21: 2,5-dioxopyrrolidin-1-yl (14S,19S)-1-
({α-D-mannopyranosyl-(1→3)-[α-D-mannopyrano-
syl-(1→6)]-α-D-mannopyranosyl}oxy)-14,19-bis
[(6-{[2-({α-D-mannopyranosyl-(1→3)-[α-D-
mannopyranosyl-(1→6)]-α-D-mannopyranosyl}oxy)
ethyl]amino}-6-oxohexyl)carbamoyl]-4,11,16,21,24-
pentaoxo-3,10,15,20,23-pentaazanonacosan-29-oate
(ML-21)

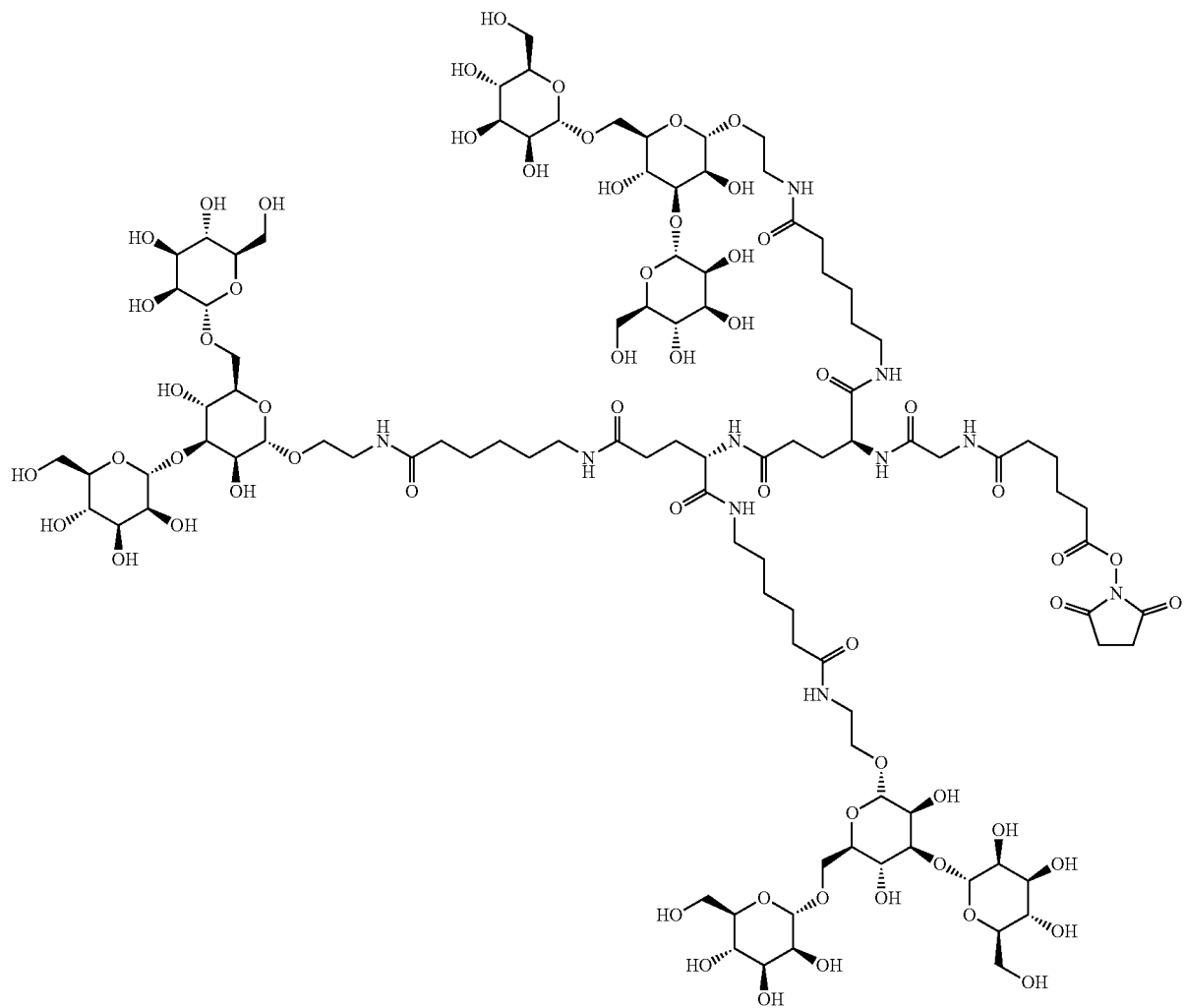

ML-21

The title compound was prepared using procedures analogous to those described for ML-1 substituting H-Gly-γGlu-Glu-OH for H-Glu-Asp-OH in Step A and 6-amino-N-[2-({α-D-mannopyranosyl-(1→3)-[α-D-mannopyranosyl-(1→6)]-α-D-mannopyranosyl}oxy)ethyl]hexanamide for 2-aminoethyl α-D-mannopyranoside in Step 2, respectively.
UPLC-MS Method A: m/z=1244.06 (z=2); $t_R$=3.88 min.

Example 22: 2,5-dioxopyrrolidin-1-yl (14S,19S)-14-
{[6-(bis{2-[(α-D-mannopyranosyl) oxy]
ethyl}amino)-6-oxohexyl]carbamoyl}-4,11,16,21,
24-pentaoxo-19-[(6-oxo-6-{[2-({α-D-
mannopyranosyl-(1→3)-[α-D-mannopyranosyl-
(1→6)]-α-D-mannopyranosyl}oxy)ethyl]
amino}hexyl)carbamoyl]-1-[(α-D-mannopyranosyl)
oxy]-3-{2-[(α-D-mannopyranosyl)oxy]ethyl}-3,10,
15,20,23-pentaazanonacosan-29-oate (ML-22)

ML-22

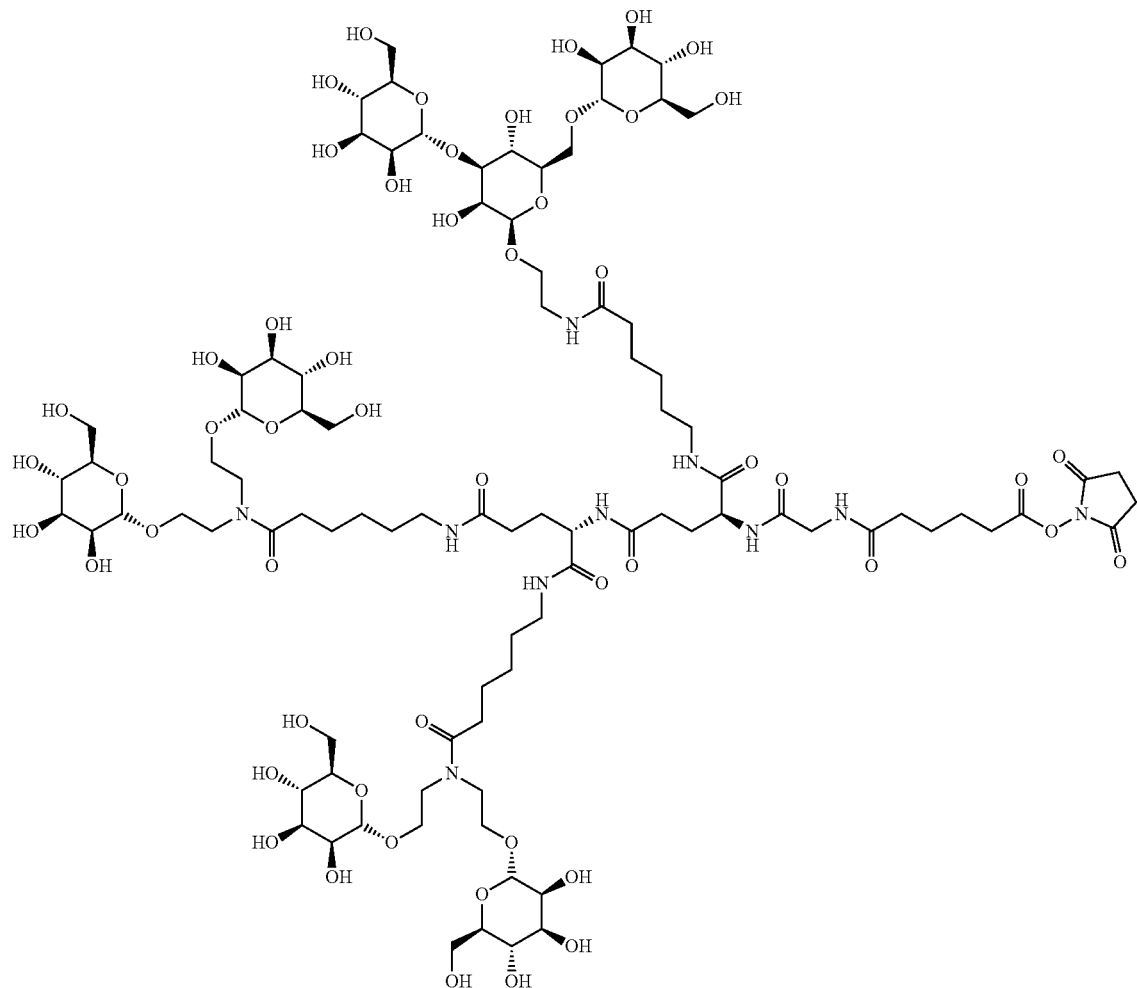

The title compound was prepared using procedures analogous to those described for ML-5 substituting 6-amino-N-[2-({α-D-mannopyranosyl-(1→3)-[α-D-mannopyranosyl-(1→6)]-α-D-mannopyranosyl} oxy)ethyl]hexanamide for 6-amino-N-[2-({α-D-mannopyranosyl-(1→3)-[α-D-mannopyranosyl-(1→6)]-α-D-mannopyranosyl}oxy)ethyl] hexanamide in Step 4. UPLC-MS Method A: m/z=1077.5947 (z=2); $t_R$=3.94 min.

Example 23: 2,5-dioxopyrrolidin-1-yl (21S,24S)-21-[6-(2-{[2-(bis{2-[(α-D-mannopyranosyl)oxy]ethyl}amino)-2-oxoethyl][2-({2-[(α-L-fucopyranosyl)oxy]ethyl}amino)-2-oxoethyl]amino}acetamido)hexanamido]-6-[2-({2-[(α-L-fucopyranosyl)oxy]ethyl}amino)-2-oxoethyl]-24-(6-[2-({2-[(α-L-fucopyranosyl)oxy]ethyl}amino)-2-oxoethyl]-4,8,15-trioxo-1-[(α-D-mannopyranosyl)oxy]-3-{2-[(α-D-mannopyranosyl)oxy]ethyl}-3,6,9,16-tetraazaicosan-20-yl)-4,8,15,22,25-pentaoxo-1-[(α-D-mannopyranosyl)oxy]-3-{2-[(α-D-mannopyranosyl)oxy]ethyl}-3,6,9,16,23,26-hexaazadotriacontan-32-oate (ML-23)

Step 1. N-(2-{[6-(benzyloxy)-6-oxohexyl]amino}-2-oxoethyl)-N-[2-(bis{2-[(2,3,4,6-tetra-O-acetyl-α-D-mannopyranosyl)oxy]ethyl}amino)-2-oxoethyl]glycine To a suspension of 2,2'-[(2-{[6-(benzyloxy)-6-oxohexyl]amino}-2-oxoethyl)azanediyl]diacetic acid (0.50 g, 1.27 mmol) in DCM (4.0 mL) at 0° C. was added TFAA (213 µL, 1.585 mmol). After stirring at 0° C. for 3 hr, the mixture was cooled to −30° C., to which was added a solution of TEA (424 µL, 3.04 mmol) in DMF (2.0 mL) and, after 30 min, a solution of bis{2-[(2,3,4,6-tetra-0-acetyl-α-D-mannopyranosyl)oxy]ethyl}amine (971 mg, 1.268 mmol) in DMF (8.0 mL) dropwise. The reaction mixture was allowed to warm over a period of 2 hr to rt and concentrated. The residue was purified by chromatography (120 g SiO$_2$ column, flow 100 mL/min, gradient solvent A-solvent B of 0-30% solvent B in 30 min followed by hold, where solvent A was EtOAc/MeOH/CH$_3$CN/H$_2$O (v/v/v/v=6/1/1/1, and solvent B was EtOAc/MeOH/CH$_3$CN/H$_2$O (v/v/v/v=2/1/1/1) to give the title compound. UPLC Method A: m/z=1142.24 (z=1); t$_R$=4.49 min.

ML-23

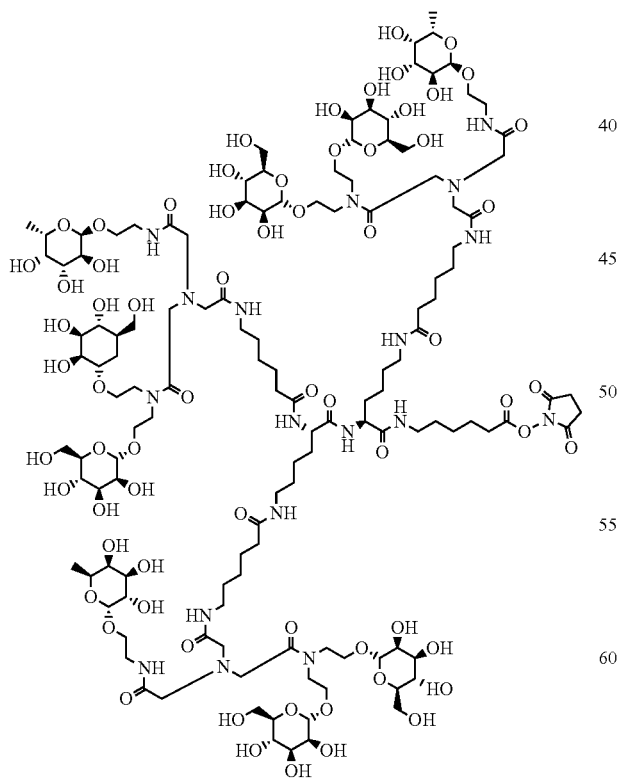

Step 2. Benzyl 6-(2-{[2-(bis{2-[(2,3,4,6-tetra-O-acetyl-α-D-mannopyranosyl)oxy]ethyl}amino)-2-oxoethyl][2-({2-[(α-L-fucopyranosyl)oxy]ethyl}amino)-2-oxoethyl]amino}acetamido)hexanoate To a solution of N-(2-{[6-(benzyloxy)-6-oxohexyl]amino}-2-oxoethyl)-N-[2-(bis{2-[(2,3,4,6-tetra-O-acetyl-α-D-mannopyranosyl)oxy]ethyl}amino)-2-oxoethyl]glycine (1.26 g, 1.103 mmol) and 2-aminoethyl α-L-fucopyranoside (297 mg, 1.434 mmol) in DMF (16 mL) was added DIPEA (578 µL, 3.31 mmol), HOBt (169 mg, 1.103 mmol) and EDC (317 mg, 1.655 mmol). After stirring at rt overnight, the reaction mixture was concentrated. The residue was purified by chromatography (120 g C18 silica gel column, flow rate=50 mL/min; gradient 0-80% AcCN/H$_2$O in 40 min) to give the title compound. UPLC Method A: m/z=1331.54 (z=1); t$_R$=3.31 min.

Step 3. 6-(2-{[2-(bis{2-[(α-D-mannopyranosyl)oxy]ethyl}amino)-2-oxoethyl][2-({2-[(α-L-fucopyranosyl)oxy]ethyl}amino)-2-oxoethyl]amino}acetamido)hexanoic Acid To a solution of benzyl 6-(2-{[2-(bis{2-[(2,3,4,6-tetra-O-acetyl-α-D-mannopyranosyl) oxy]ethyl}amino)-2-oxoethyl][2-({2-[(α-L-fucopyranosyl)oxy]ethyl}amino)-2-oxoethyl]amino}acetamido)hexanoate (980 mg, 0.736 mmol) in $CH_3OH$ (10.0 mL) was added sodium methoxide (30% wt in MeOH) (40 mg, 0.221 mmol). After stirring at rt overnight, UPLC-MS analysis of an aliquot of reaction mixture indicated removal of acyl groups and concomitant transesterification of benzyl to methyl (UPLC Method A: m/z=919.45 (z=1); $t_R$=1.75 min). The reaction mixture was concentrated, re-dissolved in $H_2O$ (5.0 mL) and treated with 5M NaOH (294 μL, 1.472 mmol). After 2 hr, the reaction mixture was neutralized with 1M HCl and freeze-dried to give the title compound. UPLC Method A: m/z=905.43 (z=1); $t_R$=1.4 min.

Step 4. N2-[N2,N6-bis(tert-butoxycarbonyl]-L-lysyl)-N6-(tert-butoxycarbonyl)-L-lysine To a solution of L-lysyl-L-lysine dihydrochloride (1.00 g, 2.88 mmol) in a mixture of 1,4-dioxane (19.2 mL) and 1M NaOH (8.64 mL, 8.64 mmol) at rt was added BOC-anhydride (2.67 g, 11.52 mmol). After stirring overnight, the mixture was partitioned between EtOAc (50 mL) and a solution of citric acid (6.64 g, 34.6 mmol) in water (100 mL). The aqueous phase was separated and extracted with EtOAc. The organic phases were combined, washed with brine, dried over $Na_2SO_4$ and concentrated. The residue was purified by chromatography (40 g $SiO_2$ column, flow rate 40 mL/min, gradient solvent A-solvent B of 0-50% solvent B in 30 min. followed by hold, where solvent A was EtOAc and solvent B was EtOAc/MeOH/AcCN/$H_2O$ (v/v/v/v=6/1/1/1) to give the title compound. UPLC Method D: m/z=575.4 (z=1); $t_R$=4.19 min.

Step 5. Benzyl (10S,13S)-10-[(tert-butoxycarbonyl)amino]-13-{4-[(tert-butoxycarbonyl)amino]butyl}-2,2-dimethyl-4,11,14-trioxo-3-oxa-5,12,15-triazahenicosan-21-oate To a solution of N2-[N2,N6-bis(tert-butoxycarbonyl]-L-lysyl)-N6-(tert-butoxycarbonyl)-L-lysine (2.00 g, 3.48 mmol) and 6-(benzyloxy)-6-oxohexan-1-aminium 4-methylbenzene sulfonate (2.054 g, 5.22 mmol) in DMF (17.0 mL) was added DIPEA (2.73 mL, 15.66 mmol), HOBt (799 mg, 5.22 mmol) and EDC (1.001 g, 5.22 mmol). After stirring overnight, the reaction mixture was partitioned between a mixture of EtOAc/hexanes (v/v=2:1, 200 mL) and 1M HCl (100 mL). The organic layer was separated and washed with saturated $NaHCO_3$ and brine, dried over $Na_2SO_4$ and evaporated. The title material was isolated by chromatography (40 g $SiO_2$ column, flow rate 40 mL/min, gradient 0-100% of EtOAc in hexanes in 30 min followed by 10 min hold with 100% EtOAc). UPLC Method D: m/z=778.52 (z=1); $t_R$=4.79 min.

Step 6. Benzyl 6-{(S)-6-amino-2-[(S)-2,6-diaminohexanamido]hexanamido}hexanoate To a solution of benzyl (10S,13S)-10-[(tert-butoxycarbonyl)amino]-13-{4-[(tert-butoxycarbonyl)amino]butyl}-2,2-dimethyl-4,11,14-trioxo-3-oxa-5,12,15-triazahenicosan-21-oate (1.89 g, 2.429 mmol) in DCM (18 mL) was added TFA (19 mL, 243 mmol). After stirring at rt for 5 hr, the mixture was concentrated. The title material was isolated by chromatography (125 g C18 silica gel column, flow rate=60 mL/min, gradient 0-40% AcCN/$H_2O$ in 30 min, followed by column wash with 100% AcCN over 10 min). UPLC Method D: m/z=478.39 (z=1); $t_R$=2.85 min.

Step 7. 2,5-dioxopyrrolidin-1-yl (21S,24S)-21-[6-(2-{[2-(bis{2-[(α-D-mannopyranosyl)oxy]ethyl}amino)-2-oxoethyl][2-({2-[(α-L-fucopyranosyl)oxy]ethyl}amino)-2-oxoethyl]amino}acetamido)hexanamido]-6-[2-({2-[(α-L-fucopyranosyl)oxy]ethyl}amino)-2-oxoethyl]-24-(6-[2-({2-[(α-L-fucopyranosyl)oxy]ethyl}amino)-2-oxoethyl]-4,8,15-trioxo-1-[(α-D-mannopyranosyl) oxy]-3-{2-[(α-D-mannopyranosyl)oxy]ethyl}-3,6,9,16-tetraazaicosan-20-yl)-4,8,15,22,25-pentaoxo-1-[(α-D-mannopyranosyl)oxy]-3-{2-[(α-D-mannopyranosyl)oxy]ethyl}-3,6,9,16,23,26-hexaazadotriacontan-32-oate The title compound was prepared using procedures analogous to those described for ML-1 substituting 6-(2-{[2-(bis{2-[(α-D-mannopyranosyl)oxy]ethyl}amino)-2-oxoethyl][2-({2-[(α-L-fucopyranosyl)oxy]ethyl}amino)-2-oxoethyl]amino}acetamido)hexanoic acid for {(S)-4-[6-(benzyloxy)-6-oxohexanamido]-4-carboxybutanoyl}-L-glutamic acid and benzyl 6-{(S)-6-amino-2-[(S)-2,6-diaminohexanamido]hexanamido}hexanoate for 2-aminoethyl α-D-mannopyranoside, respectively, in Step 2. UPLC-MS Method A: m/z=1573.74 (z=2); $t_R$=2.06 min.

Example 24: 2,5-dioxopyrrolidin-1-yl (21S,24S)-21-[6-(2-{bis[2-({2-[(α-D-mannopyranosyl)oxy]ethyl}amino)-2-oxoethyl]amino}acetamido) hexanamido]-1-[(α-D-mannopyranosyl)oxy]-24-{1-[(α-D-mannopyranosyl)oxy]-6-[2-({2-[(α-D-mannopyranosyl) oxy]ethyl}amino)-2-oxoethyl]-4,8,15-trioxo-3,6,9,16-tetraazaicosan-20-yl}-6-(2-{[(α-D-mannopyranosyl)oxy]ethyl}amino)-2-oxoethyl)-4,8,15,22,25-pentaoxo-3,6,9,16,23,26-hexaazadotriacontan-32-oate (ML-24)

ML-24

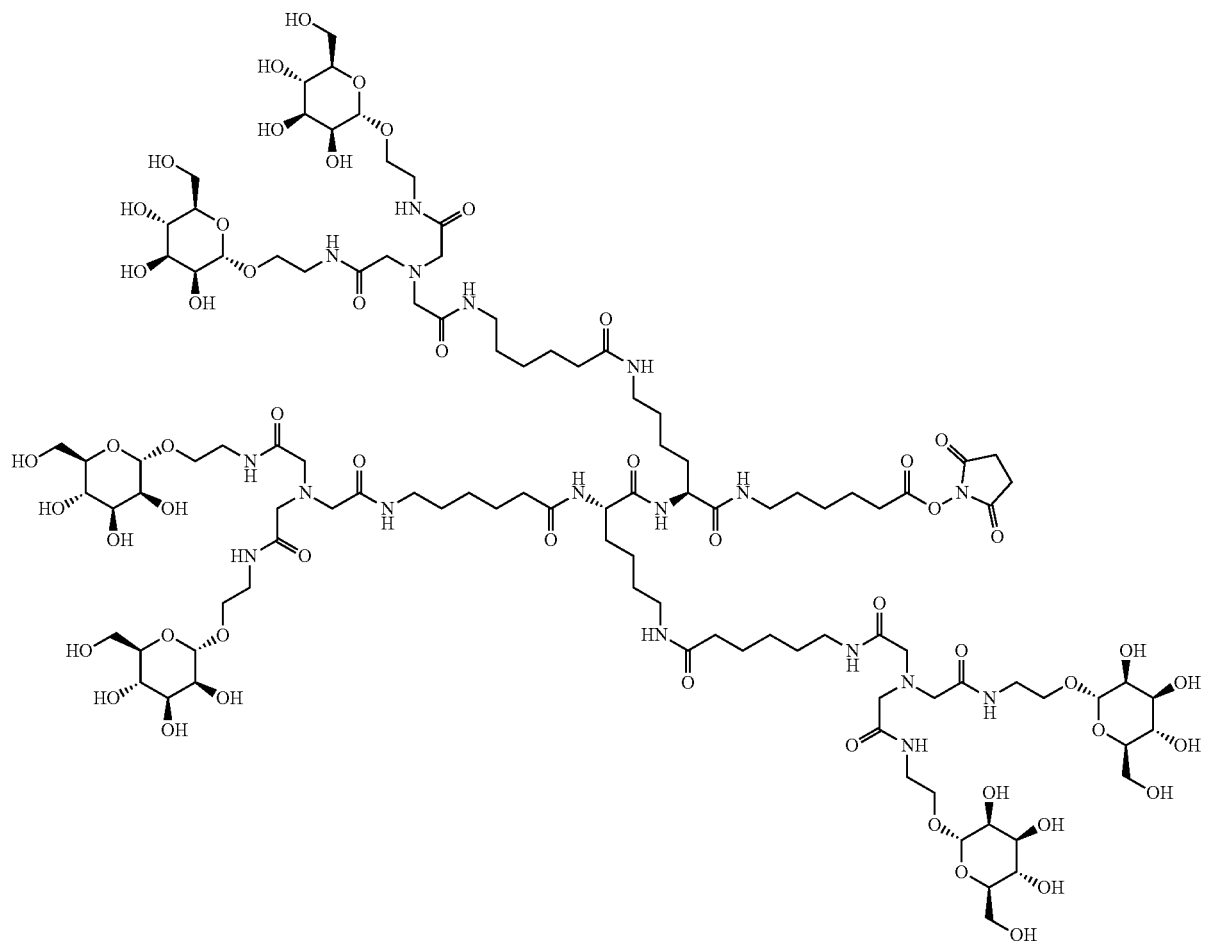

Step 1. Benzyl 6-(2-{bis[2-oxo-2-({2-[(α-D-mannopyranosyl)oxy]ethyl}amino)ethyl]amino}acetamido) hexanoate To a solution of 2,2'-[(2-{[6-(benzyloxy)-6-oxohexyl]amino}-2-oxoethyl)azanediyl]diacetic acid (1.00 g, 2.54 mmol) and 2-aminoethyl α-D-mannopyranoside (1.70 g, 7.61 mmol) in DMF (8.45 mL) at rt was added DIPEA (2.66 mL, 15.21 mmol), HOBt (1.17 g, 7.61 mmol) and EDC (1.46 g, 7.61 mmol). After stirring overnight, the reaction mixture was concentrated. The title compound was isolated by chromatography (300 g C18 silica gel column, gradient 0-40% AcCN/H$_2$O over 40 min, flow rate 100 mL/min). UPLC-MS Method A: m/z=805.4 (z=1); t$_R$=2.97 min.

Step 2. 6-(2-{bis[2-oxo-2-({2-[(α-D-mannopyranosyl)oxy]ethyl}amino)ethyl]amino}acetamido) hexanoic Acid To a solution of benzyl 6-(2-{bis[2-oxo-2-({2-[(α-D-mannopyranosyl)oxy]ethyl}amino)ethyl]amino}acetamido) hexanoate (330 mg, 0.410 mmol) in H$_2$O (50 mL) was added Pd(OH)$_2$ (115 mg, 0.164 mmol). The mixture was degassed and shaken on a Parr shaker under 344.74 kPa of H$_2$. After 3 hr, catalyst was filtered off through a cake of CELITE® and washed with H$_2$O. The filtrate was freeze-dried to give the title compound. UPLC-MS Method A: m/z=715.39 (z=1); t$_R$=1.04 min.

Step 3. 2,5-dioxopyrrolidin-1-yl 6-(2-{bis[2-oxo-2-({2-[(α-D-mannopyranosyl)oxy]ethyl}amino)ethyl]amino}acetamido)hexanoate To a solution of 6-(2-{bis[2-oxo-2-({2-[(α-D-mannopyranosyl)oxy]ethyl}amino)ethyl]amino}acetamido)hexanoic acid (300 mg, 0.420 mmol) in DMF (5 mL) at 0° C. was added TSTU (126 mg, 0.420 mmol) in DMF (5 mL) and, after 15 min, DIPEA (73 µL, 0.420 mmol). After 1 hr, the reaction mixture was added dropwise into AcCN (70 mL). Precipitate was collected by centrifugation (3500 rpm, 15 min, 4° C.) and dried to give the title compound. UPLC-MS Method A: m/z=812.39 (z=1); $t_R$=2.65 min.

Step 4. 6-{(S)-6-amino-2-[(S)-2,6-diaminohexanamido]hexanamido}hexanoic Acid To a solution of H-Lys(Z)-OMe hydrochloride (4.0 g, 12.09 mmol), Z-Lys(Z)—OH (5.61 g, 13.54 mmol) and HOBt (1.863 g, 13.78 mmol) in DCM (50 mL) and NMM (1.5 mL) at rt was added a suspension of EDC (3.94 g, 20.56 mmol) and NMM (2 mL) in DCM (50 mL) over 10 min. After stirring overnight, the reaction mixture was concentrated.

To a solution of aforementioned in MeOH/EtOH (v/v=1/1, 100 mL) was added 1N NaOH (15 mL). After 45 min, the hydrolysis was complete, and the pH of the resulting mixture was adjusted to ~7.0 using HCl. Solids were filtered off, and the filtrate was concentrated.

To a solution of the aforementioned (7.0 g, 10.34 mmol) and 6-(benzyloxy)-6-oxohexan-1-aminium 4-methylbenzenesulfonate (4.88 g, 12.41 mmol) in DMF (200 mL) at rt was add HOBt (1.69 g, 12.41 mmol), EDC (2.379 g, 12.41 mmol) and DIPEA (3.66 mL, 20.69 mmol). After stirring at rt for 4 h, to the reaction mixture was added $H_2O$ (5-6 times volume of the mixture). After stirring at 0° C. for 1 hr, the precipitate was collected and washed with sufficient $H_2O$ through filtration. The solids were dissolved in MeOH, and the resulting solution was partitioned between EtOAC (500 mL) and 1N HCl (300 mL). The organic layer was washed with saturated $NaHCO_3$ (300 mL), dried over $Na_2SO_4$ and concentrated. The residue was purified on 220 g silica gel with hexanes/EtOAc 0-100% over 60 min.

A slurry of the aforementioned (6.0 g, 6.82 mmol) in IPA (100 mL) and Pd(OH)$_2$ (957 mg, 6.82 mmol) was degassed and shaken on a Parr shaker under 344.74 kPa of $H_2$. After overnight, catalyst was filtered off through a pad of CELITE® and washed with water. The filtrate was freeze-dried to give the title compound.

Step 5. (21S,24S)-21-[6-(2-{bis[2-({2-[(α-D-mannopyranosyl)oxy]ethyl}amino)-2-oxoethyl]amino}acetamido)hexanamido]-1-[(α-D-mannopyranosyl)oxy]-24-{1-[(α-D-mannopyranosyl) oxy]-6-[2-({2-[(α-D-mannopyranosyl)oxy]ethyl}amino)-2-oxoethyl]-4,8,15-trioxo-3,6,9,16-tetraazaicosan-20-yl}-6-(2-{[(α-D-mannopyranosyl)oxy]ethyl}amino)-2-oxoethyl)-4,8,15,22,25-pentaoxo-3,6,9,16,23,26-hexaazadotriacontan-32-oic Acid To a solution of 6-{(S)-6-amino-2-[(S)-2,6-diaminohexanamido]hexanamido}hexanoic acid (38 mg, 0.098 mmol) in DMF (10 mL) was added 2,5-dioxopyrrolidin-1-yl 6-(2-{bis[2-oxo-2-({2-[(α-D-mannopyranosyl)oxy]ethyl}amino)ethyl]amino}acetamido)hexanoate (300 mg, 0.420 mmol) and DIPEA (73 µL, 0.420 mmol). After stirring overnight at rt, the reaction mixture was purified by HPLC (C4 column, flow rate=37 mL/min, 210 nm collect fractions, 0 to 15% Ac 15 CN over 30 min) to give the title compound.

Step 6. 2,5-dioxopyrrolidin-1-yl (21S,24S)-21-[6-(2-{bis[2-({2-[(α-D-mannopyranosyl)oxy]ethyl}amino)-2-oxoethyl]amino}acetamido)hexanamido]-1-[(α-D-mannopyranosyl)oxy]-24-{-[(α-D-mannopyranosyl)oxy]-6-[2-({2-[(α-D-mannopyranosyl)oxy]ethyl}amino)-2-oxoethyl]-4,8,15-trioxo-3,6,9,16-tetraazaicosan-20-yl}-6-(2-{[(α-D-mannopyranosyl)oxy]ethyl}amino)-2-oxoethyl)-4,8,15,22,25-pentaoxo-3,6,9,16,23,26-hexaazadotriacontan-32-oate The title compound was prepared using the procedure analogous to that described for ML-1 substituting (21S,24S)-21-[6-(2-{bis[2-({2-[(α-D-mannopyranosyl)oxy]ethyl}amino)-2-oxoethyl]amino}acetamido)hexanamido]-1-[(α-D-mannopyranosyl)oxy]-24-{1-[(α-D-mannopyranosyl)oxy]-6-[2-({2-[(α-D-mannopyranosyl)oxy]ethyl}amino)-2-oxoethyl]-4,8,15-trioxo-3,6,9,16-tetraazaicosan-20-yl}-6-(2-{[(α-D-mannopyranosyl)oxy]ethyl}amino)-2-oxoethyl)-4,8,15,22,25-pentaoxo-3,6,9,16,23,26-hexaazadotriacontan-32-oic acid for 6-{[(S)-5-{[(S)-1,5-dioxo-1,5-bis({2-[(α-D-mannopyranosyl)oxy]ethyl}amino)pentan-2-yl]amino}-1,5-dioxo-1-({2-[(α-D-mannopyranosyl)oxy]ethyl}amino)pentan-2-yl]amino}-6-oxohexanoic acid in Step 4. UPLC-MS Method A: m/z=1288.63 (z=2); $t_R$=1.89 min.

Example 25: 2,5-dioxopyrrolidin-1-yl (21S,24S)-21-[6-(2-{bis [2-({2-[(α-L-fucopyranosyl) oxy] ethyl}amino)-2-oxoethyl]amino}acetamido) hexanamido]-1-[(α-L-fucopyranosyl)oxy]-24-{1-[(α-L-fucopyranosyl)oxy]-6-[2-({2-[(α-L-fucopyranosyl) oxy] ethyl}amino)-2-oxoethyl]-4,8,15-trioxo-3,6,9,16-tetraazaicosan-20-yl}-6-(2-{[(α-L-fucopyranosyl)oxy]ethyl}amino)-2-oxoethyl)-4,8,15,22,25-pentaoxo-3,6,9,16,23,26-hexaazadotriacontan-32-oate (ML-25)

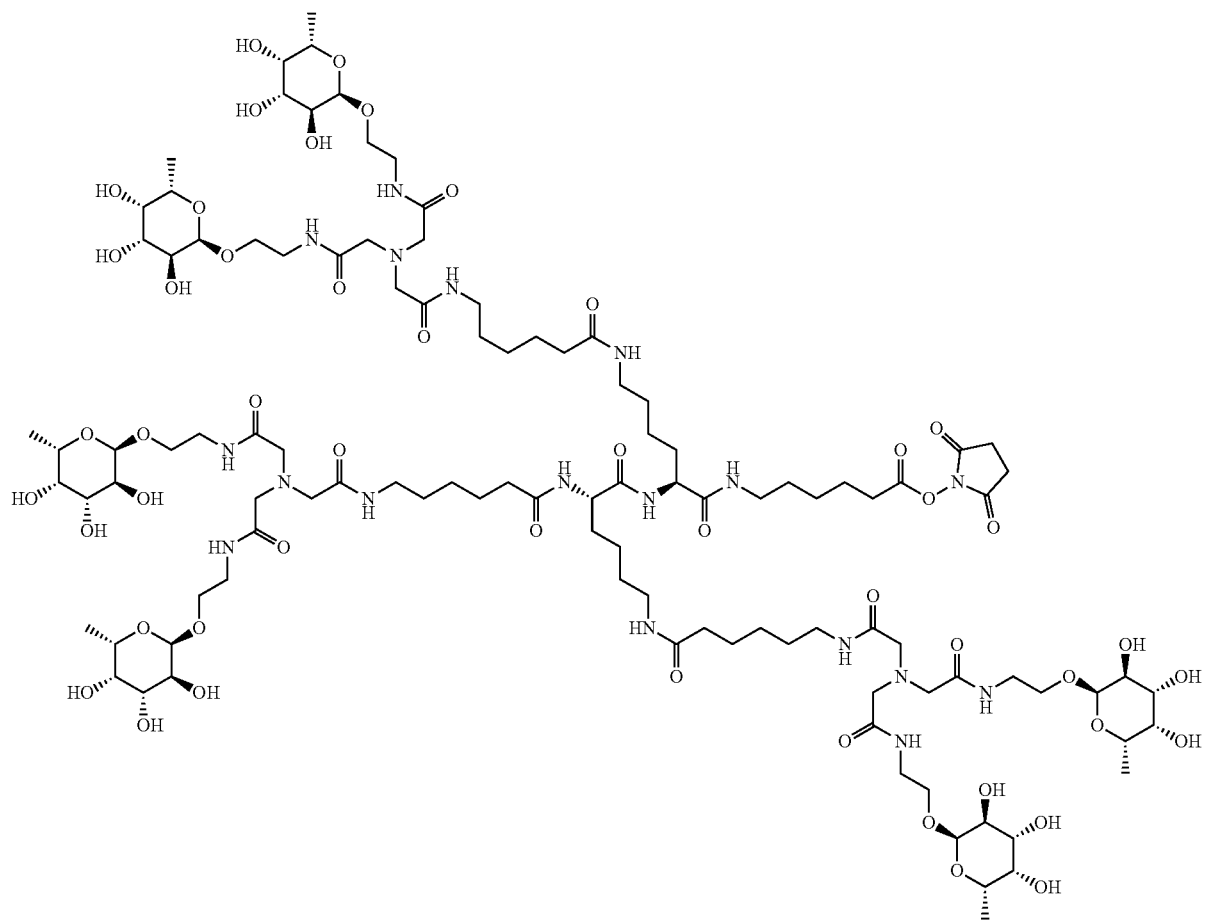

ML-25

The title compound was prepared using procedures analogous to those described for ML-24 substituting 2-aminoethyl α-L-fucopyranoside for α-D-mannopyranoside in Step 1. UPLC-MS Method A: m/z=1126.685 (z=2); $t_R$=2.86 min.

Example 26: 2,5-dioxopyrrolidin-1-yl (21S,24S)-21-(6-{2-[bis(2-{[2-({α-D-mannopyranosyl-(1→3)-[α-D-mannopyranosyl-(1→6)]-α-D-mannopyranosyl}oxy)ethyl]amino}-2-oxoethyl)amino]acetamido}hexanamido)-1-({α-D-mannopyranosyl-(1→3)-[α-D-mannopyranosyl-(1→6)]-α-D-mannopyranosyl}oxy)-24-[1-({α-D-mannopyranosyl-(1→3)-[α-D-mannopyranosyl-(1→6)]-α-D-mannopyranosyl}oxy)-6-(2-{[2-({α-D-mannopyranosyl-(1→3)-[α-D-mannopyranosyl-(1→6)]-α-D-mannopyranosyl}oxy)ethyl] amino}-2-oxoethyl)-4,8,15-trioxo-3,6,9,16-tetraazaicosan-20-yl]-6-{2-[({α-D-mannopyranosyl-(1→3)-[α-D-mannopyranosyl-(1→6)]-α-D-mannopyranosyl}oxy)ethyl]amino}-2-oxoethyl)-4,8,15,22,25-pentaoxo-3,6,9,16,23,26-hexaazadotriacontan-32-oate (ML-26)

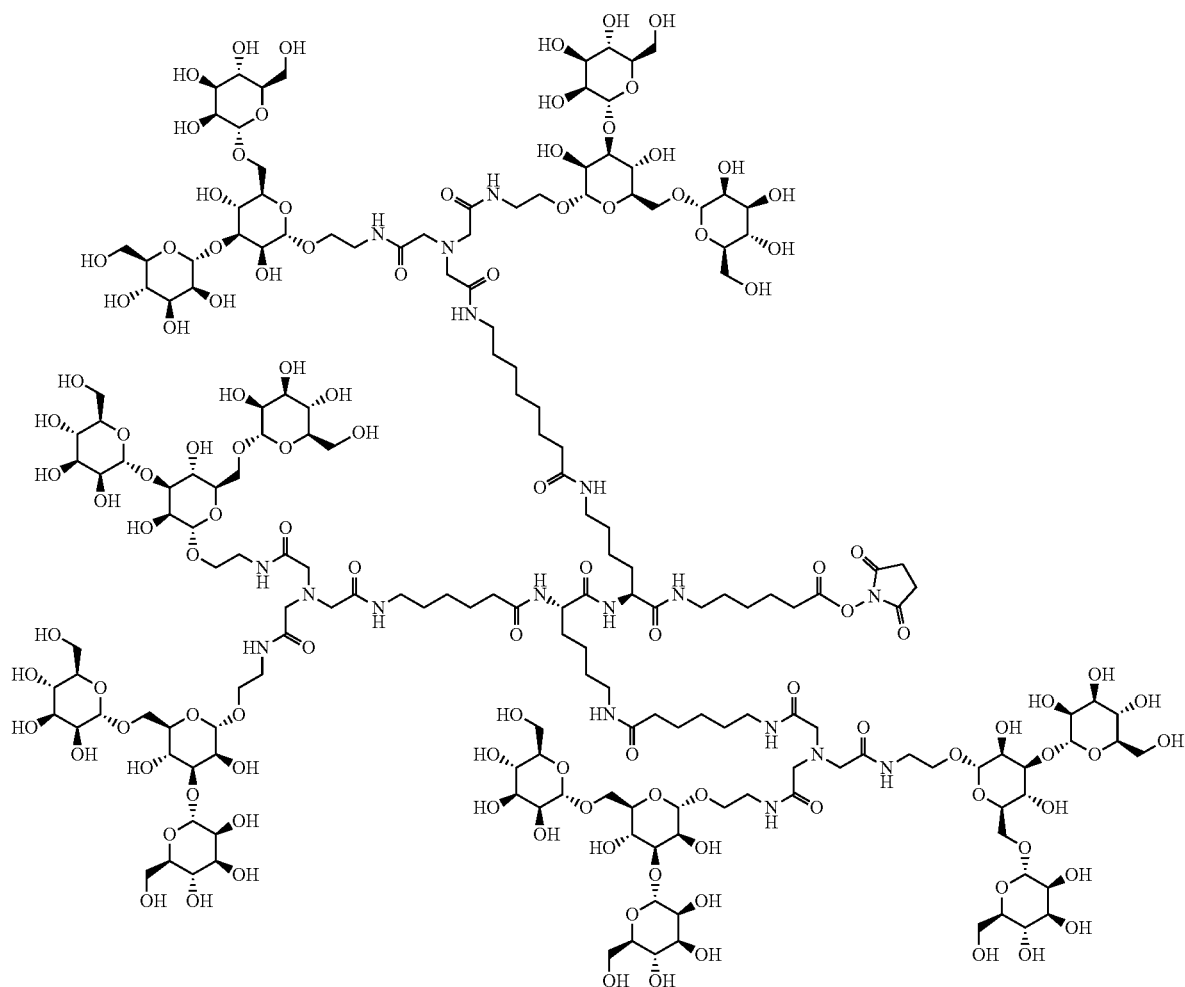

ML-26

The title compound was prepared using procedures analogous to those described for ML-24 substituting 6-amino-N-[2-({α-D-mannopyranosyl-(1→3)-[α-D-mannopyranosyl-(1→6)]-α-D-mannopyranosyl}oxy)ethyl]hexanamide for α-D-mannopyranoside in Step 1.

Example 27: 2,5-dioxopyrrolidin-1-yl (24S,27S)-1-[(α-L-fucopyranosyl)oxy]-27-{1-[(α-L-fucopyranosyl)oxy]-6-[2-({2-[(α-L-fucopyranosyl)oxy]ethyl}amino)-2-oxoethyl]-4,8,18-trioxo-12,15-dioxa-3,6,9,19-tetraazatricosan-23-yl}-24-{1-[(α-L-fucopyranosyl)oxy]-6-[2-({2-[(α-L-fucopyranosyl)oxy]ethyl}amino)-2-oxoethyl]-4,8-dioxo-12,15-dioxa-3,6,9-triazaoctadecan-18-amido}-6-[2-({2-[(α-L-fucopyranosyl)oxy]ethyl}amino)-2-oxoethyl]-4,8,18,25,28-pentaoxo-12,15-dioxa-3,6,9,19,26,29-hexaazapentatriacontan-35-oate (ML-27)
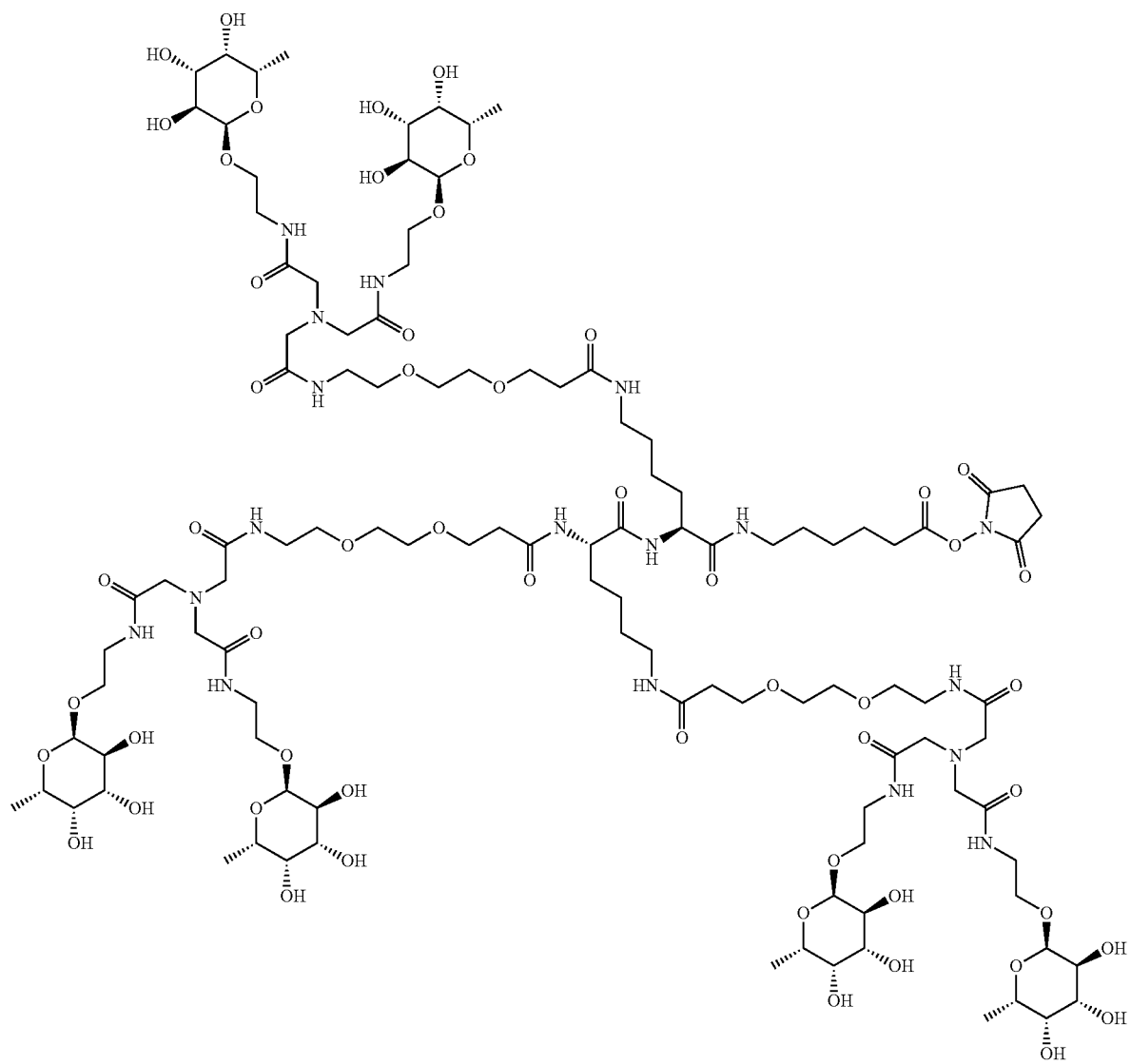
ML-27

Step 1. Benzyl 1-(9H-fluoren-9-yl)-3-oxo-2,7,10-trioxa-4-azatridecan-13-oate To a solution of 1-(9H-fluoren-9-yl)-3-oxo-2,7,10-trioxa-4-azatridecan-13-oic acid (5.0 g, 12.52 mmol) in DMF (41 mL) was added benzyl bromide (1.86 mL, 15.65 mmol) and Cs$_2$CO$_3$ (5.1 g, 15.65 mmol). After stirring overnight, the mixture was filtered, and the filtrate was diluted with EtOAc (200 mL), washed with H$_2$O (200 mL), and concentrated. The title material was isolated by chromatography (120 g SiO$_2$ column, gradient 0-100% EtOAc/Hex over 40 min, flow rate 100 mL/min). UPLC-MS Method A: m/z=490.23 (z=1); $t_R$=3.96 min.

Step 2. 15-(carboxymethyl)-3,13-dioxo-1-phenyl-2,6,9-trioxa-12,15-diazaheptadecan-17-oic Acid To a solution of benzyl 1-(9H-fluoren-9-yl)-3-oxo-2,7,10-trioxa-4-azatridecan-13-oate (2.91 g, 5.94 mmol) in DMF (30 mL) was added piperidine (5.89 mL, 59.4 mmol). After stirring for 2 hr, the reaction mixture was concentrated. The obtained solid was suspended in DMF (30 mL), treated with 2-(2,6-dioxomorpholino)acetic acid (1.029 g, 5.94 mmol). After stirring overnight, the mixture was concentrated and suspended in AcCN (100 mL). Solids were filtered off, the filtrate was concentrated, and the title compound was isolated by chromatography (C8 reverse phase silica gel 10 m 100 Å, size 250×50 mm; solvent A: water/0.05% TFA, solvent B: AcCN/0.05% TFA, Flow rate=85 mL/min, gradient solvent B in solvent A 20-40% in 20 min followed by wash with 95% solvent B). LC-MS Method A, m/z=441.32 (z=1); $t_R$=0.72 min.

Step 3. 2,5-dioxopyrrolidin-1-yl (24S,27S)-1-[(α-L-fucopyranosyl)oxy]-27-{1-[(α-L-fucopyranosyl)oxy]-6-[2-({2-[(α-L-fucopyranosyl)oxy]ethyl}amino)-2-oxoethyl]-4,8,18-trioxo-12,15-dioxa-3,6,9,19-tetraazatricosan-23-yl}-24-{1-[(α-L-fucopyranosyl)oxy]-6-[2-({2-[(α-L-fucopyranosyl)oxy]ethyl}amino)-2-oxoethyl]-4,8-dioxo-12,15-dioxa-3,6,9-triazaoctadecan-18-amido}-6-[2-({2-[(α-L-fucopyranosyl)oxy]ethyl}amino)-2-oxoethyl]-4,8,18,25,28-pentaoxo-12,15-dioxa-3,6,9,19,26,29-hexaazapentatriacontan-35-oate The title compound was prepared using procedures analogous to those described for ML-24 substituting 2-aminoethyl α-L-fucopyranoside for α-D-mannopyranoside and 15-(carboxymethyl)-3,13-dioxo-1-phenyl-2,6,9-trioxa-12,15-diazaheptadecan-17-oic acid for 2,2'-[(2-{[6-(benzyloxy)-6-oxohexyl]amino}-2-oxoethyl)azanediyl]diacetic acid, respectively, in Step 1. UPLC-MS Method A: m/z=1309.29 (z=1); $t_R$=2.20 min.

Example 28: 2,5-dioxopyrrolidin-1-yl N6-[6-(bis{2-[(α-D-mannopyranosyl)oxy]ethyl}amino)-6-oxohexanoyl]-N2-{(S)-2,5-bis[6-(bis{2-[(α-D-mannopyranosyl)oxy]ethyl}amino)-6-oxohexanamido]pentanoyl}-L-lysinate (ML-28)

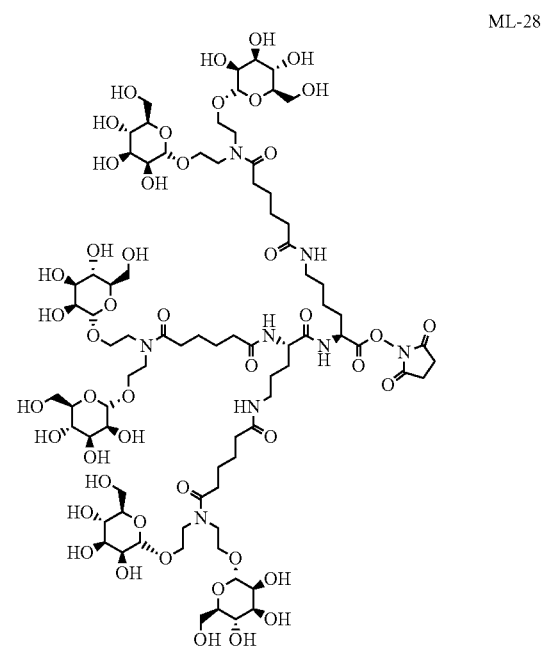

ML-28

Step 1. Benzyl 6-(bis{2-[(2,3,4,6-tetra-O-acetyl-α-D-mannopyranosyl)oxy]ethyl}amino)-6-oxohexanoate To a solution of adipic acid monobenzyl ester (1.0 g, 4.23 mmol) and bis{2-[(2,3,4,6-tetra-O-acetyl-α-D-mannopyranosyl)oxy]ethyl}amine (3.24 g, 4.23 mmol) in DMF (3.0 mL) was added DIPEA (2.22 mL, 12.70 mmol), HOBt (843 mg, 5.50 mmol) and, after stirring for 10 min, EDC (1.055 g, 5.50 mmol). After stirring at rt overnight, the mixture was concentrated. The residue was dissolved in EtOAc (100 mL) and washed with 1M HCl (100 mL), saturated NaHCO$_3$ (100 mL) and brine (100 mL). The organic layer was separated, dried over Na$_2$SO$_4$, and concentrated. The title material was isolated by chromatography (80 g SiO$_2$ column, flow rate=80 mL/min, gradient 0-100% of EtOAc in Hexanes in 30 min followed by 30 min hold with 100% EtOAc). UPLC-MS Method D: m/z=984.44 (z=1); $t_R$=4.46 min.

Step 2. 6-(bis{2-[(α-D-mannopyranosyl)oxy]ethyl}amino)-6-oxohexanoic Acid

To a solution of benzyl 6-(bis{2-[(2,3,4,6-tetra-O-acetyl-α-D-mannopyranosyl)oxy]ethyl}amino)-6-oxohexanoate (3.26 g, 3.31 mmol) in MeOH (17 mL) at rt was added NaOCH$_3$ (18 mg, 0.331 mmol). After stirring overnight, UPLC-MS analysis of an aliquot of reaction mixture indicated removal of all acetyl groups and commitant transesterefication of benzyl ester to methyl ester. The mixture was concentrated, and the residue was redissolved in H$_2$O (16.57 mL) and treated with NaOH (6.63 mL, 6.63 mmol, 1 M). After stirring for 3 hr, the pH value of the reaction mixture was adjusted to ~6 using 1N HCl. The mixture was freeze-dried to give the title compound. UPLC-MS Method A: m/z=558.286 (z=1); $t_R$=2.87 min.

Step 3. 2,5-dioxopyrrolidin-1-yl 6-(bis{2-[(α-D-mannopyranosyl)oxy]ethyl}amino)-6-oxohexanoate To a solution of 6-(bis{2-[(α-D-mannopyranosyl)oxy]ethyl}amino)-6-oxohexanoic acid (2.37 g, 3.51 mmol) in DMF (43.9 mL) at 0° C. was added TSTU (1.06 g, 3.51 mmol) and, after 5 min, DIPEA (798 μL, 4.57 mmol) dropwise. After stirring at 0° C. for 1 hr, the reaction mixture was poured in 10-fold volume of acetone. The precipitate was isolated by centrifugation and re-dissolved in H₂O (50 mL), which was freeze-dried to give the title compound. UPLC-MS Method A: m/z=655.3135 (z=1); $t_R$=3.82 min.

Step 4. N6-[6-(bis{2-[(α-D-mannopyranosyl)oxy]ethyl}amino)-6-oxohexanoyl]-N2-{(S)-2,5-bis[6-(bis{2-[(α-D-mannopyranosyl)oxy]ethyl}amino)-6-oxohexanamido]pentanoyl}-L-lysine To a solution of H-Lys-Lys-OH hydrochloride in DMSO (2 mL) and H₂O (0.2 mL) at rt was added 2,5-dioxopyrrolidin-1-yl 6-(bis{2-[(α-D-mannopyranosyl)oxy]ethyl}amino)-6-oxohexanoate (248 mg, 0.322 mmol). After stirring for 3 hr, the reaction mixture was concentrated, and the residue was purified on (120 g C18 reverse phase gel column, gradient water/AcCN=0-40% over 50 min followed by hold) to give the title compound. UPLC-MS Method A: m/z=1893.8734 (z=1); $t_R$=3.91 min.

Step 5. 2,5-dioxopyrrolidin-1-yl N6-[6-(bis{2-[(α-D-mannopyranosyl)oxy]ethyl}amino)-6-oxohexanoyl]-N2-{(S)-2,5-bis[6-(bis{2-[(α-D-mannopyranosyl)oxy]ethyl}amino)-6-oxohexanamido]pentanoyl}-L-lysinate To a solution of N6-[6-(bis{2-[(α-D-mannopyranosyl)oxy]ethyl}amino)-6-oxohexanoyl]-N2-{(S)-2,5-bis[6-(bis{2-[(α-D-mannopyranosyl)oxy]ethyl}amino)-6-oxohexanamido]pentanoyl}-L-lysine (68 mg, 0.036 mmol) in DMF (0.7 mL) at 0° C. was added TSTU (11 mg, 0.036 mmol) and, after 5 min, DIPEA (13 μl, 0.072 mmol). After stirred for 2 hr, the reaction mixture was poured into 20× volumes of acetone. A precipitate formed and was isolated by centrifugation, which was dried to give the title compound. UPLC-MS Method: m/z=995.4828 (z=2); $t_R$=4.05 min.

Example 29: 2,5-dioxopyrrolidin-1-yl (21S,28S)-21,28-bis(2-{bis[2-({2-[(α-D-mannopyranosyl)oxy]ethyl}amino)-2-oxoethyl]amino}acetamido)-1-[(α-D-mannopyranosyl)oxy]-6-(2-({2-[(α-D-mannopyranosyl)oxy]ethyl)amino}-2-oxoethyl)-4,8,15,22,29-pentaoxo-3,6,9,16,23,30-hexaazahexatriacontan-36-oate (ML-29)

ML-29

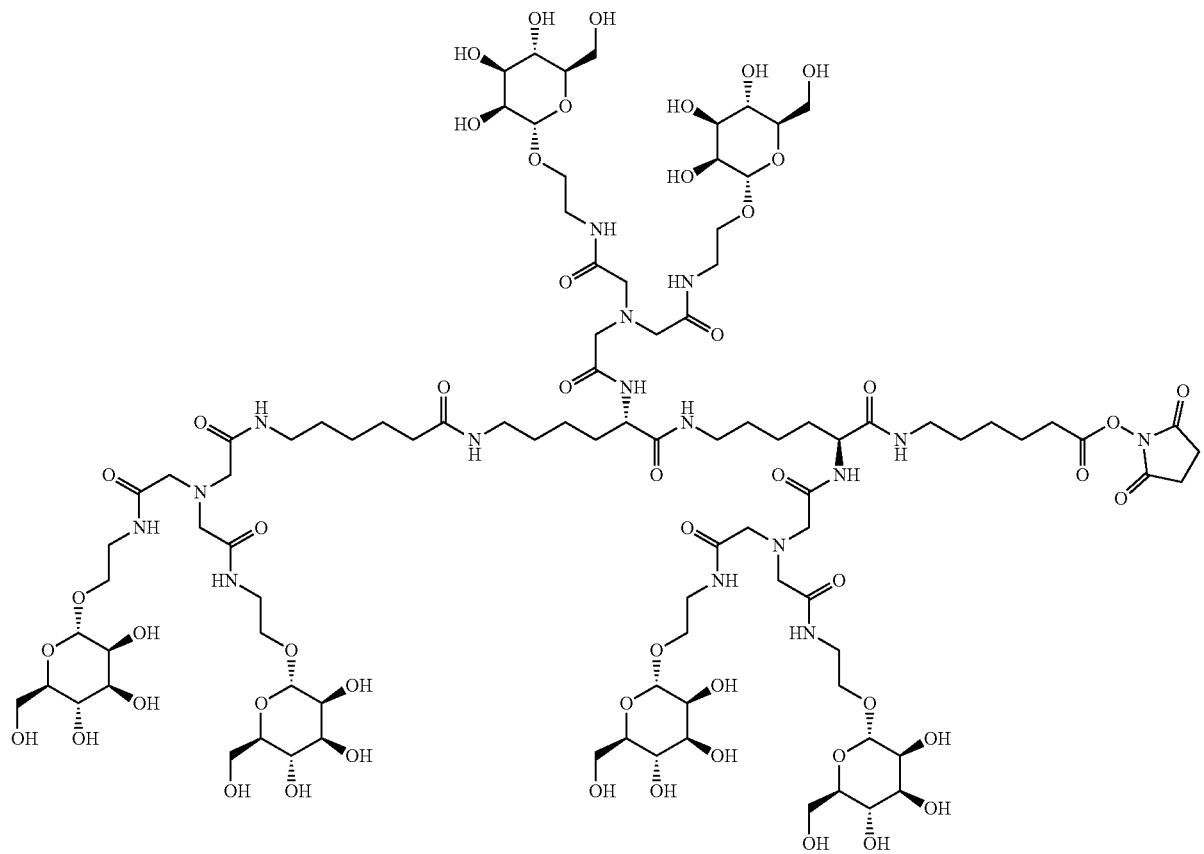

Step 1. (S)-13-(carboxymethyl)-9-(methoxycarbonyl)-3,11-dioxo-1-phenyl-2-oxa-4,10,13-triazapentadecan-15-oic Acid To a solution of H-Lys(Z)—OCH$_3$ HCl (500 mg, 1.511 mmol) in DMF (5.04 mL) at rt was added 2-(2,6-dioxomorpholin-4-yl)acetic acid (288 mg, 1.663 mmol) and TEA (253 µL, 1.814 mmol). After stirring for 1 hr, the reaction was completed, and the title compound was used without further purification. LC-MS Method A: m/z=467.83 (z=1); $t_R$=0.80 min.

Step 2. Methyl N6-[(benzyloxy)carbonyl]-N2-{bis[2-({2-[(α-D-mannopyranosyl)oxy]ethyl}amino)-2-oxoethyl]glycyl}-L-lysinate To a solution of (S)-13-(carboxymethyl)-9-(methoxycarbonyl)-3,11-dioxo-1-phenyl-2-oxa-4,10,13-triazapentadecan-15-oic acid (obtained in the previous step) was added a solution of 2-aminoethyl α-D-mannopyranoside (1.0 g, 4.49 mmol) in DMF (10 mL), HOBt (688 mg, 4.49 mmol), EDC (861 mg, 4.49 mmol) and DIPEA (785 µL, 4.49 mmol). After stirring overnight, the reaction mixture was concentrated. The title material was isolated by chromatography (120 g C18 reverse phase gel column, gradient 0-40% AcCN-water in 30 min, flow 85 mL/min). UPLC-MS Method A: m/z=878.43 (z=1); $t_R$=2.86 min.

Step 3. N6-[(benzyloxy)carbonyl]-N2-{bis[2-({2-[(α-D-mannopyranosyl)oxy]ethyl}amino)-2-oxoethyl]glycyl}-L-lysine To a solution of methyl N6-[(benzyloxy)carbonyl]-N2-{bis[2-({2-[(α-D-mannopyranosyl)oxy]ethyl}amino)-2-oxoethyl]glycyl}-L-lysinate (866 mg, 0.986 mmol) in H$_2$O (4.93 mL) was added NaOCH$_3$ (3.94 mL, 3.94 mmol). As after stirring overnight, the reaction was complete, and the pH of the resulting solution was adjusted to ~ 6.0 and then freeze-dried to give the title compound. UPLC-MS Method A: m/z=864.4 (z=1); $t_R$=2.64 min.

Step 4. Benzyl (S)-6-(6-{[(benzyloxy)carbonyl]amino}-2-[(tert-butoxycarbonyl)amino]hexanamido)hexanoate To a mixture of 6-(benzyloxy)-6-oxohexan-1-aminium 4-methylbenzenesulfonate (1.55 g, 3.94 mmol), Boc-Lys(Z)—OH (1.00 g, 2.63 mmol), HOBt (644 mg, 4.21 mmol) in DMF (13 mL) was added EDC (806 mg, 4.21 mmol) and DIPEA (735 µL, 4.21 mmol). After stirring overnight, the reaction mixture was concentrated, and the title material was isolated by chromatography (120 g C18 reverse phase gel column, gradient 0-80% AcCN/water in 25 min followed by hold). UPLC-MS Method A: m/z=584.48 (z=1); $t_R$=1.31 min.

Step 5. Benzyl (S)-6-(2-amino-6-{[(benzyloxy)carbonyl]amino}hexanamido)hexanoate To a solution of benzyl (S)-6-(6-{[(benzyloxy)carbonyl]amino}-2-[(tert-butoxycarbonyl) amino]hexanamido) hexanoate (1.244 g, 2.131 mmol) in DCM (7.10 mL) was added TFA (7.94 mL, 107 mmol). After stirring for 3 hr, the reaction mixture was concentrated. The residue was dissolved in DCM (100 mL) and washed with saturated NaHCO$_3$. The organic layer was separated, dried over Na$_2$SO$_4$, and concentrated to give the title compound. LC-MS Method A: m/z=484.38 (z=1); $t_R$=0.99 min.

Step 6. (S)-11-(4-{[(benzyloxy)carbonyl]amino}butyl)-15-(carboxymethyl)-3,10,13-trioxo-1-phenyl-2-oxa-9,12,15-triazaheptadecan-17-oic Acid To a solution of benzyl (S)-6-(2-amino-6-{[(benzyloxy)carbonyl]amino}hexanamido) hexanoate (971 mg, 2.008 mmol) in DMF (10.0 mL) was added 2-(2,6-dioxomorpholino)acetic acid (417 mg, 2.409 mmol). After stirring for 1 hr, the reaction was complete, and the title compound was used without further purification. UPLC-MS Method A: m/z=657.343 (z=1);

$$benzyl\ (S) - 10 - (4 - \{[(benzyloxy)carbonyl]amino\}butyl) - 1 - [(\alpha - D - mannopyranosyl)oxy] - 6 -.$$

Step 7. benzyl (S)-10-(4-{[(benzyloxy)carbonyl]amino}butyl)-1-[(α-D-mannopyranosyl)oxy]-6-[2-({2-[(α-D-mannopyranosyl)oxy]ethyl}amino)-2-oxoethyl]-4,8,11-trioxo-3,6,9,12-tetraazaoctadecan-18-oate To the aforementioned solution of (S)-11-(4-{[(benzyloxy)carbonyl]amino} butyl)-15-(carboxymethyl)-3,10,13-trioxo-1-phenyl-2-oxa-9,12,15-triazaheptadecan-17-oic acid (from Step 6) was added a solution of 2-aminoethyl α-D-mannopyranoside (1.35 g, 6.02 mmol) in DMF (10.0 mL), HOBt (1.23 g, 8.03 mmol), EDC (1.16 g, 6.02 mmol) and DIPEA (2.104 mL, 12.05 mmol). After stirring overnight, the reaction mixture was concentrated. The title material was isolated by chromatography (120 g C-18 reverse phase gel column, gradient 0-40% AcCN-water over 30 min, flow rate 85 mL/min). UPLC-MS Method A: m/z=1067.540 (z=1); $t_R$=2.91 min.

Step 8. Methyl (S)-10-(4-{[(benzyloxy)carbonyl]amino}butyl)-1-[(α-D-mannopyranosyl)oxy]-6-[2-({2-[(α-D-mannopyranosyl)oxy]ethyl}amino)-2-oxoethyl]-4,8,11-trioxo-3,6,9,12-tetraazaoctadecan-18-oate To a solution of benzyl (S)-10-(4-{[(benzyloxy)carbonyl]amino}butyl)-1-[(α-D-mannopyranosyl)oxy]-6-[2-({2-[(α-D-mannopyranosyl)oxy]ethyl}amino)-2-oxoethyl]-4,8,11-trioxo-3,6,9,12-tetraazaoctadecan-18-oate (1.66 g, 1.556 mmol) in MeOH (16 mL) was added NaOCH$_3$ (14 mg, 0.078 mmol, 30% in MeOH). After stirring overnight, the reaction mixture was concentrated to give the title compound, which was used without further purification. LC-MS Method A: m/z=991.09 (z=1); $t_R$=0.76 min.

Step 9. Methyl (S)-10-(4-aminobutyl)-1-[(α-D-mannopyranosyl)oxy]-6-[2-({2-[(α-D-mannopyranosyl)oxy]ethyl}amino)-2-oxoethyl]-4,8,11-trioxo-3,6,9,12-tetraazaoctadecan-18-oate The pH of a solution of methyl (S)-10-(4-{[(benzyloxy)carbonyl]amino}butyl)-1-[(α-D-mannopyranosyl)oxy]-6-

[2-({2-[(α-D-mannopyranosyl)oxy]ethyl}amino)-2-oxoethyl]-4,8,11-trioxo-3,6,9,12-tetraazaoctadecan-18-oate (from Step 8) in H$_2$O (150 mL) was adjusted pH to ~7. To this solution was added Pearlman's catalyst (109 mg, 0.156 mmol). The resulting suspension was shaken on a Parr shaker under 344.74 kPa of H$_2$ overnight. The catalyst was filtered off through a cake of CELITE®, and the filtrate was freeze-dried to give the title compound. UPLC-MS Method A: m/z=857.485 (z=1); t$_R$=2.00 min.

Step 10. methyl (10S,17S)-10-(4-{[(benzyloxy)carbonyl]amino}butyl)-17-(2-{bis[2-({2-[(α-D-mannopyranosyl)oxy]ethyl}amino)-2-oxoethyl]amino}acetamido)-1-[(α-D-mannopyranosyl) oxy]-6-[2-({2-[(α-D-mannopyranosyl)oxy]ethyl}amino)-2-oxoethyl]-4,8,11,18-tetraoxo-3,6,9,12,19-pentaazapentacosan-25-oate To a solution of N6-[(benzyloxy)carbonyl]-N2-{bis[2-({2-[(α-D-mannopyranosyl)oxy]ethyl}amino)-2-oxoethyl]glycyl}-L-lysine (300 mg, 0.309 mmol) and methyl (S)-10-(4-aminobutyl)-1-[(α-D-mannopyranosyl)oxy]-6-[2-({2-[(α-D-mannopyranosyl) oxy]ethyl}amino)-2-oxoethyl]-4,8,11-trioxo-3,6,9,12-tetraazaoctadecan-18-oate (264 mg, 0.309 mmol) in DMF (4.4 mL) was added HOBt (95 mg, 0.617 mmol), EDC (118 mg, 0.617 mmol) and DIPEA (216 μL, 1.235 mmol). After stirring overnight, the reaction mixture was concentrated. The title compound was isolated by chromatography (40 g C18 reverse phase gel column, gradient 0-40% AcCN/water over 30 min., flow rate 40 mL/min). UPLC-MS Method A: m/z=1703.00 (z=1); t$_R$=2.74 min.

Step 11. methyl (10S,17S)-10-(4-aminobutyl)-17-(2-{bis[2-({2-[(α-D-mannopyranosyl)oxy]ethyl}amino)-2-oxoethyl]amino}acetamido)-1-[(α-D-mannopyranosyl)oxy]-6-[2-({2-[(α-D-mannopyranosyl)oxy]ethyl}amino)-2-oxoethyl]-4,8,11,18-tetraoxo-3,6,9,12,19-pentaazapentacosan-25-oate A mixture of methyl (10S,17S)-10-(4-{[(benzyloxy)carbonyl]amino}butyl)-17-(2-{bis[2-({2-[(α-D-mannopyranosyl)oxy]ethyl}amino)-2-oxoethyl]amino}acetamido)-1-[(α-D-mannopyranosyl)oxy]-6-[2-({2-[(α-D-mannopyranosyl) oxy]ethyl}amino)-2-oxoethyl]-4,8,11,18-tetraoxo-3,6,9,12,19-pentaazapentacosan-25-oate (296 mg, 0.174 mmol) and Pearlman's catalyst (37 mg, 0.052 mmol) in H$_2$O (20 mL) was shaken on a Parr shaker under 344.74 kPa of H$_2$ overnight. The catalyst was filtered off through a cake of CELITE®, and the filtrate was freeze-dried to give the title compound. UPLC-MS Method A: m/z=1568.89 (z=1); t$_R$=1.96 min.

Step 12. methyl (21S,28S)-21,28-bis(2-{bis[2-({2-[(α-D-mannopyranosyl)oxy]ethyl}amino)-2-oxoethyl]amino}acetamido)-1-[(α-D-mannopyranosyl) oxy]-6-[2-({2-[(α-D-mannopyranosyl) oxy]ethyl}amino)-2-oxoethyl]-4,8,15,22,29-pentaoxo-3,6,9,16,23,30-hexaazahexatriacontan-36-oate To a solution of 6-(2-{bis[2-oxo-2-({2-[(α-D-mannopyranosyl)oxy]ethyl}amino)ethyl]amino}acetamido)hexanoic acid (55 mg, 0.077 mmol) and methyl (10S,17S)-10-(4-aminobutyl)-17-(2-{bis[2-({2-[(α-D-mannopyranosyl)oxy]ethyl}amino)-2-oxoethyl]amino} acetamido)-1-[(α-D-mannopyranosyl)oxy]-6-[2-({2-[(α-D-mannopyranosyl)oxy]ethyl}amino)-2-oxoethyl]-4,8,11,18-tetraoxo-3,6,9,12,19-pentaazapentacosan-25-oate (100 mg, 0.064 mmol) in DMF (3.0 mL) was added HOBt (20 mg, 0.128 mmol), DIPEA (45 μL, 0.255 mmol) and EDC (24 mg, 0.128 mmol). After stirring overnight, the reaction mixture was concentrated. The title material was isolated by chromatography (C8 reverse phase gel 10 m 100 Å, size 250×50 mm; solvent A=water/0.05% TFA, solvent B=AcCN/0.05% TFA, Flow=85 mL/min, gradient solvent B in solvent A 0-30% in 30 min). UPLC-MS Method A: m/z=1133.67 (z=2); t$_R$=2.22 min.

Step 13. (21S,28S)-21,28-bis(2-{bis[2-({2-[(α-D-mannopyranosyl)oxy]ethyl}amino)-2-oxoethyl]amino}acetamido)-1-[(α-D-mannopyranosyl)oxy]-6-[2-({2-[(α-D-mannopyranosyl)oxy]ethyl}amino)-2-oxoethyl]-4,8,15,22,29-pentaoxo-3,6,9,16,23,30-hexaazahexatriacontan-36-oic Acid To a solution of methyl (21S,28S)-21,28-bis(2-{bis[2-({2-[(α-D-mannopyranosyl)oxy]ethyl}amino)-2-oxoethyl]amino}acetamido)-1-[(α-D-mannopyranosyl)oxy]-6-[2-({2-[(α-D-mannopyranosyl)oxy]ethyl}amino)-2-oxoethyl]-4,8,15,22,29-pentaoxo-3,6,9,16,23,30-hexaazahexatriacontan-36-oate (94 mg, 0.041 mmol) in H$_2$O (1.0 mL) was added NaOH (207 mL, 0.207 mmol, 1M). After stirring for 1 hr, the pH of the reaction mixture was adjusted to 6.5 and the resulting solution was freeze-dried to give the title compound. UPLC-MS Method A: m/z=1126.66 (z=2); t$_R$=2.29 min.

Step 14. 2,5-dioxopyrrolidin-1-yl (21S,28S)-21,28-bis(2-{bis[2-({2-[(α-D-mannopyranosyl)oxy]ethyl}amino)-2-oxoethyl]amino}acetamido)-1-[(α-D-mannopyranosyl)oxy]-6-(2-({2-[(α-D-mannopyranosyl)oxy]ethyl)amino}-2-oxoethyl)-4,8,15,22,29-pentaoxo-3,6,9,16,23,30-hexaazahexatriacontan-36-oate To a solution of (21S,28S)-21,28-bis(2-{bis[2-({2-[(α-D-mannopyranosyl)oxy]ethyl}amino)-2-oxoethyl]amino}acetamido)-1-[(α-D-mannopyranosyl)oxy]-6-[2-({2-[(α-D-mannopyranosyl)oxy]ethyl}amino)-2-oxoethyl]-4,8,15,22,29-pentaoxo-3,6,9,16,23,30-hexaazahexatriacontan-36-oic acid (121 mg, 0.054 mmol) in DMF (1.075 mL) at 0° C. was added TSTU (24 mg, 0.081 mmol) and DIPEA (14 μL, 0.081 mmol). After stirred for 1 hr, the reaction mixture was added dropwise to a mixture of ether/acetone (v/v=1/1, 20 mL). The precipitate was collected by centrifugation and dried to give the title compound. UPLC-MS Method A: m/z=1175.170 (z=2); t$_R$=2.42 min.

Example 30: 2,5-dioxopyrrolidin-1-yl (21S,28S)-21, 28-bis(2-{bis[2-({2-[(α-L-fucopyranosyl)oxy]ethyl}amino)-2-oxoethyl]amino}acetamido)-1-[(α-L-fucopyranosyl)oxy]-6-(2-({2-[(α-L-fucopyranosyl)oxy]ethyl)amino}-2-oxoethyl)-4,8,15,22,29-pentaoxo-3,6,9,16,23,30-hexaazahexatriacontan-36-oate (ML-30)

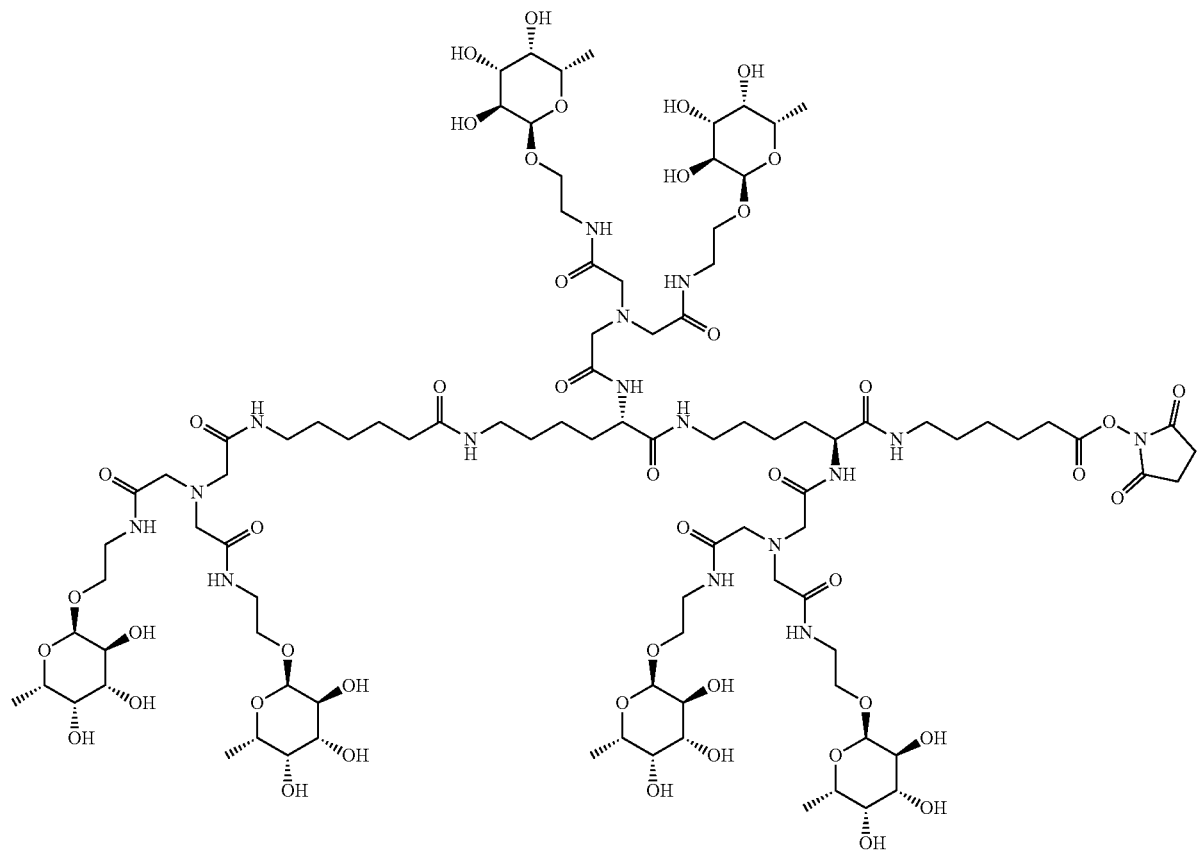

ML-30

The title compound was prepared using procedures analogous to those described for ML-29 substituting 6-aminoethyl α-L-fucopyranoside for 6-aminoethyl α-D-mannopyranoside in Step 2, 6-aminoethyl α-L-fucopyranoside for 6-aminoethyl α-D-mannopyranoside in Step 7, and 6-(2-{bis[2-oxo-2-({2-[(α-L-fucopyranosyl)oxy]ethyl}amino)ethyl]amino}acetamido)hexanoic acid for 6-(2-{bis[2-oxo-2-({2-[(α-D-mannopyranosyl)oxy]ethyl}amino)ethyl]amino}acetamido)hexanoic acid in Step 12, respectively. UPLC-MS Method A: m/z=1126.685 (z=2); $t_R$=2.86 min.

Example 31: 2,5-dioxopyrrolidin-1-yl (14S,17S)-14-
(2-{bis[2-({2-[(α-L-fucopyranosyl) oxy]
ethyl}amino)-2-oxoethyl]amino} acetamido)-17-[4-
(2-{bis [2-({2-[(α-L-fucopyranosyl) oxy]
ethyl}amino)-2-oxoethyl]amino} acetamido)butyl]-
1-[(α-L-fucopyranosyl)oxy]-6-[2-({2-[(α-L-
fucopyranosyl)oxy]ethyl}amino)-2-oxoethyl]-4,8,15,
18-tetraoxo-3,6,9,16,19-pentaazapentacosan-25-oate
(ML-31)

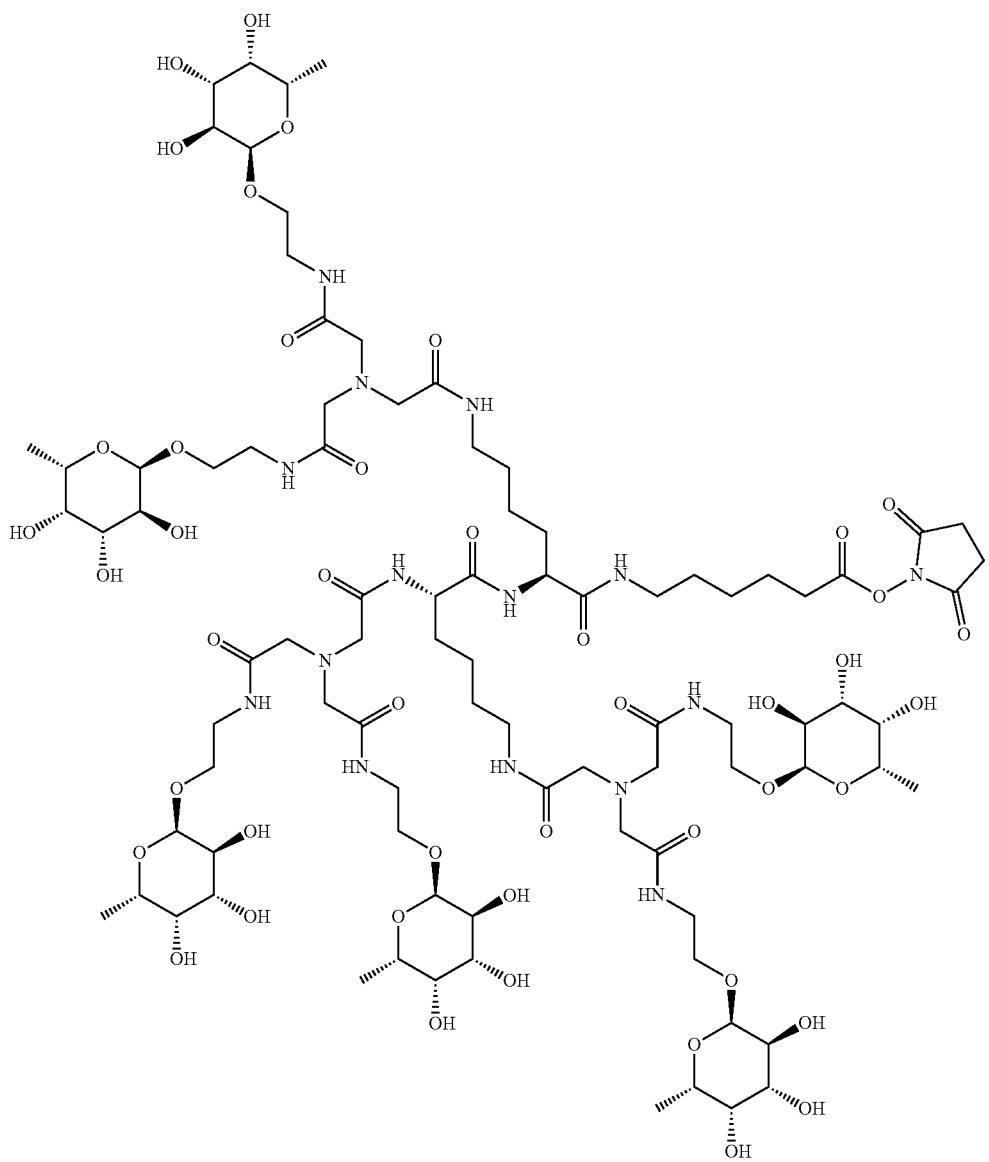

ML-31

Step 1. Bis[2-({2-[(α-L-fucopyranosyl)oxy]ethyl}amino)-2-oxoethyl]glycine

To a solution of 2-(2,6-dioxomorpholino)acetic acid (200 mg, 1.155 mmol) in DMF (5.776 mL) at 0° C. was added TSTU (348 mg, 1.155 mmol) and, after 5 min, DIPEA (202 µL, 1.155 mmol). After stirring for 45 min, to the reaction mixture was added 2-aminoethyl α-L-fucopyranoside hydrobromide (666 mg, 2.310 mmol) and DIPEA (1.211 mL, 6.93 mmol). After stirring overnight, the reaction mixture was concentrated. The title material was isolated by chromatography (40 g $SiO_2$, flow rate 35 mL/min, gradient solvent A-solvent B of 0-100% solvent B in 20 min followed by hold, solvent A was EtOAc/MeOH/AcCN/$H_2O$ (v/v/v/v=6/1/1/1), and solvent B was EtOAc/MeOH/AcCN/$H_2O$ (v/v/v/v=2/1/1/1). UPLC-MS Method A: m/z=570.287 (z=1); $t_R$=1.17 min.

Step 2. 2,5-dioxopyrrolidin-1-yl (14S,17S)-14-(2-{bis[2-({2-[(α-L-fucopyranosyl)oxy]ethyl}amino)-2-oxoethyl]amino}acetamido)-17-[4-(2-{bis[2-({2-[(α-L-fucopyranosyl)oxy]ethyl}amino)-2-oxoethyl]amino}acetamido)butyl]-1-[(α-L-fucopyranosyl)oxy]-6-[2-({2-[(α-L-fucopyranosyl)oxy]ethyl}amino)-2-oxoethyl]-4,8,15,18-tetraoxo-3,6,9,16,19-pentaazapentacosan-25-oate The title compound was prepared using procedures analogous to those described for ML-7 substituting bis[2-({2-[(α-L-fucopyranosyl)oxy]ethyl}amino)-2-oxoethyl]glycine for 6-[(2,5-Dioxopyrrolidin-1-yl)oxy]-N-(2-{[(α-D-mannopyranosyl-(1→3)-[α-D-mannopyranosyl-(1→6)]-α-D-mannopyranosyl]oxy}ethyl)-6-oxohexanamide in Step D. UPLC-MS Method A: m/z=1070.61 (z=2); $t_R$=3.43 min.

Example 32: 2,5-dioxopyrrolidin-1-yl (14S,19S)-14,19-bis{[6-(bis{2-[(α-D-mannopyranosyl)oxy]ethyl}amino)-6-oxohexyl] carbamoyl}-1-[(α-D-mannopyranosyl)oxy]-3-{2-[(α-D-mannopyranosyl)oxy]ethyl}-4,11,16,21,24-pentaoxo-3,10,15,20,23-pentaazanonacosan-29-oate (ML-32)

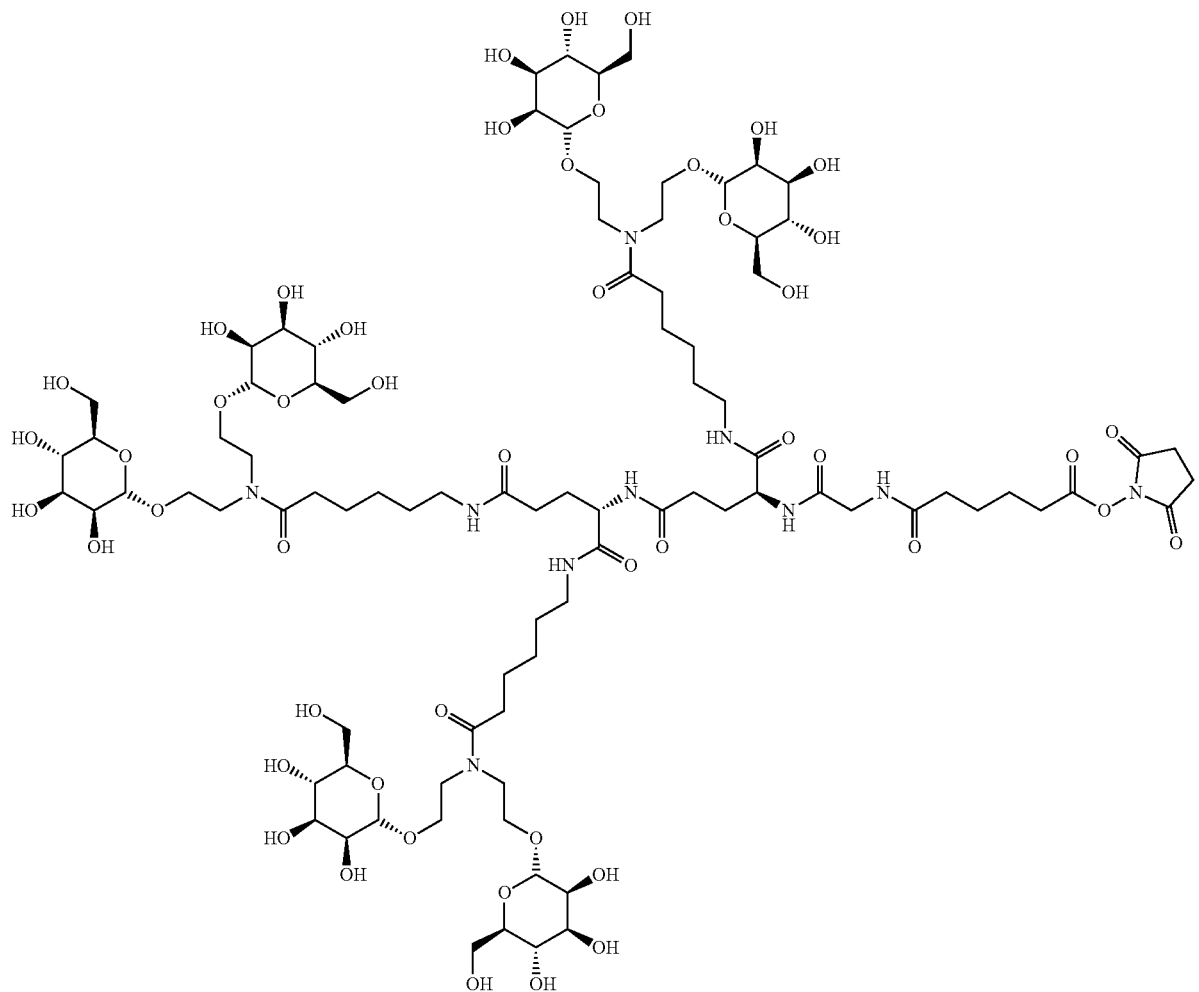

ML-32

The title compound was prepared using procedures analogous to those described for ML-1 substituting H-Gly-γGlu-Glu-OH for H-Glu-Asp-OH in Step 1 and 6-amino-N,N-bis{2-[(α-D-mannopyranosyl)oxy]ethyl}hexanamide for 2-aminoethyl α-D-mannopyranoside in Step 2, respectively. UPLC-MS Method A: m/z=1066.996 (z=2); $t_R$=4.01 min.

Example 33: 2,5-dioxopyrrolidin-1-yl (12S,15S, 18S)-15,18-bis(3-{[6-(bis{2-[(α-D-mannopyranosyl)oxy]ethyl}amino)-6-oxohexyl]amino}-3-oxopropyl)-1-[(α-D-mannopyranosyl)oxy]-3-{2-[(α-D-mannopyranosyl)oxy]ethyl}-12-isobutyl-4,11,14,17,20-pentaoxo-3,10,13,16,19-pentaazapentacosan-25-oate (ML-33)

ML-33

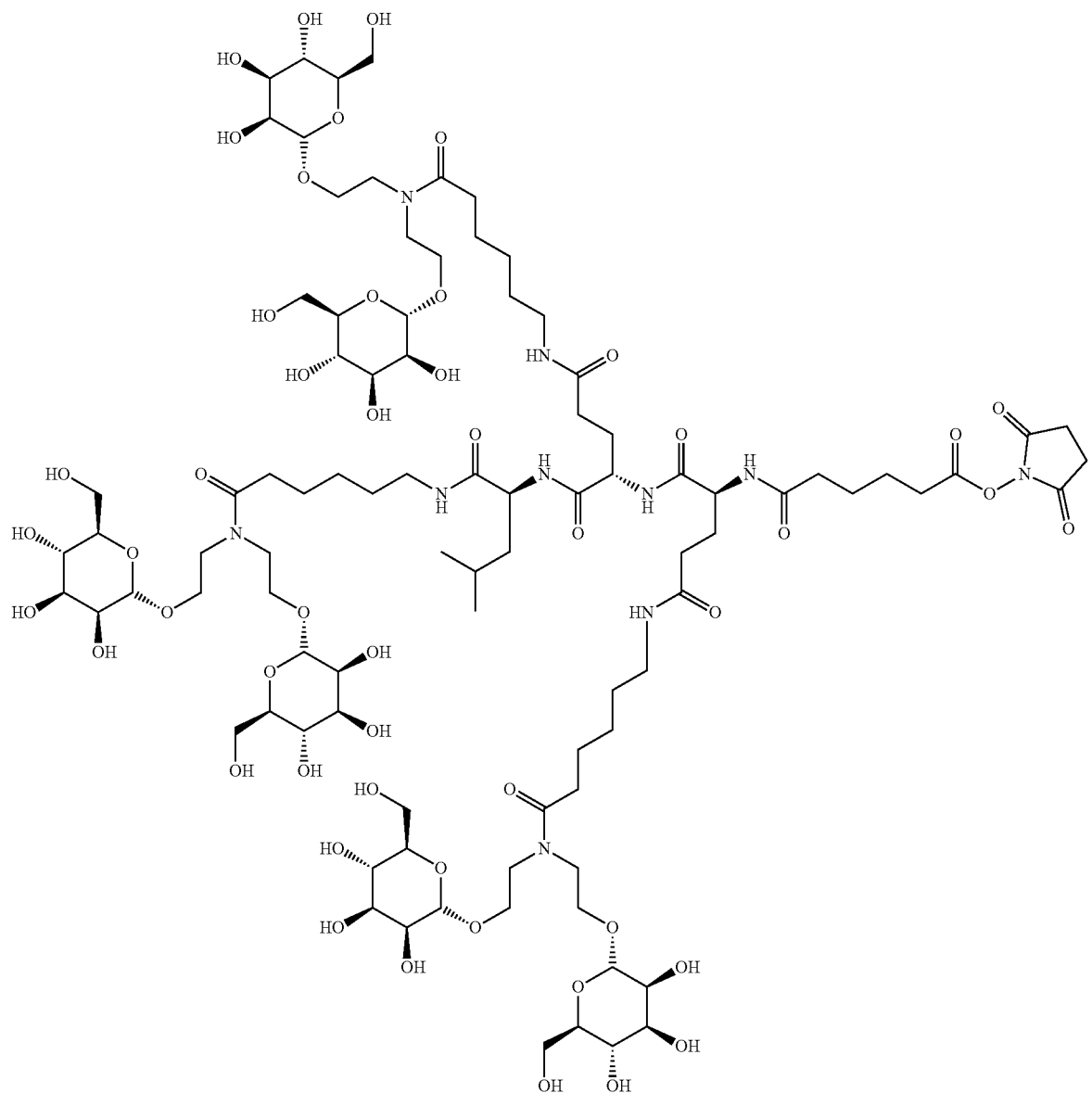

The title compound was prepared using procedures analogous to those described for ML-4 substituting 6-amino-N,N-bis{2-[(α-D-mannopyranosyl)oxy]ethyl}hexanamide for 6-amino-N-[2-({α-D-mannopyranosyl-(1→3)-[α-D-mannopyranosyl-(1-6)]-α-D-mannopyranosyl}oxy) ethyl] hexanamide in Step 2. UPLC-MS Method A: m/z=1095.042 (z=2); $t_R$=3.96 min.

Example 34: 2,5-dioxopyrrolidin-1-yl (17S,22S)-1-[(α-L-fucopyranosyl)oxy]-17,22-bis[(6-{[2-({2-[(α-L-fucopyranosyl)oxy]ethyl}amino)-2-oxoethyl][2-oxo-2-({2-[(α-D-mannopyranosyl)oxy]ethyl}amino)ethyl]amino}-6-oxohexyl)carbamoyl]-4,7,14,19,24,27-hexaoxo-6-[2-oxo-2-({2-[(α-D-mannopyranosyl)oxy]ethyl}amino)ethyl]-3,6,13,18,23,26-hexaazadotriacontan-32-oate (ML-34)

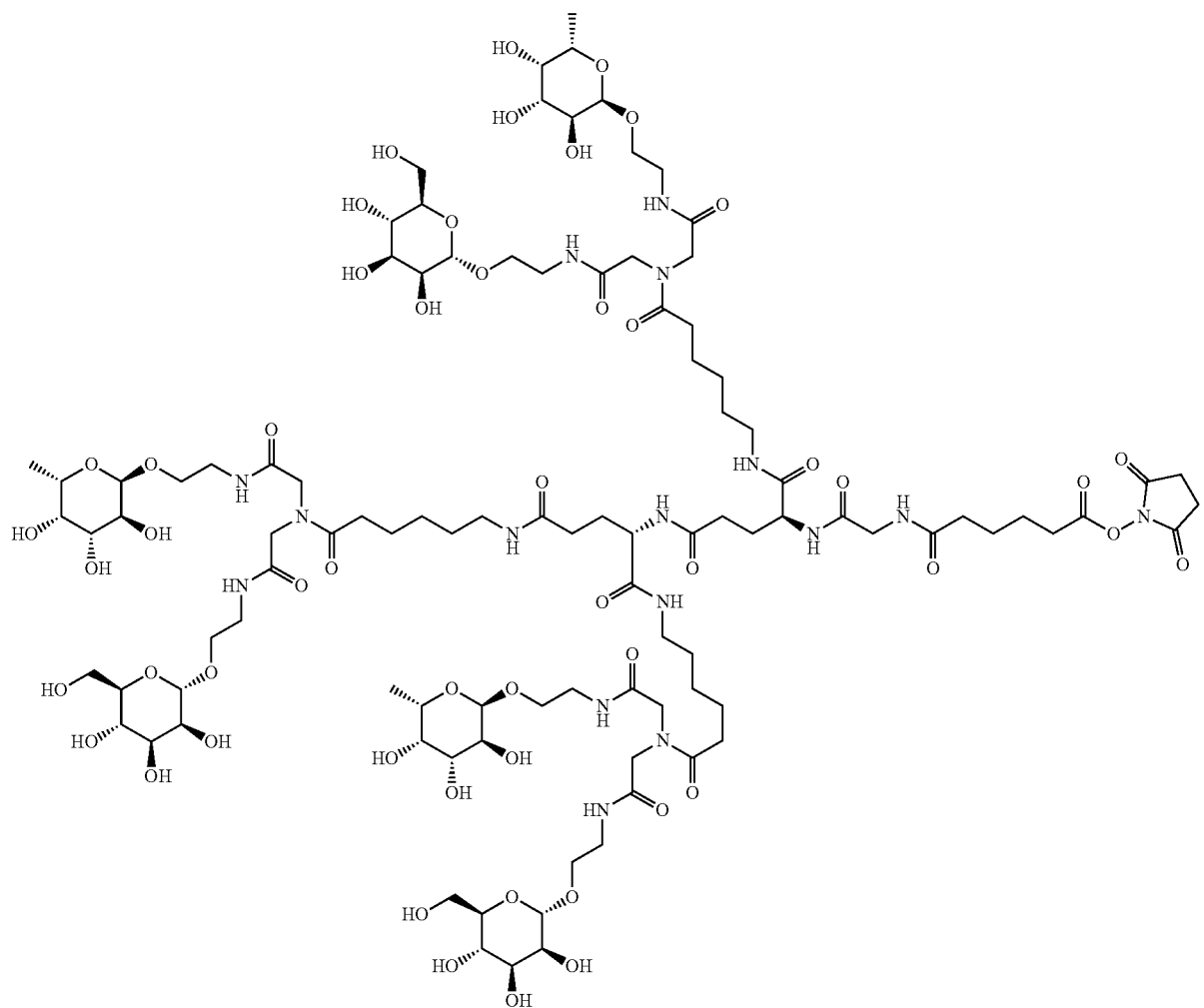

ML-34

Step 1. Tert-butyl N-{[(9H-fluoren-9-yl)methoxy]carbonyl}-N-[2-({2-[(α-L-fucopyranosyl)oxy]ethyl}amino)-2-oxoethyl]glycinate To a solution of Fmoc-N-(tert-butyloxycarbonylmethyl)-glycine (4.98 g, 12.11 mmol) in DMF (25 mL) at 0° C. was added EDC (3.48 g, 18.17 mmol), HOBt (557 mg, 3.63 mmol) and, after 30 min, 2-aminoethyl α-L-fucopyranoside (2.761 g, 13.32 mmol). The mixture was gradually warmed up to rt and stirred overnight. The reaction mixture was concentrated, and the residue was purified by column chromatography on 240 g C18 reverse phase silica gel, eluting with AcCN/H$_2$O (gradient from 0% to 50% in 20 CV), to give the title compound. UPLC-MS Method A: m/z=601.347 (z=1); t$_R$=4.35.

Step 2. N-{[(9H-fluoren-9-yl)methoxy]carbonyl}-N-[2-({2-[(α-L-fucopyranosyl)oxy]ethyl}amino)-2-oxoethyl]glycine To a solution of tert-butyl N-{[(9H-fluoren-9-yl)methoxy]carbonyl}-N-[2-({2-[(α-L-fucopyranosyl)oxy]ethyl}amino)-2-oxoethyl]glycinate (2.10 g, 3.50 mmol) in DCM (20 mL) at rt was added TFA (20 mL, 260 mmol). After stirring at 0° C. for 3 hr, the reaction mixture was concentrated. The residue was purified by column chromatography on 130 g C18 reverse phase silica gel, eluting with AcCN/H$_2$O (gradient from 0% to 45% in 20 CV), to give the title compound. UPLC-MS Method A: m/z=545.29 (z=1); t$_R$=3.31 min.

Step 3. (9H-fluoren-9-yl)methyl [2-({2-[(α-L-fucopyranosyl)oxy]ethyl}amino)-2-oxoethyl][2-oxo-2-({2-[(α-D-mannopyranosyl)oxy]ethyl}amino)ethyl]carbamate To a solution of N-{[(9H-fluoren-9-yl)methoxy]carbonyl}-N-[2-({2-[(α-L-fucopyranosyl)oxy]ethyl}amino)-2-oxoethyl]glycine (1.57 g, 2.88 mmol) in DMF (25 mL) at 0° C. was added EDC (829 mg, 4.32 mmol), HOBt (132 mg, 0.865 mmol) and, after 30 min, 2-aminoethyl α-D-mannopyranoside (772 mg, 3.46 mmol). The mixture then was gradually warmed up to rt and stirred overnight. The reaction mixture was concentrated, and the residue was purified by column chromatography on 240 g C18 reverse phase silica gel, eluting with AcCN/H$_2$O (gradient from 0% to 40% in 20 CV), to give the title compound. UPLC-MS Method A: m/z=750.394 (z=1); t$_R$=2.87 min.

Step 4. N-{2-[(α-L-fucopyranosyl)oxy]ethyl}-2-{[2-oxo-2-({2-[(α-D-mannopyranosyl)oxy]ethyl}amino)ethyl]amino}acetamide To a solution of (9H-fluoren-9-yl)methyl [2-({2-[(α-L-fucopyranosyl)oxy]ethyl}amino)-2-oxoethyl][2-oxo-2-({2-[(α-D-mannopyranosyl)oxy]ethyl}amino)ethyl]carbamate (4.00 g, 5.34 mmol) in DMF (60 mL) was added piperidine (3.42 mL, 34.5 mmol). After stirring at rt for 30 min, the mixture was concentrated, and the residue was purified by column chromatography on 130 g C18 reverse phase silica gel, eluting with AcCN/H$_2$O (gradient from 0% to 30% in 10 CV), to give the title compound. UPLC-MS Method A: m/z=528.264 (z=1); t$_R$=1.10 min.

Step 5. Benzyl (6-{[2-({2-[(α-L-fucopyranosyl)oxy]ethyl}amino)-2-oxoethyl][2-oxo-2-({2-[(α-D-mannopyranosyl)oxy]ethyl}amino)ethyl]amino}-6-oxohexyl)carbamate To a solution of N-{2-[(α-L-fucopyranosyl)oxy]ethyl}-2-{[2-oxo-2-({2-[(α-D-mannopyranosyl)oxy]ethyl}amino)ethyl]amino}acetamide (2.70 g, 5.12 mmol) in DMF (40 mL) at 0° C. was added 2,5-dioxopyrrolidin-1-yl 6-{[(benzyloxy)carbonyl]amino}hexanoate (2.41 g, 6.19 mmol) in DMF (20 mL) portionwise over a period of 15 min and then TEA (1.077 mL, 7.73 mmol) dropwise over a period of 10 min. After stirring at rt for 48 hr, the mixture was concentrated, and the residue was purified by column chromatography on 240 g C18 reverse phase silica gel, eluting with AcCN/H$_2$O (gradient from 0% to 60% in 20 CV), to give the title compound. UPLC-MS Method A: m/z=775.392 (z=1); t$_R$=2.85 min.

Step 6. 6-amino-N-[2-({2-[(α-L-fucopyranosyl)oxy]ethyl}amino)-2-oxoethyl]-N-[2-oxo-2-({2-[(α-D-mannopyranosyl)oxy]ethyl}amino)ethyl]hexanamide To a solution of benzyl (6-{[2-({2-[(α-L-fucopyranosyl)oxy]ethyl}amino)-2-oxoethyl][2-oxo-2-({2-[(α-D-mannopyranosyl)oxy]ethyl}amino)ethyl]amino}-6-oxohexyl) carbamate (1.85 g, 2.388 mmol) in H$_2$O (35 mL) was added Pd/C (254 mg, 0.239 mmol). The resulting solution was degassed and stirred under H$_2$ at rt for 6 hr. The catalyst was filtered off through a cake of CELITE®, and the filtrate was freeze-dried to give the title compound. UPLC-MS Method A: m/z=641.353 (z=1); t$_R$=1.10 min.

Step 7. 2,5-dioxopyrrolidin-1-yl (17S,22S)-1-[(α-L-fucopyranosyl)oxy]-17,22-bis[(6-{[2-({2-[(α-L-fucopyranosyl)oxy]ethyl}amino)-2-oxoethyl][2-oxo-2-({2-[(α-D-mannopyranosyl)oxy]ethyl}amino)ethyl]amino}-6-oxohexyl)carbamoyl]-4,7,14,19,24,27-hexaoxo-6-[2-oxo-2-({2-[(α-D-mannopyranosyl)oxy]ethyl}amino)ethyl]-3,6,13,18,23,26-hexaazadotriacontan-32-oate The title compound was prepared using procedures analogous to those described for ML-1 substituting H-Gly-γGlu-Glu-OH for H-Glu-Asp-OH in Step 1 and 6-amino-N-[2-({2-[(α-L-fucopyranosyl)oxy]ethyl}amino)-2-oxoethyl]-N-[2-oxo-2-({2-[(α-D-mannopyranosyl)oxy]ethyl}amino)ethyl]hexanamide for 2-aminoethyl α-D-mannopyranoside in Step 2, respectively. UPLC-MS Method A: m/z=1214.115 (z=2); t$_R$=2.01 min.

Example 35: 2,5-dioxopyrrolidin-1-yl (14S,19S)-19-
[(6-{bis[2-({2-[(α-L-fucopyranosyl) oxy]
ethyl}amino)-2-oxoethyl]amino}-6-oxohexyl) car-
bamoyl]-14-{[6-(bis{2-[(α-D-mannopyranosyl)oxy]
ethyl}amino)-6-oxohexyl]carbamoyl}-4,11,16,21,
24-pentaoxo-1-[(α-D-mannopyranosyl)oxy]-3-{2-
[(α-D-mannopyranosyl)oxy]ethyl}-3,10,15,20,23-
pentaazanonacosan-29-oate (ML-35)

ML-35

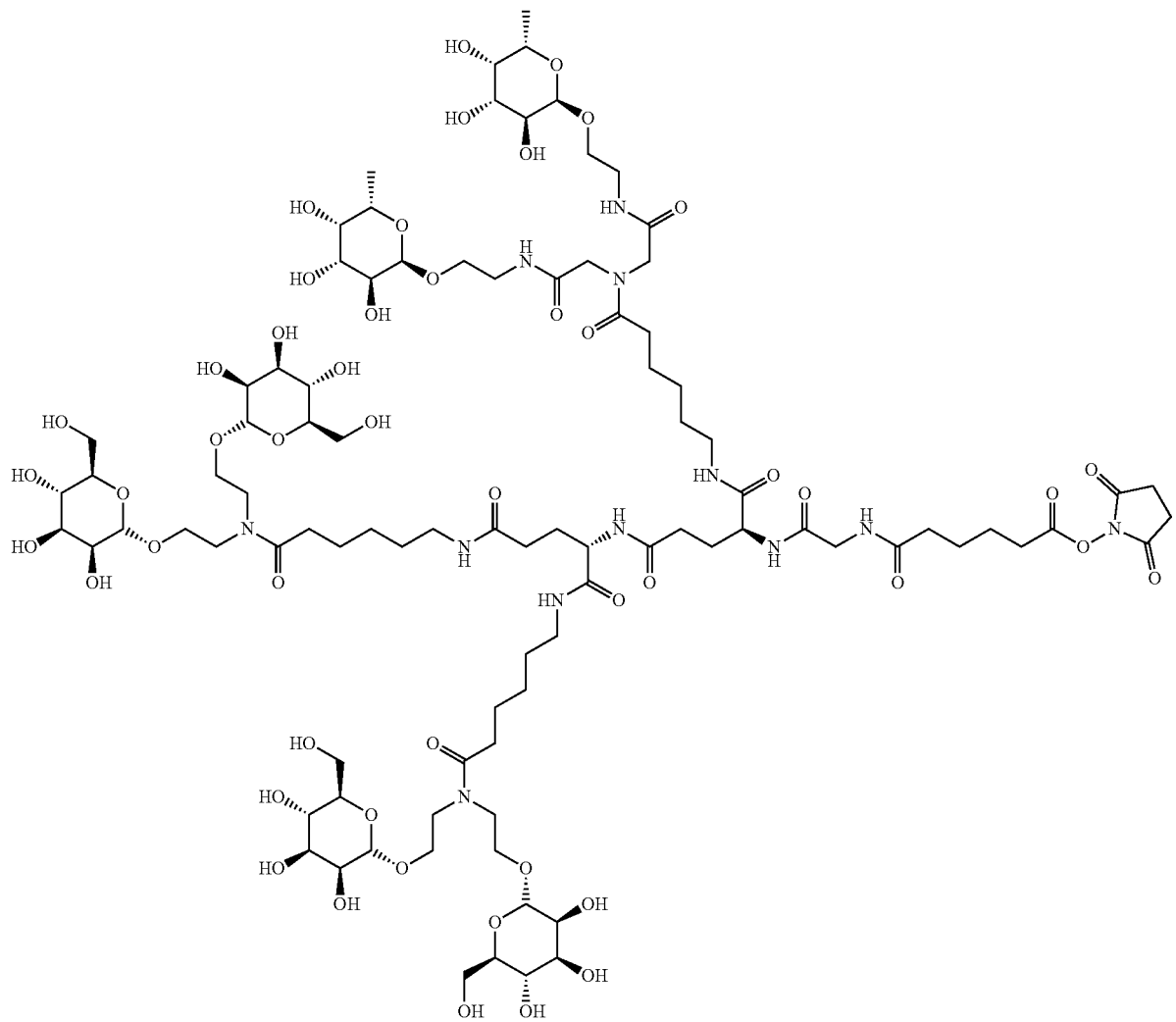

Step 1. Benzyl [5-(2-{bis[2-({2-[(α-L-fucopyrano-
syl)oxy]ethyl}amino)-2-oxoethyl]amino}acetamido)
pentyl]carbamate To a solution of 13-(carboxymethyl)-3,11-dioxo-1-phe-
nyl-2-oxa-4,10,13-triazapentadecan-15-oic acid (1.00 g, 2.442 mmol) in DMF (30 mL) at 0° C. was added EDC (1.41 g, 7.33 mmol), HOBt (224 mg, 1.465 mmol) and after 30 min, 2-aminoethyl α-L-fucopyranoside (1.22 g, 5.86 mmol). The mixture then was gradually warmed up to rt, stirred overnight, and then concentrated. The residue was purified by column chromatography on 150 g C18 reverse phase silica gel, eluting with AcCN/H$_2$O (gradient from 0% to 50% in 25 CV), to give the title compound. UPLC-MS Method A: m/z=788.453 (z=1); t$_R$=2.99 min.

Step 2. 2,2'-({2-[(5-aminopentyl)amino]-2-
oxoethyl}azanediyl)bis(N-{2-[(α-L-fucopyranosyl)
oxy]ethyl}acetamide)

To a solution of benzyl [5-(2-{bis[2-({2-[(α-L-fucopyra-
nosyl)oxy]ethyl}amino)-2-oxoethyl]amino}acetamido)pen-
tyl]carbamate (1.41 g, 1.788 mmol) in H$_2$O (20 mL) was added Pd/C (190 mg, 0.179 mmol). The resulting mixture was degassed and stirred under H$_2$ at rt for 4 hr. The catalyst was filtered off through a cake of CELITE®, and the filtrate was freeze-dried to give the title compound. UPLC-MS Method A: m/z=654.39 (z=1); $t_R$=1.06 min.

Step 3. 2,5-dioxopyrrolidin-1-yl (14S,19S)-19-[(6-{bis[2-({2-[(α-L-fucopyranosyl)oxy]ethyl}amino)-2-oxoethyl]amino}-6-oxohexyl)carbamoyl]-14-{[6-(bis{2-[(α-D-mannopyranosyl)oxy]ethyl}amino)-6-oxohexyl]carbamoyl}-4,11,16,21,24-pentaoxo-1-[(α-D-mannopyranosyl)oxy]-3-{2-[(α-D-mannopyranosyl)oxy]ethyl}-3,10,15,20,23-pentaazanonacosan-29-oate The title compound was prepared using procedures analogous to those described for ML-5 substituting 2,2'-({2-[(5-aminopentyl)amino]-2-oxoethyl}azanediyl)bis(N-{2-[(α-L-fucopyranosyl)oxy]ethyl}acetamide) for 6-amino-N-[2-({α-D-mannopyranosyl-(1→3)-[α-D-mannopyranosyl-(1→6)]-α-D-mannopyranosyl}oxy)ethyl]hexanamide in Step 4. UPLC-MS Method A: m/z=1122.603 (z=2); $t_R$=2.07 min.

Example 36: 2,5-dioxopyrrolidin-1-yl (S)-28-((S)-21-[6-(2-{bis[2-({2-[(α-D-mannopyranosyl)oxy]ethyl}amino)-2-oxoethyl]amino}acetamido) hexanamido]-1-[(α-D-mannopyranosyl)oxy]-6-[2-({2-[(α-D-mannopyranosyl)oxy]ethyl}amino)-2-oxoethyl]-4,8,15-trioxo-3,6,9,16-tetraazadocosan-22-amido)-1-[(α-D-mannopyranosyl)oxy]-6-[2-({2-[(α-D-mannopyranosyl)oxy]ethyl}amino)-2-oxoethyl]-4,8,15,22,29-pentaoxo-3,6,9,16,23,30-hexaazahexatriacontan-36-oate (ML-36)

ML-36

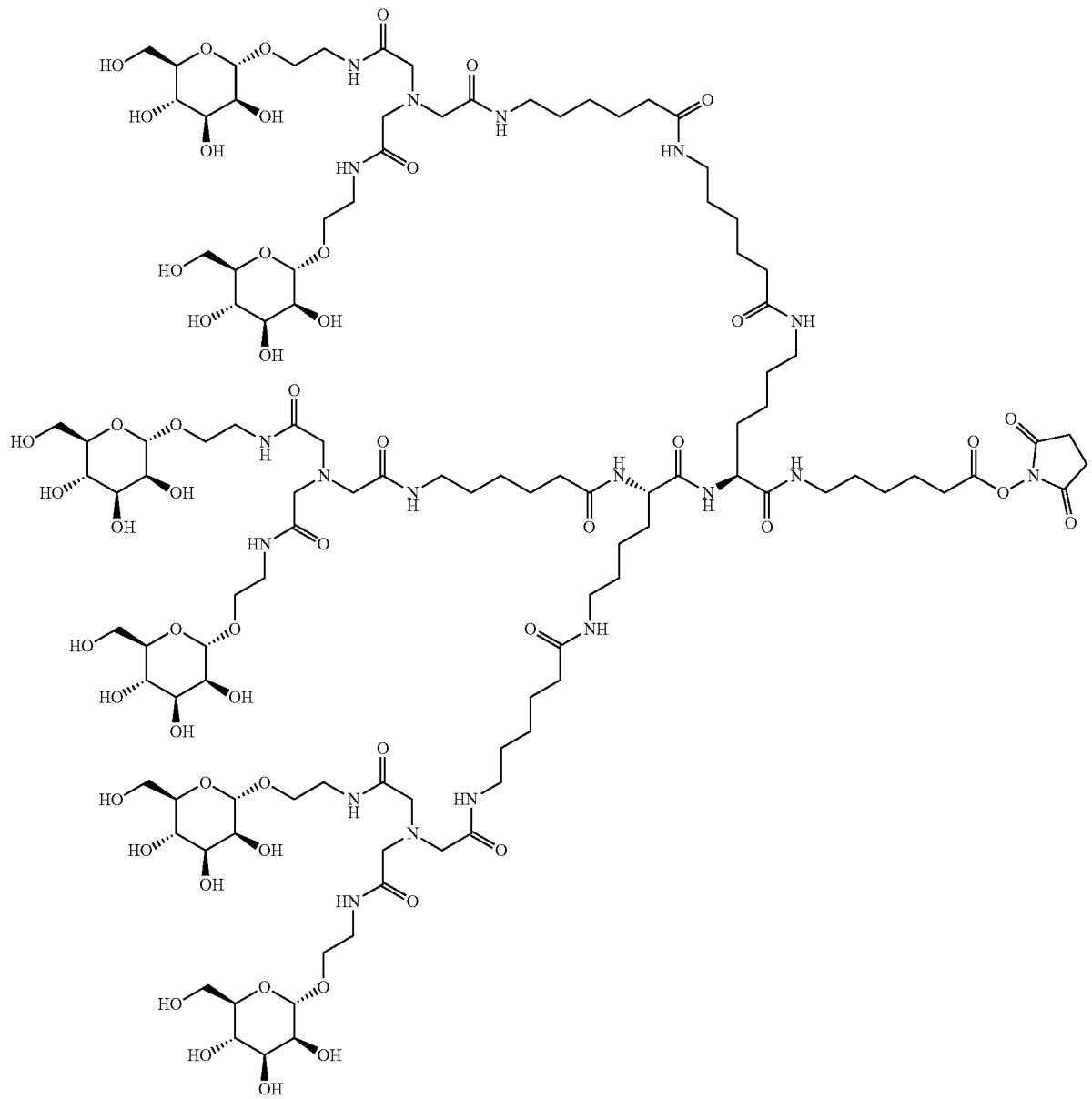

The title compound was prepared using procedures analogous to those described for ML-7 substituting 2,5-dioxopyrrolidin-1-yl 6-(2-{bis[2-({2-[(α-D-mannopyranosyl)oxy]ethyl}amino)-2-oxoethyl]amino}acetamido)hexanoate for 6-[(2,5-dioxopyrrolidin-1-yl)oxy]-N-(2-{[α-D-mannopyranosyl-(1→3)-[α-D-mannopyranosyl-(1→6)]-α-D-mannopyranosyl]oxy} ethyl)-6-oxohexanamide in Step 4. UPLC-MS Method A: m/z=1288.2451 (z=2); $t_R$=3.53 min.

Example 37: 2,5-dioxopyrrolidin-1-yl (S)-1-[(α-L-fucopyranosyl)oxy]-28-{(S)-1-[(α-L-fucopyranosyl) oxy]-21-[6-(2-{[2-({2-[(α-L-fucopyranosyl) oxy] ethyl}amino)-2-oxoethyl][2-oxo-2-({2-[(α-D-mannopyranosyl)oxy]ethyl}amino)ethyl] amino}acetamido)hexanamido]-4,8,15-trioxo-6-[2-oxo-2-({2-[(α-D-mannopyranosyl)oxy]ethyl} amino)ethyl]-3,6,9,16-tetraazadocosan-22-amido}-4,8,15,22,29-pentaoxo-6-[2-oxo-2-({2-[(α-D-mannopyranosyl) oxy]ethyl}amino)ethyl]-3,6,9,16,23,30-hexaazahexatriacontan-36-oate (ML-37)

ML-37

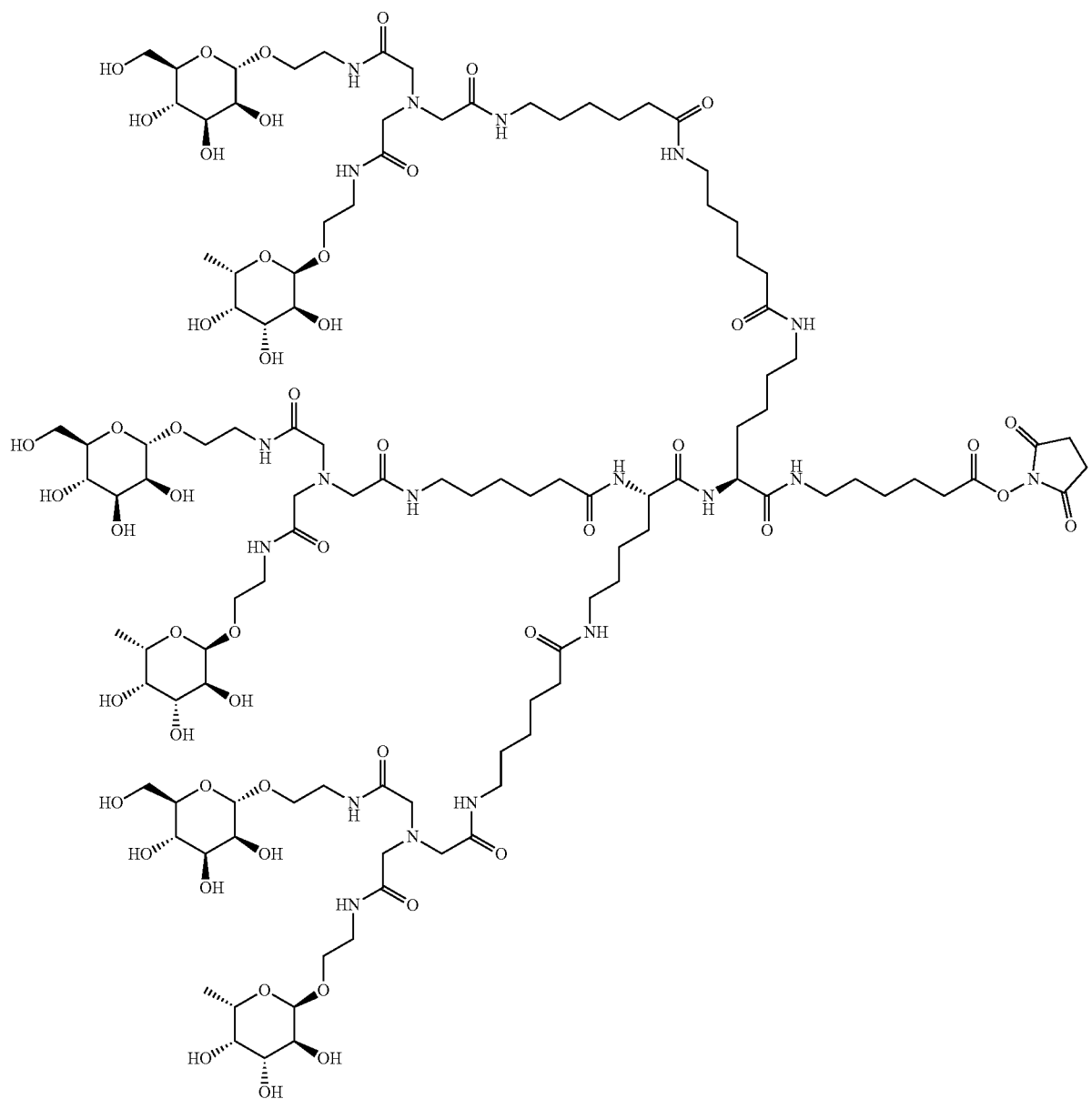

The title compound was prepared using procedures analogous to those described for ML-7 substituting 2,5-dioxopyrrolidin-1-yl 6-(2-{[2-({2-[(α-L-fucopyranosyl)oxy]ethyl}amino)-2-oxoethyl][2-oxo-2-({2-[(α-D-mannopyranosyl)oxy]ethyl}amino)ethyl]amino}acetamido) hexanoate for 6-[(2,5-dioxopyrrolidin-1-yl)oxy]-N-(2-{[α-D-mannopyranosyl-(1→3)-[α-D-mannopyranosyl-(1→6)]-α-D-mannopyranosyl]oxy}ethyl)-6-oxohexanamide in Step 4. UPLC-MS Method A: m/z=1264.2667 (z=2); $t_R$=3.85 min.

Example 38: 2,5-dioxopyrrolidin-1-yl (7S,12S,17S, 22S,27S)-1-[(α-L-fucopyranosyl)oxy]-7,12,17,22, 27-pentakis({2-[(α-L-fucopyranosyl)oxy]ethyl} carbamoyl)-4,9,14,19,24,29-hexaoxo-3,8,13,18,23,28-hexaazatetratriacontan-34-oate (ML-38)

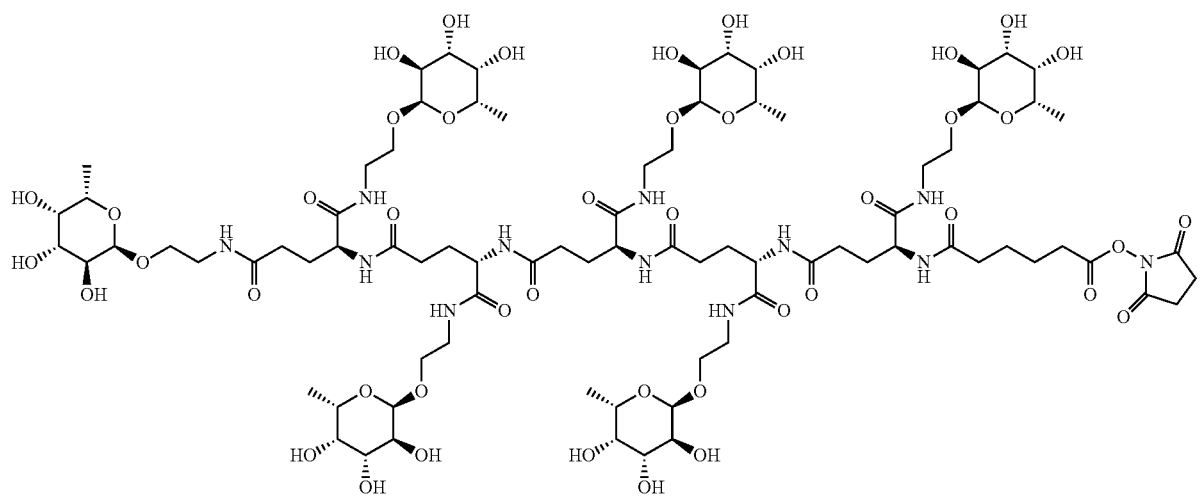

ML-38

The title compound was prepared using procedures analogous to those described for ML-1 substituting isoGlu-isoGlu-isoGlu-isoGlu-isoGlu for H-Glu-Asp-OH in Step 1 and 2-aminoethyl α-L-fucopyranoside for 2-aminoethyl α-D-mannopyranoside in Step 2, respectively. UPLC-MS Method A: m/z=1012.975 (z=2); $t_R$=2.00 min.

Example 39: 2,5-dioxopyrrolidin-1-yl (14S,19S, 24S)-14,19,24-tris{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,21,26-pentaoxo-3,10,15,20,25-pentaazahentriacontan-31-oate (ML-39)

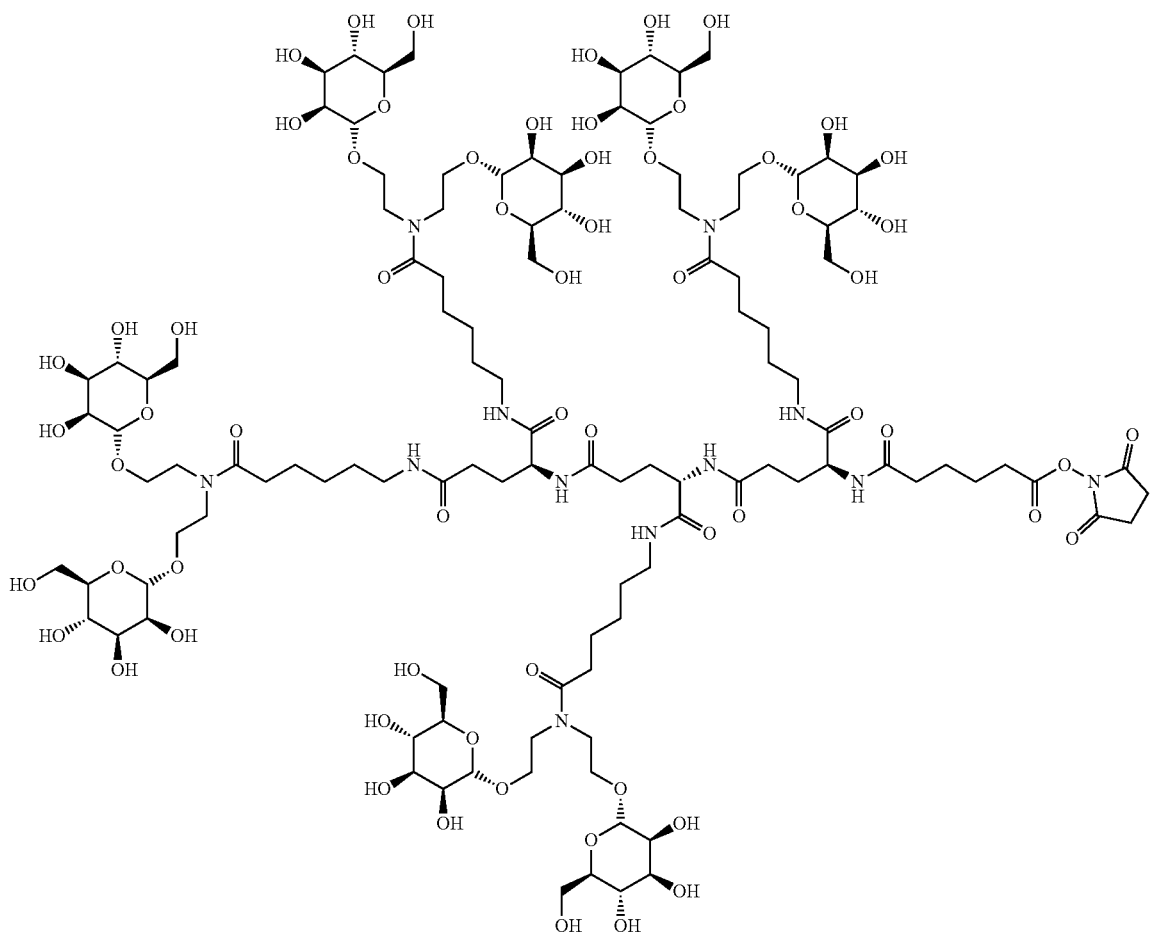

ML-39

The title compound was prepared using procedures analogous to those described for ML-1 substituting isoGlu-isoGlu-isoGlu for H-Glu-Asp-OH in Step 1 and 6-amino-N,N-bis{2-[(α-D-mannopyranosyl)oxy]ethyl}hexanamide for 2-aminoethyl α-D-mannopyranoside in Step 2, respectively. UPLC-MS Method A: m/z=1365.14 (z=2); $t_R$=4.16 min.

Example 40: 2,5-dioxopyrrolidin-1-yl (7S,14S,17S,20S)-17,20-bis({3-{[(S)-5-{bis[2-({2-[(α-D-mannopyranosyl)oxy]ethyl}amino)-2-oxoethyl]amino}-6-({2-[(α-D-mannopyranosyl) oxy]ethyl}amino)-6-oxohexyl]amino}-3-oxopropyl)-1-[(α-D-mannopyranosyl)oxy]-6-[2-({2-[(α-D-mannopyranosyl)oxy]ethyl}amino)-2-oxoethyl]-7-({2-[(α-D-mannopyranosyl)oxy]ethyl}carbamoyl)-14-isobutyl-4,13,16,19,22-pentaoxo-3,6,12,15,18,21-hexaazaheptacosan-27-oate (ML-40)

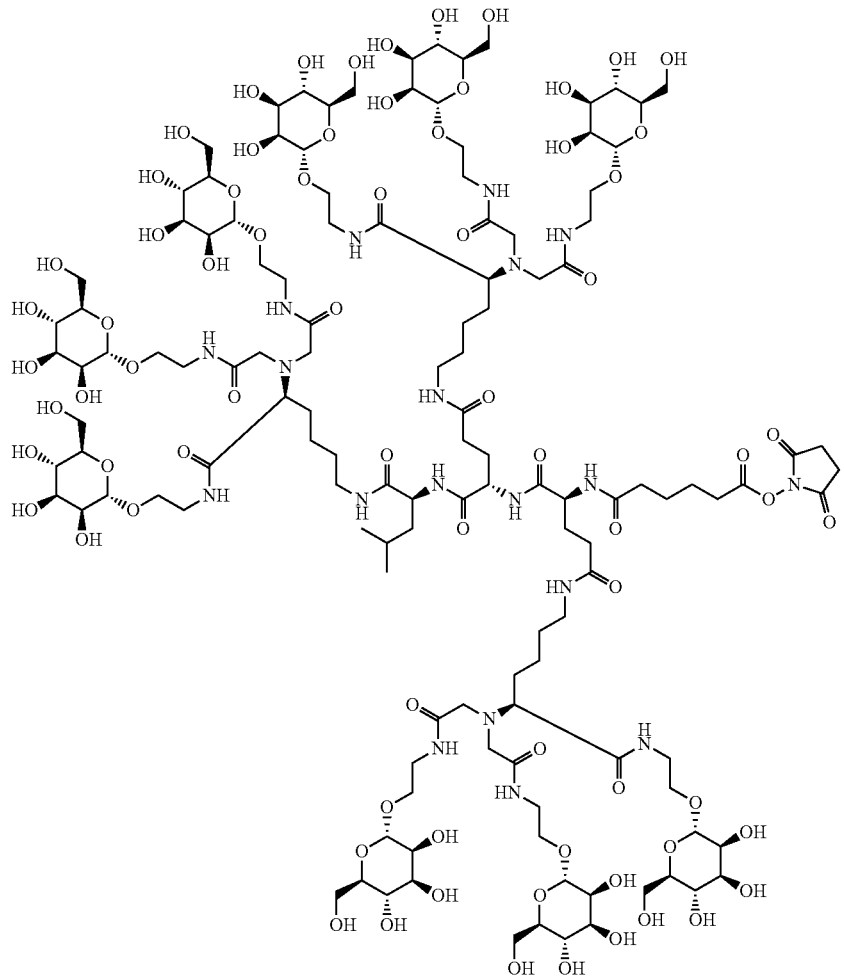

ML-40

Step 1. N6-[(benzyloxy)carbonyl]-N-[2-(α-D-mannopyranosyloxy)ethyl]-N2,N2-bis[2-({2-[(α-D-mannopyranosyl)oxy]ethyl}amino)-2-oxoethyl]-L-lysinamide To a solution of N6-[(benzyloxy)carbonyl]-N2,N2-bis(carboxymethyl)-L-lysine (1.0 g, 2.52 mmol) in DMF (15 mL) at rt was added a solution of 2-aminoethyl α-D-mannopyranoside (2.48 g, 11.10 mmol) in H$_2$O (2 mL) and HOBt (1.78 g, 11.60 mmol). The mixture was cooled to 0° C. and EDC (2.23 g, 11.60 mmol) was added. After stirring at 0° C. for 1.5 hr, the resulting solution was stirred at rt for 48 hr. The mixture was concentrated, and the residue was purified on 120 g C18 reverse phase silica gel column, eluting with 0-30% AcCN in H$_2$O. The desired fractions were combined and freeze-dried to afford the title compound. UPLC-MS Method D: m/z=1012.32 (z=1); t$_R$=3.78 min.

Step 2. N-{2-[(α-D-mannopyranosyl)oxy]ethyl}-N2,N2-bis[2-({2-[(α-D-mannopyranosyl)oxy]ethyl}amino)-2-oxoethyl]-L-lysinamide To a solution of N6-[(benzyloxy)carbonyl]-N-{2-[(α-D-mannopyranosyl)oxy] ethyl}-N2,N2-bis[2-({2-[(α-D-mannopyranosyl)oxy]ethyl}amino)-2-oxoethyl]-L-lysinamide (700 mg, 0.69 mmol) in H$_2$O (15 mL) was added Pd/C (150 mg, 0.14 mmol). The mixture was stirred under H$_2$ at rt for 16 hr. The catalyst was filtered off through CELITE®, and the filtrate was freeze-dried to afford the title product. UPLC-MS Method D: m/z=878.28 (z=1); $t_R$=3.64 min.

Step 3. 2,5-dioxopyrrolidin-1-yl (7S,14S,17S,20S)-17,20-bis({3-{[(S)-5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]amino}-3-oxopropyl)-1-[(α-D-mannopyranosyl)oxy]-6-[2-({2-[(α-D-mannopyranosyl)oxy]ethyl}amino)-2-oxoethyl]-7-({2-[(α-D-mannopyranosyl)oxy]ethyl}carbamoyl)-14-isobutyl-4,13,16,19,22-pentaoxo-3,6,12,15,18,21-hexaazaheptacosan-27-oate The title compound was prepared using procedures analogous to those described for ML-4 substituting N-{2-[(α-D-mannopyranosyl)oxy]ethyl}-N2,N2-bis[2-({2-[(α-D-mannopyranosyl) oxy]ethyl}amino)-2-oxoethyl]-L-lysinamide for 2-({α-D-mannopyranosyl-(1→3)-[α-D-mannopyranosyl-(1→6)]-α-D-mannopyranosyl}oxy)ethan-1-amine in Step 2. UPLC-MS Method A: m/z=1597.674 (z=2); $t_R$=4.01 min.

Example 41: 2,5-dioxopyrrolidin-1-yl (7S,14S,17S,20S)-17,20-bis({3-{[(S)-5-{bis[2-({2-[(α-D-glucopyranosyl)oxy]ethyl}amino)-2-oxoethyl] amino}-6-({2-[(α-D-glucopyranosyl) oxy]ethyl}amino)-6-oxohexyl]amino}-3-oxopropyl)-1-[(α-D-glucopyranosyl)oxy]-6-[2-({2-[(α-D-glucopyranosyl)oxy]ethyl}amino)-2-oxoethyl]-7-({2-[(α-D-glucopyranosyl)oxy]ethyl}carbamoyl)-14-isobutyl-4,13,16,19,22-pentaoxo-3,6,12,15,18,21-hexaazaheptacosan-27-oate (ML-41)

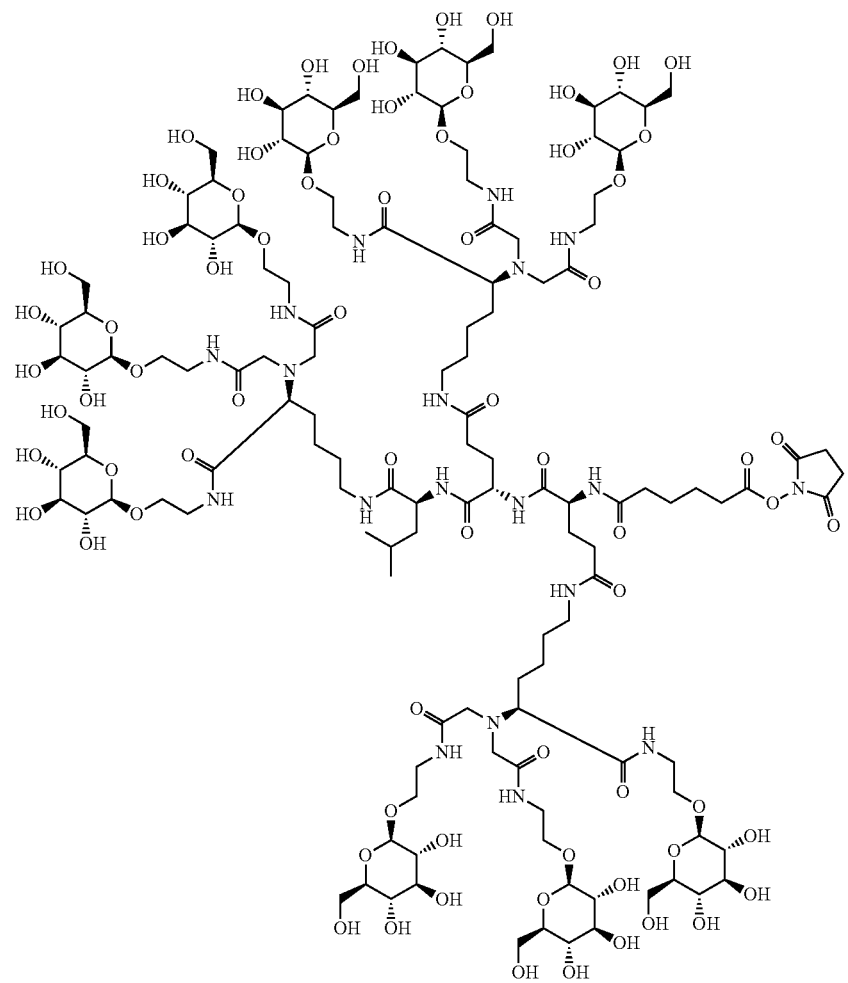

ML-41

The title compound was prepared using procedures analogous to those described for ML-40 substituting 2-aminoethyl α-D-glucopyranoside for 2-aminoethyl α-D-mannopyranoside in Step 1. UPLC-MS Method A: m/z=1597.710 (z=2); $t_R$=1.11 min.

Example 42: 2,5-dioxopyrrolidin-1-yl (7S,24S,27S)-24-(6-{[(S)-5-{bis[2-({2-[(α-L-fucopyranosyl)oxy]ethyl}amino)-2-oxoethyl]amino}-6-({2-[(α-L-fucopyranosyl)oxy]ethyl}amino)-6-oxohexyl]amino}-6-oxohexanamido)-1-[(α-L-fucopyranosyl) oxy]-27-{(S)-1-[(α-L-fucopyranosyl)oxy]-6-[2-({2-[(α-L-fucopyranosyl)oxy]ethyl}amino)-2-oxoethyl]-7-({2-[(α-L-fucopyranosyl)oxy]ethyl}carbamoyl)-4,13,18-trioxo-3,6,12,19-tetraazatricosan-23-yl}-6-[2-({2-[(α-L-fucopyranosyl)oxy]ethyl}amino)-2-oxoethyl]-7-({2-[(α-L-fucopyranosyl)oxy]ethyl}carbamoyl)-4,13,18,25,28-pentaoxo-3,6,12,19,26,29-hexaazapentatriacontan-35-oate (ML-42)

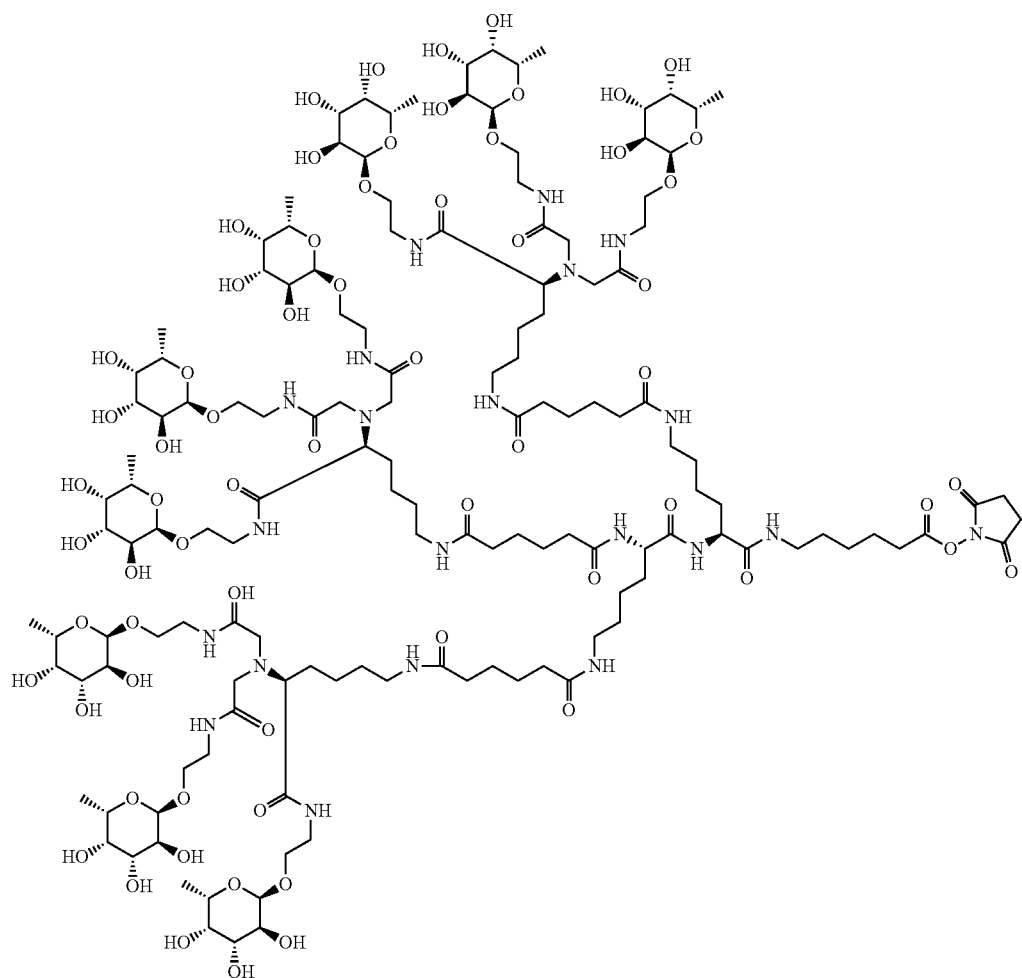

ML-42

Step 1. N6-[(benzyloxy)carbonyl]-N-[2-(α-L-fucopyranosyloxy)ethyl]-N2,N2-bis[2-({2-[(α-L-fucopyranosyl)oxy]ethyl}amino)-2-oxoethyl]-L-lysinamide To a solution of N6-[(benzyloxy)carbonyl]-N2,N2-bis(carboxymethyl)-L-lysine (600 mg, 1.514 mmol) in DMF (20 mL) at rt was added a solution of 2-aminoethyl α-L-fucopyranoside (1.19 g, 5.75 mmol) in H$_2$O (2 mL) and DMAP (758 mg, 6.21 mmol). The mixture was cooled to 0° C. and EDC (1.39 g, 7.27 mmol) was added. After stirring at 0° C. for 1.5 hr, the resulting solution was stirred at rt for 16 hr. The mixture was concentrated, and the residue was purified on 50 g C18 reverse phase silica gel column, eluting with EtOAc/MeOH/AcCN/H$_2$O (v/v/v/v=4/1/1/1), to give an enriched material, which was further purified on HPLC (C4 column, 250×50 mm, 27%-33% AcCN with 0.1% TFA in water with 0.1% TFA over 30 min) to give the title compound. UPLC-MS Method D: m/z=964.529 (z=1); t$_R$=2.52 min.

Step 2. N-{2-[(α-L-fucopyranosyl)oxy]ethyl}-N2,N2-bis[2-({2-[(α-L-fucopyranosyl)oxy]ethyl}amino)-2-oxoethyl]-L-lysinamide To a solution of N6-[(benzyloxy)carbonyl]-N-{2-[(α-L-fucopyranosyl)oxy] ethyl}-N2,N2-bis[2-({2-[(α-L-fucopyranosyl)oxy]ethyl}amino)-2-oxoethyl]-L-lysinamide (3.0 g, 3.11 mmol) in H$_2$O (50 mL) was added Pd(OH)$_2$ (219 mg, 0.311 mmol). The mixture was degassed and shaken on a Parr shaker under 344.74 kPa H$_2$ at rt overnight. The catalyst was filtered off through CELITE®, and the filtrate was freeze-dried to afford the title product. UPLC Method D: m/z=830.54 (z=1); t$_R$=1.09 min.

Step 3. Benzyl (S)-6-{[5-{bis[2-({2-[(α-L-fucopyranosyl)oxy]ethyl}amino)-2-oxoethyl]amino}-6-({2-[(α-L-fucopyranosyl)oxy]ethyl}amino)-6-oxohexyl]amino}-6-oxohexanoate To a solution of N-{2-[(α-L-fucopyranosyl)oxy]ethyl}-N2,N2-bis[2-({2-[(α-L-fucopyranosyl)oxy]ethyl}amino)-2-oxoethyl]-L-lysinamide (2.66 g, 3.21 mmol) and 6-(benzyloxy)-6-oxohexanoic acid (909 mg, 3.85 mmol) in DMF (16 mL) was added sequentially DIPEA (1.679 mL, 9.62 mmol), HOBt (589 mg, 3.85 mmol) and EDC (737 mg, 3.85 mmol). After stirring overnight, the reaction mixture was concentrated, and the residue was purified on 120 g SiO$_2$ column (flow rate 100 mL/min, gradient solvent A-solvent B of 0-100% solvent B in 30 min followed by hold, where solvent A was EtOAc, and solvent B was EtOAc/MeOH/AcCN/H$_2$O (v/v/v/v=6/1/1/1), to give the title compound. UPLC-MS Method A: m/z=1048.6133 (z=1); t$_R$=2.72.

Step 4. (S)-6-{[5-{bis[2-({2-[(α-L-fucopyranosyl)oxy]ethyl}amino)-2-oxoethyl]amino}-6-({2-[(α-L-fucopyranosyl)oxy]ethyl}amino)-6-oxohexyl]amino}-6-oxohexanoic Acid To a solution of benzyl (S)-6-{[5-{bis[2-({2-[(α-L-fucopyranosyl)oxy]ethyl} amino)-2-oxoethyl]amino}-6-({2-[(α-L-fucopyranosyl)oxy]ethyl}amino)-6-oxohexyl]amino}-6-oxohexanoate (2.4 g, 2.290 mmol) in H$_2$O (23 mL) and added aq. NaOH (687 µL, 3.43 mmol, 5.0M). After stirring overnight, the reaction mixture was neutralized to pH~6 with 1M HCl and freeze-dried to give the title compound. UPLC-MS Method A: m/z=958.5002 (z=1); t$_R$=1.71 min.

Step 5. benzyl (7S,24S,27S)-24-(6-{[(S)-5-{bis[2-({2-[(α-L-fucopyranosyl)oxy]ethyl}amino)-2-oxoethyl]amino}-6-({2-[(α-L-fucopyranosyl)oxy]ethyl}amino)-6-oxohexyl]amino}-6-oxohexanamido)-1-[(α-L-fucopyranosyl)oxy]-27-{(S)-1-[(α-L-fucopyranosyl)oxy]-6-[2-({2-[(α-L-fucopyranosyl)oxy]ethyl}amino)-2-oxoethyl]-7-({2-[(α-L-fucopyranosyl)oxy]ethyl}carbamoyl)-4,13,18-trioxo-3,6,12,19-tetraazatricosan-23-yl}-6-[2-({2-[(α-L-fucopyranosyl)oxy]ethyl}amino)-2-oxoethyl]-7-({2-[(α-L-fucopyranosyl)oxy]ethyl}carbamoyl)-4,13,18,25,28-pentaoxo-3,6,12,19,26,29-hexaazapentatriacontan-35-oate To a solution of (S)-6-{[5-{bis[2-({2-[(α-L-fucopyranosyl)oxy]ethyl}amino)-2-oxoethyl]amino}-6-({2-[(α-L-fucopyranosyl)oxy]ethyl}amino)-6-oxohexyl]amino}-6-oxohexanoic acid (501 mg, 0.523 mmol) and benzyl 6-((S)-6-amino-2-[(S)-2,6-diaminohexan-amido)hexanamido]hexanoate (50 mg, 0.105 mmol) in DMF (5.0 mL) was added DIPEA (183p, 1.047 mmol), HOBt (48.1 mg, 0.314 mmol) and EDC (100 mg, 0.523 mmol). After stirring overnight, the reaction mixture was concentrated, and the residue was purified on C18 column (ISCO-C18, 130 g, flow rate=70 mL/min; gradient 0-50% AcCN in H$_2$O in 40 min followed by hold) to give the title compound. UPLC-MS Method A: m/z=1649.4575 (z=2); t$_R$=2.48 min.

Step 5. 2,5-dioxopyrrolidin-1-yl (7S,24S,27S)-24-(6-{[(S)-5-{bis[2-({2-[(α-L-fucopyranosyl) oxy]ethyl}amino)-2-oxoethyl]amino}-6-({2-[(α-L-fucopyranosyl)oxy]ethyl}amino)-6-oxohexyl]amino}-6-oxohexanamido)-1-[(α-L-fucopyranosyl)oxy]-27-{(S)-1-[(α-L-fucopyranosyl) oxy]-6-[2-({2-[(α-L-fucopyranosyl)oxy]ethyl}amino)-2-oxoethyl]-7-({2-[(α-L-fucopyranosyl) oxy]ethyl}carbamoyl)-4,13,18-trioxo-3,6,12,19-tetraazatricosan-23-yl}-6-[2-({2-[(α-L-fucopyranosyl)oxy]ethyl}amino)-2-oxoethyl]-7-({2-[(α-L-fucopyranosyl)oxy]ethyl}carbamoyl)-4,13,18,25,28-pentaoxo-3,6,12,19,26,29-hexaazapentatriacontan-35-oate The title compound was prepared using procedures analogous to those described for ML-1 substituting benzyl (7S,24S,27S)-24-(6-{[(S)-5-{bis[2-({2-[(α-L-fucopyranosyl) oxy]ethyl}amino)-2-oxoethyl]amino}-6-({2-[(α-L-fucopyranosyl)oxy]ethyl}amino)-6-oxohexyl] amino}-6-oxohexanamido)-1-[(α-L-fucopyranosyl)oxy]-27-{(S)-1-[(α-L-fucopyranosyl)oxy]-6-[2-({2-[(α-L-fucopyranosyl) oxy]ethyl}amino)-2-oxoethyl]-7-({2-[(α-L-fucopyranosyl) oxy]ethyl}carbamoyl)-4,13,18-trioxo-3,6,12,19-tetraazatricosan-23-yl}-6-[2-({2-[(α-L-fucopyranosyl)oxy] ethyl}amino)-2-oxoethyl]-7-({2-[(α-L-fucopyranosyl)oxy] ethyl}carbamoyl)-4,13,18,25,28-pentaoxo-3,6,12,19,26,29-hexaazapentatriacontan-35-oate for benzyl 6-{[(S)-5-{[(S)-1,5-dioxo-1,5-bis({2-[(α-D-mannopyranosyl)oxy] ethyl}amino)pentan-2-yl]amino}-1,5-dioxo-1-({2-[(α-D-mannopyranosyl)oxy]ethyl}amino)pentan-2-yl]amino}-6-oxohexanoate in Step 3. UPLC-MS Method A: m/z=1653.3778 (z=2); t$_R$=2.29 min.

Example 43: 2,5-dioxopyrrolidin-1-yl (21S,24S)-1-[(α-D-mannopyranosyl)oxy]-24-{1-[(α-D-mannopyranosyl)oxy]-4,8,15-trioxo-6-(2-oxo-2-{[2-({α-D-mannopyranosyl-(1→3)-[α-D-mannopyranosyl-(1→6)]-α-D-mannopyranosyl}oxy)ethyl]amino}ethyl)-3,6,9,16-tetra-azaicosan-20-yl}-21-[6-(2-{[2-({2-[(α-D-mannopyranosyl)oxy]ethyl}amino)-2-oxoethyl](2-oxo-2-{[2-({α-D-mannopyranosyl-(1→3)-[α-D-mannopyranosyl-(1→6)]-α-D-mannopyranosyl}oxy)ethyl]amino}ethyl)amino}acetamido) exanamido)-4,8,15,22,25-pentaoxo-6-(2-oxo-2-{[2-({α-D-mannopyranosyl-(1→3)-[α-D-mannopyranosyl-(1→6)]-α-D-mannopyranosyl}oxy)ethyl]amino}ethyl)-3,6,9,16,23,26-hexaazadotriacontan-32-oate (ML-43)

ML-43

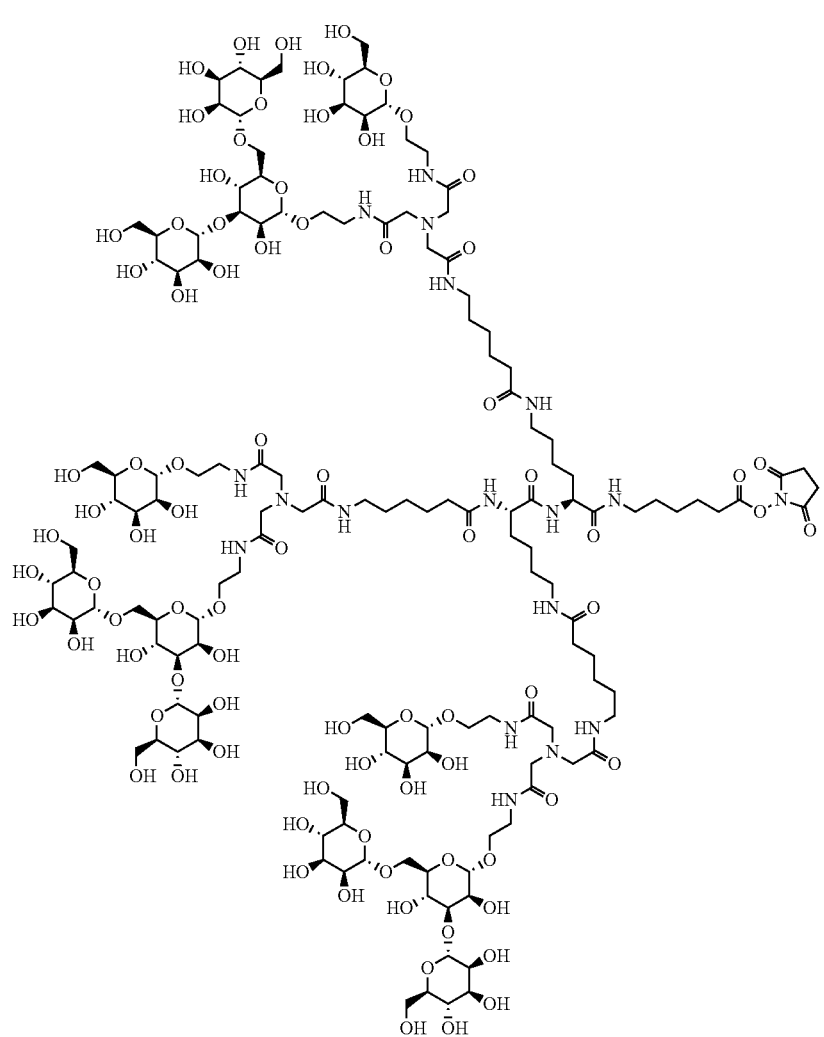

The title compound was prepared using procedures analogous to those described for ML-23 substituting 6-amino-N-[2-({α-D-mannopyranosyl-(1→3)-[α-D-mannopyranosyl-(1→6)]-α-D-mannopyranosyl}oxy)ethyl]hexanamide and 2-aminoethyl α-D-mannopyranoside for bis{2-[(2,3,4,6-tetra-O-acetyl-α-D-mannopyranosyl)oxy]ethyl}amine and 2-aminoethyl α-L-fucopyranoside in Step 1 and Step 2, respectively. UPLC-MS Method A: m/z=1774.77 (z=2); $t_R$=4.22 min.

Example 44: 2,5-dioxopyrrolidin-1-yl (22S,29S, 36S,43S)-22,29,36,43-tetrakis(2-{bis[2-({2-[(α-D-mannopyranosyl)oxy]ethyl}amino)-2-oxoethyl]amino} acetamido)-1-[(α-D-mannopyranosyl)oxy]-6-[2-({2-[(α-D-mannopyranosyl) oxy]ethyl}amino)-2-oxoethyl]-4,8,16,23,30,37,44-heptaoxo-3,6,9,17,24,31,38,45-octaazahenpentacontan-51-oate (ML-44)
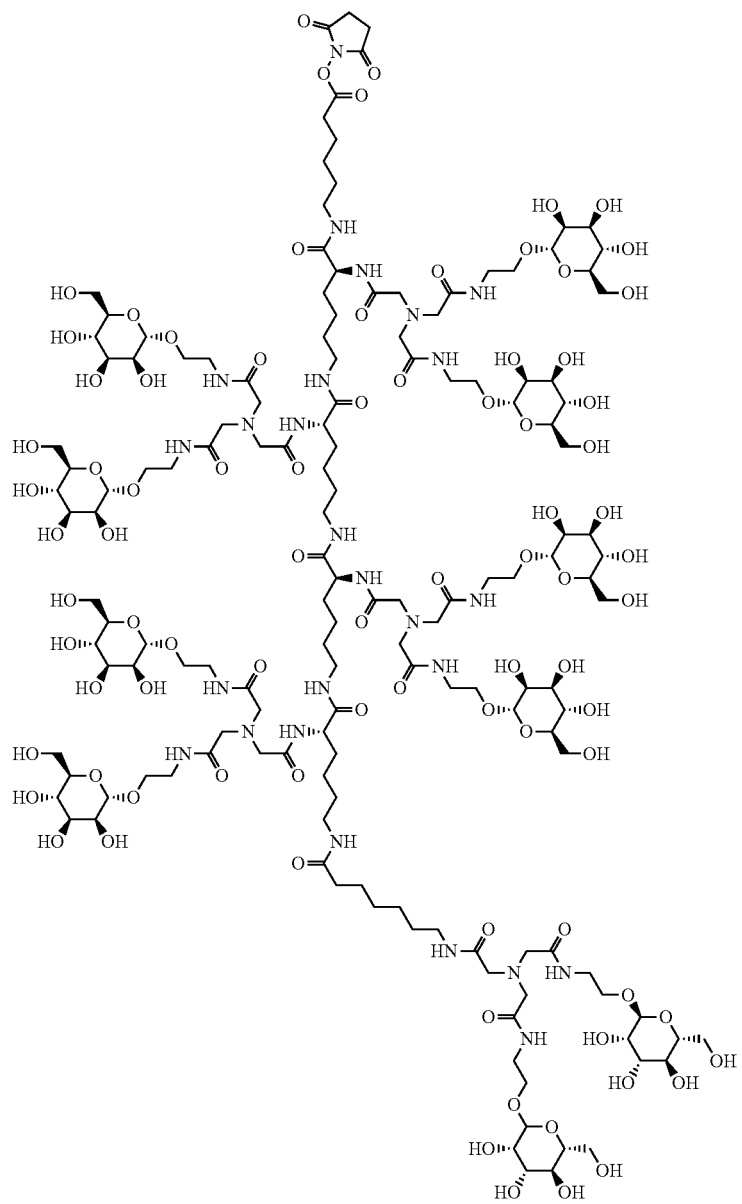
ML-44

Step 1. methyl (10S,17S,24S)-10-(4-{[(benzyloxy) carbonyl]amino}butyl)-17,24-bis(2-{bis[2-({2-[(α-D-mannopyranosyl)oxy]ethyl}amino)-2-oxoethyl] amino}acetamido)-1-[(α-D-mannopyranosyl)oxy]-6-[2-({2-[(α-D-mannopyranosyl)oxy]ethyl}amino)-2-oxoethyl]-4,8,11,18,25-pentaoxo-3,6,9,12,19,26-hexaazadotriacontan-32-oate To a solution of N6-[(benzyloxy)carbonyl]-N2-{bis[2-({2-[(α-D-mannopyranosyl)oxy]ethyl}amino)-2-oxoethyl] glycyl}-L-lysine (100 mg, 0.103 mmol) and methyl (10S, 17S)-10-(4-aminobutyl)-17-(2-{bis[2-({2-[(α-D-mannopyranosyl)oxy]ethyl} amino)-2-oxoethyl] amino}acetamido)-1-[(α-D-mannopyranosyl)oxy]-6-[2-({2-[(α-D-mannopyranosyl)oxy]ethyl}amino)-2-oxoethyl]-4,8,11,18-tetraoxo-3,6,9,12,19-pentaazapentacosan-25-oate (161 mg, 0.103 mmol, mL-29 Step 11) in DMF (5.144 mL) was added HOBt (31.5 mg, 0.206 mmol), DIPEA (53.9 µL, 0.309 mmol) and EDC (29.6 mg, 0.154 mmol). After stirring overnight, the reaction mixture was concentrated, and the residue was purified by reverse-phase chromatography on C-8 phase (C8 reverse phase gel 10 µm 100 Å, size 250×50 mm; solvent A=water/0.05% TFA, solvent B=AcCN/0.05% TFA), Flow rate=85 mL/min, gradient B in A 0-30% in 30 min) to give the title compound. UPLC-MS Method A: m/z=1207.6863 (z=2); $t_R$=3.75 min.

Step 2. methyl (10S,17S,24S)-10-(4-aminobutyl)-17,24-bis(2-{bis[2-({2-[(α-D-mannopyranosyl) oxy]ethyl}amino)-2-oxoethyl]acetamido)-1-[(α-D-mannopyranosyl)oxy]-6-[2-({2-[(α-D-mannopyranosyl)oxy]ethyl}amino)-2-oxoethyl]-4,8,11,18,25-pentaoxo-3,6,9,12,19,26-hexaazadotriacontan-32-oate A mixture of methyl (10S,17S,24S)-10-(4-{[(benzyloxy) carbonyl]amino}butyl)-17,24-bis(2-{bis[2-({2-[(α-D-mannopyranosyl)oxy]ethyl}amino)-2-oxoethyl] amino}acetamido)-1-[(α-D-mannopyranosyl)oxy]-6-[2-({2-[(α-D-mannopyranosyl)oxy]ethyl}amino)-2-oxoethyl]-4,8,11,18,25-pentaoxo-3,6,9,12,19,26-hexaazadotriacontan-32-oate (80 mg, 0.033 mmol) in H$_2$O (8.3 mL) and Pd(OH)$_2$ (4.7 mg, 6.63 µmol) was degassed and shaken on a Parr shaker at 344.74 kPa of H$_2$ overnight. The catalyst was removed by filtration, and the filtrate was freeze-dried to give the title compound. UPLC-MS Method A: m/z=1141.1532 (z=2); $t_R$=3.90 min.

Step 3. methyl (10S,17S,24S,31S)-10-(4-{[(benzyloxy)carbonyl]amino}butyl)-17,24,31-tris(2-{bis[2-({2-[(α-D-mannopyranosyl)oxy]ethyl}amino)-2-oxoethyl]amino}acetamido)-1-[(α-D-mannopyranosyl)oxy]-6-[2-({2-[(α-D-mannopyranosyl)oxy]ethyl}amino)-2-oxoethyl]-4,8,11,18,25,32-hexaoxo-3,6,9,12,19,26,33-heptaazanonatriacontan-39-oate To a stirred solution of methyl (10S,17S,24S)-10-(4-aminobutyl)-17,24-bis(2-{bis[2-({2-[(α-D-mannopyranosyl)oxy]ethyl}amino)-2-oxoethyl]amino}acetamido)-1-[(α-D-mannopyranosyl)oxy]-6-[2-({2-[(α-D-mannopyranosyl) oxy]ethyl}amino)-2-oxoethyl]-4,8,11,18,25-pentaoxo-3,6,9,12,19,26-hexaazadotriacontan-32-oate (84 mg, 0.037 mmol), N6-[(benzyl oxy)carbonyl]-N2-{bis[2-({2-[(α-D-mannopyranosyl)oxy]ethyl}amino)-2-oxoethyl] glycyl}-L-lysine (41.4 mg, 0.048 mmol) in DMF (1.473 mL) was added HOBt (7 mg, 0.048 mmol), DIPEA (19.30 µl, 0.111 mmol), and EDC (9.2 mg, 0.048 mmol). After stirring at rt overnight, the reaction mixture was concentrated, and the residue was purified by reverse-phase chromatography C8 reverse phase gel 10 µM 100 A, size 250×50 mm; solvent A=water/0.05% TFA, solvent B=AcCN/0.05% TFA, Flow=85 mL/min, gradient B in A 0-30% in 30 min) to give the title compound. UPLC-MS Method A: m/z=1563.8967 (z=2); $t_R$=2.95 min.

Step 4. methyl (10S,17S,24S,31S)-10-(4-aminobutyl)-17,24,31-tris(2-{bis[2-({2-[(α-D-mannopyranosyl)oxy]ethyl}amino)-2-oxoethyl] amino}acetamido)-1-[(α-D-mannopyranosyl) oxy]-6-[2-({2-[(α-D-mannopyranosyl)oxy]ethyl}amino)-2-oxoethyl]-4,8,11,18,25,32-hexaoxo-3,6,9,12,19,26, 33-heptaazanonatriacontan-39-oate A mixture of methyl (10S,17S,24S,31S)-10-(4-{[(benzyloxy)carbonyl]amino} butyl)-17,24,31-tris(2-{bis[2-({2-[(α-D-mannopyranosyl)oxy]ethyl}amino)-2-oxoethyl] amino}acetamido)-1-[(α-D-mannopyranosyl)oxy]-6-[2-({2-[(α-D-mannopyranosyl)oxy]ethyl}amino)-2-oxoethyl]-4,8,11,18,25,32-hexaoxo-3,6,9,12,19,26,33-heptaazanonatriacontan-39-oate (90 mg, 0.029 mmol) and Pd(OH)$_2$ (4.0 mg, 5.76 µmol) was shaken on a Parr shaker at 344.74 kPa of H$_2$ overnight. The catalyst was filtered out, and the filtrate was freeze-dried to give the title compound. UPLC-MS Method A: m/z=1496.8593 (z=2); $t_R$=3.39 min.

Step 5. methyl (21S,28S,35S,42S)-21,28,35,42-tetrakis(2-{bis[2-({2-[(α-D-mannopyranosyl)oxy] ethyl}amino)-2-oxoethyl]amino}acetamido)-1-[(α-D-mannopyranosyl)oxy]-6-[2-({2-[(α-D-mannopyranosyl)oxy]ethyl}amino)-2-oxoethyl]-4,8, 15,22,29,36,43-heptaoxo-3,6,9,16,23,30,37,44-octaazapentacontan-50-oate To a solution of methyl (10S,17S,24S,31S)-10-(4-aminobutyl)-17,24,31-tris(2-{bis[2-({2-[(α-D-mannopyranosyl)oxy]ethyl}amino)-2-oxoethyl]amino}acetamido)-1-[(α-D-mannopyranosyl)oxy]-6-[2-({2-[(α-D-mannopyranosyl) oxy]ethyl}amino)-2-oxoethyl]-4,8,11,18,25,32-hexaoxo-3, 6,9,12,19,26,33-heptaazanonatriacontan-39-oate (79 mg, 0.026 mmol), 6-(2-{bis[2-({2-[(α-D-mannopyranosyl)oxy] ethyl}amino)-2-oxoethyl]amino}acetamido)hexanoic acid (22.64 mg, 0.032 mmol) in DMF (1.320 mL) was added HOBt (6.07 mg, 0.040 mmol), DIPEA (13.83 µL, 0.079 mmol) and EDC (6.58 mg, 0.034 mmol). After stirring overnight, the reaction mixture was concentrated, and the residue was purified by reverse-phase chromatography on C8 reverse phase gel 10 µm 100 A, size 250×50 mm; solvent A=water/0.05% TFA, solvent B=AcCN/0.05% TFA, Flow=85 mL/min, gradient B in A 1-30% in 30 min) to give the title compound. UPLC-MS Method A: m/z=1844.9913 (z=2); $t_R$=4.06 min.

Step 6. (21S,28S,35S,42S)-21,28,35,42-tetrakis(2-{bis[2-({2-[(α-D-mannopyranosyl)oxy] ethyl}amino)-2-oxoethyl]amino}acetamido)-1-[(α-D-mannopyranosyl)oxy]-6-[2-({2-[(α-D-mannopyranosyl)oxy]ethyl}amino)-2-oxoethyl]-4,8, 15,22,29,36,43-heptaoxo-3,6,9,16,23,30,37,44-octaazapentacontan-50-oic Acid To a solution of methyl (21S,28S,35S,42S)-21,28,35,42-tetrakis(2-{bis[2-({2-[(α-D-mannopyranosyl)oxy] ethyl}amino)-2-oxoethyl]amino}acetamido)-1-[(α-D-mannopyranosyl) oxy]-6-[2-({2-[(α-D-mannopyranosyl)oxy] ethyl}amino)-2-oxoethyl]-4,8,15,22,29,36,43-heptaoxo-3,6, 9,16,23,30,37,44-octaazapentacontan-50-oate (69 mg, 0.019 mmol) in H$_2$O (1.871 mL) was added NaOH (187 µl, 0.187 mmol, 1.0 M). After 30 min, the reaction mixture was diluted with H₂O (10 mL), the pH was adjusted to ~ 6.5, and freeze-dried to give the title compound. UPLC-MS Method A: 1838.0414 (z=2); $t_R$=4.31 min.

Step 7. 2,5-dioxopyrrolidin-1-yl (22S,29S,36S,43S)-22,29,36,43-tetrakis(2-{bis[2-({2-[(α-D-mannopyranosyl)oxy]ethyl}amino)-2-oxoethyl]amino}acetamido)-1-[(α-D-mannopyranosyl) oxy]-6-[2-({2-[(α-D-mannopyranosyl)oxy]ethyl}amino)-2-oxoethyl]-4,8,16,23,30,37,44-heptaoxo-3,6,9,17,24,31,38,45-octaazahenpentacontan-51-oate To a solution of (21S,28S,35S,42S)-21,28,35,42-tetrakis (2-{bis[2-({2-[(α-D-mannopyranosyl)oxy]ethyl}amino)-2-oxoethyl]amino}acetamido)-1-[(α-D-mannopyranosyl)oxy]-6-[2-({2-[(α-D-mannopyranosyl)oxy]ethyl}amino)-2-oxoethyl]-4,8,15,22,29,36,43-heptaoxo-3,6,9,16,23,30,37,44-octaazapentacontan-50-oic acid (85 mg, 0.023 mmol) in DMF (1.5 mL) at 0° C. was added TSTU (7.0 mg, 0.023 mmol) and TEA (6.5 μl, 0.046 mmol). After stirring for 40 min, the reaction mixture was poured into a mixture of ether-acetone (v/v=1:1, 30 mL). The precipitate was collected by centrifugation and dried to give the title compound. UPLC-MS Method A: m/z=1886.4711 (z=2); $t_R$=4.23 min.

Example 45: 2,5-dioxopyrrolidin-1-yl (21S,24S)-21 [6-(2-{bis[2-(bis{2-[(α-D-manno-pyranosyl)oxy]ethyl}amino)-2-oxoethyl]amino}acetamido) hexanamido]-6-[2-(bis{2-[(α-D-mannopyranosyl)oxy]ethyl}amino)-2-oxoethyl]-24-(6-[2-(bis{2-[(α-D-mannopyranosyl)oxy]ethyl}amino)-2-oxoethyl]-1-[(α-D-mannopyranosyl)oxy]-3-{2-[(α-D-mannopyranosyl)oxy]ethyl}-4,8,15-trioxo-3,6,9,16-tetraazaicosan-20-yl)-1-[(α-D-mannopyranosyl)oxy]-3-{2-[(α-D-mannopyranosyl)oxy]ethyl}-4,8,15,22,25-pentaoxo-3,6,9,16,23,26-hexaazadotriacontan-32-oate (ML-45)

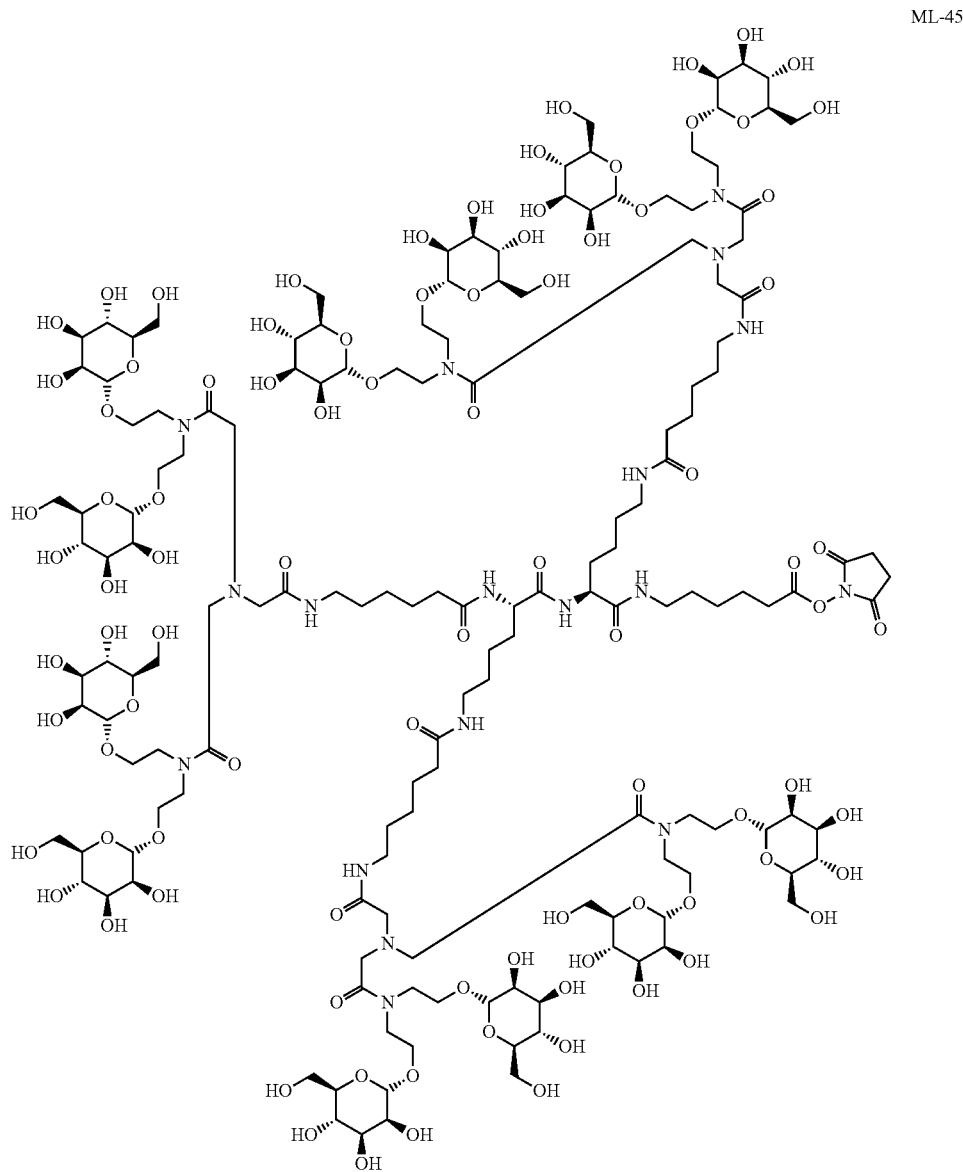

ML-45

Step 1. Benzyl 6-(2-{bis[2-(bis{2-[(2,3,4,6-tetra-O-acetyl-α-D-mannopyranosyl)oxy]ethyl}amino)-2-oxoethyl]amino}cetamido)hexanoate To a solution of bis{2-[(2,3,4,6-tetra-O-acetyl-α-D-mannopyranosyl)oxy]ethyl} amine (8.15 g, 10.65 mmol) and 2,2'-[(2-{[6-(benzyloxy)-6-oxohexyl]amino}-2-oxoethyl)azanediyl]diacetic acid (1.4 g, 3.55 mmol) in DMF (35.5 mL) was added DIPEA (3.72 mL, 21.30 mmol) followed by HOBt (1.631 g, 10.65 mmol) and, after 5 min, EDC (2.041 g, 10.65 mmol). After stirring overnight, the reaction mixture was concentrated. The residue was dissolved in EtOAc (100 mL), washed with 1M HCl (100 mL), saturated NaHCO$_3$ (100 mL), and brine (100 mL). The organic layer was separated, dried over Na$_2$SO$_4$ and concentrated. The residue was purified on 120 g SiO$_2$ column, flow rate 100 mL/min, gradient 0-100% solvent A-solvent B in 30 min followed by hold, where solvent A was pure EtOAc and solvent B was 5% MeOH/EtOAc, to give the title compound. UPLC-MS Method A: m/z=1889.7793 (z=1); t$_R$=4.48 min.

Step 2. 6-(2-{bis[2-(bis{2-[(α-D-mannopyranosyl)oxy]ethyl}amino)-2-oxoethyl]amino}cetamido)hexanoic Acid To a solution of benzyl 6-(2-{bis[2-(bis{2-[(2,3,4,6-tetra-O-acetyl-α-D-mannopyranosyl) oxy]ethyl}amino)-2-oxoethyl]amino}cetamido)hexanoate (4.95 g, 2.62 mmol) in MeOH (26 mL) was added NaOCH$_3$ (142 mg, 2.62 mmol). After stirring for 3 hr, UPLC-MS analysis of an aliquot of the reaction mixture indicated the complete removal of acetate groups and concomitant transesterification of benzyl ester to methyl ester. The reaction mixture was concentrated, and the residue was dissolved in H$_2$O (26 mL), to which was added aq. NaOH (2.62 mL, 2.62 mmol, 1M). After 2 hr, the pH of the reaction mixture was adjusted with 1M HCl to ~ 6. The resulting solution was freeze-dried to give the title compound. UPLC-MS Method A: m/z=1127.5343 (z=1); t$_R$=3.87 min.

Step 3. benzyl (21S,24S)-21[6-(2-{bis[2-(bis{2-[(α-D-mannopyranosyl)oxy]ethyl}amino)-2-oxoethyl]amino}acetamido)hexanamido]-6-[2-(bis{2-[(α-D-mannopyranosyl)oxy]ethyl}amino)-2-oxoethyl]-24-(6-[2-(bis{2-[(α-D-mannopyranosyl)oxy]ethyl}amino)-2-oxoethyl]-1-[(α-D-mannopyranosyl)oxy]-3-{2-[(α-D-mannopyranosyl)oxy]ethyl}-4,8,15-trioxo-3,6,9,16-tetraazaicosan-20-yl)-1-[(α-D-mannopyranosyl)oxy]-3-{2-[(α-D-mannopyranosyl)oxy]ethyl}-4,8,15,22,25-pentaoxo-3,6,9,16,23,26-hexaazadotriacontan-32-oate To a solution of benzyl 6-{(S)-6-amino-2-[(S)-2,6-diaminohexanamido]hexanamido}hexanoate (72 mg, 0.094 mmol) and 6-(2-{bis[2-(bis{2-[(α-D-mannopyranosyl)oxy]ethyl}amino)-2-oxoethyl]amino}cetamido)hexanoic acid (633 mg, 0.468 mmol) in DMF (2.0 mL) was added DIPEA (164 µL, 0.937 mmol), HOBt (71.7 mg, 0.468 mmol), and EDC (90 mg, 0.468 mmol). After stirring overnight, the mixture was concentrated, and the residue was purified on reverse-phase C18 silica gel (120 g), flow rate=60 mL/min, gradient 0-40% AcCN/water over 50 min to give the title compound.

Step 4. 2,5-dioxopyrrolidin-1-yl (21S,24S)-21[6-(2-{bis[2-(bis{2-[(α-D-mannopyranosyl)oxy]ethyl}amino)-2-oxoethyl]amino}acetamido)hexanamido]-6-[2-(bis{2-[(α-D-mannopyranosyl) oxy]ethyl}amino)-2-oxoethyl]-24-(6-[2-(bis{2-[(α-D-mannopyranosyl)oxy]ethyl}amino)-2-oxoethyl]1-[(α-D-mannopyranosyl)oxy]-3-{2-[(α-D-mannopyranosyl)oxy]ethyl}-4,8,15-trioxo-3,6,9,16-tetraazaicosan-20-yl)-1-[(α-D-mannopyranosyl)oxy]-3-{2-[(α-D-mannopyranosyl)oxy]ethyl}-4,8,15,22,25-pentaoxo-3,6,9,16,23,26-hexaazadotriacontan-32-oate The title compound was prepared using procedures analogous to those described for ML-1 substituting benzyl (21S,24S)-21[6-(2-{bis[2-(bis{2-[(α-D-mannopyranosyl)oxy]ethyl}amino)-2-oxoethyl]amino}acetamido)hexanamido]-6-[2-(bis{2-[(α-D-mannopyranosyl)oxy]ethyl}amino)-2-oxoethyl]-24-(6-[2-(bis{2-[(α-D-mannopyranosyl)oxy]ethyl}amino)-2-oxoethyl]-1-[(α-D-mannopyranosyl)oxy]-3-{2-[(α-D-mannopyranosyl)oxy]ethyl}-4,8,15-trioxo-3,6,9,16-tetraazaicosan-20-yl)-1-[(α-D-mannopyranosyl)oxy]-3-{2-[(α-D-mannopyranosyl)oxy] ethyl}-4,8,15,22,25-pentaoxo-3,6,9,16,23,26-hexaazadotriacontan-32-oate for benzyl 6-{[(S)-5-{[(S)-1,5-dioxo-1,5-bis({2-[(α-D-mannopyranosyl)oxy]ethyl}amino)pentan-2-yl]amino}-1,5-dioxo-1-({2-[(α-D-mannopyranosyl)oxy]ethyl}amino)pentan-2-yl]amino}-6-oxohexanoate in Step 3. UPLC-MS Method A: m/z=1271.2062 (z=3); t$_R$=4.31 min.

Example 46: 2,5-dioxopyrrolidin-1-yl (7S,19S,22S)-7-(bis{2-[(α-D-mannopyranosyl)oxy]ethyl}carbamoyl)-19-(5-{[(S)-1,5-bis(bis{2-[(α-D-mannopyranosyl) oxy]ethyl}amino)-1,5-dioxopentan-2-yl]amino}-5-oxopentanamido)-22-[4-(5-{[(S)-1,5-bis(bis {2-[(α-D-mannopyranosyl)oxy]ethyl}amino)-1,5-dioxopentan-2-yl]amino}-5-oxopentanamido) butyl]-1-[(α-D-mannopyranosyl)oxy]-3-{2-[(α-D-mannopyranosyl)oxy]ethyl}-4,9,13,20,23-pentaoxo-3,8,14,21,24-pentaazatriacontan-30-oate (ML-46)

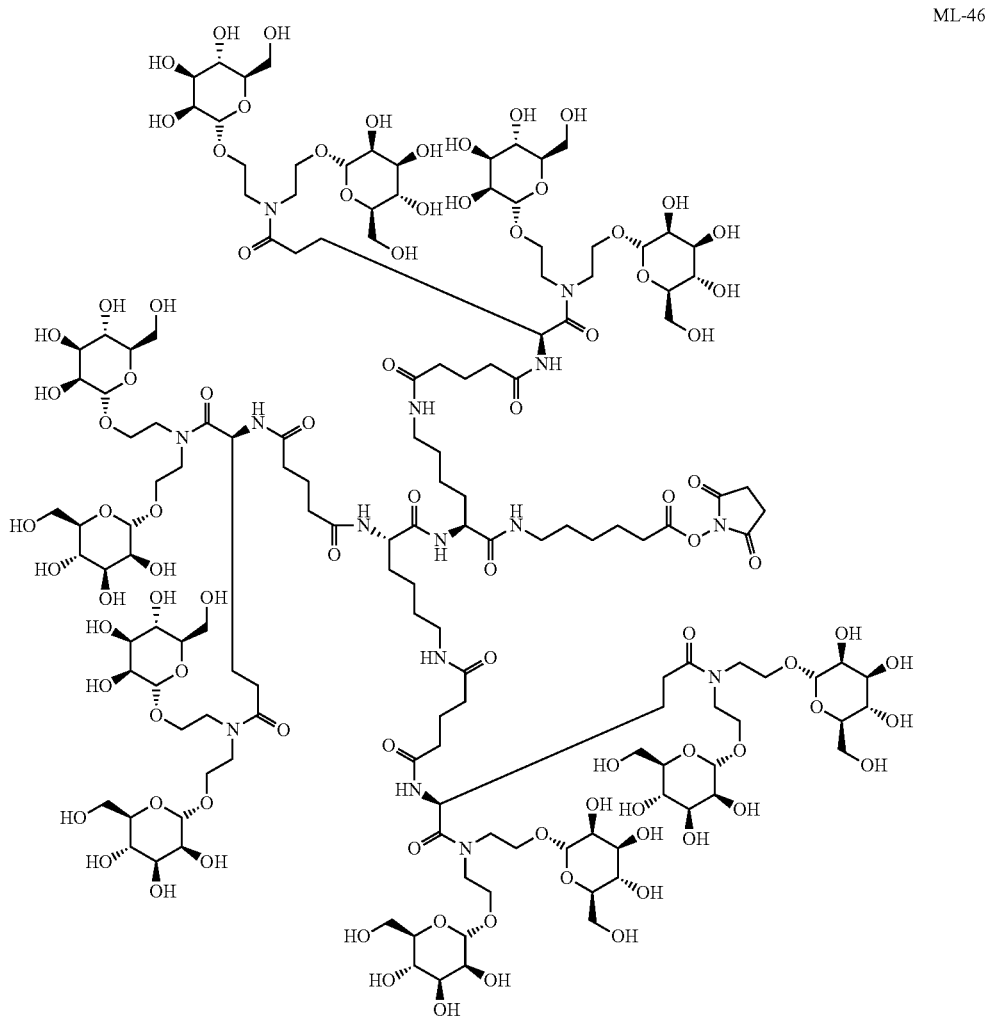

ML-46

The title compound was prepared using procedures analogous to those described for ML-45 substituting Z-Glu-OH for 2,2'-[(2-{[6-(benzyloxy)-6-oxohexyl]amino}-2-oxoethyl) azanediyl]diacetic acid in Step 1.

Example 47: Synthesis of IOC-1

To a 20 mL scintillation vial containing human insulin (400 mg, 0.069 mmol) at rt was added DMSO (4.0 mL) and TEA (67.2 µL, 0.482 mmol). The mixture was stirred gently until the human insulin dissolved. In a separate vial, linker ML-1 (205 mg, 0.186 mmol) was dissolved in DMSO (2.0 mL) at rt. To the solution containing human insulin was added the solution of ML-1 in three equal portions in 20-30 min intervals. The reaction was quenched by adding 2-aminoethanol (125 µL, 2.066 mmol). After stirring at rt for 15 min, the resulting mixture was carefully diluted with cold $H_2O$ (70 mL) at 0° C. The pH of the resulting mixture was adjusted to a final pH of 2.5 using 1N HCl (or 0.1N NaOH). The resulting solution was purified by reverse phase prepare HPLC (C8 column; Buffer A: 0.05-0.1% TFA in deionized water; Buffer B: 0.05-0.1% TFA in AcCN). The combined desired fractions were lyophilized. The solids were dissolved in water, and the pH was adjusted to 7 using 0.1N NaOH solution to provide a solution of IOC-1. UPLC-MS Method A: $t_R$=3.64 min; m/z=1946.61 (z=4).

EXAMPLES 48 through 55, Conjugates IOC-8 to IOC-15, as listed in Table 1, were prepared according to procedures analogous to those described above for EXAMPLE 47, IOC-1, with the appropriate linkers.

TABLE 1

| EXAMPLE | Conjugate | Linker |
|---|---|---|
| 48 | IOC-8 | ML-8 |
| 49 | IOC-9 | ML-9 |
| 50 | IOC-10 | ML-11 |
| 51 | IOC-11 | ML-10 |
| 52 | IOC-12 | ML-12 |
| 53 | IOC-13 | ML-13 |
| 54 | IOC-14 | ML-14 |
| 55 | IOC-15 | ML-15 |

Example 56: Synthesis of IOC-2

To a solution of $N^{41}$-Trifluoroacetyl Human Insulin (90 mg, 0.015 mmol; prepared according to the procedures disclosed in WO2015/051052 A2) in DMSO (1.5 mL) at rt was added TEA (21 μL, 0.152 mmol) and a solution of ML-2 (48.9 mg, 0.046 mmol) in DMSO (300 μL). After stirring at rt for 4 hrs, the mixture was added to AcCN (42 mL). The precipitate was collected through centrifugation. The collected solids were dissolved in water (5 mL, pH=3.00), and the mixture was cooled down to 0° C., to which a solution of $NH_4OH$ (5 mL, 28% in water) was added. The mixture was stirred at 0° C. for 2 hr and then diluted with water (20 mL, pH=3.00). The volume of the resulting solution was concentrated and reduced to 7.5 mL, and was further diafiltrated with water (100 mL, pH=3.00) to final volume about 7.5 mL, which was purified by HPLC to give the IOC-2. UPLC-MS Method A: $t_R$=3.46 min; m/z=1929.296 (z=4).

Example 57: Synthesis of IOC-6

To a solution of $N^{41}$-Trifluoroacetyl Human Insulin (100 mg, 0.017 mmol; prepared according to the procedures disclosed in WO2015/051052 A2) in DMSO (2 mL) at rt was added TEA (24 μL, 0.169 mmol) and a solution of ML-6 (50.1 mg, 0.041 mmol) in DMSO (750 μL). After stirring at rt for 2.5 hrs, the mixture was added to AcCN (42 mL). The precipitate was collected through centrifugation. The collected solids were dissolved in water (5 mL, pH=3.00), and the mixture was cooled down to 0° C., to which a solution of $NH_4OH$ (5 mL, 28% in water) was added. The mixture was stirred at 0° C. for 2 hr and then diluted with water (20 mL, pH=3.00). The volume of the resulting solution was concentrated and reduced to 5 mL, and was further diafiltrated with water (100 mL, pH=3.00) to final volume about 7.5 mL, which was purified by HPLC to give the IOC-6. UPLC Method A: $t_R$=3.49 min; m/z=1609.155 (z=5).

Example 58: Synthesis of IOC-16

Human insulin (800 mg, 0.138 mmol) was dissolved in aqueous $Na_2CO_3$ (6.85 mL, 0.1M) and AcCN (4.6 mL). The pH of the resulting solution was adjusted to 10.5, to which ML-16 (300 mg, 0.207 mmol) in DMSO (2.25 mL) in 4 portions over 80 min, the reaction mixture was quenched by adding 2-aminoethanol (41.7 μL, 0.689 mmol). After stirring at rt for 15 min, the reaction mixture was diluted with $H_2O$ and pH was adjusted to about 2.5 using 1.0N HCl solution, concentrated. The resulting solution was purified on HPLC (C4, 50×250 mm, gradient 24-28.5% AcCN in $H_2O$ with 0.1% TFA over 25 min, flow rate 85 mL/min). The combined desired fractions were lyophilized. The solids were dissolved in water and the pH adjusted to 7 using 0.1N NaOH solution to provide a solution of IOC-16. UPLC-MS Method A: $t_R$=3.71 min; m/z=1786.7 (z=4).

EXAMPLES 59 through 102, Conjugates IOC-3 to IOC-5, IOC-7, IOC-19, IOC-23 to IOC-25, and IOC-27 to IOC-62 as listed in Table 2, were prepared according to procedures analogous to those described above for EXAMPLE 58, IOC-16, with the appropriate linkers.

TABLE 2

| EXAMPLE | Conjugate | Linker |
|---|---|---|
| 59 | IOC-3 | ML-3 |
| 60 | IOC-4 | ML-4 |
| 61 | IOC-5 | ML-5 |
| 62 | IOC-7 | ML-7 |
| 63 | IOC-19 | ML-17 |
| 64 | IOC-23 | ML-18 |
| 65 | IOC-24 | ML-19 |
| 66 | IOC-25 | ML-20 |
| 67 | IOC-27 | ML-22 |
| 68 | IOC-28 | ML-22 |
| 69 | IOC-29 | ML-22 |
| 70 | IOC-30 | ML-22 |
| 71 | IOC-31 | ML-22 |
| 72 | IOC-32 | ML-22 |
| 73 | IOC-33 | ML-22 |
| 74 | IOC-34 | ML-22 |
| 75 | IOC-35 | ML-22 |
| 76 | IOC-36 | ML-22 |
| 77 | IOC-37 | ML-22 |
| 78 | IOC-38 | ML-22 |
| 79 | IOC-39 | ML-43 |
| 80 | IOC-40 | ML-24 |
| 81 | IOC-41 | ML-25 |
| 82 | IOC-42 | ML-26 |
| 83 | IOC-43 | ML-27 |
| 84 | IOC-44 | ML-28 |
| 85 | IOC-45 | ML-30 |
| 86 | IOC-46 | ML-29 |
| 87 | IOC-47 | ML-31 |
| 88 | IOC-48 | ML-32 |
| 89 | IOC-49 | ML-33 |
| 90 | IOC-50 | ML-34 |
| 91 | IOC-51 | ML-35 |
| 92 | IOC-52 | ML-36 |
| 93 | IOC-53 | ML-37 |
| 94 | IOC-54 | ML-38 |
| 95 | IOC-55 | ML-39 |
| 96 | IOC-56 | ML-40 |
| 97 | IOC-57 | ML-41 |
| 98 | IOC-58 | ML-42 |
| 99 | IOC-59 | ML-23 |
| 100 | IOC-60 | ML-44 |
| 101 | IOC-61 | ML-45 |
| 102 | IOC-62 | ML-46 |

Example 103 and Example 104: Synthesis of IOC-17 and IOC-18

IOC-16 (100.6 mg, 0.014 mmol) was dissolved in 1 ml DMSO at rt. To this solution was added TEA (14.25 mg, 0.141 mmol). 6-[(2,5-dioxopyrrolidin-1-yl)oxy]-N-[2-(α-D-mannopyrano-syloxy)ethyl]-6-oxohexanamide (10.7 mg, 0.024 mmol; prepared according to the procedures disclosed in WO2015/051052 A2) was dissolved in 500 μL DMSO and added to the reaction mixture in 3 portions over 60 min. The reaction mixture was quenched by adding 2-aminoethanol (8.5 μL, 0.141 mmol). After stirring at rt for 15 min, the reaction mixture was diluted with $H_2O$ (30 mL), and pH was adjusted to about 2.5 using 1.0N HCl solution, concentrated.

The resulting solution was purified by ion exchange chromatography. The desired fraction for the first eluting isomer (IOC-18) and the second eluting isomer (IOC-17) were collected. Both isomers were concentrated, then further purified by HPLC (C4, gradient 24-30% AcCN in H$_2$O with 0.1% TFA over 30 min, flow rate 85 mL/min) respectively. The combined desired fractions were lyophilized. Then the solids were dissolved in water, and the pH was adjusted to 7 using 0.1N NaOH solution to provide a solution of IOC-18, UPLC-MS Method A: $t_R$=3.94 min; m/z=1952.9 (z=4) and a solution of IOC-17, UPLC-MS Method A: $t_R$=3.69 min; m/z=1869.7 (z=4), respectively.

Example 105: Synthesis of IOC-20

N$^{41}$-Fmoc insulin (50 mg, 0.00829 mmol; prepared according to the procedures disclosed in WO2015/051052 A2) and linker ML-17 (57.5 mg, 0.041 mmol) were warmed up to rt for 30 min. To the N$^{\alpha 41}$-Fmoc insulin (50 mg, 0.00829 mmol) in DMSO (1.0 mL) in a 20 mL vial was added TEA (10 µL, 0.072 mmol). ML-17 (57.5 mg, 0.041 mmol) in DMSO (580 µL) was added in to the reaction vial in two equal portions at 60 min interval. The reaction was quenched by adding 2-aminoethanol (75 µL, 1.244 mmol) and stirred at rt for 30 min. The mixture was diluted into H$_2$O (10 mL) at 0° C. The pH of the reaction mixture is adjusted to be about 2.5 using 1N HCl.

The crude product was first purified by ion exchange chromatography. The desired fractions were concentrated lyophilized overnight and then further purified by reverse phase prepare HPLC (C-4 column). The combined desired fractions were lyophilized. The solids were dissolved in water, and the pH adjusted to 7 using 0.1N NaOH solution to provide a solution of IOC-20. UPLC-MS Method A: $t_R$=3.95 min; m/z=1671.406 (z=5).

Example 106: Synthesis of IOC-22

To a solution of IOC-16 (100 mg, 0.014 mmol) in water (8 mL) at rt with the pH adjusted to 6.5 using 0.1N NaOH solution was added ML-16 (24.3 mg, 0.017 mmol) in DMSO (1.0 mL) in portions over 25 min, while the pH of reaction mixture was maintained at 6.5 using 0.1N NaOH solution. The reaction mixture was stirred at rt for 5 hrs and quenched by adding 2-aminoethanol (4.2 µL, 0.07 mmol). After stirring at rt for 15 min, the reaction mixture was diluted with H$_2$O (10 mL), and the pH was adjusted to about 2.5 using 1.0N HCl solution. The resulting mixture was purified by ion exchange chromatography. The desired fractions were combined and concentrated. The resulting mixture was purified on HPLC (C4 column, gradient 24-28% AcCN in H$_2$O with 0.1% TFA over 30 min, flow rate 85 mL/min). The combined desired fractions were lyophilized. The solids were dissolved in water, and the pH adjusted to 7 using 0.1N NaOH solution to provide a solution of IOC-22. UPLC-MS Method A: $t_R$=3.45 min; m/z=1696.762 (z=5).

Example 107: Synthesis of IOC-26

To a solution of N$^{41}$/N$^{B1}$-Acetyl human insulin (152 mg, 0.026 mmol; prepared according to the procedures disclosed in WO 2016/081670 A2) and TEA (54 µL, 0.387 mmol) in DMSO (2 mL) at rt was added a solution of ML-20 in DMSO (440 µL) in portions over 45 min. The reaction was quenched by adding 2-aminoethanol (7.8 µL, 0.13 mmol). After stirring at rt for 15 min, the reaction mixture was diluted with H$_2$O (15 mL) and the pH was adjusted to about 2.5 using 1.0N HCl solution. The resulting mixture was purified by HPLC (C8 column, gradient 26-32% AcCN in H$_2$O with 0.1% TFA over 30 min, flow rate 85 mL/min). The combined desired fractions were lyophilized. The solids were dissolved in water, and the pH adjusted to 7 using 0.1N NaOH solution to provide a solution of IOC-26. UPLC-MS Method A: $t_R$=3.53 min; m/z=1871.934 (z=4).

Example 108: Synthesis of N$^{41}$/NB-Tetrakis(dimethyl) Human Insulin

Human insulin (100 mg, 0.017 mmol) was dissolved in water (5 mL) and adjusted to pH~4.0 by acetic acid solution, then formaldehyde (9.6 µL, 0.129 mmol) was added, followed by addition of a freshly prepared solution of sodium cyanoborohydride (8.7 mg, 0.138 mmol) in water (1 mL). 1 mL DMSO was added, and the pH was adjusted to pH~4.0 by acetic acid. The mixture was gently stirred. After completion of the reaction about 1 hr, the mixture was carefully acidified by dropwise addition of 1N HCl to pH-2.9. The mixture was purified by ion exchange chromatography. The desired fractions were combined, concentrated, then further purified by HPLC (C8, 50×250 mm, gradient 28-36% AcCN in H$_2$O with 0.1% TFA over 25 min, flow rate 85 mL/min). The combined desired fractions were lyophilized to produce the title compound. UPLC-MS Method A: $t_R$=3.55 min, m/z=1466.605 (z=4).

Example 109: Synthesis of IOC-31

N$^{41}$/N$^{B1}$-Tetrakis(dimethyl) human insulin (105 mg, 0.018 mmol) was dissolved in aqueous Na$_2$CO$_3$ (1.28 mL, 0.1M) and AcCN (0.8 mL). The pH of the resulting solution was adjusted to 10.8, followed by addition of a solution of ML-5 (41 mg, 0.018 mmol) in DMSO (390 µL) in portions in 45 min. The reaction progress was monitored by UPLC-MS. The reaction mixture was diluted with H$_2$O (15 mL), and pH was adjusted to about 2.5 using 1.0N HCl solution. The resulting mixture was purified by ion exchange chromatography. The desired fractions were combined, concentrated, then further purified by HPLC (C8 column, gradient 26-33% AcCN in H$_2$O with 0.1% TFA over 25 min, flow rate 85 mL/min). The combined desired fractions were lyophilized. The solids were dissolved in water, and the pH adjusted to 7 using 0.1N NaOH solution to provide a solution of IOC-31. UPLC-MS Method A: $t_R$=3.32 min; m/z=1600.563 (z=5).

Binding Assays

Insulin Receptor Phosphorylation Assays

CHO cells stably expressing human IR(B) were in grown in in F12 cell media containing 10% FBS and antibiotics (G418, Penicillin/Strepavidin) for at least 8 hr, and then serum starved by switching to F12 media containing 0.5% BSA (insulin-free) in place of FBS for overnight growth. Cells were harvested and frozen in aliquots for use in the MSD pIR assay. Briefly, the frozen cells were plated in either 96-well (40,000 cells/well, Methods A) or 384-well (10,000 cells/well, Method B) clear tissue culture plates and allowed to recover. IOC molecules at the appropriate concentrations were added and the cells incubated for 8 min at 37° C. The media was aspirated and chilled MSD cell lysis buffer was added as per MSD kit instructions. The cells were lysed on ice for 40 min and the lysate then mixed for 10 min at rt. The lysate was transferred to the MSD kit pIR detection plates. The remainder of the assay was carried out following the MSD kit recommended protocol.

Insulin Receptor Binding Assays

Two competition binding assays were utilized to determine IOC affinity for the human insulin receptor type B (IR(B)) against the endogenous ligand, insulin, labeled with $^{125}$[I].

Method C: IR binding assay was a whole cell binding method using CHO cells overexpressing human IR(B). The cells were grown in F12 media containing 10% FBS and antibiotics (G418, Penicillin/Strepavidin), plated at 40,000 cells/well in a 96-well tissue culture plate for at least 8 hrs. The cells were then serum starved by switching to DMEM media containing 1% BSA (insulin-free) overnight. The cells were washed twice with chilled DMEM media containing 1% BSA (insulin-free) followed by the addition of IOC molecules at appropriate concentration in 90 µL of the same media. The cells were incubated on ice for 60 min. The $^{125}$[I]-insulin (10 µL) was added at 0.015 nm final concentration and incubated on ice for 4 hrs. The cells were gently washed three times with chilled media and lysed with 30 µL of Cell Signaling lysis buffer (cat #9803) with shaking for 10 min at rt. The lysate was added to scintillation liquid and counted to determine $^{125}$[I]-insulin binding to IR and the titration effects of IOC molecules on this interaction.

Method D: IR binding assay was run in a scintillation proximity assay (SPA) in 384-well format using cell membranes prepared from CHO cells overexpressing human IR(B) grown in F12 media containing 10% FBS and antibiotics (G418, Penicillin/Strepavidin). Cell membranes were prepared in 50 mM Tris buffer, pH 7.8 containing 5 mM MgCl$_2$. The assay buffer contained 50 mM Tris buffer, pH 7.5, 150 mM NaCl, 1 mM CaCl$_2$, 5mgCl$_2$, 0.1% BSA and protease inhibitors (Complete-Mini-Roche). Cell membranes were added to WGA PVT PEI SPA beads (5 mg/mL final concentration) followed by addition of IOC molecules at appropriate concentrations. After 5-15 min incubation at rt, $^{125}$[I]-insulin was added at 0.015 nm final concentration for a final total volume of 50 µL. The mixture was incubated with shaking at rt for 1 to 12 hours followed by scintillation counting to determine $^{125}$[I]-insulin binding to IR and the titration effects of IOC molecules on this interaction.

Human Macrophage Mannose Receptor 1 (MRC1) Binding Assays

The competition binding assay for Human macrophage mannose receptor 1 (MRC1) utilized a ligand, mannosylated-BSA labeled with the DELFIA Eu-N1-ITC reagent, as reported in the literature. Assay was performed either in a 96-well plate with 100 µL well volume (Method E) or in a 384-well plate with 25 µL well volume (Method F). Anti-MRC1 antibody (2 ng/µl) in PBS containing 1% stabilizer BSA was added to a Protein G plate that had been washed three times with 100 µl of 50 mM Tris buffer, pH 7.5 containing 100 mM NaCl, 5 mM CaCl$_2$, 1 mM MgCl$_2$ and 0.1% Tween-20 (wash buffer). The antibody was incubated in the plate for 1 hr at rt with shaking. The plate was washed with wash buffer 3-5 times followed by addition of MRC1 (2 ng/µl final concentration) in PBS containing 1% stabilizer BSA. The plate was incubated at rt with gentle shaking for 1 hr. The plate was washed three times with wash buffer. The IOC molecules in 12.5 µL (or 50 µL depending on plate format) buffer at appropriate concentrations were added followed by 12.5 µL (or 50 µL) Eu-mannosylated-BSA (0.1 nm final concentration) in 50 mM Tris, pH 7.5 containing 100 mM NaCl, 5 mM CaCl$_2$, 1 mM MgCl$_2$ and 0.2% stabilizer BSA. The plate was incubated for 2 hrs at rt with shaking followed by washing three times with wash buffer. Perkin Elmer Eu-inducer reagent was added and incubated for 30 min at rt prior to detection of the Eu signal (Excitation=340 nm: Emission=615 nm).

The following table lists conjugates that were prepared using appropriate intermediates following one of the General Methods described above. These conjugates were characterized using UPLC Method E or UPLC Method G noted by an asterisk (*) or UPLC Method F noted by a dagger (?), exhibiting either four charged, i.e. [(M+4)/4], (or five charged, i.e. [(M+5)/5]) species of parent compound at certain retention time ($t_R$). The in vitro biological activities towards insulin receptor (IR) were measured by either ligand competition assays or functional phosphorylation assays, as described above, labeled as following: Method A: IR phosphorylation assay based on 96-well; Method B: IR phosphorylation assay based on 384-well with automated liquid dispense; Method C: cell-based IR binding assay; Method D: SPA IR binding assay method E; Method E: MRC1 assay was performed in a 96-well plate; Method F: MRC1 assay was performed in a 384-well plate. The results are shown in Table 3.

TABLE 3

| | | UPLC-MS | | | | | | |
|---|---|---|---|---|---|---|---|---|
| | | Mass [(m + 4)/4 | IR Activation | | IR Binding | | MRC1 Binding | |
| IOC # | $T_R$ (min) | or (m + 5)/5] | IP† (nM) | Method | IP‡ (nM) | Method | IP‡ (nM) | Method |
| IOC-1 | 3.64* | 1946.61 | 24.36 | A | 6.25 | C | 31.49 | E |
| IOC-2 | 3.46* | 1929.30 | 1.98 | B | 2.01 | D | 2.56 | F |
| IOC-3 | 3.62 | 1776.23 | 9.85 | A | 0.76 | C | 42.24 | E |
| IOC-4 | 3.37* | 1647.85 | 8.85 | A | 2.52 | C | 7.56 | E |
| IOC-5 | 4.52* | 1636.43 | 5.71 | A | 1.28 | C | 9.12 | E |
| IOC-6 | 3.49 | 1609.16 | 1.69 | B | 1.36 | D | 9.47 | F |
| IOC-7 | 2.88 | 1630.91 | 0.87 | B | 1.89 | C | 7.17 | E |
| IOC-8 | 3.26* | 1597.93 | 6.79 | B | 4.92 | D | 51.35 | F |
| IOC-9 | 3.43* | 1968.60 | 7.86 | B | 11.82 | D | 34.99 | F |
| IOC-10 | 3.23* | 1602.93 | 5.47 | B | 3.01 | D | 16.62 | F |
| IOC-11 | 3.22* | 1603.26 | 5.74 | B | 2.67 | D | 241.30 | F |
| IOC-12 | 3.26* | 1590.59 | 4.96 | B | 3.24 | D | 4.74 | F |
| IOC-13 | 3.36* | 1603.10 | 12.08 | B | 5.76 | D | 70.25 | F |
| IOC-14 | 3.38* | 1603.11 | 5.84 | B | 4.08 | D | 610.30 | F |
| IOC-15 | 3.58* | 1979.92 | 5.20 | B | 3.94 | D | 0.94 | F |
| IOC-16 | 3.71* | 1786.70 | 2.09 | A | 0.19 | C | 86.72 | E |

TABLE 3-continued

| | UPLC-MS | | IR Activation | | IR Binding | | MRC1 Binding | |
|---|---|---|---|---|---|---|---|---|
| IOC # | $T_R$ (min) | Mass [(m + 4)/4 or (m + 5)/5] | IP† (nM) | Method | IP‡ (nM) | Method | IP‡ (nM) | Method |
| IOC-17 | 3.69* | 1869.95 | 10.33 | A | 1.66 | C | 182.10 | E |
| IOC-18 | 3.94* | 1953.56 | 15.56 | A | 2.04 | C | 184.60 | E |
| IOC-19 | 3.46* | 1770.39 | 0.81 | A | 0.29 | C | 16.05 | E |
| IOC-20 | 3.95* | 1671.41 | 3.14 | A | 2.83 | C | 0.63 | E |
| IOC-21 | 3.45* | 1770.60 | 8.30 | A | 1.45 | C | 42.43 | E |
| IOC-22 | 3.45* | 1696.76 | 4.71 | A | 1.68 | C | 13.91 | E |
| IOC-23 | 3.79* | 1867.07 | 3.27 | A | 1.07 | C | 37.16 | E |
| IOC-24 | 3.50* | 1779.54 | 8.81 | A | 1.85 | C | 3.32 | E |
| IOC-25 | 3.36* | 1849.99 | 0.32 | B | 1.31 | D | 7.27 | E |
| IOC-26 | 3.53* | 1871.93 | 6.29 | B | 8.48 | D | 6.61 | F |
| IOC-27 | 3.32* | 1986.75 | 1.06 | B | 2.82 | D | 20.74 | F |
| IOC-28 | 4.111 | 1986.55 | 0.58 | B | 3.36 | D | 10.92 | F |
| IOC-29 | 3.29 | 1961.94 | 1.67 | B | 0.95 | D | 18.49 | F |
| IOC-30 | 3.31 | 1986.62 | 1.43 | B | 0.79 | D | 37.01 | F |
| IOC-31 | 3.32 | 1600.56 | 0.96 | B | 0.50 | D | 46.35 | F |
| IOC-32 | 3.37 | 1947.27 | 1.25 | B | 2.07 | D | 603.80 | F |
| IOC-33 | 3.33 | 1640.56 | 2.35 | B | 2.67 | D | 10.04 | F |
| IOC-34 | 3.31 | 1976.76 | NA | | NA | | 7.93 | F |
| IOC-35 | 3.37 | 1972.36 | NA | | NA | | 16.62 | F |
| IOC-36 | 3.34 | 1971.89 | 1.00 | B | 1.53 | D | 19.78 | F |
| IOC-37 | 3.33 | 1600.88 | 0.70 | B | 0.43 | D | 20.71 | F |
| IOC-38 | 2.96 | 1660.11 | 3.62 | B | 4.97 | D | 9.78 | F |
| IOC-39 | 4.87 | 1848.65 | 8.99 | A | 1.87 | C | 2.38 | E |
| IOC-40 | 3.49 | 1654.38 | 1.09 | B | 1.58 | D | 24.69 | F |
| IOC-41 | 3.96 | 1634.53 | 1.61 | B | 2.19 | D | 6.09 | F |
| IOC-42 | 3.14 | 1702.85 | 1.72 | B | 1.95 | D | 1.99 | F |
| IOC-43 | 3.49 | 1662.19 | 2.24 | B | 6.82 | D | 8.25 | F |
| IOC-44 | 4.36 | 1921.35 | 8.40 | A | 1.15 | C | 31.35 | E |
| IOC-45 | 4.11† | 1986.40 | 1.92 | B | 6.12 | D | 8.91 | F |
| IOC-46 | 4.08 | 1609.24 | 2.02 | B | 2.72 | D | 58.27 | F |
| IOC-47 | 3.72 | 1958.74 | 2.68 | B | 9.07 | D | 10.59 | F |
| IOC-48 | 4.30* | 1956.74 | 1.66 | B | 1.21 | C | 9.12 | E |
| IOC-49 | 4.41* | 1970.95 | 0.71 | B | 1.48 | C | 54.48 | E |
| IOC-50 | 3.44* | 1624.87 | 0.84 | B | 3.47 | D | 13.05 | F |
| IOC-51 | 3.27 | 1984.77 | 3.84 | B | 8.46 | D | 28.77 | F |
| IOC-52 | 3.82 | 1654.05 | 2.54 | B | 5.53 | D | 49.06 | F |
| IOC-53 | 4.23 | 1644.88 | 2.77 | B | 6.55 | D | 9.22 | F |
| IOC-54 | 3.40* | 1929.92 | 1.14 | B | 0.78 | D | 8.91 | F |
| IOC-55 | 4.45* | 1684.85 | 1.38 | B | 1.85 | C | 7.21 | E |
| IOC-56 | 3.65* | 1778.32 | 16.93 | A | 2.93 | C | 30.94 | E |
| IOC-57 | 3.97* | 1777.93 | 11.09 | A | 3.09 | C | 1556.00 | E |
| IOC-58 | 2.52 | 1800.50 | 1.17 | B | 0.92 | D | 0.87 | F |
| IOC-59 | 3.38 | 1768.35 | 1.98 | B | 1.52 | D | 2.58 | F |
| IOC-60 | 3.55 | 1893.20 | 2.71 | B | 7.30 | D | 86.41 | F |
| IOC-61 | 3.16 | 1902.11 | 1.12 | B | 1.68 | C | 1.89 | E |
| IOC-62 | 3.20 | 1884.49 | 2.11 | B | 2.43 | C | 11.53 | E |

The effect of Methyl α-d-Mannopyranoside (αMM) on PK and PD of IOCs in non-diabetic minipigs was evaluated.

Male Yucatan miniature pigs, non-diabetic, instrumented with two Jugular vein vascular access ports (VAP), were used in these studies. Animals are fasted overnight prior to the study. On the day of the study, animals are restrained in slings, and VAPs accessed for infusion and sampling. At t=−60 min, a constant infusion of PBS (n=3) or 21.2% α-methyl mannose (αMM) (n=3) is started, at a rate of 2.67 mL/kg/hr. This infusion was maintained for the duration of the study. At t=0 min, and after collecting a baseline blood sample for plasma glucose measurement, animals were administered IOC as a single bolus IV. Sampling continued for 90 minutes, with final readouts of plasma glucose and compound levels.

IOCs were formulated at 17-69 nmol/mL in NaCl (87 mM), phenol (21 mM), dibasic sodium phosphate (26.5 mM), Osmolality=275 mOsm, pH=7.4; QS with Water for Injection.

Time points for sample collection: −60 min, 0 min, 1 min, 2 min, 4 min, 6 min, 8 min, 10 min, 15 min, 20 min, 25 min, 30 min, 35 min, 45 min, 60 min, and 90 min.

Blood was collected in K3-EDTA tubes, supplemented with 10 g/ml aprotinin, and kept on an ice bath until processing, within 30 min of collection. After centrifugation at 3000 rpm, 4° C., for 8 min, plasma was collected and aliquoted for glucose measurement using a Beckman Coulter AU480 Chemistry analyzer and for compound levels measurement by LC-MS.

Figure 2:
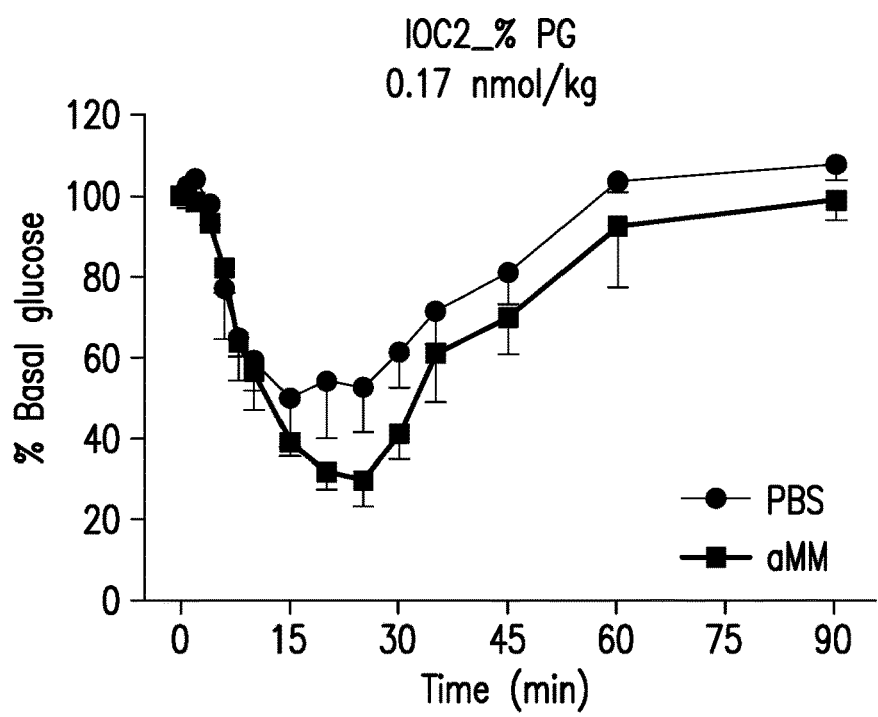
FIG. 2 shows plasma glucose depression curves in non-diabetic male Yucatan minipigs equipped with dual vascular access ports (n=3 per study) following i.v. injection of conjugate IOC-2 at 0.17 nmol/kg under conditions of PBS infusion or i.v. alpha methyl mannose (αMM) infusion.
Figure 3:
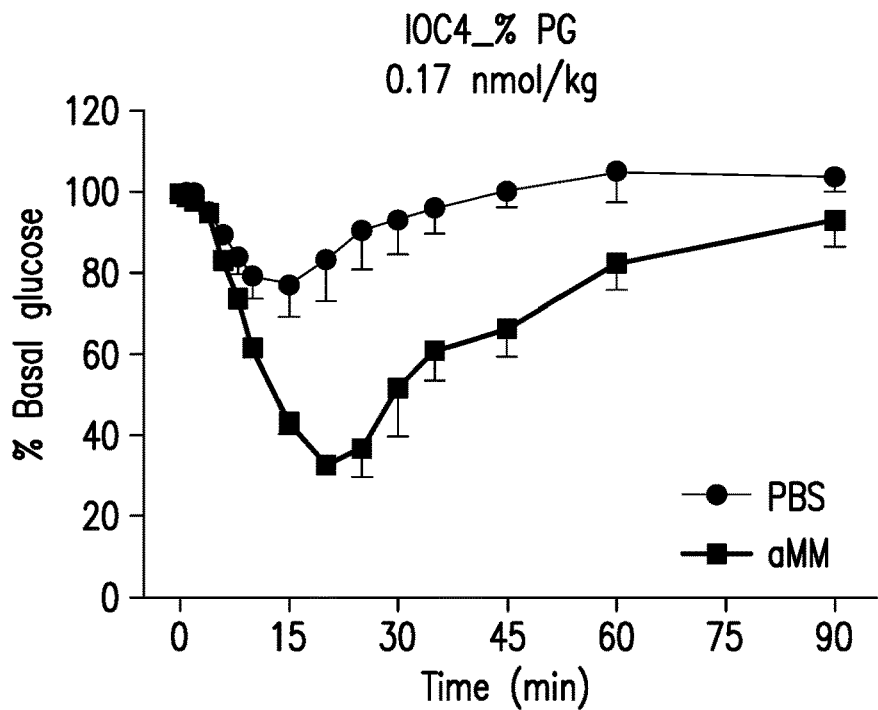
FIG. 3 shows plasma glucose depression curves in non-diabetic male Yucatan minipigs equipped with dual vascular access ports (n=3 per study) following i.v. injection of conjugate IOC-4 at 0.17 nmol/kg under conditions of PBS infusion or i.v. alpha methyl mannose (αMM) infusion.
Figure 4:
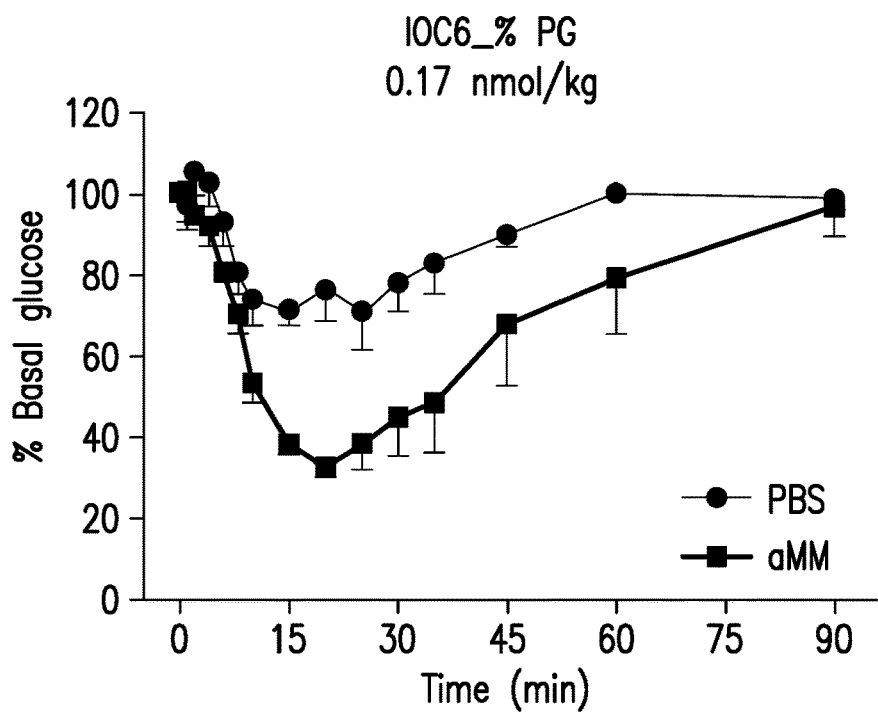
FIG. 4 shows plasma glucose depression curves in non-diabetic male Yucatan minipigs equipped with dual vascular access ports (n=3 per study) following i.v. injection of conjugate IOC-6 at 0.17 nmol/kg under conditions of PBS infusion or i.v. alpha methyl mannose (αMM) infusion.
Figure 5:
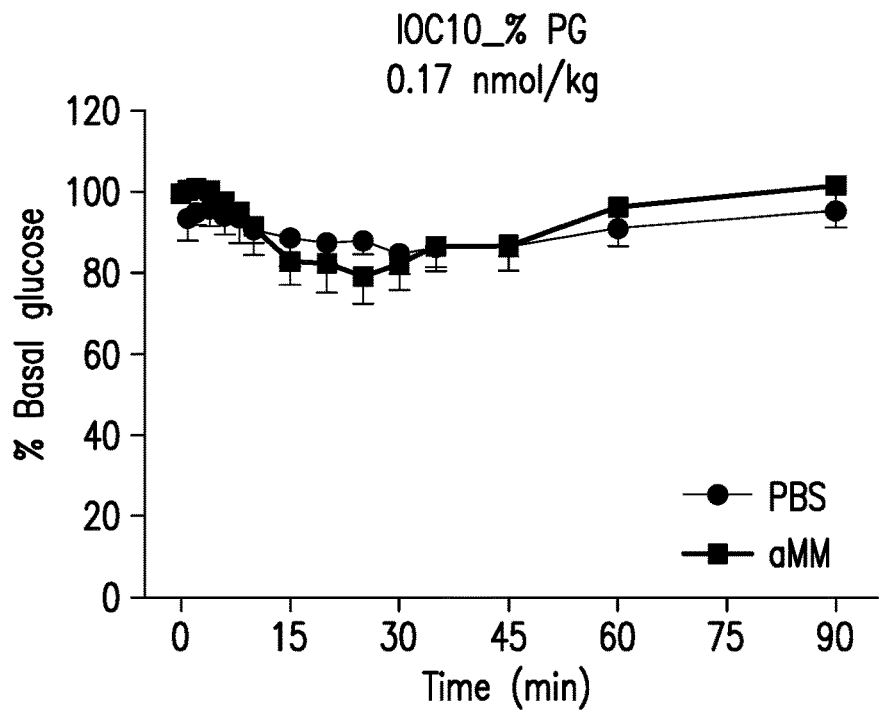
FIG. 5 shows plasma glucose depression curves in non-diabetic male Yucatan minipigs equipped with dual vascular access ports (n=3 per study) following i.v. injection of conjugate IOC-10 at 0.17 nmol/kg under conditions of PBS infusion or i.v. alpha methyl mannose (αMM) infusion.
Figure 6:
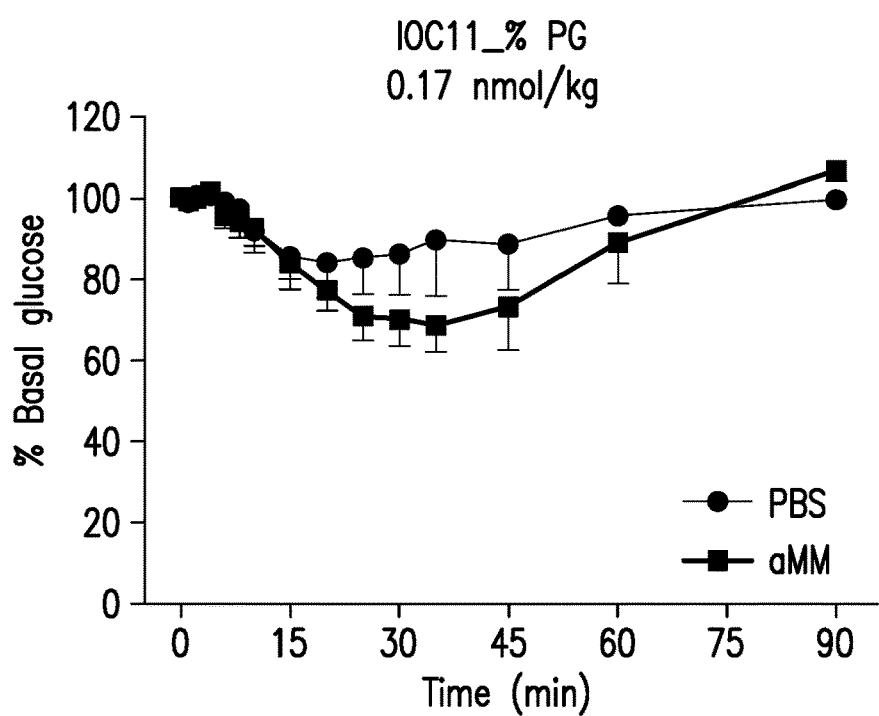
FIG. 6 shows plasma glucose depression curves in non-diabetic male Yucatan minipigs equipped with dual vascular access ports (n=3 per study) following i.v. injection of conjugate IOC-11 at 0.17 nmol/kg under conditions of PBS infusion or i.v. alpha methyl mannose (αMM) infusion.
Figure 7:
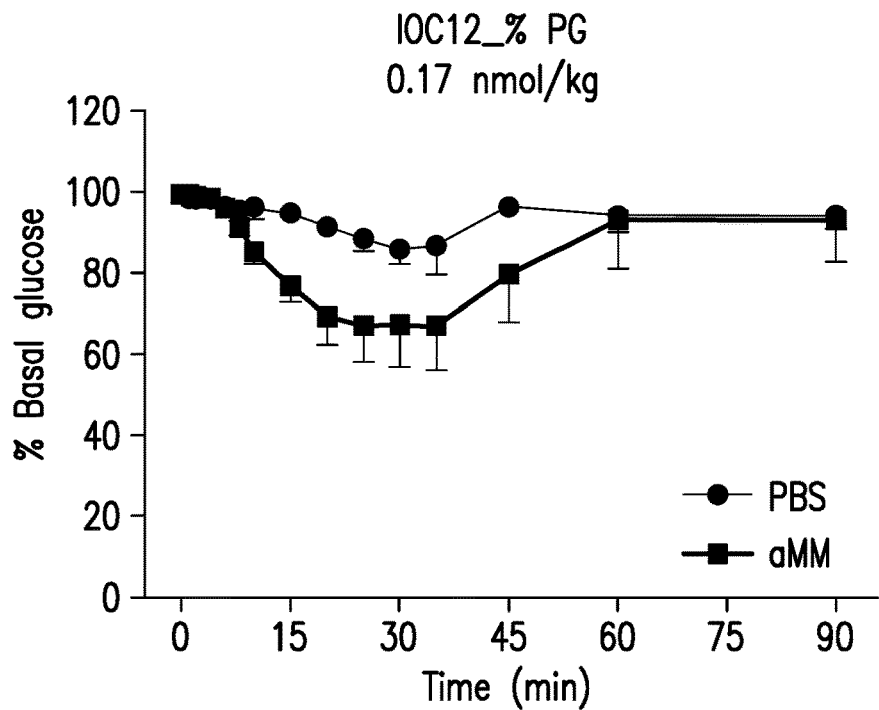
FIG. 7 shows plasma glucose depression curves in non-diabetic male Yucatan minipigs equipped with dual vascular access ports (n=3 per study) following i.v. injection of conjugate IOC-12 at 0.17 nmol/kg under conditions of PBS infusion or i.v. alpha methyl mannose (αMM) infusion.
Figure 8:
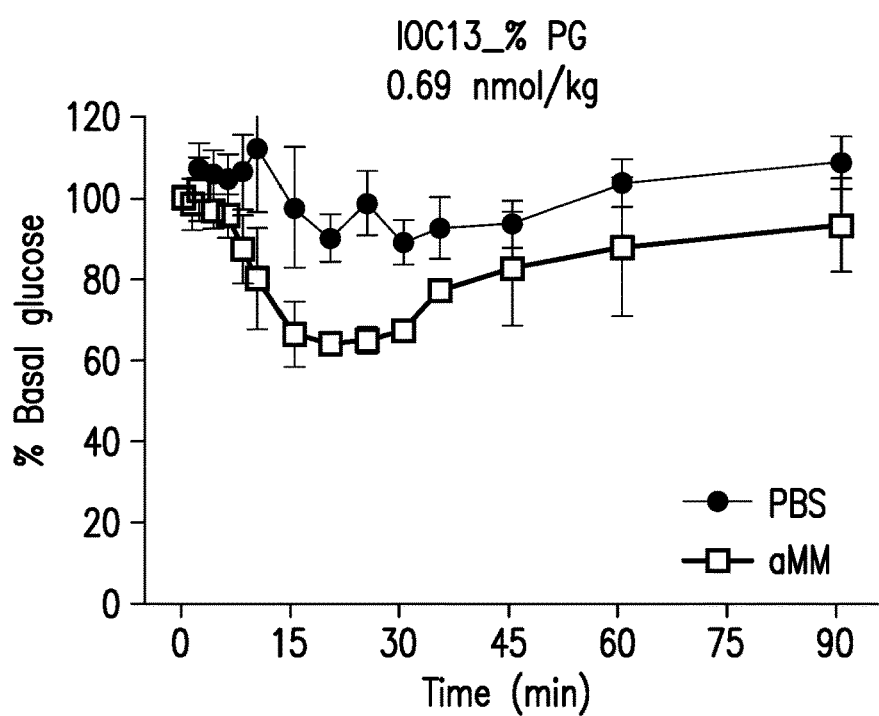
FIG. 8 shows plasma glucose depression curves in non-diabetic male Yucatan minipigs equipped with dual vascular access ports (n=3 per study) following i.v. injection of conjugate IOC-13 at 0.69 nmol/kg under conditions of PBS infusion or i.v. alpha methyl mannose (αMM) infusion.
Figure 9:
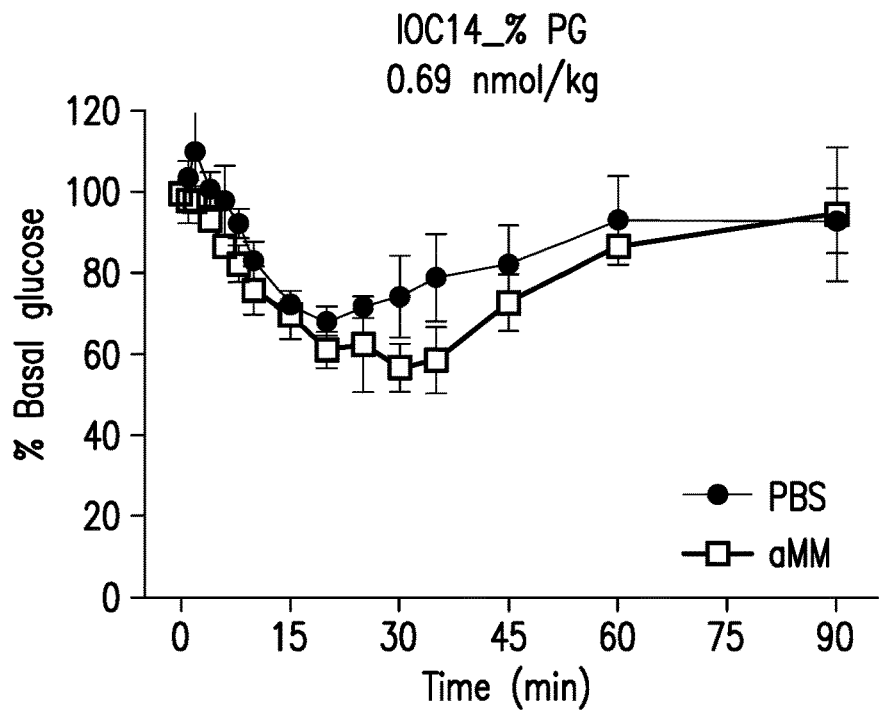
FIG. 9 shows plasma glucose depression curves in non-diabetic male Yucatan minipigs equipped with dual vascular access ports (n=3 per study) following i.v. injection of conjugate IOC-14 at 0.69 nmol/kg under conditions of PBS infusion or i.v. alpha methyl mannose (αMM) infusion.
Figure 10:
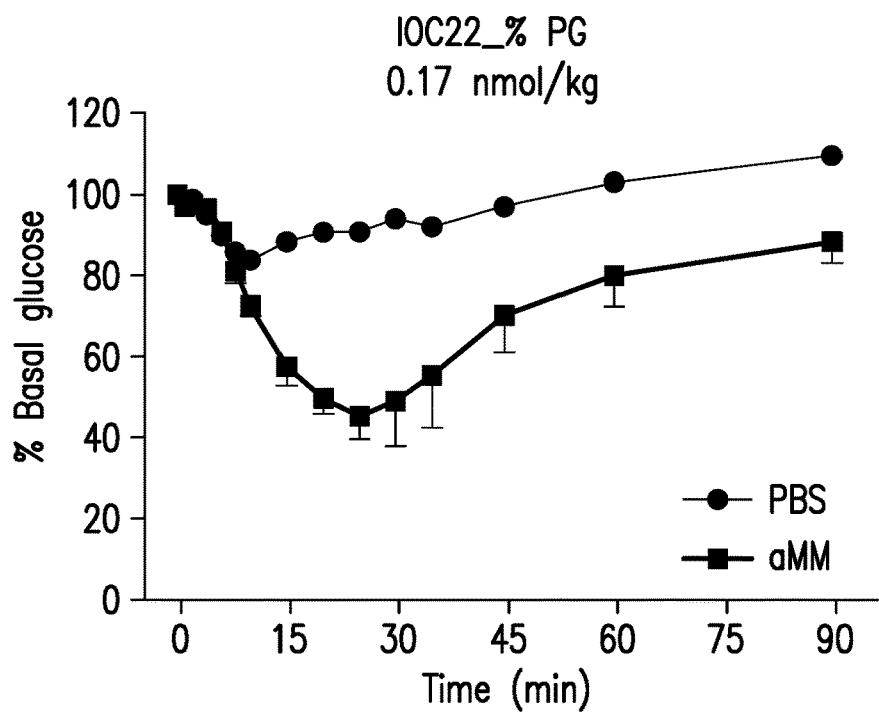
FIG. 10 shows plasma glucose depression curves in non-diabetic male Yucatan minipigs equipped with dual vascular access ports (n=3 per study) following i.v. injection of conjugate IOC-22 at 0.17 nmol/kg under conditions of PBS infusion or i.v. alpha methyl mannose (αMM) infusion.
Figure 11:
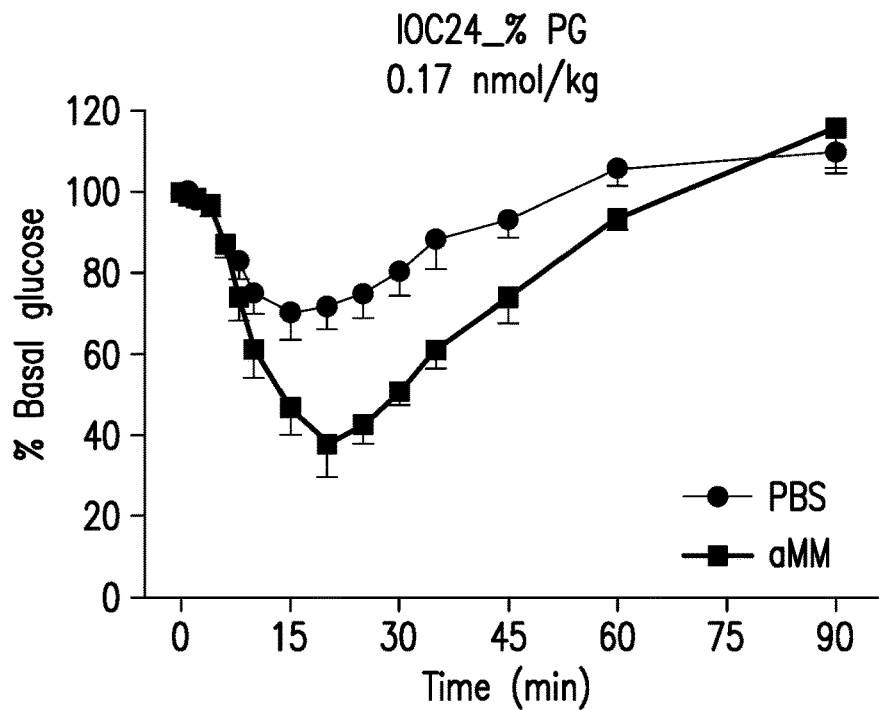
FIG. 11 shows plasma glucose depression curves in non-diabetic male Yucatan minipigs equipped with dual vascular access ports (n=3 per study) following i.v. injection of conjugate IOC-24 at 0.17 nmol/kg under conditions of PBS infusion or i.v. alpha methyl mannose (αMM) infusion.
Figure 12:
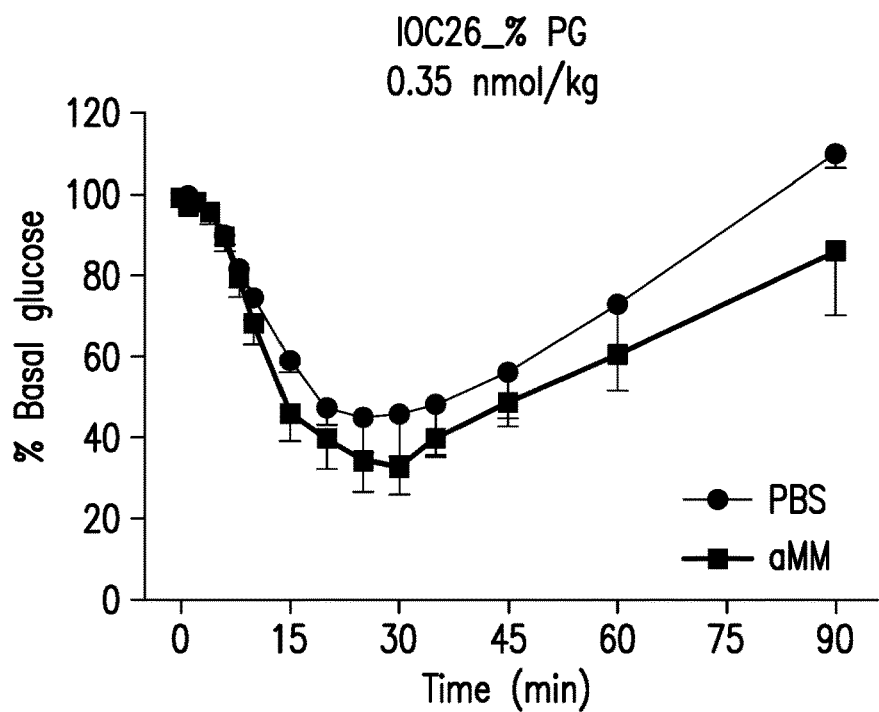
FIG. 12 shows plasma glucose depression curves in non-diabetic male Yucatan minipigs equipped with dual vascular access ports (n=3 per study) following i.v. injection of conjugate IOC-26 at 0.35 nmol/kg under conditions of PBS infusion or i.v. alpha methyl mannose (αMM) infusion.
Figure 13:
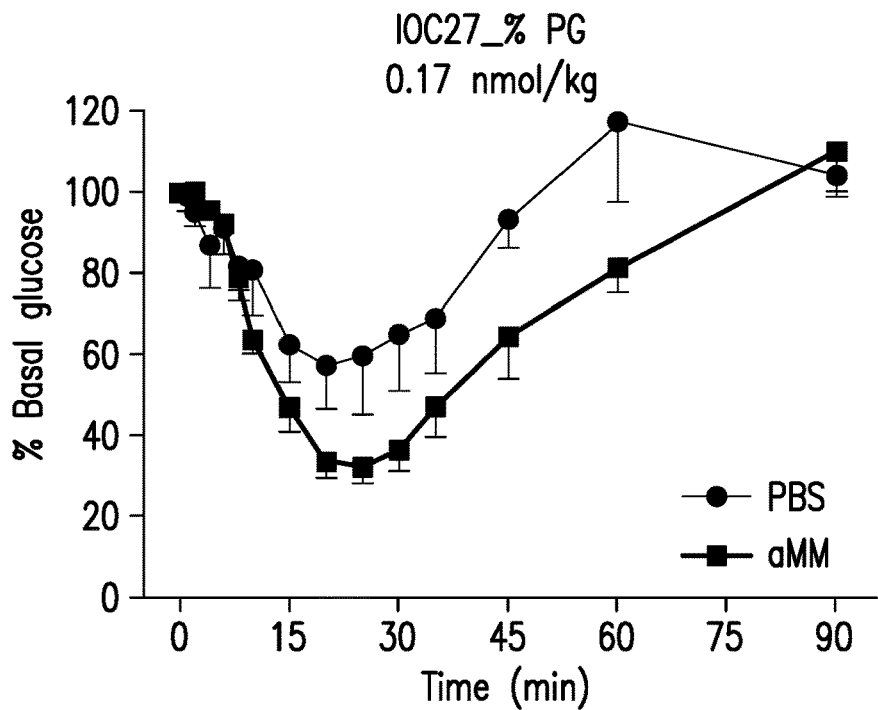
FIG. 13 shows plasma glucose depression curves in non-diabetic male Yucatan minipigs equipped with dual vascular access ports (n=3 per study) following i.v. injection of conjugate IOC-27 at 0.17 nmol/kg under conditions of PBS infusion or i.v. alpha methyl mannose (αMM) infusion.
Figure 14:
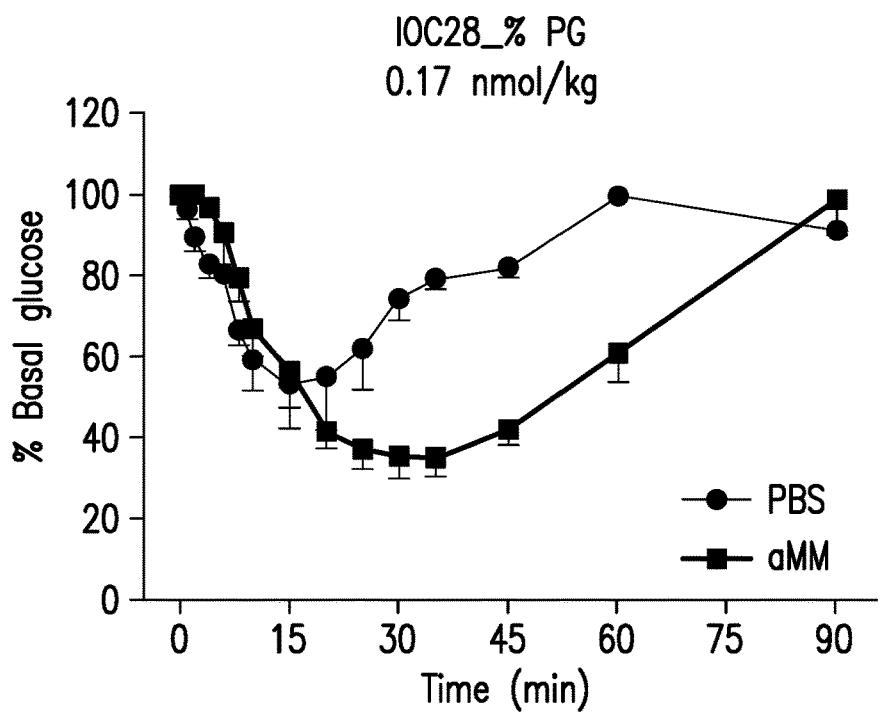
FIG. 14 shows plasma glucose depression curves in non-diabetic male Yucatan minipigs equipped with dual vascular access ports (n=3 per study) following i.v. injection of conjugate IOC-28 at 0.17 nmol/kg under conditions of PBS infusion or i.v. alpha methyl mannose (αMM) infusion.
Figure 15:
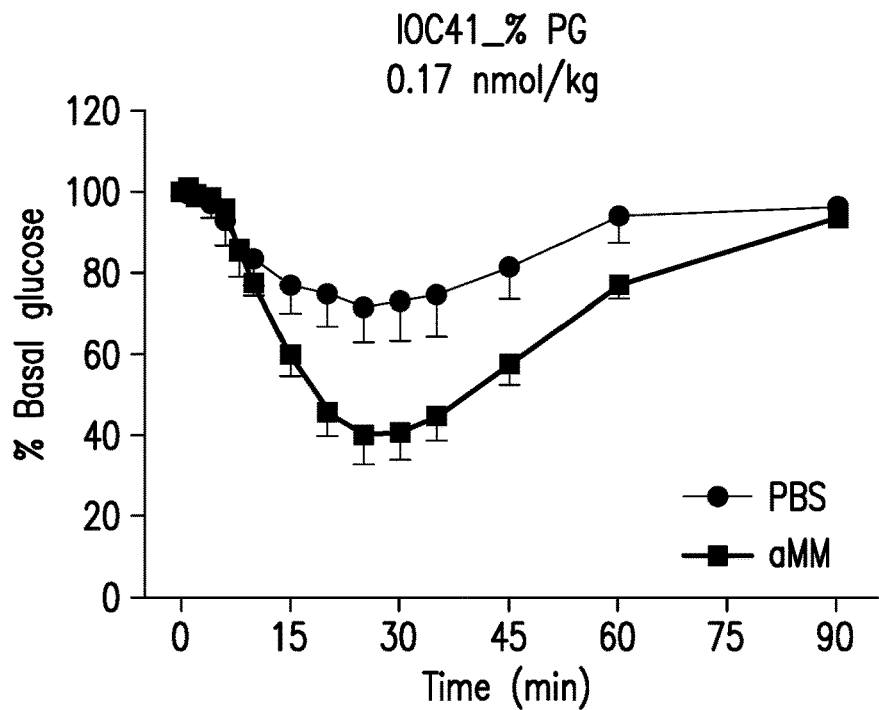
FIG. 15 shows plasma glucose depression curves in non-diabetic male Yucatan minipigs equipped with dual vascular access ports (n=3 per study) following i.v. injection of conjugate IOC-41 at 0.17 nmol/kg under conditions of PBS infusion or i.v. alpha methyl mannose (αMM) infusion.
Figure 16:
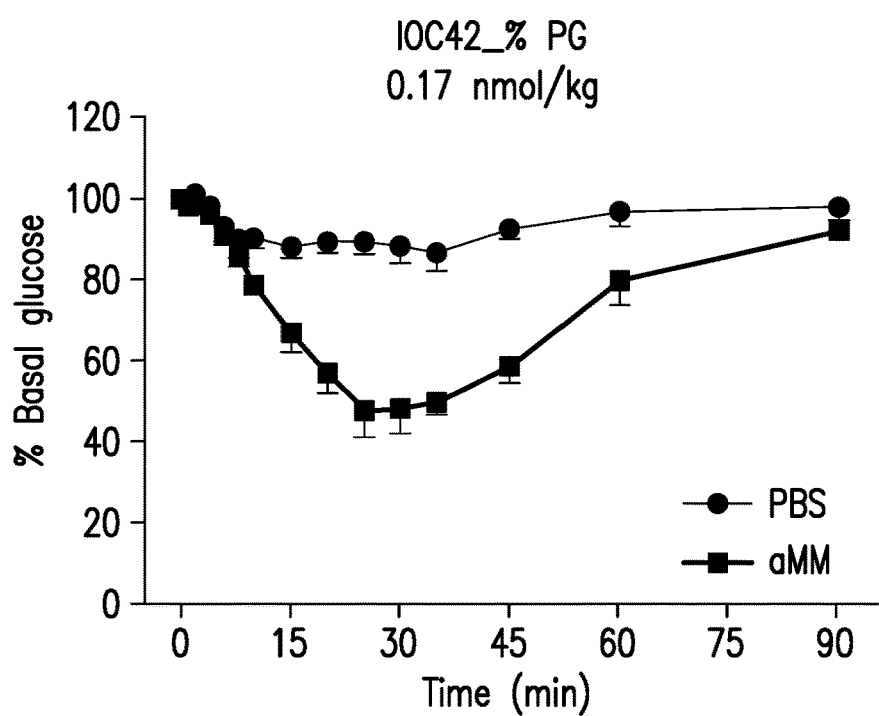
FIG. 16 shows plasma glucose depression curves in non-diabetic male Yucatan minipigs equipped with dual vascular access ports (n=3 per study) following i.v. injection of conjugate IOC-42 at 0.17 nmol/kg under conditions of PBS infusion or i.v. alpha methyl mannose (αMM) infusion.
Figure 17:
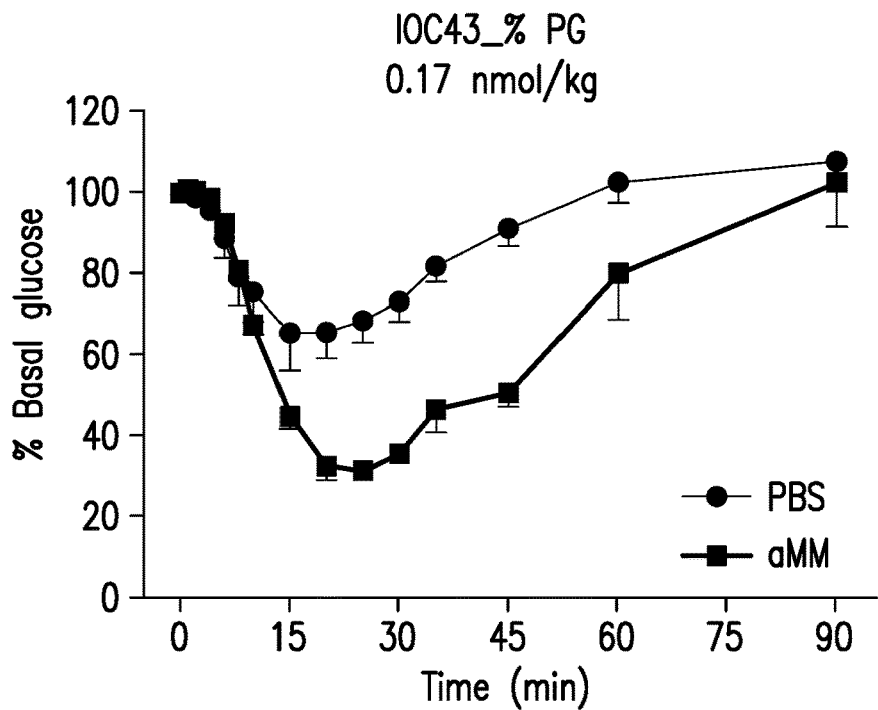
FIG. 17 shows plasma glucose depression curves in non-diabetic male Yucatan minipigs equipped with dual vascular access ports (n=3 per study) following i.v. injection of conjugate IOC-43 at 0.17 nmol/kg under conditions of PBS infusion or i.v. alpha methyl mannose (αMM) infusion.
Figure 18:
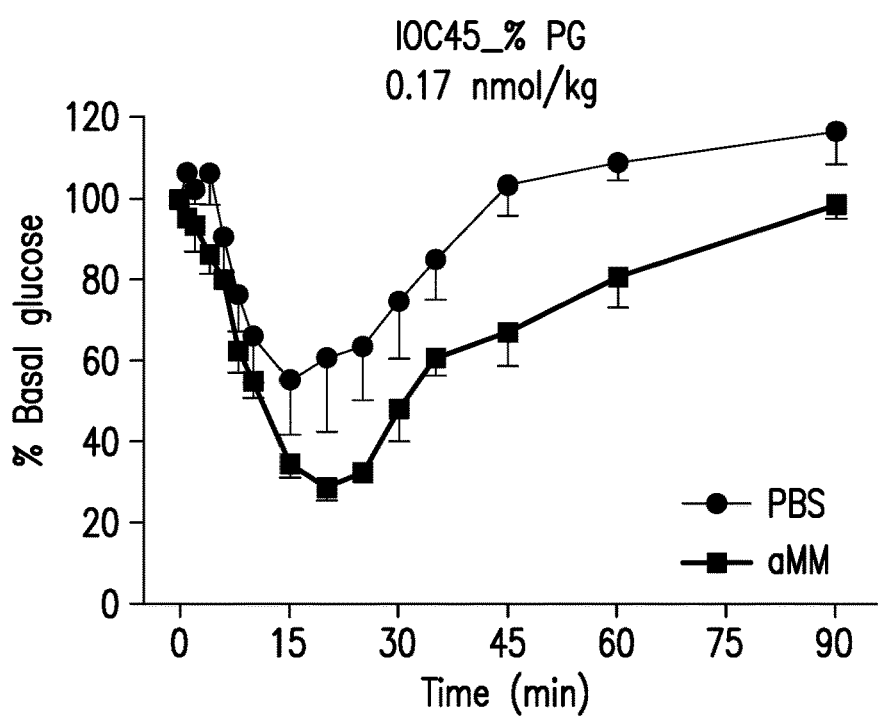
FIG. 18 shows plasma glucose depression curves in non-diabetic male Yucatan minipigs equipped with dual vascular access ports (n=3 per study) following i.v. injection of conjugate IOC-45 at 0.17 nmol/kg under conditions of PBS infusion or i.v. alpha methyl mannose (αMM) infusion.
Figure 19:
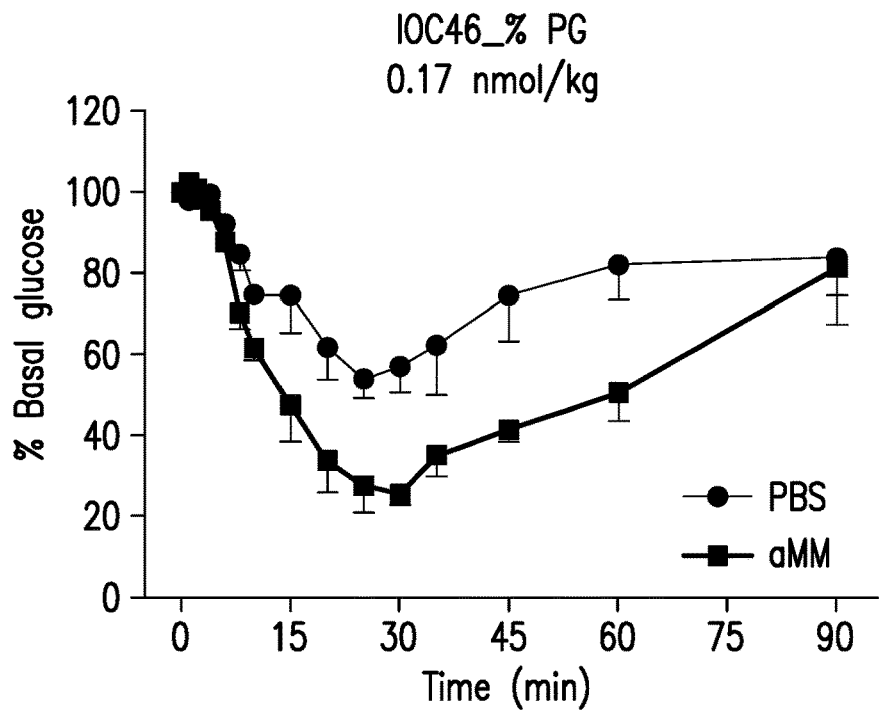
FIG. 19 shows plasma glucose depression curves in non-diabetic male Yucatan minipigs equipped with dual vascular access ports (n=3 per study) following i.v. injection of conjugate IOC-46 at 0.17 nmol/kg under conditions of PBS infusion or i.v. alpha methyl mannose (αMM) infusion.
Figure 20:
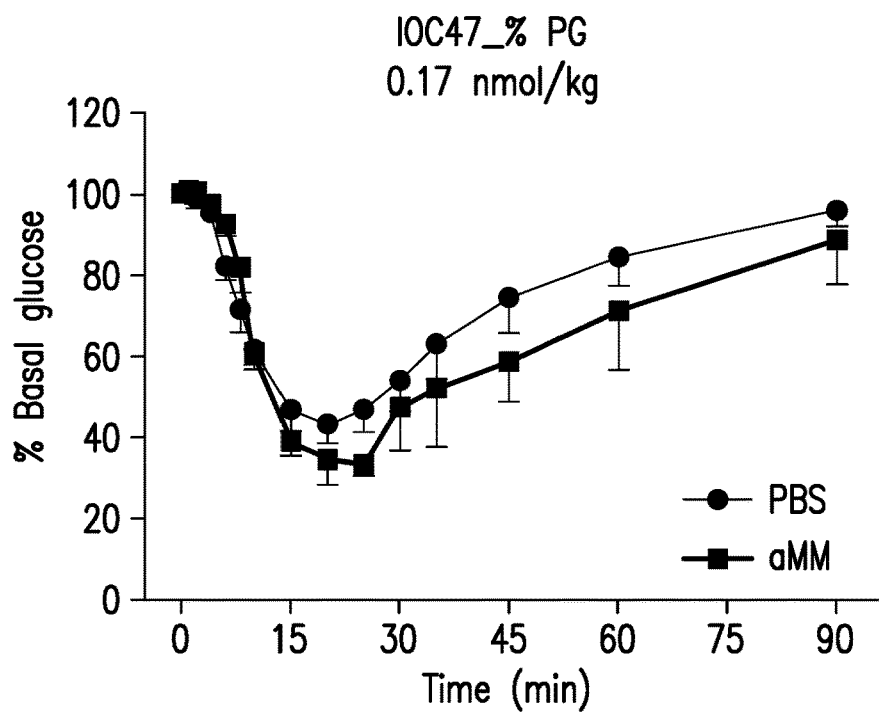
FIG. 20 shows plasma glucose depression curves in non-diabetic male Yucatan minipigs equipped with dual vascular access ports (n=3 per study) following i.v. injection of conjugate IOC-47 at 0.17 nmol/kg under conditions of PBS infusion or i.v. alpha methyl mannose (αMM) infusion.
Figure 21:
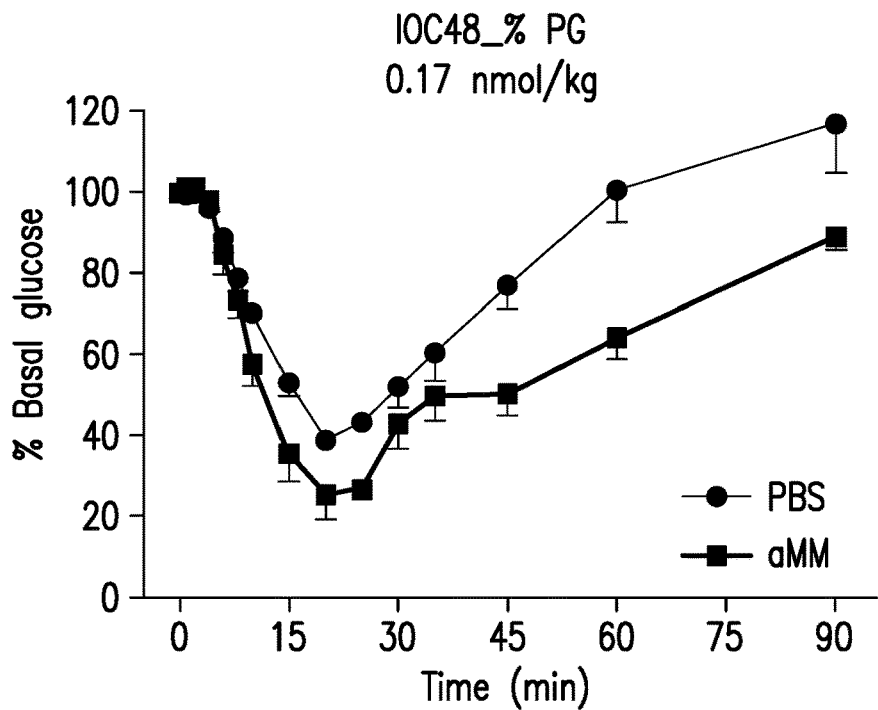
FIG. 21 shows plasma glucose depression curves in non-diabetic male Yucatan minipigs equipped with dual vascular access ports (n=3 per study) following i.v. injection of conjugate IOC-48 at 0.17 nmol/kg under conditions of PBS infusion or i.v. alpha methyl mannose (αMM) infusion.
Figure 22:
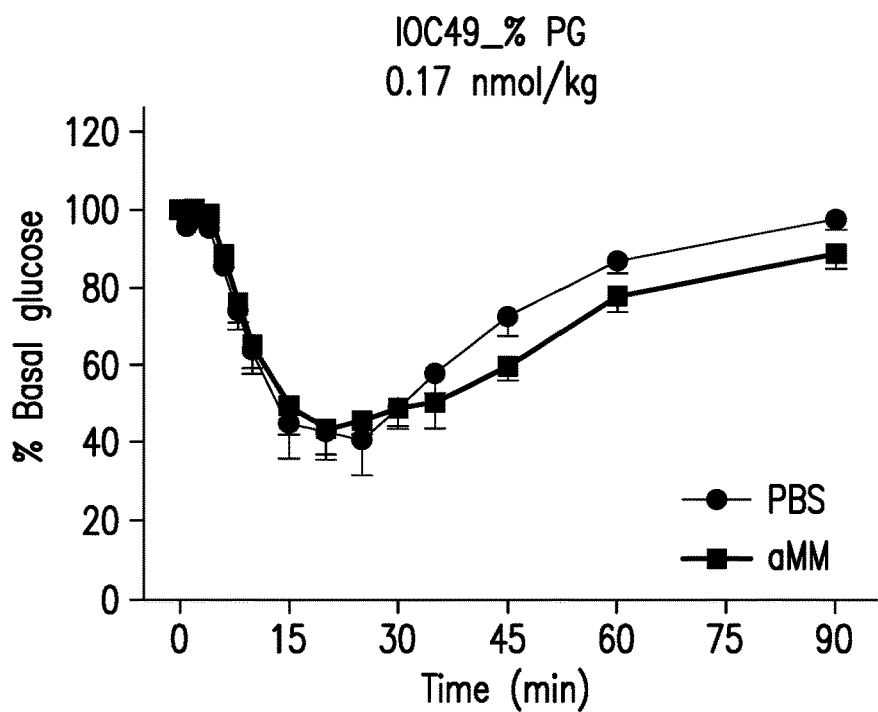
FIG. 22 shows plasma glucose depression curves in non-diabetic male Yucatan minipigs equipped with dual vascular access ports (n=3 per study) following i.v. injection of conjugate IOC-49 at 0.17 nmol/kg under conditions of PBS infusion or i.v. alpha methyl mannose (αMM) infusion.
Figure 23:
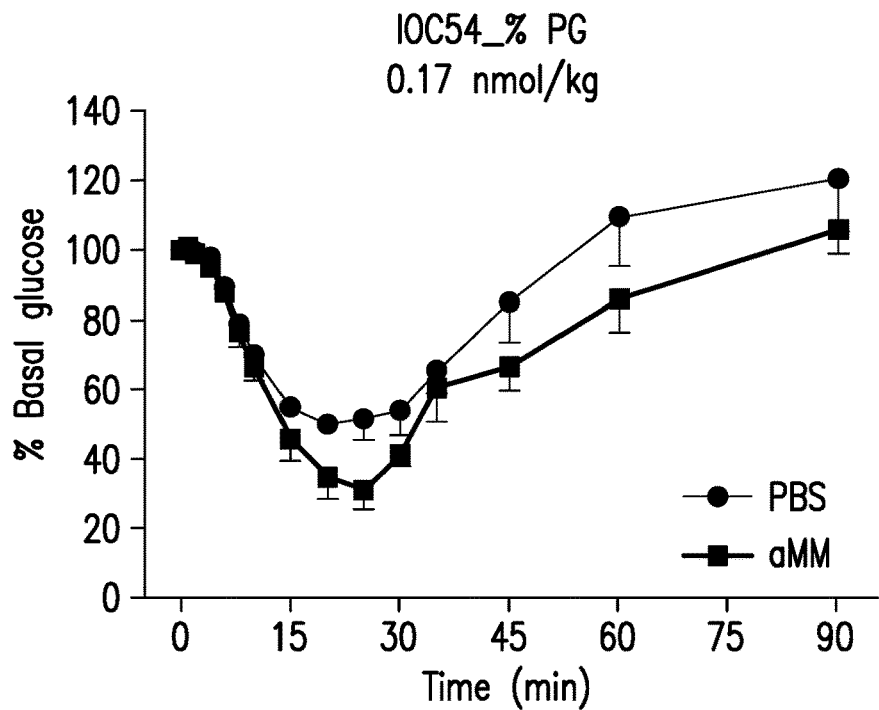
FIG. 23 shows plasma glucose depression curves in non-diabetic male Yucatan minipigs equipped with dual vascular access ports (n=3 per study) following i.v. injection of conjugate IOC-54 at 0.17 nmol/kg under conditions of PBS infusion or i.v. alpha methyl mannose (αMM) infusion.
Figure 24:
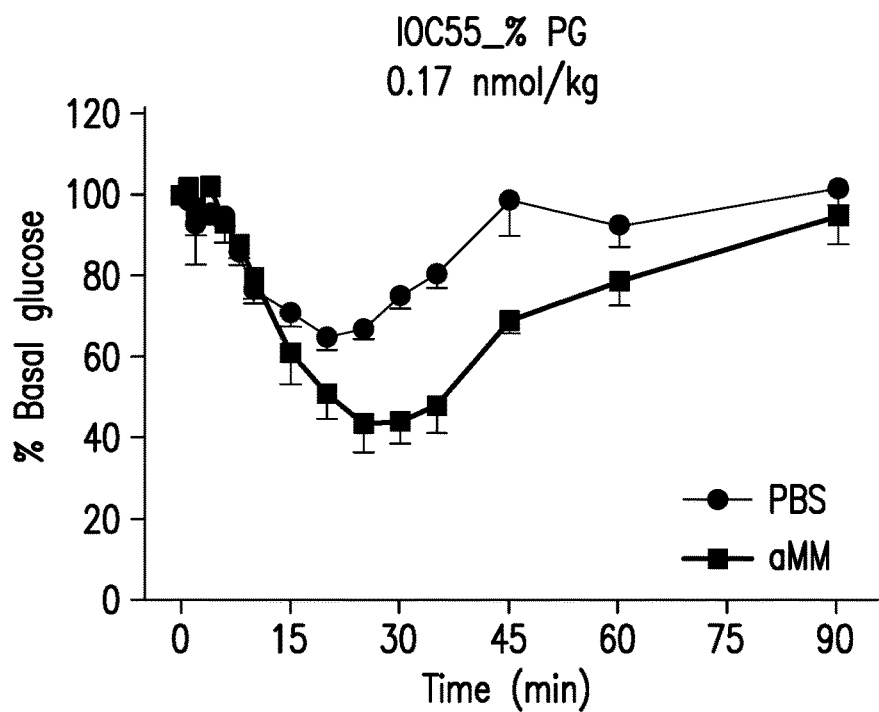
FIG. 24 shows plasma glucose depression curves in non-diabetic male Yucatan minipigs equipped with dual vascular access ports (n=3 per study) following i.v. injection of conjugate IOC-55 at 0.17 nmol/kg under conditions of PBS infusion or i.v. alpha methyl mannose (αMM) infusion.
Figure 25:
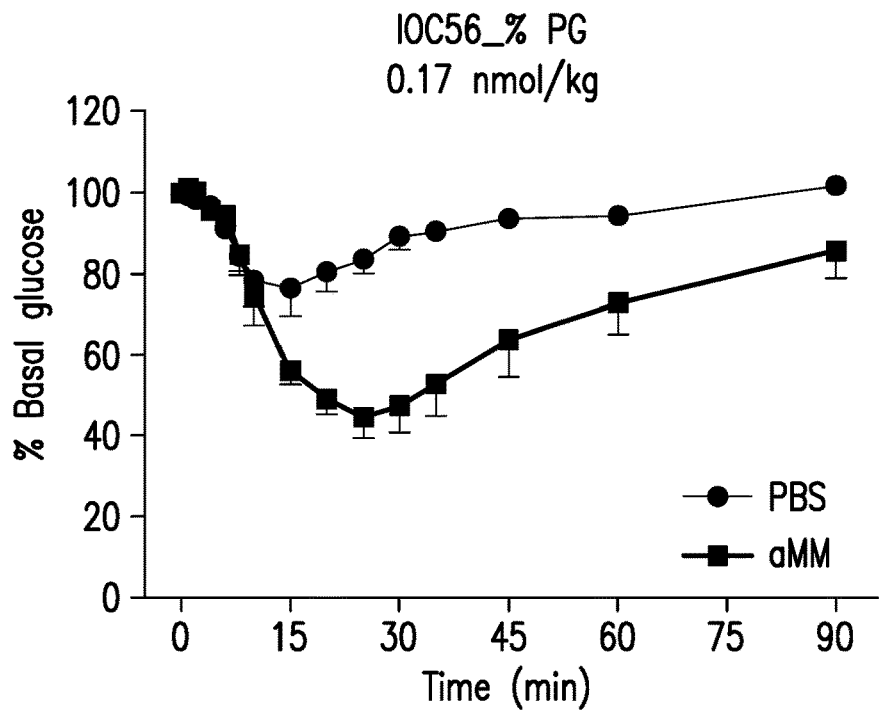
FIG. 25 shows plasma glucose depression curves in non-diabetic male Yucatan minipigs equipped with dual vascular access ports (n=3 per study) following i.v. injection of conjugate IOC-56 at 0.17 nmol/kg under conditions of PBS infusion or i.v. alpha methyl mannose (αMM) infusion.
Figure 26:
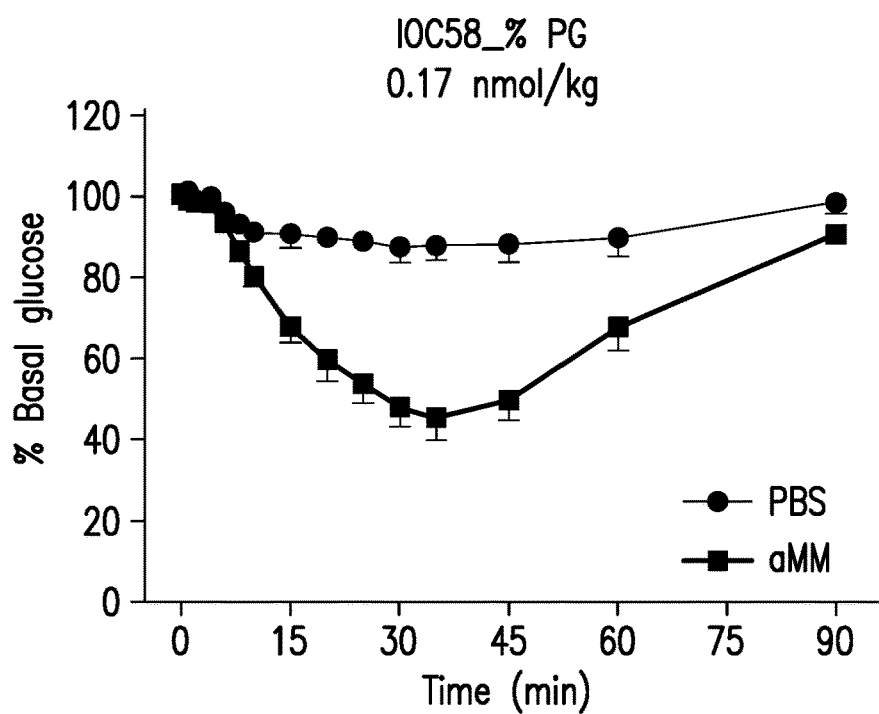
FIG. 26 shows plasma glucose depression curves in non-diabetic male Yucatan minipigs equipped with dual vascular access ports (n=3 per study) following i.v. injection of conjugate IOC-58 at 0.17 nmol/kg under conditions of PBS infusion or i.v. alpha methyl mannose (αMM) infusion.
Figure 27:
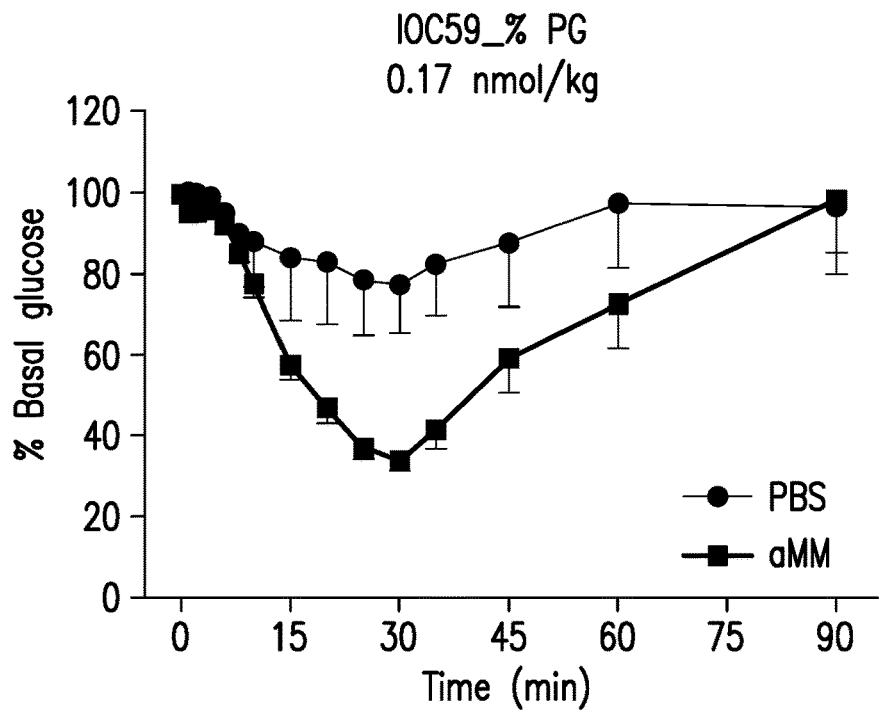
FIG. 27 shows plasma glucose depression curves in non-diabetic male Yucatan minipigs equipped with dual vascular access ports (n=3 per study) following i.v. injection of conjugate IOC-59 at 0.17 nmol/kg under conditions of PBS infusion or i.v. alpha methyl mannose (αMM) infusion.
Figure 28:
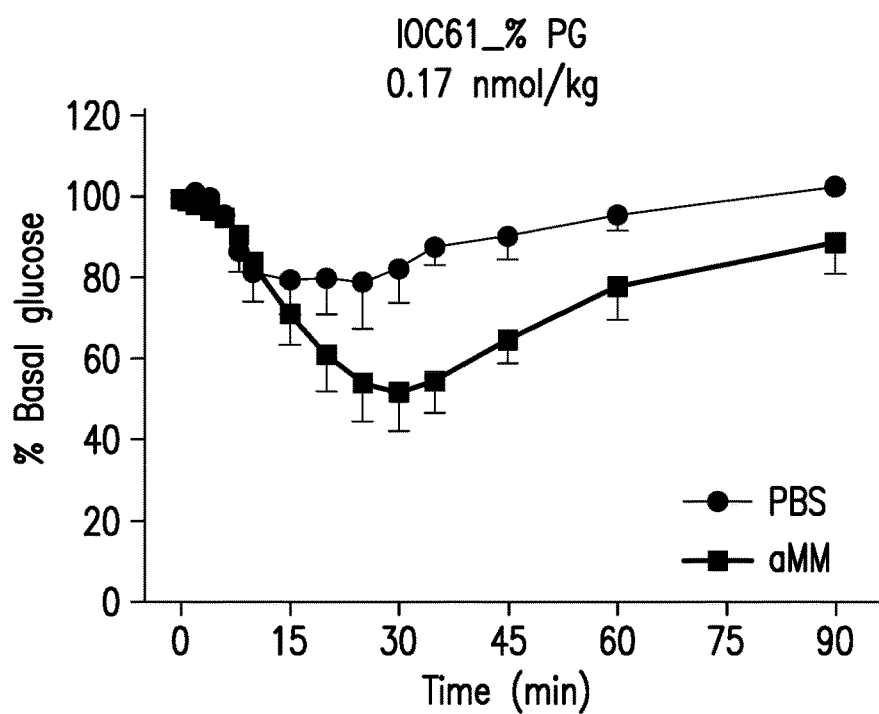
FIG. 28 shows plasma glucose depression curves in non-diabetic male Yucatan minipigs equipped with dual vascular access ports (n=3 per study) following i.v. injection of conjugate IOC-61 at 0.17 nmol/kg under conditions of PBS infusion or i.v. alpha methyl mannose (αMM) infusion.

Glucose results were expressed as % changes over baseline values at t=0 min and are shown for IOC-1, IOC-2, IOC-4, IOC-6, IOC-10, IOC-11, IOC-12, IOC-13, IOC-14, IOC-22, IOC-24, IOC-26, IOC-27, IOC-28, IOC-41, IOC-42, IOC-43, IOC-45, IOC-46, IOC-47, IOC-48, IOC-49, IOC-54, IOC-55, IOC-56, IOC-58, IOC-59, and IOC-61, in FIGS. 1-28, respectively.

It will be appreciated that various of the above-discussed and other features and functions, or alternatives thereof, may be desirably combined into many other different systems or applications. It will also be appreciated that various presently unforeseen or unanticipated alternatives, modifications, variations or improvements therein may be subsequently made by those skilled in the art, which are also intended to be encompassed by the following claims.

What is claimed is:

1. A conjugate having the general formula (I):

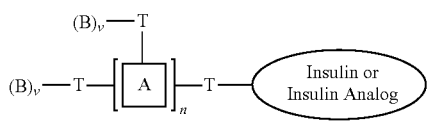
(I)

wherein
(a) the insulin or insulin analog is selected from human insulin, porcine insulin, insulin lispro, insulin aspart, insulin glulisine, insulin glargine, insulin detemir, GlyA21 human insulin, GlyA3 human insulin, LysA22 human insulin, LysB3 human insulin, HisA8 human insulin, GlyA21 ArgA22 human insulin, DesB30 human insulin, LysA9 DesB30 human insulin, GlyA21 DesB30 human insulin, LysA22 DesB30 human insulin, LysB3 DesB30 human insulin, LysA1 ArgB29 DesB30 human insulin, LysA5 ArgB29 DesB30 human insulin, LysA9 ArgB29 DesB30 human insulin, LysA10 ArgB29 DesB30 human insulin, LysA13 ArgB29 DesB30 human insulin, LysA14 ArgB29 DesB30 human insulin, LysA15 ArgB29 DesB30 human insulin, LysA18 ArgB29 DesB30 human insulin, LysA22 ArgB29 DesB30 human insulin, LysA1 GlyA21 ArgB29 DesB30 human insulin, GlyA21 ArgB29 DesB30 human insulin, LysB1 ArgB29 DesB30 human insulin, LysB3 ArgB29 DesB30 human insulin, LysB4 ArgB29 DesB30 human insulin, LysB16 ArgB29 DesB30 human insulin, LysB17 ArgB29 DesB30 human insulin, LysB25 ArgB29 DesB30 human insulin, GlyA21 ArgB31 ProB32 ArgB33 ProB34 ArgB35 human insulin, GlyA21 ArgA22 ArgB31 ProB32 ArgB33 human insulin, and insulin analogs that comprise
   (i) an A chain polypeptide sequence comprising a sequence of $X_1I X_2E X_3CCX_4 X_5 X_6CS X_7 X_8 X_9LE X_{10}YC X_{11}X_{12}$ (SEQ ID NO: 3) and
   (ii) a B chain polypeptide sequence comprising a sequence of $X_{13}VX_{14}X_{15}HLCGSHL VEALX_{16}X_{17}VCGERGFX_{18}YTX_{19}X_{20}X_{21}X_{22}X_{23} X_{24}X_{25}X_{26}$ (SEQ ID NO: 4)
wherein:
$X_1$ is glycine (G) or lysine (K);
$X_2$ is valine (V), glycine (G), or lysine (K);
$X_3$ is glutamine (Q) or lysine (K);
$X_4$ is threonine (T), histidine (H), or lysine (K);
$X_5$ is serine(S) or lysine (K);
$X_6$ is isoleucine (I) or lysine (K);
$X_7$ is leucine (L) or lysine (K);
$X_8$ is tyrosine (Y) or lysine (K);
$X_9$ is glutamine (Q) or lysine (K);
$X_{10}$ is asparagine (N) or lysine (K):
$X_{11}$ is asparagine (N), glycine (G), or lysine (K);
$X_{12}$ is arginine (R), lysine (K), or absent;
$X_{13}$ is phenylalanine (F) or lysine (K);
$X_{14}$ is asparagine (N) or lysine (K);
$X_{15}$ is glutamine (Q) or lysine (K);
$X_{16}$ is tyrosine (Y) or lysine (K);
$X_{17}$ is leucine (L) or lysine (K);
$X_{18}$ is phenylalanine (F) or lysine (K);
$X_{19}$ is proline (P) or lysine (K):
$X_{20}$ is lysine (K), proline (P), arginine (R), or is absent;
$X_{21}$ is threonine (T) or absent;
$X_{22}$ is arginine (R) if $X_{21}$ is threonine (T), or absent;
$X_{23}$ is proline (P) if $X_{22}$ is arginine (R), or absent;
$X_{24}$ is arginine (R) if $X_{23}$ is proline (P), or absent;
$X_{25}$ is proline (P) if $X_{24}$ is arginine (R), or absent; and
$X_{26}$ is arginine (R) if $X_{25}$ is proline (P), or absent,
with the proviso that at least one of $X_1$, $X_3$, $X_5$, $X_6$, $X_7$, $X_8$, $X_9$, $X_{10}$, $X_{12}$, $X_{13}$, $X_{14}$, $X_{15}$, $X_{16}$, $X_{17}$, $X_{18}$, and $X_{19}$ is a lysine (K) and when $X_{19}$ is lysine (K) then $X_{20}$ is absent or if $X_{20}$ is present then at least one of $X_1$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, and $X_{17}$ is lysine (K), or $X_4$ is histidine (H), or $X_{11}$ is glycine (G); or at least one of $X_{12}$ or $X_{21}$ is present;
(b) the group

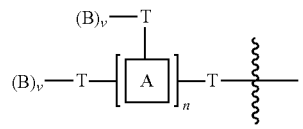

is covalently linked to the amino group at position A1 of the insulin or insulin analog molecule; position B1 of the insulin or insulin analog molecule; position B29 of the insulin or insulin analog molecule; or other lysine residue of the insulin or insulin analog molecule;
(c) each occurrence of spacer T is selected independently from the group consisting of a covalent bond or a bivalent, straight or branched, saturated or unsaturated, optionally substituted $C_{1-30}$ hydrocarbon chain wherein one or more methylene units of the hydrocarbon chain are optionally and independently replaced by —O—, —S—, —N(R)—, —C(O)—, —C(O)O—, —OC(O)—, —N(R)C(O)—, —C(O)N(R)—, —S(O)—, —S(O)₂—, —N(R)SO₂—, —SO₂N(R)—, a heterocyclic group, an aryl group, or a heteroaryl group, wherein each occurrence of R is independently hydrogen, a suitable protecting group, or an acyl moiety, arylalkyl moiety, aliphatic moiety, aryl moiety, heteroaryl moiety, or heteroaliphatic moiety;

(d) each occurrence of 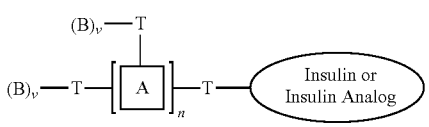 is independently an optionally substituted monomeric amino acid unit selected from the group consisting of aspartic acid and glutamic acid, where either α-carboxylic acid or side chain carboxylic acid group or both carboxylic acids are conjugated to a sugar, or lysine, where either α-amino group or ε-amino group or both amino groups are conjugated to a sugar;

(e) each occurrence of B is a sugar-containing moiety having a valence v that is independently 0, 1, 2, 3, or 4;

(f) n is the number of individual, independently selected monomeric amino acid units 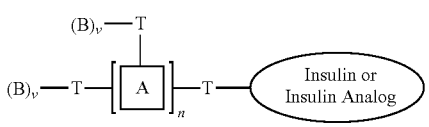, and is selected from 0, 1, 2, 3, or 4, wherein the conjugate prepared using a reagent having a formula selected from the group consisting of ML-1, ML-2, ML-3, ML-4, ML-5, ML-6, ML-7, ML-8, ML-9, ML-10, ML-11, ML-12, ML-13, ML-14, ML-15, ML-16, ML-17, ML-18, ML-19, ML-20, ML-21, ML-22, ML-23, ML-24, ML-25, ML-26, ML-27, ML-28, ML-29, ML-30, ML-31, ML-32, ML-33, ML-34, ML-35, ML-36, ML-37, ML-38, ML-39, ML-40, ML-41, ML-42, ML-43, ML-44, ML-45, and ML-46.

2. A conjugate having the general formula (I):

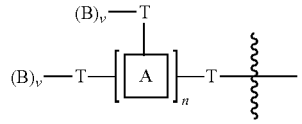

(I)

wherein
(a) the insulin or insulin analog is selected from human insulin, porcine insulin, insulin lispro, insulin aspart, insulin glulisine, insulin glargine, insulin detemir, GlyA21 human insulin, GlyA3 human insulin, LysA22 human insulin, LysB3 human insulin, HisA8 human insulin, GlyA21 ArgA22 human insulin, DesB30 human insulin, LysA9 DesB30 human insulin, GlyA21 DesB30 human insulin, LysA22 DesB30 human insulin, LysB3 DesB30 human insulin, LysA1 ArgB29 DesB30 human insulin, LysA5 ArgB29 DesB30 human insulin, LysA9 ArgB29 DesB30 human insulin, LysA10 ArgB29 DesB30 human insulin, LysA13 ArgB29 DesB30 human insulin, LysA14 ArgB29 DesB30 human insulin, LysA15 ArgB29 DesB30 human insulin, LysA18 ArgB29 DesB30 human insulin, LysA22 ArgB29 DesB30 human insulin, LysA1 GlyA21 ArgB29 DesB30 human insulin, GlyA21 ArgB29 DesB30 human insulin, LysB1 ArgB29 DesB30 human insulin, LysB3 ArgB29 DesB30 human insulin, LysB4 ArgB29 DesB30 human insulin, LysB16 ArgB29 DesB30 human insulin, LysB17 ArgB29 DesB30 human insulin, LysB25 ArgB29 DesB30 human insulin, GlyA21 ArgB31 ProB32 ArgB33 human insulin, GlyA21 ArgB31 ProB32 ArgB33 ProB34 ArgB35 human insulin, GlyA21 ArgA22 ArgB31 ProB32 ArgB33 human insulin, and insulin analogs that comprise (i) an A chain polypeptide sequence comprising a sequence of XII X₂E X₃CCX4 X₅ X₆CS X₇ X₈ X₉LE X₁₀YC X₁₁X₁₂ (SEQ ID NO: 3) and (ii) a B chain polypeptide sequence comprising a sequence of X₁₃VX₁₄X₁₅HLCGSHL VEALX₁₆X₁₇VCGERGFX₁₈YTX₁₉X₂₀X₂₁X₂₂ X₂₃X₂₄X₂₅X₂₆ (SEQ ID NO: 4)

wherein:
X₁ is glycine (G) or lysine (K);
X₂ is valine (V), glycine (G), or lysine (K);
X₃ is glutamine (Q) or lysine (K);
X₄ is threonine (T), histidine (H), or lysine (K);
X₅ is serine(S) or lysine (K);
X₆ is isoleucine (I) or lysine (K);
X₇ is leucine (L) or lysine (K);
X₈ is tyrosine (Y) or lysine (K);
X₉ is glutamine (Q) or lysine (K);
X₁₀ is asparagine (N) or lysine (K);
X₁₁ is asparagine (N), glycine (G), or lysine (K);
X₁₂ is arginine (R), lysine (K), or absent;
X₁₃ is phenylalanine (F) or lysine (K);
X₁₄ is asparagine (N) or lysine (K);
X₁₅ is glutamine (Q) or lysine (K);
X₁₆ is tyrosine (Y) or lysine (K);
X₁₇ is leucine (L) or lysine (K);
X₁₈ is phenylalanine (F) or lysine (K);
X₁₉ is proline (P) or lysine (K):
X₂₀ is lysine (K), proline (P), arginine (R), or is absent;
X₂₁ is threonine (T) or absent;
X₂₂ is arginine (R) if X₂₁ is threonine (T), or absent;
X₂₃ is proline (P) if X₂₂ is arginine (R), or absent;
X₂₄ is arginine (R) if X₂₃ is proline (P), or absent;
X₂₅ is proline (P) if X₂₄ is arginine (R), or absent; and
X₂₆ is arginine (R) if X₂₅ is proline (P), or absent, with the proviso that at least one of X₁, X₃, X₅, X₆, X₇, X₈, X₉, X₁₀, X₁₂, X₁₃, X₁₄, X₁₅, X₁₆, X₁₇, X₁₈, and X₁₉ is a lysine (K) and when X₁₉ is lysine (K) then X₂₀ is absent or if X₂₀ is present then at least one of X₁, X₃, X₄, X₅, X₆, X₇, X₈, X₉, X₁₀, X₁₁, X₁₂, X₁₃, X₁₄, X₁₅, X₁₆, and X₁₇ is lysine (K), or X₄ is histidine (H), or X₁₁ is glycine (G); or at least one of X₁₂ or X₂₁ is present;

(b) the group

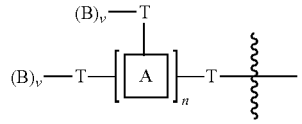

is covalently linked to the amino group at position A1 of the insulin or insulin analog molecule; position B1 of the insulin or insulin analog molecule; position B29 of the insulin or insulin analog molecule; or other lysine residue of the insulin or insulin analog molecule;

(c) each occurrence of spacer T is selected independently from the group consisting of a covalent bond or a bivalent, straight or branched, saturated or unsaturated, optionally substituted C₁₋₃₀ hydrocarbon chain wherein one or more methylene units of the hydrocarbon chain are optionally and independently replaced by —O—, —S—, —N(R)—, —C(O)—, —C(O)O—, —OC(O)—, —N(R)C(O)—, —C(O)N(R)—, —S(O)—, —S(O)₂—, —N(R)SO₂—, —SO₂N(R)—, a heterocyclic group, an aryl group, or a heteroaryl group, wherein each occurrence of R is independently hydrogen, a suitable protecting group, or an acyl moiety, arylalkyl moiety, aliphatic moiety, aryl moiety, heteroaryl moiety, or heteroaliphatic moiety;

(d) each occurrence of $\boxed{A}$ is independently an optionally substituted monomeric amino acid unit selected from the group consisting of aspartic acid and glutamic acid, where either α-carboxylic acid or side chain carboxylic acid group or both carboxylic acids are conjugated to a sugar, or lysine, where either a-amino group or E-amino group or both amino groups are conjugated to a sugar;

(e) each occurrence of B is a sugar-containing moiety having a valence v that is independently 0, 1, 2, 3, or 4;

(f) n is the number of individual, independently selected monomeric amino acid units $\boxed{A}$, and is selected from 0, 1, 2, 3, or 4, wherein the conjugate has a formula selected from the group consisting of IOC-1, 10C-2, IOC-3, IOC-4, IOC-5, IOC-6, IOC-7, IOC-8, IOC-9, IOC-10, IOC-11, IOC-12, IOC-13, IOC-14, IOC-15, IOC-16, IOC-17, IOC-18, IOC-19, IOC-20, IOC-21, IOC-22, IOC-23, IOC-24, IOC-25, IOC-26, IOC-27, IOC-28, IOC-29, IOC-30, IOC-31, IOC-32, IOC-33, IOC-34, IOC-35, IOC-36, IOC-37, IOC-38, IOC-39, IOC-40, IOC-41, IOC-42, IOC-43, IOC-44, IOC-45, IOC-46, IOC-47, IOC-48, IOC-49, IOC-50, IOC-51, IOC-52, IOC-53, IOC-54, IOC-55, IOC-56, IOC-57, IOC-58, IOC-59, IOC-60, IOC-61, and IOC-62.

\* \* \* \* \*

```
                          SEQUENCE LISTING

<160> NUMBER OF SEQ ID NOS: 4

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 22
<212> TYPE: PRT
<213> ORGANISM: Artificial Sequence
<220> FEATURE:
<223> OTHER INFORMATION: Generic A-chain Polypeptide
<220> FEATURE:
<221> NAME/KEY: MISC_FEATURE
<222> LOCATION: (1)..(1)
<223> OTHER INFORMATION: Xaa is G or K
<220> FEATURE:
<221> NAME/KEY: MISC_FEATURE
<222> LOCATION: (3)..(3)
<223> OTHER INFORMATION: Xaa is V, G, or K
<220> FEATURE:
<221> NAME/KEY: MISC_FEATURE
<222> LOCATION: (5)..(5)
<223> OTHER INFORMATION: Xaa is Q or K
<220> FEATURE:
<221> NAME/KEY: MISC_FEATURE
<222> LOCATION: (8)..(8)
<223> OTHER INFORMATION: Xaa is T, H, or K
<220> FEATURE:
<221> NAME/KEY: MISC_FEATURE
<222> LOCATION: (9)..(9)
<223> OTHER INFORMATION: Xaa is S or K
<220> FEATURE:
<221> NAME/KEY: MISC_FEATURE
<222> LOCATION: (10)..(10)
<223> OTHER INFORMATION: Xaa is I or K
<220> FEATURE:
<221> NAME/KEY: MISC_FEATURE
<222> LOCATION: (13)..(13)
<223> OTHER INFORMATION: Xaa is L or K
<220> FEATURE:
<221> NAME/KEY: MISC_FEATURE
<222> LOCATION: (14)..(14)
<223> OTHER INFORMATION: Xaa is Y or K
<220> FEATURE:
<221> NAME/KEY: MISC_FEATURE
<222> LOCATION: (15)..(15)
<223> OTHER INFORMATION: Xaa is Q or K
<220> FEATURE:
```

```
<221> NAME/KEY: MISC_FEATURE
<222> LOCATION: (18)..(18)
<223> OTHER INFORMATION: Xaa is N or K
<220> FEATURE:
<221> NAME/KEY: MISC_FEATURE
<222> LOCATION: (21)..(21)
<223> OTHER INFORMATION: Xaa is N, G, or K
<220> FEATURE:
<221> NAME/KEY: MISC_FEATURE
<222> LOCATION: (22)..(22)
<223> OTHER INFORMATION: Xaa is R, K, or absent

<400> SEQUENCE: 3

Xaa Ile Xaa Glu Xaa Cys Cys Xaa Xaa Xaa Cys Ser Xaa Xaa Xaa Leu
1               5                   10                  15

Glu Xaa Tyr Cys Xaa Xaa
            20

<210> SEQ ID NO 4
<211> LENGTH: 35
<212> TYPE: PRT
<213> ORGANISM: Artificial Sequence
<220> FEATURE:
<223> OTHER INFORMATION: Generic B-chain polypeptide
<220> FEATURE:
<221> NAME/KEY: MISC_FEATURE
<222> LOCATION: (1)..(1)
<223> OTHER INFORMATION: Xaa is F or K
<220> FEATURE:
<221> NAME/KEY: MISC_FEATURE
<222> LOCATION: (3)..(3)
<223> OTHER INFORMATION: Xaa is N or K
<220> FEATURE:
<221> NAME/KEY: MISC_FEATURE
<222> LOCATION: (4)..(4)
<223> OTHER INFORMATION: Xaa is Q or K
<220> FEATURE:
<221> NAME/KEY: MISC_FEATURE
<222> LOCATION: (16)..(16)
<223> OTHER INFORMATION: Xaa is Y or K
<220> FEATURE:
<221> NAME/KEY: MISC_FEATURE
<222> LOCATION: (17)..(17)
<223> OTHER INFORMATION: Xaa is L or K
<220> FEATURE:
<221> NAME/KEY: MISC_FEATURE
<222> LOCATION: (25)..(25)
<223> OTHER INFORMATION: Xaa is F or K
<220> FEATURE:
<221> NAME/KEY: MISC_FEATURE
<222> LOCATION: (28)..(28)
<223> OTHER INFORMATION: Xaa is P or K
<220> FEATURE:
<221> NAME/KEY: MISC_FEATURE
<222> LOCATION: (29)..(29)
<223> OTHER INFORMATION: Xaa is K, P, R, or absent
<220> FEATURE:
<221> NAME/KEY: MISC_FEATURE
<222> LOCATION: (30)..(30)
<223> OTHER INFORMATION: Xaa is T or absent
<220> FEATURE:
<221> NAME/KEY: MISC_FEATURE
<222> LOCATION: (31)..(31)
<223> OTHER INFORMATION: Xaa is R if X30 is T, or absent
<220> FEATURE:
<221> NAME/KEY: MISC_FEATURE
<222> LOCATION: (32)..(32)
<223> OTHER INFORMATION: Xaa is P if X31 is R, or absent
<220> FEATURE:
<221> NAME/KEY: MISC_FEATURE
<222> LOCATION: (33)..(33)
<223> OTHER INFORMATION: Xaa is R if X32 is P, or absent
<220> FEATURE:
<221> NAME/KEY: MISC_FEATURE
<222> LOCATION: (34)..(34)
<223> OTHER INFORMATION: Xaa is P if X33 is R, or absent
```

```
<220> FEATURE:
<221> NAME/KEY: MISC_FEATURE
<222> LOCATION: (35)..(35)
<223> OTHER INFORMATION: Xaa is R if X34 is P, or absent

<400> SEQUENCE: 4

Xaa Val Xaa Xaa His Leu Cys Gly Ser His Leu Val Glu Ala Leu Xaa
1               5                   10                  15

Xaa Val Cys Gly Glu Arg Gly Phe Xaa Tyr Thr Xaa Xaa Xaa Xaa Xaa
            20                  25              30

Xaa Xaa Xaa
        35
```